United States Patent
Lyon et al.

(10) Patent No.: US 11,103,593 B2
(45) Date of Patent: *Aug. 31, 2021

(54) PEGYLATED DRUG-LINKERS FOR IMPROVED LIGAND-DRUG CONJUGATE PHARMACOKINETICS

(71) Applicant: SEAGEN INC., Bothell, WA (US)

(72) Inventors: Robert Lyon, Sammamish, WA (US); Patrick Burke, Seattle, WA (US); Joshua Hunter, Lynnwood, WA (US)

(73) Assignee: SEAGEN INC., Bothell, WA (US)

( * ) Notice: Subject to any disclaimer, the term of this patent is extended or adjusted under 35 U.S.C. 154(b) by 380 days.

This patent is subject to a terminal disclaimer.

(21) Appl. No.: 15/029,584

(22) PCT Filed: Oct. 14, 2014

(86) PCT No.: PCT/US2014/060477
§ 371 (c)(1),
(2) Date: Apr. 14, 2016

(87) PCT Pub. No.: WO2015/057699
PCT Pub. Date: Apr. 23, 2015

(65) Prior Publication Data
US 2016/0310612 A1    Oct. 27, 2016

Related U.S. Application Data

(60) Provisional application No. 61/891,320, filed on Oct. 15, 2013, provisional application No. 61/941,904, (Continued)

(51) Int. Cl.
*A61K 47/68* (2017.01)
*C07K 16/28* (2006.01)
(Continued)

(52) U.S. Cl.
CPC ........ *A61K 47/6817* (2017.08); *A61K 47/549* (2017.08); *A61K 47/60* (2017.08);
(Continued)

(58) Field of Classification Search
None
See application file for complete search history.

(56) References Cited

U.S. PATENT DOCUMENTS 4,816,397 A    3/1989  Boss
4,816,567 A    3/1989  Cabilly
(Continued)

FOREIGN PATENT DOCUMENTS

EP    0171496 A3    11/1987
EP    0173494 A3    11/1987
(Continued)

OTHER PUBLICATIONS

Venonese et al. ("Veronese", Drug Discovery Today, 2005, 10(21), 1451-1458) (Year: 2005).*
(Continued)

*Primary Examiner* — Karl J Puttlitz
(74) *Attorney, Agent, or Firm* — Morrison & Foerster LLP

(57) ABSTRACT

The present invention provides Ligand-Drug Conjugates comprising a PEG Unit in a parallel orientation to the Drug Unit. The invention provides inter alia, Ligand-Drug Conjugates (LDCs), methods of preparing and using them, and intermediates thereof. The Ligand-Drug Conjugates are stable in circulation, yet capable of inflicting cell death on targeted cells or inhibiting proliferation of targeted cells once its drug cargo is released in the vicinity or within targeted cells. In principle embodiments, an LDC of the (Continued)

present invention is represented by the structure of Formula I.

26 Claims, 23 Drawing Sheets

Specification includes a Sequence Listing.

Related U.S. Application Data filed on Feb. 19, 2014, provisional application No. 61/947,742, filed on Mar. 4, 2014, provisional application No. 61/975,318, filed on Apr. 4, 2014.

(51) Int. Cl.
*A61K 47/60* (2017.01)
*A61K 47/54* (2017.01)
*A61K 39/00* (2006.01)

(52) U.S. Cl.
CPC ...... *A61K 47/6819* (2017.08); *A61K 47/6851* (2017.08); *A61K 47/6883* (2017.08); *A61K 47/6885* (2017.08); *C07K 16/28* (2013.01); *C07K 16/2878* (2013.01); *A61K 2039/505* (2013.01); *C07K 2317/94* (2013.01)

(56) References Cited

U.S. PATENT DOCUMENTS

| | | |
|---|---|---|
| 4,880,935 A | 11/1989 | Thorpe |
| 5,122,368 A | 6/1992 | Greenfield |
| 5,225,539 A | 7/1993 | Winter |
| 5,585,089 A | 12/1996 | Queen |
| 5,605,976 A | 2/1997 | Martinez et al. |
| 5,622,929 A | 4/1997 | Willner |
| 5,672,662 A | 9/1997 | Harris |
| 5,681,567 A | 10/1997 | Martinez et al. |
| 5,756,593 A | 5/1998 | Martinez et al. |
| 5,757,078 A | 5/1998 | Matsuda |
| 5,824,805 A | 10/1998 | King |
| 5,851,527 A | 12/1998 | Hansen |
| 5,919,455 A | 7/1999 | Greenwald et al. |
| 5,965,119 A | 10/1999 | Greenwald et al. |
| 6,077,499 A | 6/2000 | Griffiths et al. |
| 6,077,939 A | 6/2000 | Wei |
| 6,113,906 A | 9/2000 | Greenwald et al. |
| 6,124,431 A | 9/2000 | Sakakibara et al. |
| 6,153,655 A | 11/2000 | Martinez et al. |
| 6,214,330 B1 | 4/2001 | Greenwald et al. |
| 6,214,345 B1 | 4/2001 | Firestone et al. |
| 6,261,537 B1 | 7/2001 | Klaveness et al. |
| 6,303,569 B1 | 10/2001 | Greenwald et al. |
| 6,323,322 B1 | 11/2001 | Filpula et al. |
| 6,331,289 B1 | 12/2001 | Klaveness et al. |
| 6,361,774 B1 | 3/2002 | Griffiths et al. |
| 6,395,266 B1 | 5/2002 | Martinez et al. |
| 6,556,506 B2 | 5/2003 | Greenwald et al. |
| 6,569,834 B1 | 5/2003 | Petit et al. |
| 6,602,498 B2 | 8/2003 | Shen |
| 6,624,142 B2 | 9/2003 | Greenwald et al. |
| 6,638,499 B2 | 10/2003 | Martinez et al. |
| 6,643,575 B2 | 11/2003 | Ishida et al. |
| 6,680,047 B2 | 1/2004 | Klaveness et al. |
| 6,743,896 B2 | 6/2004 | Filpula et al. |
| 6,743,908 B2 | 6/2004 | Filpula et al. |
| 6,777,387 B2 | 8/2004 | Greenwald et al. |
| 6,824,782 B2 | 11/2004 | Whitlow et al. |
| 6,872,393 B2 | 3/2005 | Whitlow et al. |
| 7,011,812 B1 | 3/2006 | Griffiths et al. |
| 7,026,440 B2 | 4/2006 | Bentley et al. |
| 7,090,843 B1 | 8/2006 | Francisco |
| 7,091,186 B2 | 8/2006 | Senter et al. |
| 7,150,872 B2 | 12/2006 | Whitlow et al. |
| 7,273,845 B2 | 9/2007 | Zhao et al. |
| 7,300,644 B2 | 11/2007 | Griffiths et al. |
| 7,332,164 B2 | 2/2008 | Greenwald et al. |
| 7,374,762 B2 | 5/2008 | Amphlett et al. |
| 7,375,078 B2 | 5/2008 | Feng |
| 7,462,687 B2 | 12/2008 | Greenwald et al. |
| 7,494,649 B2 | 2/2009 | Amphlett et al. |
| 7,498,298 B2 | 3/2009 | Doronina |
| 7,501,120 B2 | 3/2009 | Amphlett et al. |
| 7,514,066 B2 | 4/2009 | Griffiths et al. |
| 7,514,080 B2 | 4/2009 | Amphlett et al. |
| 7,553,816 B2 | 6/2009 | Senter et al. |
| 7,595,304 B2 | 9/2009 | Zhao et al. |
| 7,632,504 B2 | 12/2009 | Whitlow et al. |
| 7,659,241 B2 | 2/2010 | Senter |
| 7,754,681 B2 | 7/2010 | Feng |
| 7,754,885 B2 | 7/2010 | Hoefle et al. |
| 7,767,205 B2 | 8/2010 | Mao et al. |
| 7,785,618 B2 | 8/2010 | Elmaleh et al. |
| 7,872,072 B2 | 1/2011 | Bentley et al. |
| 7,884,869 B2 | 2/2011 | Shurboff et al. |
| 7,888,536 B2 | 2/2011 | Davis et al. |
| 7,931,890 B2 | 4/2011 | Griffiths et al. |
| 7,947,839 B2 | 5/2011 | Gazzard et al. |
| 7,989,434 B2 | 8/2011 | Feng |
| 7,989,598 B2 | 8/2011 | Steeves et al. |
| 7,994,135 B2 | 8/2011 | Doronina et al. |
| 8,012,485 B2 | 9/2011 | Amphlett et al. |
| 8,012,488 B2 | 9/2011 | Sakanoue et al. |
| 8,039,273 B2 | 10/2011 | Jeffrey |
| 8,088,387 B2 | 1/2012 | Steeves et al. |
| 8,163,888 B2 | 4/2012 | Steeves et al. |
| 8,168,605 B2 | 5/2012 | Zhao et al. |
| 8,198,417 B2 | 6/2012 | Steeves et al. |
| 8,257,706 B2 | 9/2012 | Mcdonagh |
| 8,268,317 B2 | 9/2012 | Govindan et al. |
| 8,273,833 B2 | 9/2012 | Bentley et al. |
| 8,367,065 B2 | 2/2013 | Zhao et al. |
| 8,440,816 B2 | 5/2013 | Bentley et al. |
| 8,455,622 B2 | 6/2013 | Mcdonagh et al. |
| 8,563,509 B2 | 10/2013 | Chari et al. |
| 8,568,728 B2 | 10/2013 | Jeffrey |
| 8,609,092 B2 | 12/2013 | Torgov et al. |
| 9,061,074 B2 | 6/2015 | Carter et al. |
| 9,242,013 B2 | 1/2016 | Howard et al. |
| 2002/0102215 A1 | 8/2002 | Klaveness |
| 2004/0001820 A1 | 1/2004 | Hahn et al. |
| 2004/0009166 A1 | 1/2004 | Filpula et al. |
| 2004/0053976 A1 | 3/2004 | Martinez et al. |
| 2004/0141922 A1 | 7/2004 | Klaveness et al. |
| 2005/0002865 A1 | 1/2005 | Klaveness et al. |
| 2005/0042680 A1 | 2/2005 | Filpula et al. |
| 2006/0130160 A1 | 6/2006 | Dumas Milne Edwards et al. |
| 2007/0134243 A1 | 6/2007 | Gazzard et al. |
| 2008/0241128 A1 | 10/2008 | Jeffrey |
| 2009/0136526 A1 | 5/2009 | Mcdonagh |
| 2009/0148942 A1 | 6/2009 | Mcdonagh |
| 2009/0202573 A1 | 8/2009 | Zhao et al. |
| 2009/0203706 A1 | 8/2009 | Zhao et al. |
| 2009/0221471 A1 | 9/2009 | Greenwald et al. |
| 2010/0062008 A1 | 3/2010 | Senter et al. |
| 2010/0158909 A1 | 6/2010 | McDonagh et al. |
| 2010/0203007 A1 | 8/2010 | Li et al. |
| 2010/0203066 A1 | 8/2010 | Zhao et al. |
| 2010/0260786 A1 | 10/2010 | Doronina et al. |
| 2010/0278842 A1 | 11/2010 | Mao et al. |
| 2011/0014151 A1 | 1/2011 | Nilsson et al. |
| 2011/0206658 A1 | 8/2011 | Crowley et al. |
| 2011/0243880 A1 | 10/2011 | Yurkovetskiy et al. |
| 2011/0245295 A1 | 10/2011 | Chai et al. |
| 2011/0256157 A1 | 10/2011 | Howard |
| 2011/0263650 A1 | 10/2011 | Ellman et al. |
| 2011/0268751 A1 | 11/2011 | Sievers et al. |
| 2011/0281856 A1 | 11/2011 | Chari et al. |
| 2011/0300162 A1 | 12/2011 | Amphlett et al. |
| 2012/0107332 A1 | 5/2012 | Jeffrey |
| 2012/0226025 A1 | 9/2012 | Chari et al. |
| 2012/0328555 A1 | 12/2012 | Patil et al. |
| 2013/0217638 A1 | 8/2013 | Wessjohann et al. |
| 2013/0225789 A1 | 8/2013 | Sun et al. |

(56) References Cited

U.S. PATENT DOCUMENTS

| | | |
|---|---|---|
| 2013/0259860 A1 | 10/2013 | Smith |
| 2013/0295639 A1 | 11/2013 | Bentley et al. |
| 2013/0309223 A1 | 11/2013 | Sutherland |
| 2013/0309256 A1 | 11/2013 | Lyon et al. |
| 2013/0338231 A1 | 12/2013 | Godwin et al. |
| 2014/0086942 A1 | 3/2014 | Carter et al. |
| 2015/0352224 A1 | 12/2015 | Naito et al. |

FOREIGN PATENT DOCUMENTS

| | | |
|---|---|---|
| EP | 0184187 A3 | 12/1987 |
| EP | 0401384 A4 | 9/1991 |
| EP | 1029551 A2 | 8/2000 |
| EP | 1029551 A3 | 3/2001 |
| JP | 2015227891 A | 12/2015 |
| TW | 201420118 A | 6/2014 |
| WO | 198601533 A1 | 3/1986 |
| WO | 198702671 A1 | 5/1987 |
| WO | 199012874 A2 | 11/1990 |
| WO | 199012874 A3 | 1/1991 |
| WO | 199734631 A1 | 9/1997 |
| WO | 2003026577 | 4/2003 |
| WO | 2004010957 | 2/2004 |
| WO | 2004085386 | 10/2004 |
| WO | 2005081711 | 9/2005 |
| WO | 2005099768 A2 | 10/2005 |
| WO | 2005099768 A3 | 10/2005 |
| WO | 2005112919 A2 | 12/2005 |
| WO | 2006066020 A2 | 6/2006 |
| WO | 2006066020 A3 | 6/2006 |
| WO | 2006132670 A2 | 12/2006 |
| WO | 2007001968 A2 | 1/2007 |
| WO | 2007008848 A2 | 1/2007 |
| WO | 2007011968 | 1/2007 |
| WO | 2005112919 A3 | 2/2007 |
| WO | 2006132670 A3 | 7/2007 |
| WO | 200701968 A3 | 8/2007 |
| WO | 2007085930 A1 | 8/2007 |
| WO | 2007103288 A2 | 9/2007 |
| WO | 2007103288 A3 | 11/2007 |
| WO | 2008034124 | 3/2008 |
| WO | WO2008/056346 A2 | 5/2008 |
| WO | 2008070593 A2 | 6/2008 |
| WO | 2009002993 A1 | 12/2008 |
| WO | 2009009712 A1 | 1/2009 |
| WO | 2009009716 A1 | 1/2009 |
| WO | 2009025669 A1 | 2/2009 |
| WO | 2007008848 A3 | 4/2009 |
| WO | 2009117531 A1 | 9/2009 |
| WO | 2010048018 | 4/2010 |
| WO | 2010091150 A1 | 8/2010 |
| WO | 2010126551 | 11/2010 |
| WO | 2011023883 A1 | 3/2011 |
| WO | 2011038159 A2 | 3/2011 |
| WO | 2011038159 A3 | 8/2011 |
| WO | 2011109308 A1 | 9/2011 |
| WO | 2011130599 | 10/2011 |
| WO | 2011130613 A1 | 10/2011 |
| WO | 2011130616 | 10/2011 |
| WO | 2012078688 A2 | 6/2012 |
| WO | 2012078688 A3 | 8/2012 |
| WO | 2012112708 A1 | 8/2012 |
| WO | WO2012/113847 A1 | 8/2012 |
| WO | 2012166560 A1 | 12/2012 |
| WO | 2013033476 A1 | 3/2013 |
| WO | 2013041606 A1 | 3/2013 |
| WO | 2013053873 | 4/2013 |
| WO | 2013055990 | 4/2013 |
| WO | 2013055993 | 4/2013 |
| WO | 2013123152 A2 | 8/2013 |
| WO | 2013170272 | 11/2013 |
| WO | 2013173337 | 11/2013 |
| WO | 2013173391 | 11/2013 |
| WO | 2013173392 | 11/2013 |
| WO | 2013173393 | 11/2013 |
| WO | 2014061277 A1 | 4/2014 |
| WO | 2014064423 | 5/2014 |
| WO | 2013123152 A3 | 11/2014 |
| WO | WO2015/057699 A2 | 4/2015 |
| WO | WO2016/046574 A1 | 3/2016 |

OTHER PUBLICATIONS

Greenwald, et al., "Effective drug delivery by PEGylated drug conjugates", Advanced Drug Delivery Reviews, 55, pp. 217-250, (2003).

Miller et al., "Potent antigen-specific anti-tumor activity obserbed with antibody-drug conjugates (ADCs) made using a new class of DNA-crosslinking agents," Poster, Nov. 2009.

Jeffrey et al., "Expanded Utility of the Beta-Glucuronide Linker: ADCs That Deliver Henolic Cytotoxic Agents," ACS Medicinal Chemistry Letters, 1:277-280, 2010.

Molineaux, "Pegylation: engineering improved pharmaceuticals for enhanced therapy," Cancer Treatment Reviews 28 (Supp. A):13-16, 2002.

King et al., "Monoclonal Antibody Conjugates of Doxorubicin Prepared with Branched Peptide Linkers: Inhibition of Aggregation by Methoxytriethyleneglycol Chains," J. Med. Chem. 45:4336-4343, 2002.

Sperker et al., "The Role of Beta-Glucuronidase in Drug Disposition and Drug Targeting in Humans," Clin. Pharmocokinet, 33(1):18-31, 1997.

Huang et al., "Drug-targeting strategies in cancer therapy," Current Opinion in Genetics & Development 11:104-110, 2001.

Allen, "Ligand-Targeted Therapeutics in Anticancer Therapy," Nature Reviews, 2:750-765, 2002.

Chen et al., Glucuronides in Anti-Cancer Therapy, Curr. Med. Chem. 3:139-150, 2003.

Kirschke, "Lysosomal Cysteine Peptidases and Malignant Tumours," Cellular Peptidases in Immune Functions and Diseases, edited by Ansorge and Langner plenum Press, New York, 1997.

G.M. Dubowchik, M.A. Walker, Pharmacology & Therapeutics 83:67-123, 1999.

De Graff et al., "Beta-Glucuronidase-Mediated Drug Release," Current Pharmaceutical Design 8:1391-1403, 2002.

Papot et al., "Design of Selectively Activated Anticancer Prodrugs: Elimination and Cyclization Strategies," Curr. Med Chem. Anti-Cancer Agents 2:155-185, 2002.

Sanderson et al., "In Vivo Drug-Linker Stability of an Anti-CD30 Dipeptide-Linked Auristatin Immunoconjugate," Clin. Cancer Res. 11:843-852, 2005.

Jeffrey et al, "Development and Properties of Beta-Glucuronide Linkers for Monoclonal Antibody-Drug Conjugates," American Chemical Society, 2006.

Jeffrey et al., "Development and Properties of Beta-Glucuronide Linkers for Monoclonal antibody-Drug Conjugates," Bioconjugate Chem. 17:831-840, 2006.

Alley et al., "Contribution of Linker Stability to the Activities of Anticancer Immunoconjugates," Bioconjugate Chem. 19:759-765, 2008.

Baldwin et al., "Tunable Degradation of Maleimide—Thiol Adducts in Reducing Environments," Bioconjugate Chem. 22:1946-1953, 2011.

Lyon et al., "Self-hydrolyzing maleimides improve the stability and pharmacological properties of antibody-drug conjugates," Nature Biotechnology, 1-7, 2014.

Translation of Taiwan Patent Office Search Report for Appl. Ser. No. 103135737 dated Feb. 11, 2019.

Amsberry, K.L. et al. (1990) "The Lactonizatin of 2'-Hydroxyhydrocinnamic Acid Amides: A Potential Prodrug for Amines," J. Org. Chem. 55:5867-5877.

Beidler, C.B. et al. (Dec. 1, 1988). "Cloning High Level Expression of a Chimeric Antibody With Specificity For Human Carcinoembryonic Antigen," J. Immunol. 141(11):4053-4060.

Better, M. et al. (May 20, 1988). "*Escherichia coli* Secretion of an Active Chimerica Antibody Fragment," Science 240:1041-1043.

(56) References Cited

OTHER PUBLICATIONS

Chari, R.V.J. et al. (Jan. 1, 1992). "Immunoconjugates Containing Noveal maytansinoids: Promissing Anticancer Drugs," Cancer Res. 52:127-131.
Chen, X. et al. (Mar. 2003). "Glucuronides in Anti-Cancer Therapy," Curr. Med. Chem. 3(2):139-150.
Extended European Search Report, dated Aug. 16, 2017, for European Patent Application No. 14853953.9, 16 pages.
Extended European Search Report, dated Oct. 20, 2020, for European Patent Application No. 20186727.2, 15 pages.
Gaertner, H.F. et al. (Mar. 11, 1994). "Chemo-Enzymic Backbone Engineering of Proteins," J. Biol. Chem. 269 (10):7224-7230.
Goodson, R.J. et al. (Apr. 1990). Site-Directed Pegylation of Recombinatnt Interleukin-2 at its Glycosylation Site, Bio/Technology 8:343-346.
Hamblett, K.J. et al. (Oct. 15, 2004). "Effects Drug Loading the Antitumor Activity Monoclonal Antibody Drug Conjugate," Clin. Cancer Res. 10:7063-7070.
Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1, 2-dihydro-3H-benz[e]indole (amino-seco-CBI-TMI) for Use With ADEPT and GDEPT," Bioorganic & Medicinal Chemistry Letter 9(15):2237-2242.
International Preliminary Report on Patentability, dated Apr. 19, 2016, for PCT Application No. PCT/US2014/060477, filed Oct. 14, 2015, 10 pages.
International Search Report and Written Opinion, dated Jul. 30, 2015, for PCT Application No. PCT/US2014/060477, filed Oct. 14, 2015. 22 pages.
Jones, P.T. et al. (May 29, 1986). "Replacing the Complementarity-Determining Regions in a Human Antibody With Those From a Mouse," Nature 321:522-525.
Junutula, J.R. et al. (2010, e-pub. Aug. 30, 2010). "Engineered Thio-Trastuzumab-DM1 Conjugate With an Improved Therapeutic Index to Target Human Epidermal Growth Factor Receptor 2-Postitive Breast Cancer," Clinical Cancer Res. 16(19):4769-4778.
Kabat, E.A. et al. (1991). Sequences of Proteins of Immunological Interest, Fifth Edition, National Institute of Health, Bethesda, Md., 10 pages.
Kabat, E.A. et al. (Sep. 1980). "Origins of Antibody Complementarity and Specificity-Hypervariable Regions and the Minigene Hypothesis," J Immunology 125(3):961-969.
Kaneko, T. et al. (May-Jun. 1991). "New Hydrazone Derivatives Of Adriamycin and Their Immunoconjugates—A Correlation Between Acid Stability and Cytotoxicity," Bioconjugate Chem. 2(3):133-141.
Khandare, J. et al. (2006). "Polymer-Drug Conjugates: Progress in Polymeric Prodrugs," Prog. Polym. Sci. 31:359-397.
Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451.
Kozbor, D. et al. (1983). "The Production of Monoclonal Antibodies From Human Lymphocytes," Immunology Today 4(3):72-79.
Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.
Li, W. et al. (2013; e-pub. Aug. 11, 2012). "Current Drug Research on Pegylation With Small Molecular Agents," Progress in Polymer Science 38:421-444.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.
Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035.

Morrison, S.L. (Sep. 1985). "Transfectomas Provide Novel Chimeric Antibodies," Science 229 (4719):1202-1207.
Neville, D.M. et al. (Sep. 5, 1989). "Enhancement of Immunotoxin Efficacy by Acid-cleavable Crosslinking Agents Utilizing Diphtheria Toxin and Toxin Mutants," The Journal of Biological Chemistry 264(25):14653-14661.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
Oi, V.T. et al. (1986). "Chimeric Antibodies," Bio Techniques 4:214-219.
Olsson, L. et al. (1983), "[1] Human-Human Monoclonal Antibody-Producing Hybridomas: Technical Aspects," Meth Enzymol. 92:3-16.
Page, B. et al. (Sep. 1993). "A New Fluorometric Assay for Cytotoxicity Measurements In-Vitro," Intl. J. of Oncology 3(3):473-476.
Quiles, S. et al. (2010; e-pub. Dec. 3, 2009). "Synthesis and Preliminary Biological Evaluation of High-Drug-Load Paclitaxel-Antibody Conjugates for Tumor-Targeted Chemotherapy," J. Med. Chem. 53:586-594.
Rodrigues, M.L. et al. (Apr. 1995). "Synthesis and β-Lactamase-Mediated Activation of a Cephalosporine-Taxol Prodrug," Chem. Biol. 2:223-227.
Rose, K. et al. (May-Jun. 1991). "Preparation of Well-Defined Protein Conjugates Using Enzyme-Assisted Reverse Proteolysis," Bioconjugate Chem. 2(3):154-159.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwartz, A. et al. (1990). "Enzymatic C-Terminal Biotinylation of Proteins," Methods Enzymol. 184:160-162.
Shaw, D.R. et al. (Dec. 7, 1988). "Mouse/Human Chimeric Antibodies to a Tumor-Associated Antigen: Biologic Activity of the Four Human IgG Subclasses," J. Natl. Cancer Inst. 80(19):1553-1559.
Skehan, P. et al. (Jul. 4, 1990). "New Colorlmetric Cytotoxicity Assay for Anticancer-Drug Screening,"J. Nat'l Cancer Inst. 82(13):1107-1112.
Storm, D.R. et al. (Aug. 9, 1972). "Effect of Small Changes in Orientation on Reaction Rate," Journal of the American Chemical Society 94(16):5815-5825.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Teng, N.N.H. et al. (Dec. 1983). "Construction and Testing of Mouse-Human Heteromyelomas for Human Monoclonal Antibody Production," Proc. Natl. Acad. Sci. USA. 80:7308-7312.
Thorpe, et al. (Nov. 15, 1987). "New Coupling Agents for the Synthesis of Immunotoxins Containing a Hindered Disulfide Bond with Improved Stability in Vivo," Cancer Research 47:5924-5931.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
Verhoeyan, M. et al. (Mar. 25, 1988). "Reshaping Human Antibodies: Grafting an Antilysozyme Activity," Science 239:1534-1536.
Veronese, F.M. (2001). "Peptide and Protein PEGylation: A Review of Problems and Solutions," Biomaterials 22:405-417.
Veronese, F.M. et al. (Apr. 1985). "Surface Modification of Proteins: Activation of Monomethoxy-Polyethylene Glycols by Phenylchloroformates and Modification of Ribonuclease and Superoxide Dismutase," Appl. Bioechnol 11(2):141-142.
Wan, L. et al. (Apr. 24, 2006). "Novel Multi-Component Nanopharmaceuticals Derived From poly (ethylene) glycol, retro-inverso-Tat Nonapeptide and Saquinavir Demostrate Combined Anti-HIV Effects," AIDS Research and Therapy, pp. 1-15.
Wildman, S.A. et al. (1999, e-pub. Aug. 19, 1999). "Prediction of Physiochemical Parameters by Atomic Contributions," J. Chem. Inf. Comput Sci. 39(5):868-873.

(56) References Cited

OTHER PUBLICATIONS

Wood, C.R. et al. (Apr. 4-10, 1985). "The Synthesis and in vivo Assembly of Functional Antibodies in Yeast," Nature 314(6010):446-449.
Yokoyama, M. et al. (1989) "Molecular Design for Missile Drug: Synthesis of Adriamycin Conjugate With Immunoglobulin G Using Poly(ethylene glycol)-Block-poly(aspartic acid) as Intermediate Carrier," Makromol. Chem. 190:2041-2054.
Consolidated List for European Opposition for European Application No. EP14853953.9, 1 page.
European Notice of Opposition, dated Apr. 30, 2021, for European Application No. 14853953.9, 76 pages.
Grounds for Opposition, dated Apr. 21, 2021, for European Patent No. EP3057585, 66 pages.
Kahn, C.R. et al., (1988) "The Insulin Receptor and the Molecular Mechanism of Insulin Action," Insulin Receptor and Insulin Action 82:1151-1156.
Lyon, R.P. (May 5, 2014) "Novel ADC Chemistry for Improved Stability and Pharmacokinetics," Characterization for Antibody-Drug Conjugates, Seattle Genetics Presentation, PEGS Boston, 25 pages.
Notice of Opposition, dated Apr. 22, 2021, for European Application No. EP14853953.9, 7 pages.
Proprietors Submission dated Aug. 19, 2019, European Opposition for European Application No. EP14853953.9, 79 pages.
Proprietors Submission dated Jul. 3, 2018, European Opposition for European Application No. EP14853953.9, 40 pages.
Proprietors Submission dated Mar. 12, 2018, European Opposition for European Application No. EP14853953.9, 43 pages.
Proprietors Submission dated Nov. 15, 2019, European Opposition for European Application No. EP14853953.9, 99 pages.
U.S. Appl. No 61/891,320, Provisional Application, filed Oct. 15, 2013, 254 pages.
U.S. Appl. No 61/941,304, Provisional Application, filed Feb. 19, 2014, 269 pages.
U.S. Appl. No 61/947,742, Provisional Application, filed Mar. 4, 2014, 279 pages.
U.S. Appl. No 61/975,318, Provisional Application, filed Apr. 4, 2014, 280 pages.
Banerjee, S.S. et al. (May 7, 2012). "Poly(ethylene glycol)-Prodrug Conjugates: Concepts Design, and Applications," Journal of Drug Delivery 2012(103973):1-17.

\* cited by examiner

PEGYLATED DRUG-LINKERS FOR IMPROVED LIGAND-DRUG CONJUGATE PHARMACOKINETICS

CROSS REFERENCE TO RELATED APPLICATIONS

This non-provisional application claims priority under 35 USC § 119(e) to U.S. Appl. Ser. Nos. 61/891,320, filed Oct. 15, 2013, 61/941,904, filed Feb. 19, 2014, 61/947,742, filed Mar. 4, 2014 and 61/975,318, filed Apr. 4, 2014, all of which are incorporated herein by reference in their entireties.

SEQUENCE LISTING

A sequence listing designated 2700-00114PC-ST25.txt of 13 KB created Oct. 9, 2014, is incorporated herein by reference.

BACKGROUND OF THE INVENTION

A great deal of interest has surrounded the use of monoclonal antibodies (mAbs) for the targeted delivery of cytotoxic agents to cancer cells. The design of antibody drug conjugates, by attaching a cytotoxic agent to an antibody, typically via a linker, involves consideration of a variety of factors. These factors include the identity and location of the chemical group for conjugation of the cytotoxic agent, the mechanism of agent release, the structural element(s) (if any) providing release of the cytotoxic agent, and structural modification of the released free agent, if any. In addition, if the cytotoxic agent is to be released after antibody internalization, the structural elements and mechanism of agent release must be consonant with the intracellular trafficking of the conjugate.

While a number of different drug classes have been evaluated for delivery via antibodies, only a few drug classes have proved sufficiently active as antibody drug conjugates, while having a suitable toxicity profile, to warrant clinical development. One such class is the auristatins, related to the natural product dolastatin 10. Representative auristatins include MMAE (N-methylvaline-valine-dolaisoleuine-dolaproine-norephedrine) and MMAF (N-methylvaline-valine-dolaisoleuine-dolaproine-phenylalanine).

MMAE is an example of a cytotoxic agent that is active as a free drug, and is highly potent when conjugated to a monoclonal antibody (mAb) and is released after internalization into cells. MMAE has been successfully conjugated to a mAb at the N-terminal amino acid of MMAE via a cathepsin B cleavable peptide-based linker containing maleimidocaproyl-valine-citrulline (mc-vc-) and a self-immolative group p-aminobenzyl-carbamoyl (PABC) to produce antibody drug conjugates of the following structure, mAb-(mc-vc-PABC-MMAE)$_p$. (In the preceding formula, p refers to the number of (mc-vc-PABC-MMAE) units per antibody.) Upon cleavage of the bond between the vc peptide and the self-immolative PABC group, the PABC group releases itself from MMAE, liberating free MMAE.

Another auristatin, MMAF, is relatively less active as a free drug (compared to MMAE), yet is highly potent when conjugated to an antibody and internalized into cells. MMAF has been successfully conjugated to a monoclonal antibody (mAb) at the N-terminal amino acid of MMAF via a cathepsin B cleavable peptide-based linker containing maleimidocaproyl-valine-citrulline (mc-vc-) and a self-immolative group p-aminobenzyl-carbamoyl (PABC) to produce antibody-drug conjugates of the structure, mAb-(mc-vc-PABC-MMAF)$_p$, wherein p refers to the number of (mc-vc-PABC-MMAF) units per antibody. Upon cleavage of the peptide linker, the self-immolative PABC group releases itself from MMAF, liberating free MMAF.

MMAF was also found to be active as a non-cleavable conjugate, containing the drug-linker maleimidocaproyl MMAF (mcMMAF). When this conjugate, mAb-(mcMMAF)$_p$, is internalized into cells, the active species released is cys-mcMMAF. Because the linker is non-cleavable, the maleimidocaproyl and a cysteine residue of the antibody remain attached to the N-terminus of MMAF. MMAF was also reported to be active as a C-terminal conjugate, attached at its C-terminal amino acid, phenylalanine, to a peptide-maleimidocaproyl linker. When this conjugate, (MMAF-peptide-mc)$_p$-mAb is internalized into cells, the active species, MMAF, is released following cleavage of the MMAF (phenylalanine)-peptide bond.

In animal models, these MMAE and MMAF conjugates exhibited a drug loading-dependent decrease in pharmacokinetic properties. In particular, as the number of drug-linker units attached to each antibody increased, the PK of the conjugates decreased.

Therefore, another important factor in the design of conjugates is the amount of drug that can be delivered per targeting agent (i.e., the number of cytotoxic agents attached to each targeting agent (e.g., an antibody), referred to as the drug load or drug loading). Historically, assumptions were that higher drugs loads were superior to lower drug loads (e.g., 8-loads vs 4-loads). The rationale was that higher loaded conjugates would deliver more drug (cytotoxic agents) to the targeted cells. This rationale was supported by the observations that conjugates with higher drug loadings were more active against cell lines in vitro. Certain later studies revealed, however, that this assumption was not confirmed in animal models. Conjugates having drug loads of 4 or 8 of certain auristatins were observed to have similar activities in mouse models. Hamblett et al., *Clinical Cancer Res.* 10:7063-70 (2004). Hamblett et al. further reported that the higher loaded ADCs were cleared more quickly from circulation in animal models. This faster clearance suggested a PK liability for higher loaded species as compared to lower loaded species. Hamblett et al. In addition, higher loaded conjugates had lower MTDs in mice, and as a result had narrower reported therapeutic indices. Id. In contrast, ADCs with a drug loading of 2 at engineered sites in a monoclonal antibody were reported to have the same or better PK and therapeutic indices as compared to certain 4-loaded ADCs. For example, see Junutula et al., *Clinical Cancer Res.* 16:4769 (2010). Thus, recent trends are to develop ADCs with low drug loadings.

There is a need, therefore, for antibody drug conjugate formats (and more generally for formats for other conjugates), that allow for higher drug loading, but will maintain other characteristics of lower loaded conjugates, such as favorable PK properties. Surprisingly, the present invention addresses those needs.

BRIEF SUMMARY OF THE INVENTION

Figure 1:
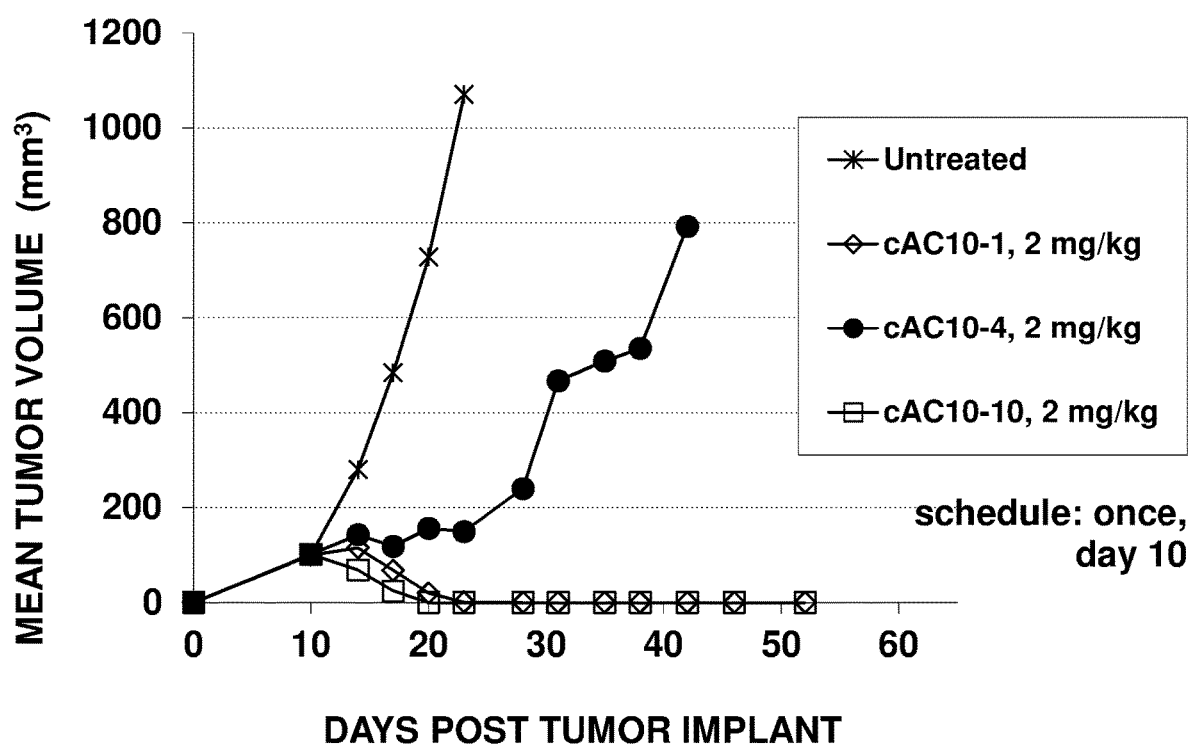
FIG. 1. Mean tumor volume versus days post implant for xenograft L540cy model (Hodgkin Lymphoma) dosed at higher single dose (2 mg/kg) with non-PEGylated ADC, cAC10-[mc-PAB(gluc) MMAE]$_p$, (cAC10-1), Parallel-oriented PEGylated ADC (cAC10-10), and serial-oriented PEGylated ADC (cAC10-4) compositions with average drug loading of 8 drugs/Ab.

The invention provides inter alia, Ligand-Drug Conjugates (LDCs), methods of preparing and using them, and intermediates thereof. The Ligand-Drug Conjugates are stable in circulation, yet capable of inflicting cell death on targeted cells or inhibiting proliferation of targeted cells once its drug cargo is released in the vicinity or within targeted cells.

In principle embodiments, an LDC of the present invention is represented by the structure of Formula I below:

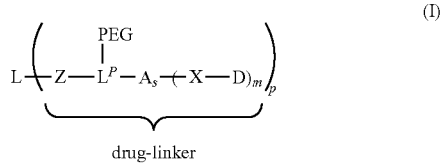

(I)

drug-linker wherein D is a drug unit, PEG is the polyethylene glycol unit that masks the hydrophobicity of the drug-linker, L$^P$ is the parallel connector unit that allows for a PEG Unit to be in a parallel orientation with respect to X-D, A is a branching unit when m is greater than 1, optionally comprised of subunits, or A is absent when m is 1, X is a Releasable Assembly unit that provides for release of each D from the LDC and Z is an optional spacer unit through which L$^P$ is bonded to L, which is the targeting ligand.

In other principle embodiments, an LDC of the present invention is represented by the structure of Formula II below:

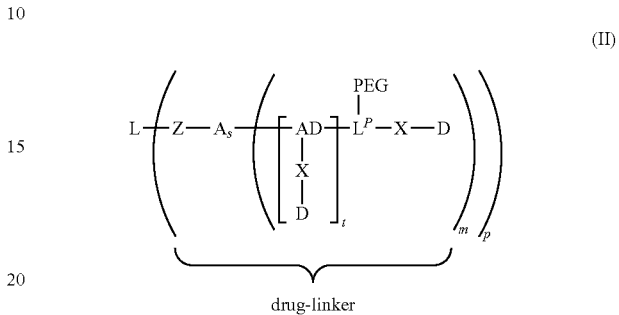

(II)

drug-linker wherein AD is a drug attachment unit that allows for additional attachment of X-D moieties indicated by t in parallel orientation to the PEG Unit and L, L$^P$, Z, A, X, D, m, p and s are as defined for Formula I In yet other principle embodiments an LDC of the present invention is represented by the structure of Formula III below:

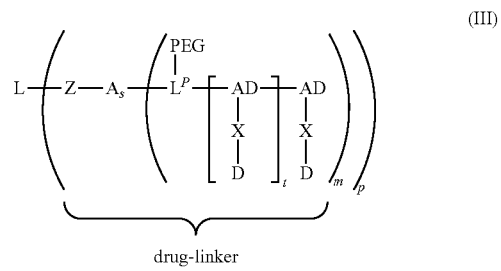

(III)

drug-linker wherein AD, L, L$^P$, PEG, Z, A, X, D, m, p, s and t are as defined for Formula II.

DESCRIPTION OF THE INVENTION

General

The present invention is based, in part, on the surprising discovery that the orientation of a polyethylene glycol component (PEG Unit) of a Ligand-Drug Conjugate, can have a profound influence on the resulting pharmacokinetics of the conjugate. Specifically, the present inventors have discovered that a parallel placement of a PEG Unit in relation to the Drug unit of a Ligand-Drug Conjugate can improve the pharmacokinetics of the conjugate as compared to conjugates having either no PEG Unit or a PEG Unit placed in a serial orientation with the Drug unit. The present inventors have further discovered that the number of repeating polyethylene glycol subunits present on the PEG Unit influences the resulting pharmacokinetics of the conjugate. By designing the conjugates to have a PEG Unit in a parallel placement and of an appropriate size to mask the hydrophobicity of the drug and, in some cases, components of the linker, ligand-drug conjugate formats that allow for higher drug loading, while maintaining other characteristics of lower loaded conjugates, such as favorable PK properties, can be prepared. The Ligand-Drug Conjugates are further designed in such a manner that they release "free" drug.

Definitions

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

"Parallel Connector Unit" as used herein refers to a branched Linker Unit component that connects a PEG Unit in parallel orientation to the Drug Unit. As used herein, the phrase "parallel orientation", "parallel placement", "parallel connection" and like terms refers to a configuration wherein the parallel-placed or parallel-oriented or parallel-connected components are attached to the parallel connector unit ($L^P$) in such a manner that each has one end tethered to $L^P$ and one free end. Typically $L^P$ connects a Drug Unit through one or more linker unit components, of which one (or the only one) is a Releasable Assembly Unit, and a PEG unit so that the Drug and PEG Units are in a parallel orientation such that the hydrophobicity of the Drug Unit is masked by the PEG Unit. In some aspects, further branching is provided by one or more Drug Attachment Units (ADs) that are connected to a $L^P$ so that the Drug Unit connected to AD is in parallel orientation to a PEG unit in that $L^P$. Only those PEG units required to mask hydrophobicity for a given linker-drug moiety need be in parallel orientation to its drug unit, which does not necessarily require all of the drug and polyethyelene glycol units connected to $L^P$ be in parallel orientations to one another.

The term "parallel" is used herein to denote branching of two components of a Ligand-Drug Conjugate (LDC) from a $L^P$ that comprises the LDC and is not being used to denote that the two components are side-by-side in space or have the same distance between them throughout some or their entire lengths. In instances where a parallel-oriented component is itself branched and thus has multiple ends, it still has only one tethered end.

A LDC having a PEG Unit that is in a parallel orientation in relation to the Drug Unit of the LDC refers to a LDC comprising a PEG Unit that has one terminus that is connected to a component of a Linker unit (i.e., a Parallel Connector Unit) and one or more free untethered terminus (termini). The free untethered terminus of the PEG unit can take the form, for example, of an unreacted functional group, e.g., alkoxy, carboxylic acid, alkylenecarboxylic acid, alcohol, or other functional group. The parallel orientation of the PEG Unit in relationship to the Drug Unit acts to minimize the number of atoms between the Ligand Unit and the Drug Unit as the atoms of the PEG Unit are not interposed between the Drug Unit and the Ligand Unit. In LDCs, the Linker Unit is comprised of a Releasable Assembly Unit capable of releasing a biologically active drug moiety from the LDC at a target site (e.g., via intraceullar cleavage). In some instances, the drug moiety that is released is the parent drug that had been incorporated into the Drug Unit and thus does not remain attached to the PEG Unit or a degradant product of the Ligand Unit. In other instances the biologically active drug moiety that is released is the parent drug having part of the Linker Unit (other than the PEG Unit), retained.

The Linker Unit component having the release mechanism, which is referred to as the Releasable Assembly Unit, is interposed between $L^P$ and the Drug Unit. As with the PEG Unit, the Drug Unit has one end that is attached (albeit indirectly through a Releasable Assembly Unit) to the Parallel Connector Unit and one or more free untethered termini (or in the case of some cyclic drugs, no free termini). An exemplary graphical representation of a LDC having a PEG Unit that is in a parallel (i.e., branched) orientation in relation to the Drug Unit is as follows:

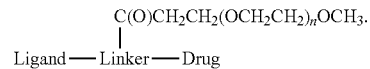

Ligand—Linker—Drug

The phrase "serial orientation" or "serial placement" or "serial connection" refers to a configuration of a component in a LDC wherein the serially-oriented component is attached in such a manner that it has two tethered ends with each end connected to a different component of the LDC. A LDC having a PEG Unit that is in a serial orientation in relation to the Ligand Unit and Drug Unit of the LDC refers to a LDC comprising a PEG Unit that is tethered to the Ligand at one termini (typically indirectly via components of a Linker Unit) and to the Drug Unit at another termini (typically indirectly via other components of a Linker unit). The serial placement of the PEG Unit increases the number of atoms between the Ligand Unit and the Drug Unit since at least some of the atoms of the PEG Unit are interposed between the Drug Unit and the Ligand Unit. For example, one or more ($OCH_2CH_2$) subunits, which characterize a PEG unit, are interposed between the Drug Unit and the Ligand Unit. An exemplary graphical representation of a Ligand-Drug Conjugate having a PEG Unit that is in a serial orientation in relation to the Ligand Unit and Drug Unit is as follows:

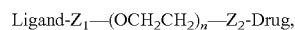

wherein $Z_1$ and $Z_2$ are optional stretcher components of a Linker Unit.

The term "antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system. (see, e.g., Janeway et al., 2001, Immuno. Biology, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some aspects, the antibody is of human or murine origin. An antibody can be, for example, human, humanized or chimeric.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. In order to be of use in the present invention, the antibody fragment must have the requisite number of sites for attachment to a drug-linker. The attachment sites can be naturally occurring or non-naturally occurring.

An "antigen" is an entity to which an antibody specifically binds.

The terms "specific binding" and "specifically binds" mean that the antibody or antibody derivative will bind, in a highly selective manner, with its corresponding target antigen and not with a multitude of other antigens. Typically, the antibody or antibody derivative binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The term "inhibit" or "inhibition of" means to reduce by a measurable amount, or to prevent entirely.

The term "therapeutically effective amount" refers to an amount of a conjugate effective to treat a disease or disorder in a mammal. In the case of cancer, the therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

Unless otherwise indicated by context, the term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The terms "intracellularly cleaved" and "intracellular cleavage" refer to a metabolic process or reaction inside a cell on a Ligand-Drug conjugate (e.g., an Antibody Drug Conjugate (ADC) or the like), whereby the covalent attachment, between the Drug moiety (D) and the Ligand unit (e.g., an antibody (Ab)) is broken e.g., by action of a Releasable Assembly Unit, resulting in free Drug being dissociated from the LDC, including degradant products thereof, inside the cell. The moieties resulting from that dissociation are thus intracellular metabolites.

The term "cytotoxic activity" refers to a cell-killing effect of a drug or Ligand-Drug Conjugate or an intracellular metabolite of a Ligand-Drug Conjugate. Cytotoxic activity may be expressed by an $IC_{50}$ value, which is the concentration (molar or mass) per unit volume at which half the cells survive exposure to a cytotoxic agent.

The term "cytostatic activity" refers to an anti-proliferative effect other than cell killing of a cytostatic agent, or a Ligand-Drug Conjugate having a cytostatic agent as its Drug Unit or an intracellular metabolite thereof wherein the metabolite is a cytostatic agent.

The term "cytotoxic agent" as used herein refers to a substance that has cytotoxic activity and causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof.

The term "cytostatic agent" as used herein refers to a substance that has cytostatic activity e.g., inhibits a function of cells responsible for or that contributes to cell growth or multiplication. Cytostatic agents include inhibitors such as protein inhibitors, e.g., enzyme inhibitors.

The terms "cancer" and "cancerous" refer to or describe the physiological condition or disorder in mammals that is typically characterized by unregulated cell growth. A "tumor" comprises one or more cancerous cells.

An "autoimmune disease" herein is a disease or disorder arising from and directed against an individual's own tissues or proteins.

"Patient" as used herein refers to a subject to which an LDC is administered. Examples of a "patient" include, but are not limited to, a human, rat, mouse, guinea pig, non-human primate, pig, goat, cow, horse, dog, cat, bird and fowl. Typically, a patient is a rat, mouse, dog, non-human primate or human. In an some aspects, the patient is a human in need of an effective amount of an LDC.

The terms "treat" or "treatment," unless otherwise indicated by context, refer to therapeutic treatment and prophylactic measures to prevent relapse, wherein the object is to inhibit or slow down (lessen) an undesired physiological change or disorder, such as, for example, the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder.

In the context of cancer, the term "treating" includes any or all of: inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of: inhibiting replication of cells associated with an autoimmune disease state including, but not limited to, cells that produce an autoimmune antibody, lessening the autoimmune-antibody burden and ameliorating one or more symptoms of an autoimmune disease.

The phrase "pharmaceutically acceptable salt," as used herein, refers to pharmaceutically acceptable organic or inorganic salts of a compound (e.g., a Drug, Drug-Linker, or a Ligand-Drug Conjugate). The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise indicated, the term "alkyl" by itself or as part of another term refers to a substituted or unsubstituted straight chain or branched, saturated or unsaturated hydrocarbon having the indicated number of carbon atoms (e.g., "—$C_1$-$C_8$ alkyl" or "—$C_1$-$C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_1$-$C_8$ alkyl" groups include, but are not limited to, -methyl, -ethyl, -n-propyl, -n-butyl, -n-pentyl, -n-hexyl, -n-heptyl and -n-octyl; while branched —$C_1$-$C_8$ alkyls include, but are not limited to, -isopropyl, -sec-butyl, -isobutyl, -tert-butyl, -isopentyl, and -2-methylbutyl; unsaturated —$C_2$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexyl, 2-hexyl, -3-hexyl, -acetylenyl, -propynyl, -1-butynyl, -2-butynyl, -1-pentynyl, -2-pentynyl and -3-methyl-1 butynyl. In some aspects, an alkyl group is unsubstituted. An alkyl group can be substituted with one or more groups. In other aspects, an alkyl group will be saturated.

Unless otherwise indicated, "alkylene," by itself of as part of another term, refers to a substituted or unsubstituted saturated or unsaturated branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like. In preferred aspects, an alkylene is a branched or straight chain hydrocarbon (i.e., it is not a cyclic hydrocarbon). In any of the embodiments provided herein, the alkylene can be a saturated alkylene.

Unless otherwise indicated, "aryl," by itself or as part of another term, means a substituted or unsubstituted monovalent carbocyclic aromatic hydrocarbon radical of 6-20 carbon (preferably 6-14 carbon) atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group.

Unless otherwise indicated, an "arylene," by itself or as part of another term, is an aryl group as defined above wherein one of the aryl group's hydrogen atoms is replaced with a bond (i.e., it is divalent) and can be in the ortho, meta, or para orientations as shown in the following structures, with phenyl as the exemplary group:

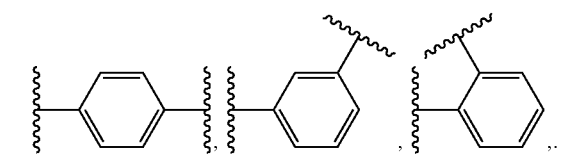

In select embodiments, e.g., when a Parallel Connector Unit, Branching Unit or Drug Attachment Unit comprises an arylene, the arylene is an aryl group defined above wherein one or two of the aryl group's hydrogen atoms is replaced with a bond (i.e., the arylene can be divalent or trivalent).

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Unless otherwise noted, the heterocycle is attached to its pendant group at any heteroatom or carbon atom that results in a stable structure. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl.

Unless otherwise indicated, "$C_3$-$C_8$ heterocyclo", by itself or as part of another term, refers to a $C_3$-$C_8$ heterocycle group defined above wherein one of the heterocycle group's hydrogen atoms is replaced with a bond (i.e., it is divalent). In select embodiments, e.g., when a Parallel Connector Unit, Branching Unit or Drug Attachment Unit comprises a heterocyclo, the heterocyclo is a heterocycle group defined above wherein one or two of the heterocycle group's hydrogen atoms is replaced with a bond (i.e., the heterocyclo can be divalent or trivalent).

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo", by itself or as part of another term, refers to a $C_3$-$C_8$ carbocycle group defined above wherein another of the carbocycle groups' hydrogen atoms is replaced with a bond (i.e., it is divalent). In select embodiments, e.g., when a Parallel Connector Unit, Branching Unit or Drug Attachment Unit comprises a carbocyclo, the carbocyclo is a carbocycle group defined above wherein one or two of the carbocycle group's hydrogen atoms is replaced with a bond (i.e., the carbocyclo can be divalent or trivalent).

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. In preferred embodiments, a $C_1$ to $C_4$ heteroalkyl or heteroalkylene has 1 to 4 carbon atoms and 1 or 2 heteroatoms and a $C_1$ to $C_3$ heteroalkyl or heteroalkylene has 1 to 3 carbon atoms and 1 or 2 heteroatoms. In some aspects, a heteroalkyl or heteroalkylene is saturated.

Unless otherwise indicated, the term "heteroalkylene" by itself or as part of another substituent means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied. In select embodiments, e.g., when a Parallel Connector Unit, Branching Unit or Drug Attachment Unit comprises a heteroalkylene, the heteroalkylene is a heteroalkyl group defined above wherein one or two of the heteroalkyl group's hydrogen atoms is replaced with a bond (i.e., the heteroalkylene can be divalent or trivalent).

"Substituted alkyl" and "substituted aryl" mean alkyl and aryl, respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)$_2$R, —OS(=O)$_2$OR, —S(=O)$_2$ NR, —S(=O)R, —OP(=O)(OR)$_2$, —P(=O)(OR)$_2$, —PO$^-_3$, —PO$_3$H$_2$, —AsO$_2$H$_2$, —C(=O)R, —C(=O)X, —C(=S)R, —CO$_2$R, —CO$_2^-$, —C(=S)OR, C(=O)SR, C(=S)SR, C(=O)NR$_2$, C(=S)NR$_2$, or C(=NR)NR$_2$, where each X is independently a halogen: —F, —Cl, —Br, or —I; and each R is independently —H, —$C_1$-$C_{20}$ alkyl, —$C_6$-$C_{20}$ aryl, —$C_3$-$C_{14}$ heterocycle, a protecting group or a prodrug moiety. Typical substitutents also include (=O). Alkylene, carbocycle, carbocyclo, arylene, heteroalkyl, heteroalkylene, heterocycle, and heterocyclo groups as described above may also be similarly substituted.

As used herein, the term "free drug" refers to a biologically active drug moiety that is not covalently attached either directly or indirectly to a PEG Unit or to a degradant product of a Ligand Unit. Free Drug can refer to the drug, as it exists immediately upon cleavage from the Linker Unit via the release mechanism, which is provided by the Releasable Assembly Unit in the LDC, or to subsequent intracellular conversion or metabolism. In some aspects, the free drug will have the form H-D or may exist a as a charged moiety. The free drug is a pharmacologically active species which can exert the desired biological effect. In some aspects, the pharmacologically active species may not be the parent drug and may include a component of the Linker Unit, which has not undergone subsequent intracellular metabolism.

Ligand-Drug Conjugate Compounds and Related Intermediates

The present invention is based, in part, on the discovery that Ligand-Drug Conjugates (LDCs) that have unfavorable PK properties can have their PK properties improved by placement of a PEG Unit in a parallel orientation with respect to its Drug Unit as described herein. In some aspects, the clearance profile of the PEGylated conjugates is similar to that of the unconjugated Ligand (i.e., the targeting agent, such as an antibody or related antigen binding fragment) even at high drug loading. LDCs comprise a Ligand Unit (i.e., a targeting Ligand), a Linker Unit, and a Drug Unit. A Linker Unit prior to or after its attachment to a targeting Ligand connects the Drug Unit to a Ligand Unit and comprises a PEG Unit in parallel configuration relative to the Drug Unit. That parallel configuration results from attachment of Drug Unit, through a Releasable Assembly Unit, and PEG Unit to a Parallel Connector Unit. A Linker Unit when connected to a Drug Unit can be referred to as a Drug-Linker. A population of LDCs will preferably have an average drug-linker loading of at least about 6, about 7 or about 8 drug-linkers per Ligand Unit.

The PEG units are designed to impart an optimized level of hydrophobicity masking of hydrophobic components of the drug-linker. For that reason, the incorporation of PEG Unit as taught herein is particularly suitable for drug-linkers that otherwise would have sufficient hydrophobicity to negatively impact the pharmacokinetics of the resultant conjugate as compared to the unconjugated ligand. Those poorer pharmokinetic include greater plasma clearance. Thus, ligand drug conjugates which display significantly greater plasma clearance and correspondingly lower plasma exposure relative to the unconjugated Ligand will be benefited by the present invention.

Ligand-Drug conjugates have more favorable pharmokinetic properties due to the parallel orientation within a hydrophobic drug-linker moiety of a Drug Unit and a PEG Unit whereby the negative impact of hydrophobicity of the Drug Unit and/or other components of the drug-linker moiety on plasma clearance is reduced or eliminated (i.e., hydrophobicity of a drug-linker moiety is masked). The parallel orientation is accomplished by the Parallel Connector Unit ($L^P$) as the Parallel Connector Unit acts to connect a Drug Unit, A PEG Unit and a Ligand in the appropriate branching configuration to provide the requisite parallel orientation. The Parallel Connector Unit can be considered a scaffold having attachment sites for components of the conjugates, which can be multiplexed to have multiple drug units in parallel orientation with PEG units to provide a PEGylated multiplexed scaffold. In some embodiments the hydrophobic component in a drug-linker moiety whose hydrophobicity is masked by the parallel-oriented PEG Unit is a hydrophobic Drug Unit.

The Drug Unit is attached to the Parallel Connector Unit via a Releasable Assembly Unit. The Releasable Assembly Unit allows efficient release of the drug at the target cell, sufficient to induce, e.g., cytotoxicity or cytostaticity. Typically, the Releasable Assembly Unit is designed for efficient release of the free drug once the conjugate has been internalized into the target cell, but may also be designed to release free drug within the vicinity of target cells. Suitable recognition sites for cleavage are those that allow efficient release of an LDC's Drug Unit(s). Typically, the recognition site is a peptide cleavage site (such as in a peptide-based Releasable Assembly Units), a sugar cleavage site (such as in sugar-based Releasable Assembly Units), or a disulfide cleavage site (such as in disulfide-based Releasable Assembly Units). Examples of peptide cleavage sites include those recognized by intracellular proteases, such as those present is lysosomes. Examples of sugar cleavage site include those recognized by glycosidases, including glucuronidases, such as beta-glucuronidase.

Any bioactive compound (i.e., Drug) can be used as a Drug Unit in the present invention. A bioactive compound may have a suitable site for its incorporation as a Drug Unit into a LDC or may be modified for that purpose while substantially retaining the desired biological activity of the parent drug when the modified drug, which may or may not retain part of the Linker Unit, is released from the LDC. Preferred Drug Units provide for release of the parent bioactive compound. The Drug Unit can be an auristatin or non-auristatin drug, which is the hydrophobic component of a drug-linker moiety whose hydrophobicity is to be masked by the parallel-oriented Drug Unit The effects of the present invention will be more pronounced in embodiments wherein the Drug Unit, Releasable Assembly Unit, or Drug Unit/Releasable Assembly Unit combination are hydrophobic in nature thereby negatively impacting the pharmacokinetics of the resultant conjugate. Examples of hydrophobic drugs, include monomethyl auristatin E and drugs having a hydrophobicity comparable to or greater than monomethyl auristatin E. Examples of hydrophobic Releasable Assembly Units include the peptide-based and sugar based Releasable Assembly Units that have a hydrophobic self-immolative component specifically exemplified herein as well as Releasable Assembly Units having a hydrophobicity comparable to or greater than such Releasable Assembly Units.

Hydrophobicity can be measured using SlogP. SlogP is defined as the log of the octanol/water partition coefficient (including implicit hydrogens) and can be calculated using the program MOE™ from the Chemical Computing group (SlogP values calculated using Wildman, S. A., Crippen, G. M.; Prediction of Physiochemical Parameters by Atomic Contributions; *J. Chem. Inf. Comput. Sci.* 39 No. 5 (1999) 868-873). When referring to a Drug Unit or a Releasable Assembly Unit having a hydrophobicity comparable to a reference Drug Unit or Releasable Assembly Unit, the SlogP value will be within 20%, preferably within 10%, of the SlogP value of the reference Drug Unit or Releasable Assembly Unit.

In view of the above, the present invention provides in one group of embodiments, a Ligand-Drug Conjugate composition comprising a population of Ligand-Drug Conjugates. The Ligand-Drug Conjugates comprise a Ligand unit and multiple Drug-Linker units attached thereto. Preferably, there is an average of from about 6 to about 14, about 6 to about 12, about 6 to about 10, about 8 to about 14, about 8 to about 12, about 8 to about 10 Drug-Linker Units per Ligand in the composition. Exemplary attachment to the Ligand is via thioether linkages. Exemplary conjugation sites on a Ligand are the thiol groups obtained from reduction of interchain disulfide residues and/or thiol-containing residues introduced into the Ligand such as introduced cysteines. Attachment can be, for example, via thiol residues derived from an interchain disulfide and from 0 to 8 introduced cysteine residues.

In a related group of embodiments, methods are provided for administering the Ligand-Drug Conjugates to a patient for the treatment of a disease. The disease can be, for example, a cancer or an autoimmune disease. The Ligand-Drug Conjugates are administered in a therapeutically effective amount and on a therapeutically effective schedule.

EMBODIMENTS

A number of embodiments of the invention are described below followed by a more detailed discussion of the components that make of the Ligand-Drug Conjugates and Intermediates thereof. Any of the selected embodiments for the components of the Ligand-Drug Conjugates and Intermediates thereof can apply to each and every aspect of the invention as described herein or they may relate to a single aspect. The selected embodiments may be combined together in any combination.

Ligand-Drug Conjugate Compounds

In one group of embodiments, provided herein are LDC compounds capable of releasing free drug wherein the LDC compound is represented by Formula AA below:

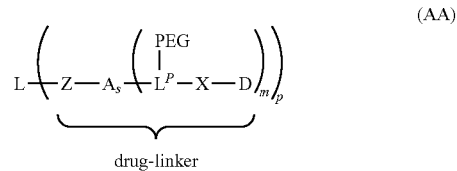

(AA)

drug-linker or a pharmaceutically acceptable salt thereof, wherein,
L is a Ligand Unit;
D is a Drug Unit;
PEG is a Polyethylene Glycol Unit;
Z is a Stretcher Unit;
X is a Releasable Assembly Unit;
$L^P$ is a Parallel Connector Unit;
A is an optional Branching Unit;
the subscript p is an integer ranging from 1 to 14, preferably from 2 to 12 (preferably from 6 to 14, from 6 to 12, 8 to 14 or 8 to about 12);
the subscript m is an integer ranging from 1 to 4; and preferably is 1 or 2; and
the subscript s is 0 or 1, with the proviso that when s is 0, m is 1 and when s is 1, m is 2, 3 or 4.

In another group of embodiments, Formula AA represents not individual LDC compounds but a LDC composition (i.e., a composition comprising a population of individual LDC compounds). In such embodiments, p represents the average number of drug-linkers per ligand in the composition. In such embodiments, p is typically not an integer value and can range from 1 to about 14, preferably from about 2 to about 12 (preferably from about 6 to about 14, from about 6 to about 12, from about 8 to about 14 or from about 8 to about 12). The other variables (e.g., L, Z, A, $L^P$, PEG, X, D, s, and m) remain the same.

In another group of embodiments, a LDC composition comprises a population of LDC compounds, the individual LDC compounds represented by Formula AA where for each individual LDC compound, p is independently selected from an integer ranging from 1 to 14, preferably from 2 to 12 (preferably from 6 to 14, from 6 to 12, 8 to 14 or 8 to about 12) and the average number of drug-linkers per ligand in the composition is from 1 to about 14, preferably from about 2 to about 12 (preferably from about 6 to about 14, from about 6 to about 12, from about 8 to about 14 or from about 8 to about 12).

In some aspects, from 1 to 32, or from 2 to 32 (preferably from 6 to 32 or from 8 to 32) Drug Units are attached to each Ligand Unit. A population of Ligand-Drug conjugates can have an average of from 1 to 32 or from about 2 to 32 (preferably from about 6 to 32 or from about 8 to 32) Drug Units per Ligand.

Selected embodiments of LDC compounds or LDC compositions represented by Formula AA include those wherein:
1) m is 1 and s is 0;
2) m is 2 to 4 and s is 1;
3) m is 2 and s is 1;
4) m is 1; s is 0; and p is an integer ranging from 6 to 14, from 8 to 14, or 8 to 12 for an LDC compound, or p is a number ranging from 6 to about 14, from about 8 to about 14, or about 8 to about 12 for an LDC composition;
5) m is 2-4; s is 1; and p is an integer ranging from 6 to 14, from 8 to 14, or 8 to 12 for an LDC compound or, or p is a number ranging from 6 to about 14, from about 8 to about 14, or about 8 to about 12 from an LDC composition;
6) m is 2; s is 1; and p is a integer ranging from 6 to 14, form 8 to 14, or 8 to 12 for an LDC compound or; p is a number ranging from 6 to about 14, form about 8 to about 14, or about 8 to about 12 for an LDC composition;
7) m is 2; s is 1; and p is 8
8) m is 1; s is 0; and p is 8
9) Any one of the embodiments set forth in 1-8 of this paragraph wherein there are from 1 to 32 or from about 2 to 32 (preferably from about 6 to about 32 or about 8 to about 32) Drug Units attached to the Ligand Unit.
10) Any one of the embodiments set forth in 1-9 of this paragraph wherein $L^P$ is a natural or non-natural amino acid, amino alcohol, amino aldehyde, or polyamine.

Selected embodiments of LDC compounds or LDC compositions that are represented by Formula AA have formulas AA1 and AA2 below:

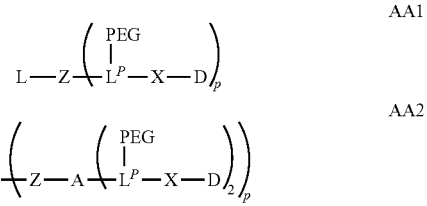

or a pharmaceutically acceptable salt thereof, wherein,
L is a Ligand Unit;
D is a Drug Unit;
PEG is a Polyethylene Glycol Unit;
Z is a Stretcher Unit;
X is a Releasable Assembly Unit;
$L^P$ is a Parallel Connector Unit;
A is a Branching Unit that is present; and
the subscript p is an integer ranging from 1 to 14, and preferably ranges from 2 to 12 (preferably 6 to 14, 6 to 12, 8 to 14 or from 8 to 12) for an Ligand-Drug Conjugate compound, or p is a number ranging from 1 to about 14, and preferably ranges from about 2 to about 12 (preferably about 6 to about 14, about 6 to about 12, about 8 to about 14 or from about 8 to about 12) for an Ligand-Drug Conjugate composition.

In any of the selected embodiments for LDC compounds provided herein where a p value is present, including those above, p can be an integer ranging from 1 to 14, from 2 to 14, 2 to 10, 4 to 12, 6 to 14, 6 to 12, 8 to 12 or 8 to 10. The subscript p can be 1, or 2, or 3, or 4, or 5, or 6, or 7, or 8, or 9, or 10, or 11, or 12, or 13, or 14.

In any of the selected embodiments for LDC compositions provided herein where a p value is present, including those above, p ranges from 1 to about 14, from about 2 to about 14, about 2 to about 10, about 4 to about 12, about 6 to about 14, about 6 to about 12, about 8 to about 12 or about 8 to about 10. The subscript p can be 1 or about 1, or 2 or about 2 or 3 or about 3 or 4, or about 4 or 5, or about 5 or 6, or about 6 or 7, or about 7 or 8, or about 8 or 9, or about 9 or 10, or about 10 or 11, or about 11 or 12, or about 12 or 13, or about 13 or 14 or about 14.

In another group of embodiments, provided herein are ligand-drug conjugates (LDCs) capable of releasing free drug, wherein from one to thirty-two Drug Units (preferably 2 to 32 Drug Units, 6 to 32 Drug Units, 8 to 32 Drug Units, 6 to 14 Drug Units, about 8 to about 14 Drug Units, or about 8 to about 12 Drug Units) are conjugated to the targeting Ligand of an LDC through Linker Units wherein each Drug Unit of a Drug-Linker moiety is attached to its Linker Unit through a cleavable component (i.e., the Releasable Assembly unit) that releases free drug in proximity to a site targeted by the Ligand (L), and wherein the LDCs further comprise a parallel connector unit ($L^P$) to which the Ligand Unit is connected, and a Polyethylene Glycol (PEG) Unit, wherein the PEG and Drug Units of a Linker-Drug moiety are connected in parallel orientation to each other. The Polyethylene Glycol Unit has from 4 to 72 (preferably from 6 to 72 repeating —OCH$_2$CH$_2$— units, more preferably from 6 to 36, or from 8 to 24) repeating units. The ligand can be an antibody unit, preferably an intact antibody unit. The cleavable linker can comprise, for example, a peptide cleavage site, a sugar cleavage site, or a disulfide cleavage site. The drug can be an auristatin or a non-auristatin. The auristatin or non-auristatin can have a hydrophobicity comparable to or greater than monomethyl auristatin E. The auristatin can be monomethyl auristatin E. In some aspects, the ADC exhibits improved pharmacokinetic properties as compared to the same or substantially the same ADC lacking the PEG Unit or containing the PEG Unit but placed in a serial orientation in relation to the antibody and drug. In some aspects, the ADC exhibits pharmacokinetic properties the same or substantially the same as the antibody component when unconjugated.

Drug-Linker Compounds

In some aspects, when designing the Ligand-Drug Conjugates, it will be desirable to synthesize the full drug-linker prior to conjugation to the Ligand Unit. In such embodiments, Drug-Linker Compounds act as Intermediate Compounds. Exemplary Drug-Linker Compounds are provided as follows whose structure are represented by Formula BB:

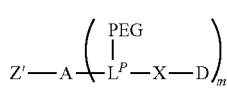
(BB)

or a pharmaceutically acceptable salt thereof, wherein
  D is a Drug Unit;
  PEG is a Polyethylene Glycol Unit;
  Z' is a Stretcher Unit capable of forming a covalent attachment to a Ligand Unit;
  X is a Releasable Assembly Unit;
  $L^P$ is a Parallel Connector Unit;
  A is an optional Branching Unit;
  the subscript m is an integer ranging from 1 to 4; and preferably is 1 or 2;
  the subscript s is 0 or 1, with the proviso that when s is 0, m is 1 and when s is 1, m is 2 to 4.

Selected embodiments of Formula BB include those wherein:
  1) m is 1 and s is 0;
  2) m is 2, 3 or 4 and s is 1;
  3) m is 2 and s is 1;
  4) Any one of the embodiments set forth in 1-3 of this paragraph wherein $L^P$ is a natural or non-natural amino acid, amino alcohol, amino aldehyde, or polyamine.

Selected embodiments of formulas BB include the following formulas:

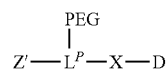
BB1

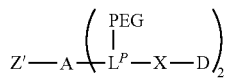
BB2 or a pharmaceutically acceptable salt thereof, wherein
  D is a Drug Unit;
  PEG is a Polyethylene Glycol Unit;
  Z' is a Stretcher Unit capable of forming a covalent attachment to a Ligand Unit;
  X is a Releasable Assembly Unit;
  $L^P$ is a Parallel Connector Unit; and
  A is an Branching Unit that is present.

Intermediate Linker Compounds

In some aspects, when designing the Ligand-Drug Conjugates, it may be desirable to conjugate components of the linker to the Ligand Unit (e.g., antibody) prior to attaching the -X-D component of the Ligand-Drug Conjugate. For example, in embodiments where a thiol containing substituent, e.g., cysteine, is being used to attach the -X-D component, it may be desirable to conjugate components of the linker to the Ligand Unit (e.g., antibody) prior to attaching the -X-D component of the Ligand-Drug Conjugate. In some such embodiments, the parallel connector unit is capable of forming a covalent linkage to the Releasable Assembly Unit but is not yet attached thereto. The Parallel Connector Unit can be protected by protecting groups for ease of synthesis. The protecting group can be removed just prior to attachment to the Releasable Assembly Unit.

Exemplary Intermediate Linker Compounds are provided as follows having Formula CC:

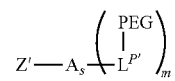
(CC)

or a pharmaceutically acceptable salt thereof wherein
  PEG is a Polyethylene Glycol Unit;
  Z' is a Stretcher Unit capable of forming a covalent attachment to a Ligand Unit;
  A is an optional Branching Unit;
  $L^{P'}$ is a Parallel Connector Unit capable of forming a covalent attachment to a Drug-Release Unit;
  the subscript m is an integer ranging from 1 to 4; and preferably is 1 or 2; and
  the subscript s is 0 or 1, with the proviso that when s is 0, m is 1 and when s is 1, m is 2, 3 or 4.

Selected embodiments of Formula CC include the following formulas.

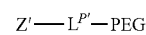
CC1

CC2 or a pharmaceutically acceptable salt thereof wherein
  PEG is a Polyethylene Glycol Unit;
  Z' is a Stretcher Unit capable of forming a covalent attachment to a Ligand Unit;
  -X-D is a Releasable Assembly Unit attached to a Drug Unit;
  A is a Branching Unit; and
  $L^{P'}$ is a Parallel Connector Unit capable of forming a covalent attachment to -X-D.

In some aspects, the Intermediate Linker Compounds will be conjugated to the Ligand Unit to form Intermediate Ligand-Linker Compounds. Exemplary embodiments of Intermediate Ligand-Linker compounds are represented by the structure shown below:

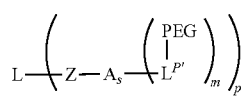
(DD)

or a pharmaceutically acceptable salt thereof wherein
  L is a Ligand Unit;
  PEG is a Polyethylene Glycol Unit;
  Z is a Stretcher Unit;
  $L^{P'}$ is a Parallel Connector Unit capable of forming a covalent attachment to -X-D;
  A is an optional Branching Unit;
the subscript p an integer ranging from 1 to 14, preferably from 2 to 12 (preferably from 6 to 14, 6 to 12, 8 to 14 or 8 to 12);
  the subscript m is an integer ranging from 1 to 4; preferably 1 or 2; and
  the subscript s is 0 or 1, with the proviso that when s is 0, m is 1 and when s is 1, m is 2, 3 or 4.

In another group of embodiments, Formula DD represents not individual Intermediate Ligand-Linker Compounds but a composition comprising a population of individual Intermediate Ligand-Linker Compounds. In such embodiments, p represents the average number of intermediate linkers per ligand in the composition. In such embodiments, p is typically not an integer value and can range from 1 to about 14, preferably from about 2 to about 12 (preferably from about 6 to about 14, from about 6 to about 12, from about 8 to about 14 or from about 8 to about 12). The other variables (e.g., L, Z, A, $L^{P}$, PEG, s, and m) remain the same.

Selected embodiments of Formula DD include the following formulas.

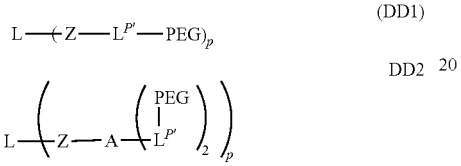

or a pharmaceutically acceptable salt thereof wherein

L is a Ligand Unit;

PEG is a Polyethylene Glycol Unit;

Z— is a Stretcher Unit;

-X-D is a Releasable Assembly Unit attached to a Drug Unit;

$L^{P'}$ is a Parallel Connector Unit capable of forming a covalent attachment to -X-D;

A is a Branching Unit; and the subscript p is an integer ranging from 1 to 14, preferably from 2 to 12 (preferably from 6 to 14, 6 to 12, 8 to 14 or 8 to 12) for an Intermediate Ligand-Linker compound, or the subscript p is a number ranging from 1 to about 14, preferably from about 2 to about 12 (preferably from about 6 to about 14, about 6 to about 12, about 8 to about 14 or about 8 to about 12) for an Intermediate Ligand-Linker composition.

Additional Embodiments

The Conjugates of Formula AA and Intermediates thereof permit the inclusion of one Drug unit per PEG Unit, a ratio of 1:1. It may be desirable, however, to provide drug conjugates having either 1 drug per PEG Unit or 2 or more drugs per PEG Unit. Accordingly, the present invention provides Ligand-Drug Conjugates having at least one drug per PEG Unit and intermediates thereof.

One of skill in the art will appreciate that as long as the core components of the Ligand-Drug conjugates are present, (i.e., Ligand Unit, Stretcher Unit, a Parallel Connector Unit, a PEG Unit, a Releasable Assembly Unit, and a Drug Unit), synthesis of Ligand-Drug Conjugates comprising additional Drug Units can be readily accomplished using the teachings provided herein. Inclusion of additional Branching Units and/or Drug Attachment Units allow for the attachment of multiple drugs per PEG Unit. The additional -X-D Units are attached via the Branching Units or Drug Attachment Units.

In one group of embodiments, such LDC compounds capable of releasing free drug, are represented by formulas (I), (II), or (III):

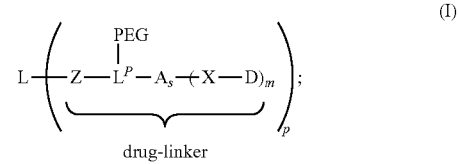

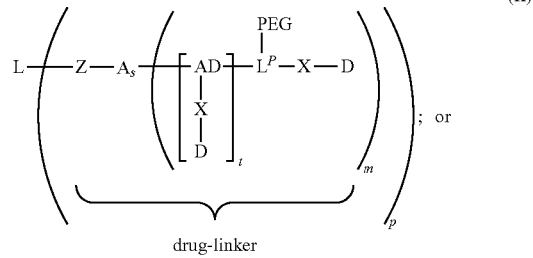

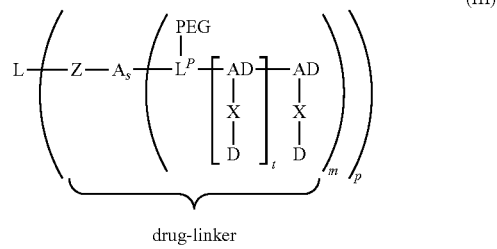

or a pharmaceutically acceptable salt thereof, wherein,

L is a Ligand Unit;

D is a Drug Unit;

PEG is a Polyethylene Glycol Unit;

Z is a Stretcher Unit;

X is a Releasable Assembly Unit;

$L^P$ is a Parallel Connector Unit;

A is an optional Branching Unit;

AD is a Drug Attachment Unit;

the subscript p is an integer ranging from 1 to 14, preferably from 2 to 12 (preferably from 6 to 14, 6 to 12, 8 to 14 or 8 to 12)

the subscript t is an integer ranging from 0 to 8, and preferably is 0, 1, 2 or 3;

the subscript m is an integer ranging from 1 to 4; and preferably is 1 or 2; and the subscript s is 0 or 1, with the proviso that when s is 0, m is 1 and when s is 1, m is 2, 3 or 4.

In another group of embodiments, Formulas I, II and III represent not individual LDC compounds but a LDC composition (i.e., a composition comprising a population of individual LDC compounds). In such embodiments, p represents the average number of drug-linkers per ligand in the composition. In such embodiments, p is typically not an integer value and can range from 1 to about 14, preferably from about 2 to about 12 (preferably from about 6 to about 14, from about 6 to about 12, from about 8 to about 14 or from about 8 to about 12). The other variables (e.g., L, Z, A, $L^P$, PEG, X, D, AD, s, m, and t) remain the same.

In another group of embodiments, a LDC composition comprises a population of LDC compounds, the individual LDC compounds represented by Formula I, II or II where for each individual LDC compound, p is independently selected from an integer ranging from 1 to 14, preferably from 2 to 12 (preferably from 6 to 14, from 6 to 12, 8 to 14 or 8 to about 12) and the average number of drug-linkers per ligand in the composition is from 1 to about 14, preferably from about 2 to about 12 (preferably from about 6 to about 14, from about 6 to about 12, from about 8 to about 14 or from about 8 to about 12).

In some aspects, from 1 to 32, or from 2 to 32 (preferably from 6 to 32 or from 8 to 32) Drug Units are attached to each Ligand Unit. A population of Ligand-Drug conjugates can have an average of from 1 to 32 or from about 2 to 32 (preferably from about 6 to 32 or from about 8 to 32) Drug Units per Ligand.

Selected embodiments of formulas I, II, and III include those wherein:

1) m is 1 and s is 0;
2) m is 2, 3 or 4 and s is 1;
3) m is 2 and s is 1;
4) m is 1; s is 0; and p is an integer ranging from 2 to 12, 4 to 12, 8 to 14, or 8 to 12 for a Ligand-Drug Conjugate compound or p is an number ranging from about 2 to about 12, about 4 to about 12, about 8 to about 14, or about 8 to about 12 for a Ligand-Drug Conjugate composition;
5) m is 2, 3 or 4; s is 1; and is p is an integer ranging from about 2 to about 12, about 4 to about 12, about 8 to about 14, or about 8 to about 12 for a Ligand-Drug Conjugate compound, or p is a number ranging from about 2 to about 12, about 4 to about 12, about 8 to about 14, or about 8 to about 12 Ligand-Drug Conjugate composition;
6) m is 2; s is 1; and p is an integer ranging from 2 to 12, 4 to 12, 6 to 14, 6 to 12, 8 to 14, or about 8 to about 12 for a Ligand-Drug Conjugate compound, or p is a number ranging from about 2 to about 12, about 4 to about 12, about 6 to about 14, about 6 to about 12, about 8 to about 14, or about 8 to about 12 for a Ligand-Drug Conjugate composition;
7) m is 2; s is 1; and p is 8;
8) m is 1; s is 0; and p is 8;
9) any one of the embodiments set forth in 1-8 of this paragraph wherein t is 0;
10) any one of the embodiments set forth in 1-8 of this paragraph wherein t is 1-8;
11) any one of the embodiments set forth in 1-8 of this paragraph wherein t is 1;
12) any one of the embodiments set forth in 1-8 of this paragraph wherein t is 2;
13) any one of the embodiments set forth in 1-8 of this paragraph wherein t is 3;
14) any one of the embodiments set forth in 1-8 of this paragraph wherein t is 4;
15) any one of the embodiments set forth in 1-8 of this paragraph wherein t is 5;
16) any one of the embodiments set forth in 1-8 of this paragraph wherein t is 6;
17) any one of the embodiments set forth in 1-8 of this paragraph wherein t is 7;
18) any one of the embodiments set forth in 1-8 of this paragraph wherein t is 8;
19) any one of the embodiments set forth in 1-18 of this paragraph wherein there are from 1 to 32, or from about 2 to 32 Drug Units attached to the Ligand Unit;
20) any one of the embodiments set forth in 1-18 of this paragraph wherein there are from 6 to 32 or from about 8 to 32 Drug Units attached to the Ligand Unit; and
21) any one of the embodiments set forth in 1-20 of this paragraph wherein $L^P$ is a natural or non-natural amino acid, amino alcohol, amino aldehyde, or polyamine.

In any of the selected embodiments for LDC compounds provided herein where a p value is present, including those above, p can be an integer ranging from 1 to 14, from 2 to 14, 2 to 10, 4 to 12, 6 to 14, 6 to 12, 8 to 12 or 8 to 10. The subscript p can be 1, or 2, or 3, or 4, or 5, or 6, or 7, or 8, or 9, or 10, or 11, or 12, or 13, or 14.

In any of the selected embodiments for LDC compositions provided herein where a p value is present, including those above, p ranges from 1 to about 14, from about 2 to about 14, about 2 to about 10, about 4 to about 12, about 6 to about 14, about 6 to about 12, about 8 to about 12 or about 8 to about 10. The subscript p can be 1 or about 1, or 2 or about 2 or 3 or about 3 or 4, or about 4 or 5, or about 5 or 6, or about 6 or 7, or about 7 or 8, or about 8 or 9, or about 9 or 10, or about 10 or 11, or about 11 or 12, or about 12 or 13, or about 13 or 14 or about 14. The other variables (e.g., L, Z, A, $L^P$, PEG, X, D, AD, s, m, and t) remain the same.

Selected embodiments of formulas I, II, and III include formula Ia, Ib, IIa, IIb, IIb, IIIa, and IIIb below.

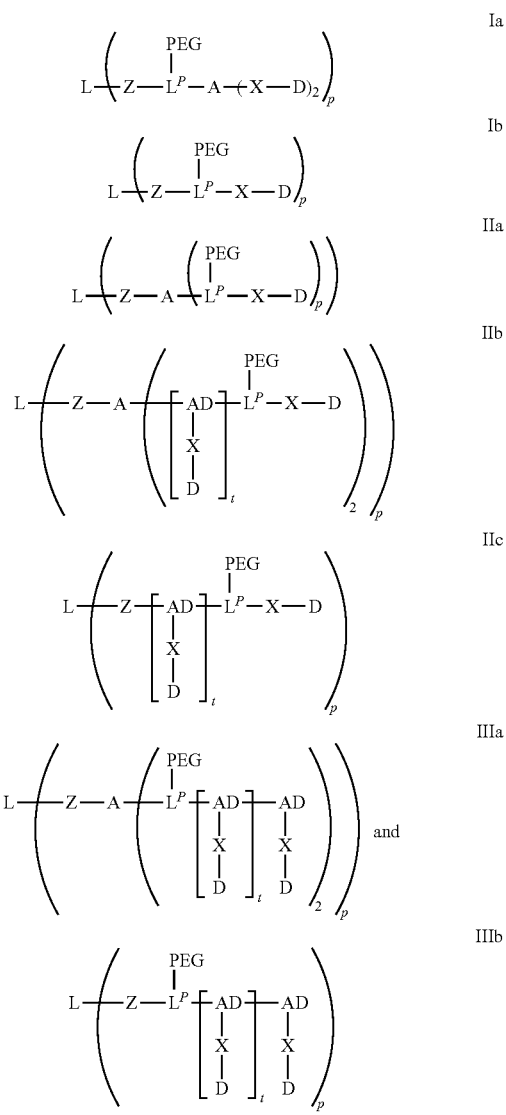

or a pharmaceutically acceptable salt thereof, wherein,

L is a Ligand Unit;
D is a Drug Unit;
PEG is a Polyethylene Glycol Unit;
Z is a Stretcher Unit;
X is a Releasable Assembly Unit;
$L^P$ is a Parallel Connector Unit;
A is an optional Branching Unit; and
AD is a Drug Attachment Unit;
the subscript p an integer ranging from 1 to 14, preferably form 2 to 12 (preferably from 6 to 14, 6 to 12, 8 to 14, or 8 to 12) for a Ligand-Drug Conjugate compound, or the subscript p is a number ranging from 1 to about 14, preferably from about 2 to about 12 (preferably from about 6 to about 14, about 6 to about 12, about 8 to about 14, or about 8 to about 12) for a Ligand-Drug Conjugate composition; and
the subscript t is an integer ranging from 0 to 8; and preferably is 0, 1, 2 or 3.

Selected embodiments of formulas Ia, Ib, IIa, IIb, IIb, IIc, IIIa, and IIIb include those wherein:
1) t is 0;
2) t is 1 to 8;
3) t is 1;
4) t is 2;
5) t is 3;
6) t is 4;
7) t is 5;
8) t is 7;
9) t is 8;
10) any of the embodiments set forth in 1-10 of this paragraph wherein there are from 1 to 32, from about 2 to 32, from 6 to 32 or from about 8 to 32 Drug Units attached to a Ligand Unit; and
11) any of the embodiments set forth in 1-11 of this paragraph wherein $L^P$ is a natural or non-natural amino acid, amino alcohol, amino aldehyde, or polyamine.

Embodiments of Formulas Ia, Ib, IIa, IIb, IIb, IIc, IIIa, and IIIb for a LDC composition include those wherein p is a number ranging from 6 to about 12; about 8 to about 12 and about 8 to about 10. For those compositions the subscript p can be 6 or about 6 or 7, or about 7 or 8, or about 8 or 9, or about 9 or 10, or about 10 or 11, or about 11 or 12, or about 12 or 13 or about 13 or 14, or about 14. In any of these embodiments, t can be from 0 to 8, from 1 to 8, or 0, 1, 2, 3, 4, 5, 6, 7, or 8.

Embodiments of Formulas Ia, Ib, IIa, IIb, IIb, IIc, IIIa, and IIIb for a LDC compound include those wherein p is an integer ranging from 6 to 12; 8 to 12 and 8 to 10. The subscript p can be 6, 7, 8, 9, 10, 11, 12, 13, or 14. In any of these embodiments, t can be from 0 to 8, from 1 to 8, or 0, 1, 2, 3, 4, 5, 6, 7, or 8.

Drug-Linker Compounds

Exemplary Drug-Linker Compounds having at least 1 drug per PEG Unit are provided as follows having formulas IV, V, VI:

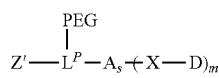

(IV)

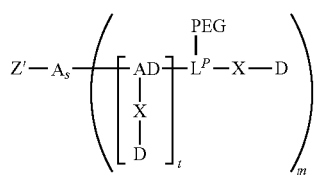

(V)

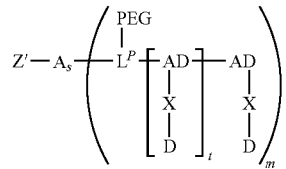

(VI)

or a pharmaceutically acceptable salt thereof, wherein
D is a Drug Unit;
PEG is a Polyethylene Glycol Unit;
Z' is a Stretcher Unit capable of forming a covalent attachment to a Ligand Unit;
X is a Releasable Assembly Unit;
$L^P$ is a Parallel Connector Unit;
A is an optional Branching;
AD is a Drug Attachment Unit;
the subscript t is an integer ranging from 0 to 8; and preferably is 0, 1, 2 or 3;
the subscript m is an integer ranging from 1 to 4; and preferably is 1 or 2;
the subscript s is 0 or 1, with the proviso that when s is 0, m is 1 and when s is 1, m is 2, 3 or 4.

Selected embodiments of formulas IV, V and VI include those wherein:
1) m is 1 and s is 0;
2) m is 2 to 4 and s is 1;
3) m is 2 and s is 1;
4) any of the embodiments set forth in 1-3 of this paragraph wherein t is 0
5) any of the embodiments set forth in 1-3 of this paragraph wherein t is 1
6) any of the embodiments set forth in 1-3 of this paragraph wherein t is 2; and
7) any of the embodiments set forth in 1-6 of this paragraph wherein $L^P$ is a natural or non-natural amino acid, amino alcohol, amino aldehyde, or polyamine.

Selected embodiments of formulas IV, V and VI include the following formulas:

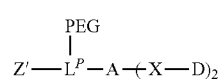

IVa

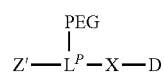

IVb

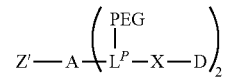

Va

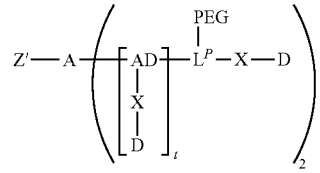

Vb

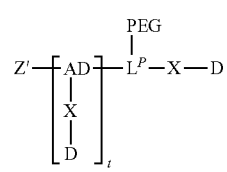

Vc

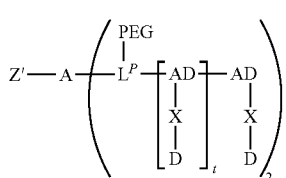
(VIa)

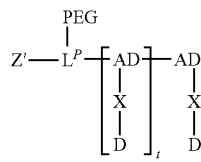
(VIb)

or a pharmaceutically acceptable salt thereof, wherein
D is a Drug Unit;
PEG is a Polyethylene Glycol Unit;
Z' is a Stretcher Unit capable of forming a covalent attachment to a Ligand Unit;
X is a Releasable Assembly Unit;
$L^P$ is a Parallel Connector Unit;
A is an optional Branching;
AD is a Drug Attachment Unit; and
the subscript t is an integer ranging from 0 to 8; and preferably is 0, 1, 2 or 3.

Intermediate Linker Compounds

Exemplary Intermediate Linker Compounds comprising at least one drug per PEG Unit are as follows having formulas VII, VIII or IX:

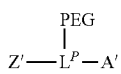
(VII)

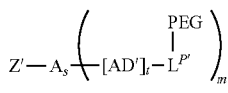
(VIII)

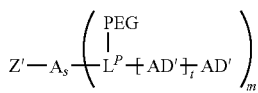
(IX)

or a pharmaceutically acceptable salt thereof wherein
PEG is a Polyethylene Glycol Unit;
Z' is a Stretcher Unit capable of forming a covalent attachment to a Ligand Unit;
A' is a Branching Unit capable of forming a covalent attachment to two to four X-D Units, preferably two X-D Units;
A is an optional Branching Unit;
AD' is a Drug Attachment Unit capable of forming a covalent attachment to a -X-D Unit;
$L^P$ is a Parallel Connector Unit;
$L^{P'}$ is a Parallel Connector Unit capable of forming a covalent attachment to -X-D;
the subscript t is an integer ranging from 0 to 8, and preferably is 0, 1, 2 or 3;
the subscript m is an integer ranging from 1 to 4; and preferably is 1 or 2;
the subscript s is 0 or 1, with the proviso that when s is 0, m is 1 and when s is 1, m is 2, 3 or 4; and
wherein -X-D is a Releasable Assembly Unit attached to a Drug Unit.

Selected embodiments of formulas VIII or IX include the following:

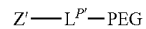
(VIIIa)

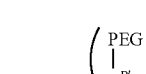
(VIIIb)

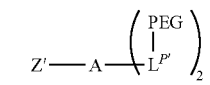

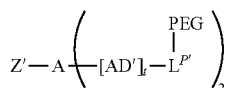
(VIIIc)

(VIIId)

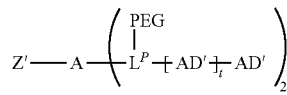
(IXa)

(IXb)

or a pharmaceutically acceptable salt thereof wherein
PEG is a Polyethylene Glycol Unit;
Z' is a Stretcher Unit capable of forming a covalent attachment to a Ligand Unit;
A is a Branching Unit;
AD' is a Drug Attachment Unit capable of forming a covalent attachment to a -X-D Unit;
$L^P$ is a Parallel Connector Unit;
$L^{P'}$ is a Parallel Connector Unit capable of forming a covalent attachment to -X-D; and
the subscript t is an integer ranging from 0 to 8; and preferably is 0, 1, 2 or 3; and
wherein -X-D is a Releasable Assembly Unit attached to a Drug Unit.

The Intermediate Linker Compounds and formulas VII, VIII, XI, VIIIa, VIIIb, VIIIc, VIIId, IXa, and IXb, the Stretcher Unit can be conjugated to the Ligand Unit (e.g., antibody) to form Intermediate Ligand-Linker Compounds that provide 1 to 14 linkers attached to each Ligand Unit. Exemplary embodiments are shown below wherein p is 1 to 14 and all of the other variable groups are as described herein for the Intermediate Linker Compounds. Exemplary Ligand-Linker Compounds and compositions comprising these compounds (i.e., Ligand-Linker compositions) are as follows having structures represented by formula X, XI, XII

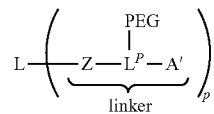
(X)

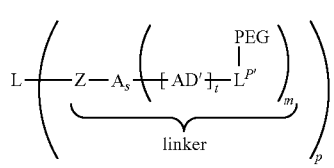
(XI)

-continued

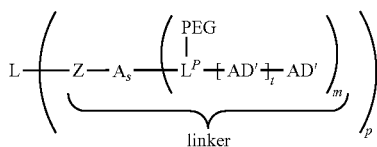
(XII)

or a pharmaceutically acceptable salt thereof wherein
L is a Ligand Unit;
PEG is a Polyethylene Glycol Unit;
Z— is a Stretcher Unit;
-X-D is a Releasable Assembly Unit attached to a Drug Unit;
$L^P$ is a Parallel Connector Unit;
$L^{P'}$ is a Parallel Connector Unit capable of forming a covalent attachment to -X-D;
A' is a Branching Unit capable of forming a covalent attachment to two to four X-D Units, preferably two X-D Units;
A is an optional Branching Unit;
AD' is a Drug Attachment Unit capable of forming a covalent attachment to a X-D Unit;
the subscript p is an integer ranging from 1 to 14, preferably from 2 to 12 (preferably from 6 to about 14, about 6 to about 12, about 8 to about 14 or about 8 to about 12) for a Ligand-Linker compound, or
the subscript p is a number ranging from 1 to about 14, preferably about 2 to about 12 (preferably about 6 to about 14, about 6 to about 12, about 8 to about 14 or about 8 to about 12) for a Ligand-Linker composition;
the subscript t is 0 to 8; and preferably is 0, 1, 2 or 3;
the subscript m is an integer ranging from 1 to 4; and preferably is 1 or 2; and
the subscript s is 0 or 1, with the proviso that when s is 0, m is 1 and when s is 1, m is 2, 3 or 4.

Selected embodiments of formulas XI and XII include the following formulas.

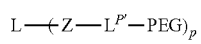
(XIa)

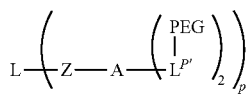
(XIb)

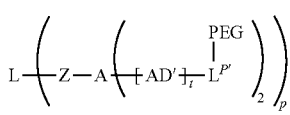
(XIc)

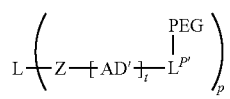
(XId)

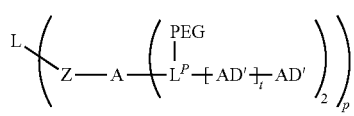
(XIIa)

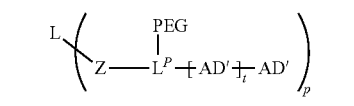
(XIIb)

or a pharmaceutically acceptable salt thereof wherein
L is a Ligand Unit;
PEG is a Polyethylene Glycol Unit;
Z— is a Stretcher Unit;
$L^P$ is a Parallel Connector Unit;
$L^{P'}$ is a Parallel Connector Unit capable of forming a covalent attachment to -X-D;
A is a Branching Unit;
AD' is a Drug Attachment Unit capable of forming a covalent attachment to a X-D Unit;
the subscript p is an integer ranging from 1 to 14, preferably from 2 to 12 (preferably from 6 to 14, 6 to 12, 8 to 14, or 8 to 12) for a Ligand-Linker compound, or
the subscript p is a number ranging from 1 to about 14, preferably from about 2 to about 12 (preferably from about 6 to about 14, about 6 to about 12, about 8 to about 14 or about 8 to about 12) for a Ligand-Linker composition; and
the subscript t is 0 to 8; and
wherein -X-D is a Releasable Assembly Unit attached to a Drug Unit.

Component Groups

Central to the Ligand-Drug Conjugates and Intermediate Compounds described herein is the placement of a PEG unit in parallel orientation with its Drug Unit in order to influence the pharmacokinetics of the resulting LDC. Placement of the PEG unit is accomplished by the Parallel Connector Unit. The Parallel Connector Unit serves to connect a Ligand, to a Polyethylene Glycol Unit and a Drug Unit so that the PEG and Drug Units are in a parallel configuration, which arranges the Ligand, PEG and Drug Units in a branched configuration. Accordingly, the Parallel Connector Unit can be considered a scaffold having attachment sites for components of the Ligand-Drug Conjugates, and Intermediate Compounds for their preparation.

In order to act as a parallel connector, the $L^P$ unit is attached via three attachment sites within the linker. One of the attachment sites attaches the $L^P$ Unit to the PEG Unit. A second attachment site attaches the $L^P$ Unit to the Releasable Assembly Unit (in some instances via the Branching Unit A or Drug Attachment Unit AD). A third attachment site attaches the $L^P$ Unit to the Stretcher Unit (in some instances via the Drug Attachment Unit, AD, and/or Branching Unit, A). The Parallel Connector Unit is a unit that is distinct from the PEG Unit and is attached thereto via the PEG Attachment Unit component of the PEG Unit. In other words, the Parallel Connector Unit is not a subunit of the PEG Unit.

For the Ligand-Drug Conjugates and intermediates thereof having more than one drug per PEG Unit, attachment of the Parallel Connector Unit to the Releasable Assembly Unit can be through a Branching Unit or a Drug Attachment Unit. Attachment of the Parallel Connector Unit to the Stretcher Unit can be via a Drug Attachment Unit AD and/or optionally an additional Branching Unit. In all of these embodiments, the $L^P$ unit can be considered a tri-functional chemical moiety that is capable of covalently linking together three spaced chemical moieties. As will be appreciated, for select Intermediate Compounds, the $L^P$ unit is represented by $L^{P'}$ and is not yet attached to the Drug via the Drug-Release Unit but has an optionally protected functional group for attachment to the Drug (e.g., via the Drug-Release Unit.) As will also be appreciated, the term tri-functional is used to denote the three attachment sites and not the number of functional groups present on the $L^P$ or $L^{P'}$ Unit.

A Parallel Connector Unit can be prepared from one or more (typically from 1 to 5 or 1 to 4 or 1 to 3 or 1 or 2) natural or non-natural amino acid, amino alcohol, amino aldehyde, or polyamines.

It will be appreciated that when referring to the natural or non-natural amino acid, amino alcohol, amino aldehyde, or polyamines as present in the Conjugate or Intermediates of the present invention (whether they be part of a $L^P$ Unit or other component of the Conjugates or Intermediates described herein), the amino acid, amino alcohol, amino aldehyde, or polyamines will exist in residual form, also referred to herein as assembled form. For example, in embodiments, wherein the Parallel Connector Unit is two amino acids, the two amino acids will exist as residues with a peptide bond between them. In embodiments where the Parallel connector unit is comprised of an amino alcohol, the amino alcohol will exist as a residue where, for example, its amino group is bonded to another residue of the Parallel Connector Unit or another component of the Conjugate through a carbonyl-containing functional group of that other residue/component while its hydroxyl group is bonded as an ether to, or is bonded through a carbonyl-containing functional group, of yet another residue of the Parallel Connector Unit or another component of the Conjugate. In embodiments where the Parallel Connector Unit is comprised of an amino aldehyde, the amino aldehyde will exist as a residue where, for example, its amino group is bonded to another residue of the Parallel Connector Unit or another component of the Conjugate through a carbonyl-containing functional group of that other residue/component while its aldehyde functional group is converted to an immino functional group or through subsequent reduction to provide a nitrogen-carbon bond when bonded to an amino group of yet another residue of the Parallel Connector Unit or another component of the Conjugate. An amino alcohol or amino aldehyde may be derived from a natural or unnatural amino acid by reduction of its carboxylic acid functional group to an aldehyde or an hydroxyl functional group.

When a Parallel Connector Unit residue is the branching residue for that unit, it will be understood that residue will have a third functional group to which another residue of the Parallel Connector Unit, a -X-D moiety, or a PEG Unit or other component of a Linker Unit is bonded. For example, an amino acid or other amine-containing acid residue of the Parallel Connecting Unit can have or can be substituted with a functionalized side chain to provide the requisite three points of attachment required for a branching residue. For example, serine has three functional groups, i.e., acid, amino and hydroxyl functional groups and may be viewed as a combined amino acid and amino alcohol residue for purposes of its incorporation into a Parallel Connector Unit. Tyrosine also contains a hydroxyl group, in this instance in its phenolic side chain, and may also be view similarly to serine for purposes of its incorporation as a branching residue into a Parallel Connector Unit.

In another example, when the branching residue of a Parallel Connector unit is cysteine, its amino and carboxylic acid group will exist in residual form in a manner previously discussed for amino acids or amine-containing acids to provide two of the three requisite points of attachment for a braching residue while its thiol group will exist in residual form when bonded to a -X-D moiety, or a PEG Unit or other component of a Linker Unit as a disulfide or in a sulfur-carbon bond as, for example, when the thiol functional group reacts with a maleimide-containing group of a Linker Unit component. In some instances, the residual thiol group is in its oxidized form (i.e., —S(=O)— or —S(=O)$_2$—) when bonded to another residue of the Parallel Connector Unit or to another component of the Linker Unit. In yet another example, the alpha amino and carboxylic acid group of a lysine will exist in residual form to provide two of the three requisite points of attachment required of a branching residue of a Parallel Connector Unit while it epsilon amino group in its residual form provides the third point of attachment. Histidine may also be viewed as an amino acid with two amino groups, where the second amino group is the NH of the imidazole-containing side chain.

In another example, when the branching residue of a Parallel Connector unit is aspartic or glutamic acid, the alpha amino and C-terminal carboxylic acid groups of the amino acid in their residual forms provide two of the three requisite points of attachment required for a branching residue of a Parallel Connector Unit, while its beta or gamma carboxylic acid group in its residual form provides the third point of attachment. In those instances when a naturally occurring amino acid is recited as a residue of a Parallel Connector Unit, but does not naturally contain a functionalized amino acid side chain, yet is required to be a branching residue, it is understood that the amino acid structure is modified to have an additional functional group besides its amino and carboxylic acid functional groups when in residual form in order to provide the requisite third point of attachment. For example, an amino acid having an aliphatic side chain may be substituted at a carbon of that side chain with a hydroxyl, amino, aldehyde, thiol, carboxylic acid group or other functional group or other moiety (e.g., an aryl or arylalkyl) substituted with any one of these functional groups to provide an unnatural amino acid having the requisite three points of attachment. Such unnatural amino acids are incorporated into a Parallel Connector Unit as described above for amino acids and residual forms of the introduced functional groups.

Similarly, when an amino aldehyde or amino alcohol is incorporated into a Parallel Connecting Unit as a branching residue that amino aldehyde or amino alcohol will have a third functional group to provide, along with its amino and aldehyde functional groups, the requisite three points of attachment. In those instances, an amino aldehyde or amino alcohol may correspond in structure to a natural amino acid that has a functionalized side chain or an unnatural amino acid having an functional group that was introduced into the side chain of a natural amino acid as described above in which a carboxylic acid of the natural or unnatural amino acid is reduced to an hydroxy or aldehyde functional group.

The amino acid can be an alpha, beta, or gamma amino acid or other amine-containing acid compound and can be in its D or L isomer if it contains a chiral carbon to which is bonded a natural or unnatural amino acid side chain. When the Parallel Connector Unit is made up of more than one natural or non-natural amino acid, amino alcohol, amino aldehyde, or polyamines, the amino acids, amino alcohols, amino aldehydes, polyamines or combinations thereof are linked together via covalent bonds to form the Parallel Connector Unit.

The amino acid, amino alcohol, or amino aldehyde can be non-natural and can be modified to have a functionalized side chain for attachment to components of the Conjugates or Intermediate Compounds (as described above for a branching residue of a Parallel Connector Unit), as the case may be. Exemplary functionalized amino acids, amino alcohols, or amino aldehydes include, for example, azido or alkyne functionalized amino acids, amino alcohols, or amino aldehydes (e.g., amino acid, amino alcohol, or amino aldehyde modified to have an azide group or alkyne group for attachment using click chemistry). Methods for the independent activation and reaction of the functional groups present on an amino acid—e.g., the amine portion, the carboxylic acid portion and the side chain portion (whether, for example, an amino moiety, a hydroxyl group, another carboxylic acid, thiol, azide or alkyne) are well known in the art.

The Parallel Connector Unit can comprise 1 or more (typically from 1 to 5 or 1 to 4 or 1 to 3 or 1 or 2) amino acids, optionally substituted $C_{1-20}$ heteroalkylenes (preferably optionally substituted $C_{1-12}$ heteroalkylene), optionally substituted $C_{3-8}$ heterocyclos, optionally substituted $C_{6-14}$ arylenes, optionally substituted $C_3$-$C_8$ carbocyclos, or combinations thereof. In some aspects, the Parallel Connector Unit comprises no more than 2 or no more than one optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo. Optional substituents include (=O), —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)2R, —OS(=O)$_2$OR, —S(=O)$_2$NR, —S(=O)R, —OP(=O)(OR)$_2$, —P(=O)(OR)$_2$, —PO$^=_3$, —PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, —$C_1$ $C_{20}$ alkyl, —$C_6$ $C_{20}$ aryl, —$C_3$ $C_{14}$ heterocycle, a protecting group or a prodrug moiety. Preferred optional substituents are (=O), —X, —R, —OR, —SR, and —NR$_2$.

A Parallel Connector Unit can be a straight chain or branched chain and can be represented by Formula A:

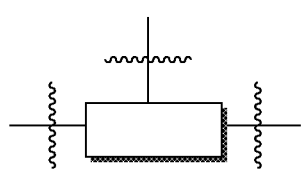

Formula A

Wherein
$AA^1$ is a subunit of $L^P$ independently selected from an amino acid, optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;
and the subscript u is independently selected from 0 to 4; and the wavy line indicates covalent attachment sites within the Ligand-Drug Conjugate or intermediate thereof. The optionally substituted heteroalkylene, heterocycle, arylene or carbocyclo will have functional groups for attachments between the subunits and within a Ligand-Drug Conjugate or intermediates thereof.

In some aspects at least one instance of $AA^1$ is an amino acid. The subscript u can be 0, 1, 2, 3, or 4. In some aspects, $AA^1$ is an amino acid and u is 0. In some aspects, the Parallel Connector Unit comprises no more than 2 optionally substituted $C_{1-20}$ heteroalkylenes, optionally substituted $C_{3-8}$ heterocyclos, optionally substituted $C_{6-14}$ arylenes, or optionally substituted $C_3$-$C_8$ carbocyclos. In some aspects, wherein the Parallel Connector Unit has formula A, the Parallel Connector Unit comprises no more than 1 optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo.

A Parallel Connector Unit or an amino acid subunit thereof can be an alpha, beta, or gamma amino acid can be natural or non-natural. The amino acid can be a D or L isomer. Attachment within the Parallel Connector Unit or with the other components of the conjugate (or linker) can be, for example, via amino, carboxy, or other functionalities. Methods for the independent activation and reaction of the functional groups are well known in the art.

A Parallel Connector Unit or an amino acid subunit thereof can be independently selected from the D or L isomer of a thiol containing amino acid. The thiol containing amino acid can be, for example, cysteine, homocysteine, or penicillamine.

A Parallel Connector Unit or an amino acid subunit thereof can be independently selected from the group consisting of the L- or D-isomers of the following amino acids: Alanine (including β-alanine), arginine, aspartic acid, asparagine, cysteine, histidine, glycine, glutamic acid, glutamine phenylalanine, lysine, leucine, methionine, serine, tyrosine, threonine, tryptophan, proline, ornithine, penicillamine, B-alanine, aminoalkynoic acid, aminoalkanedioic acid, heterocyclo-carboxylic acid, citrulline, statine, diaminoalkanoic acid, and derivatives thereof.

Preferred amino acids include cysteine, homocysteine, penicillamine, ornithine, lysine, serine, threonine, glutamine, alanine, aspartic acid, glutamic acid, selenocysteine, proline, glycine, isoleucine, leucine, methionine, valine, and alanine.

Exemplary $L^P$ or $AA^1$ subunits thereof include:

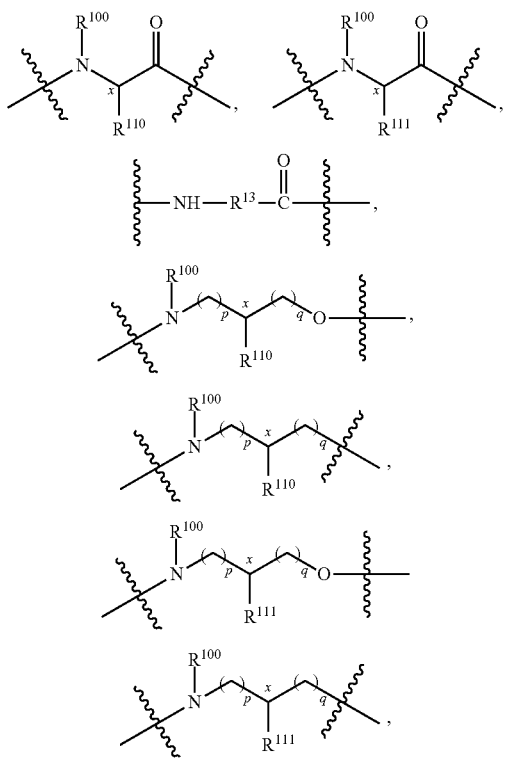

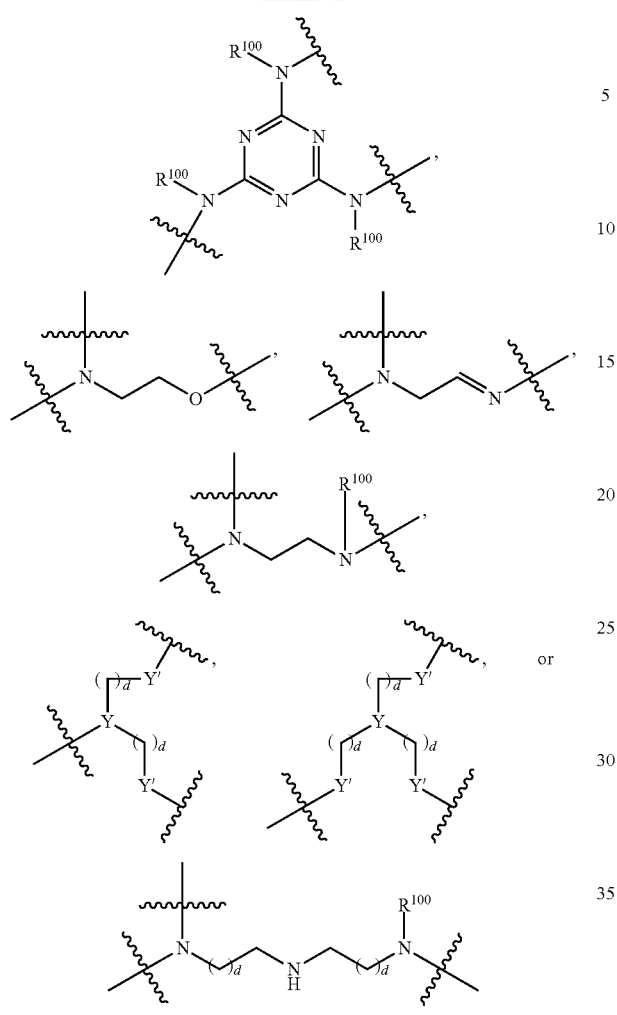

wherein $R^{110}$ is

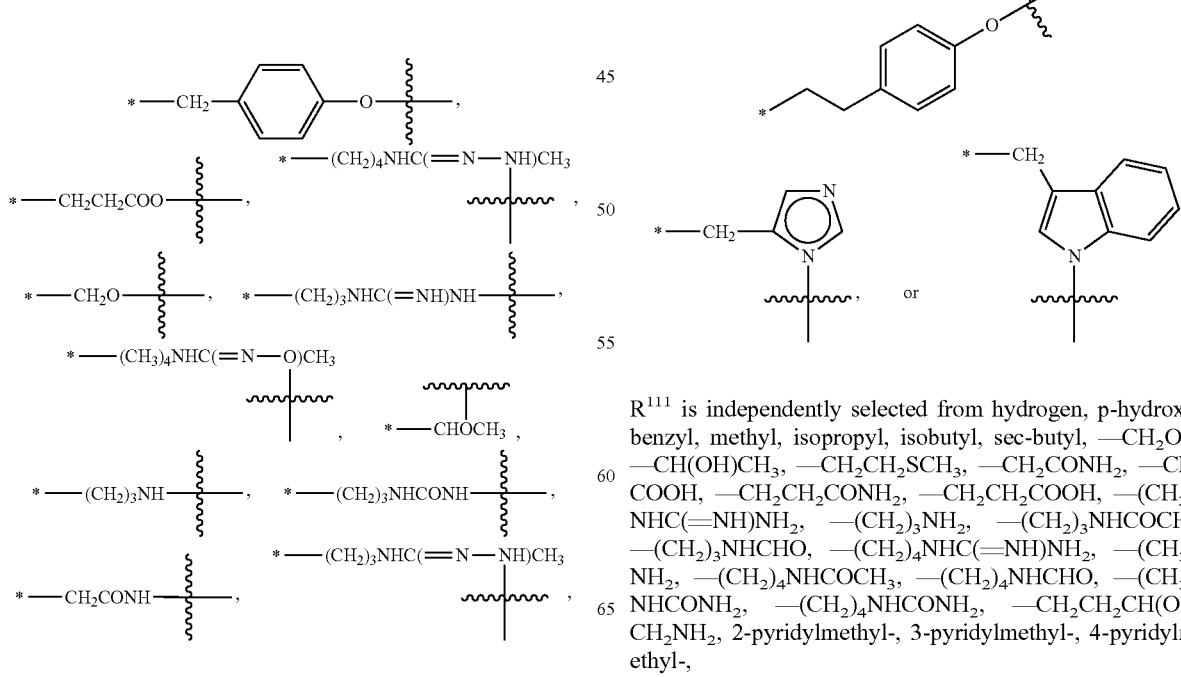

$R^{111}$ is independently selected from hydrogen, p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-,

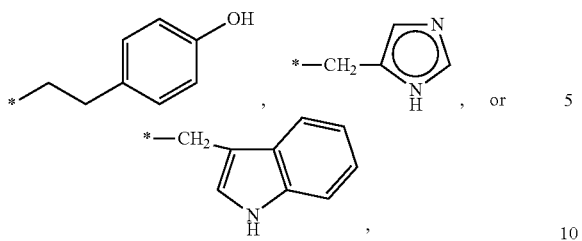

wherein the asterisk indicates attachment to the carbon labeled x;
$R^{100}$ is independently selected from hydrogen or —$C_1$-$C_3$ alkyl (preferably hydrogen or $CH_3$),
$R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene-(preferably —$CH_2$—$CH_2$—);
Y is —

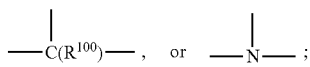

Y' is —C(=O)—, —O—, —S—, —NH—, or —N($CH_3$)—, and
the subscripts p, q, and d are integers independently selected from 0 to 5; and the wavy line indicates covalent attachment within the compound, hydrogen, OH or a $C_{1-3}$ unsubstituted alkyl group, provided that at least one of the wavy lines indicates a covalent attachment within the compound. In some aspects, all of the wavy lines indicate covalent attachment within the compound (e.g., when $L^P$ does not comprise any subunits).

In one group of embodiments, $L^P$ is a heterocyclic ring having functional groups that can independently form covalent linkages to the noted components (e.g., a triazole heterocyclic ring formed from cyanuric chloride). In another group of embodiments, $L^P$ is an alkane having attached functional groups as noted above. In still other embodiments, $L^P$ can be a nitrogen atom.

In some embodiments, -$L^P$-, once assembled, has the formula denoted below:

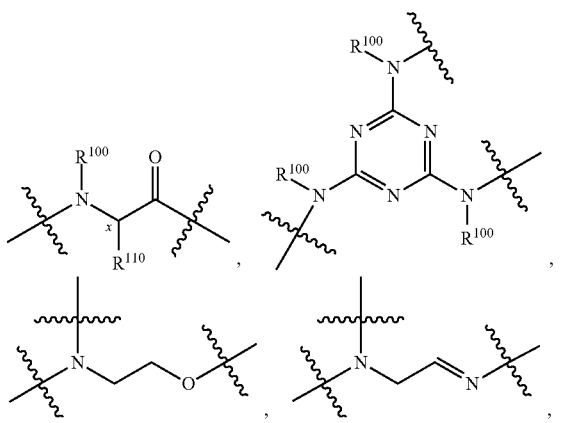

wherein the wavy line indicates the attachment sites within the Ligand-Drug Conjugate or intermediate thereof (e.g., PEG, to —X (directly or indirectly via A or AD) and to Z (directly or indirectly via A or AD) and wherein $R^{110}$ is

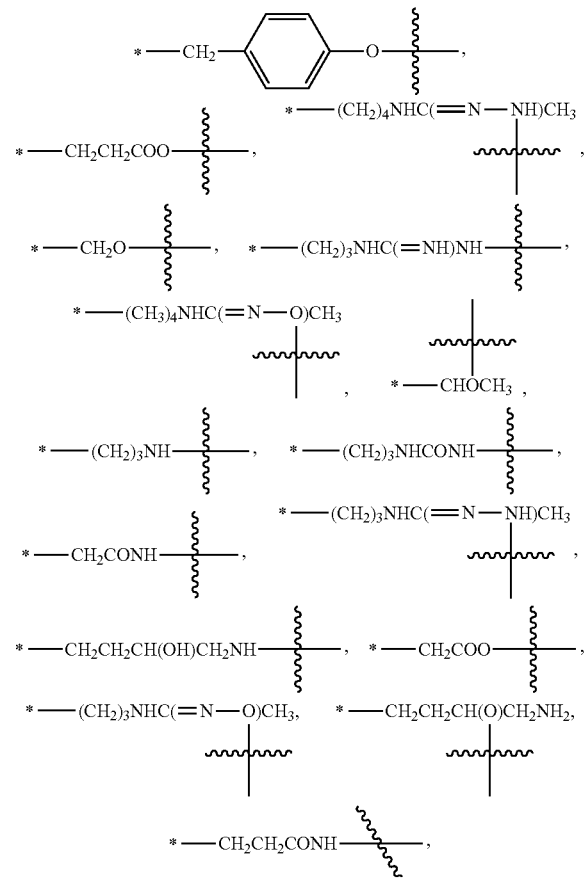

-continued

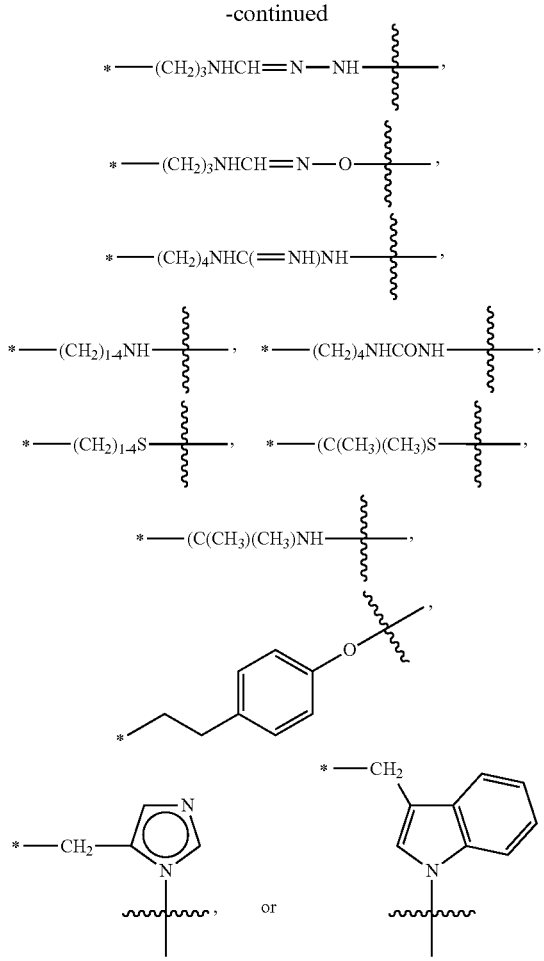

wherein the asterisk indicates attachment to the carbon labeled x and the wavy line indicates one of the three attachment sites;
$R^{100}$ is independently selected from hydrogen or —$C_1$-$C_3$ alkyl, preferably hydrogen or $CH_3$,
Y is independently selected from N or CH,
Y' is independently selected from NH, O, or S, and
the subscript c is an integer independently selected from 1 to 10, and preferably 1, 2, or 3.

In preferred embodiments, $R^{110}$ is not

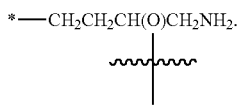

A Parallel Connector Unit or an amino acid subunit thereof can have the formula below

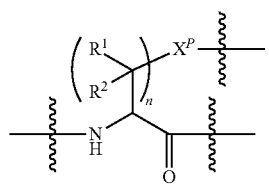

wherein, the subscript n is an integer ranging from 1 to 4;
$X^P$ is selected from the group consisting of —O—, —NR—, —S—, —S(=O)—, —C(=O)—, or —$C_2$-$C_8$ heterocyclo-; and
$R^1$ and $R^2$ are independently selected from the group consisting of —H, —$C_{1-3}$ alkyl, -phenyl, or —$C_2$-$C_5$ heterocycle (preferably H or $C_{1-3}$ alkyl), wherein the wavy line indicates covalent attachment within the compound.

In some embodiments $X^P$ is provided by a natural or un-natural amino acid side chain.

Each Parallel Connector Unit or subunit thereof can be independently selected from the D or L isomer of lysine, glutamic acid, aspartic acid, cysteine, penicillamine, serine or threonine.

Each Parallel Connector Unit or subunit thereof can be independently selected from the D or L isomer of lysine, glutamic acid, aspartic acid, cysteine, or penicillamine.

Each Parallel Connector Unit or subunit thereof can be independently selected from the group consisting of the following amino acids: arginine, aspartic acid, asparagine, histidine, glutamic acid, glutamine, lysine, serine, tyrosine, threonine, tryptophan, ornithine, penicillamine, aminoalkynoic acid, aminoalkanedioic acid, heterocyclo-carboxylic acid, citrulline, statine, diaminoalkanoic acid, and derivatives thereof.

Each Parallel Connector Unit or subunit thereof can be independently selected from the group consisting of the following L-isomers of these natural amino acids: arginine, aspartic acid, asparagine, histidine, glutamic acid, glutamine, lysine, cysteine, penicillamine, serine, tyrosine, threonine, and tryptophan.

Each Parallel Connector Unit or subunit thereof can be independently selected from the group consisting of the following D-isomers of these natural amino acids: arginine, aspartic acid, asparagine, histidine, glutamic acid, glutamine, phenylalanine, lysine, cysteine, penicillamine serine, tyrosine, threonine, and tryptophan.

Each Parallel Connector Unit or subunit thereof can be independently selected from the D or L isomer of a thiol containing amino acid. The thiol containing amino acid can be, for example, cysteine, homocysteine, or penicillamine.

Each Parallel Connector Unit or subunit thereof can be independently selected from the group consisting of the L- or D-isomers of the following amino acids: Alanine (including β-alanine), arginine, aspartic acid, asparagine, cysteine, histidine, glycine, glutamic acid, glutamine phenylalanine, lysine, leucine, methionine, serine, tyrosine, threonine, tryptophan, proline, ornithine, penicillamine, B-alanine, aminoalkynoic acid, aminoalkanedioic acid, heterocyclo-carboxylic acid, citrulline, statine, diaminoalkanoic acid, and derivatives thereof.

Preferred amino acids include cysteine, homocysteine, penicillamine, ornithine, lysine, serine, threonine, glutamine, alanine, aspartic acid, glutamic acid, selenocysteine, proline, glycine, isoleucine, leucine, methionine, and valine.

Each Parallel Connector Unit or subunit thereof can be independently selected from the group consisting of alanine derivatives provided that the appropriate number of functional units are present. Illustrative of examples of alanine derivatives include but are not limited to: dehydro-alanine, 4-thiazolylalanine, 2-pyridylalanine, 3-pyridylalanine, 4-pyridylalanine, β-(1-naphthyl)-alanine, β-(2-naphthyl)-alanine, α-aminobutyric acid, β-chloro-alanine, β-cyano-alanine, β-cyclopentyl-alanine, β-cyclohexyl-alanine, β-iodo-alanine, β-cyclopentenyl-alanine, β-tBu-alanine, β-cyclopropyl-alanine, β-diphenyl-alanine, β-fluoro-alanine, β-piperazinyl-alanine with the piperazine ring protected or not, β-(2-quinolyl)-alanine, β-(1,2,4-triazol-1-yl)-alanine, β-ureido-alanine, H-β-(3-benzothienyl)-Ala-OH, and H-β-(2-thienyl)-Ala-OH.

Each Parallel Connector Unit or subunit thereof can be independently selected from the group consisting of arginine and arginine derivatives thereof. Illustrative of examples of arginine and derivatives thereof include but are not limited to: arginine (Arg), N-alkyl-arginine, H-Arg(Me)-OH, H-Arg (NH$_2$)—OH, H-Arg(NO$_2$)—OH, H-Arg(Ac)$_2$—OH, H-Arg (Me)$_2$-OH (asymmetrical), H-Arg(Me)$_2$-OH (symmetrical), 2-amino-4-(2'-hydroxyguanidino)-butyric acid (N-ω-hydroxy-nor-arginine) and homoarginine.

Each Parallel Connector Unit or subunit thereof can be independently selected from the group consisting of aspartic acid and derivatives thereof. Illustrative of examples of aspartic acid and derivatives thereof include but are not limited to: aspartic acid (Asp), N-alkyl-aspartic acid, and H-Asp(OtBu)-OH.

Each Parallel Connector Unit or subunit thereof can be independently selected from the group consisting of asparagine and derivatives thereof. Illustrative of examples of asparagine and derivatives thereof include but are not limited to: asparagine (Asn), N-alkyl-asparagine, and isoasparagine (H-Asp-NH$_2$).

Each Parallel Connector Unit or subunit thereof can be independently selected from the group consisting of cysteine and derivatives thereof. Illustrative of examples of cysteine (Cys) derivatives (containing no free SH group) thereof include but are not limited to: Cys (StBu), H-Cys(Acm)-OH, H-Cys(Trt)-OH, H-Cys(StBu)-OH, H-Cys(Bzl)-OH, H-Cys (S-Et)-OH, H-Cys(SO$_3$H)—OH, H-Cys(aminoethyl)-OH, H-Cys(carbamoyl)-OH, H-Cys(S-phenyl)-OH, H-Cys (Boc)-OH, and H-Cys(hydroxyethyl)-OH.

Each Parallel Connector Unit or subunit thereof can be independently selected from the group consisting of histidine and derivatives thereof. Illustrative of examples of histidine and derivatives thereof include but are not limited to: histidine (His), N-alkyl-histidine, H-His(Boc)-OH, H-His(Bzl)-OH, H-His(1-Me)-OH, H-His(1-Tos)-OH, H-2, 5-diiodo-His-OH, and H-His(3-Me)-OH.

Each Parallel Connector Unit or subunit thereof can be independently selected from the group consisting of glycine derivatives. Illustrative of examples of glycine derivatives include but are not limited to: H-propargylglycine

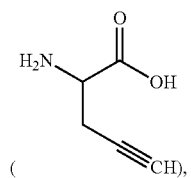

α-aminoglycine (protected or not), β-cyclopropyl-glycine, α-allylglycine, and neopentylglycine.

Each Parallel Connector Unit or subunit thereof can be independently selected from the group consisting of glutamic acid and derivatives thereof. Illustrative of examples of glutamic acid and derivatives thereof include but are not limited to: glutamic acid (Glu), N-alkyl-glutamic acid, H-Glu(OtBu)-OH, H-γ-hydroxy-Glu-OH, H-γ-methylene-Glu-OH, H-γ-carboxy-Glu(OtBu)$_2$-OH, and pyroglutamic acid.

Each Parallel Connector Unit or subunit thereof can be independently selected from the group consisting of gluta-mine and derivatives thereof. Illustrative of examples of glutamine and derivatives thereof include but are not limited to: glutamine (Gln), N-alkyl-glutamine, isoglutamine (H-Glu-NH$_2$), H-Gln(Trt)-OH, and H-Gln(isopropyl)-OH.

Each Parallel Connector Unit or subunit thereof can be independently selected from the group consisting of phenylalanine (Phe) derivatives. Illustrative of examples of phenylalanine derivatives include but are not limited to: H-p-amino-Phe-OH, H-p-amino-Phe(Z)—OH, H-p-bromo-Phe-OH, HH-p-carboxy-Phe(OtBu)-OH, H-p-carboxy-Phe-OH, H-p-cyano-Phe-OH, H-p-fluoro-Phe-OH, H-3,4-dichloro-Phe-OH, H-p-iodo-Phe-OH, H-p-nitro-Phe-OH, chloro-phenylalanine and β-homophenylalanine.

Each Parallel Connector Unit or subunit thereof can be independently selected from the group consisting of lysine and derivatives thereof. Illustrative of examples of lysine and derivatives thereof include but are not limited to: lysine (Lys), N-alkyl-lysine, H-Lys(Boc)-OH, H-Lys (Ac)-OH, H-Lys (Formyl)-OH, H-Lys (Me)$_2$-OH, H-Lys (nicotinoyl)-OH, H-Lys (Me)$_3$-OH, H-trans-4,5-dehydro-Lys-OH, H-Lys (Alloc)-OH, H—H-δ-hydroxy-Lys-OH, H-δ-hydroxy-Lys (Boc)-OH, H-Lys(acetamidoyl)-OH, and H-Lys(isopropyl)-OH.

Each Parallel Connector Unit or subunit thereof can be independently selected from the group consisting of leucine derivatives. Illustrative of examples of leucine derivatives include but are not limited to: 4,5-dehydroleucine.

Each Parallel Connector Unit or subunit thereof can be independently selected from the group consisting of methionine derivatives. Illustrative of examples of methionine derivatives include but are not limited to: methionine (Met), H-Met(=O)—OH, and H-Met(=O)$_2$—OH in which the sulfur atom of the methionine side chain is in oxidized form.

Each Parallel Connector Unit or subunit thereof can be independently selected from the group consisting of serine and derivatives thereof. Illustrative of examples of serine and derivatives thereof include but are not limited to: serine (Ser), N-alkyl-serine, H-Ser(Ac)—OH, H-Ser(tBu)-OH, H-Ser(Bzl)-OH, H-Ser(p-chloro-Bzl)-OH, H-β-(3,4-dihydroxyphenyl)-Ser-OH, H-β-(2-thienyl)-Ser-OH, isoserine N-alkyl-isoserine, and 3-phenylisoserine.

Each Parallel Connector Unit or subunit thereof can be independently selected from the group consisting of tyrosine and derivatives thereof. Illustrative of examples of tyrosine and derivatives thereof include but are not limited to: tyrosine (Tyr), N-alkyl-tyrosine, H-3,5-dinitro-Tyr-OH, H-3-amino-Tyr-OH, H-3,5-dibromo-Tyr-OH, H-3,5-diiodo-Tyr-OH, H-Tyr(Me)-OH, H-Tyr(tBu)-OH, H-Tyr(Boc)-OH, H-Tyr(Bzl)-OH, H-Tyr(Et)-OH, H-3-iodo-Tyr-OH, and H-3-nitro-Tyr-OH.

Each Parallel Connector Unit or subunit thereof can be independently selected from the group consisting of threonine and derivatives thereof. Illustrative of examples of threonine and derivatives thereof include but are not limited to: threonine (Thr), N-alkyl-threonine, allo-threonine, H-Thr (Ac)—OH, H-Thr(tBu)-OH, and H-Thr(Bzl)-OH.

Each Parallel Connector Unit or subunit thereof can be independently selected from the group consisting of tryptophan and derivatives thereof. Illustrative of examples of tryptophan and derivatives thereof include but are not limited to: tryptophan (Trp), N-alkyl-tryptophan, H-5-Me-Trp-OH, H-5-hydroxy-Trp-OH, H-4-Me-Trp-OH, H-α-Me-Trp-OH, H-Trp(Boc)-OH, H-Trp(Formyl)-OH, and H-Trp (Mesitylene-2-sulfonyl)-OH.

Each Parallel Connector Unit or subunit thereof can be independently selected from the group consisting of proline and derivatives thereof. Illustrative of examples of proline and derivatives thereof include but are not limited to: proline (Pro), N-alkyl-proline, homoproline, thioproline, hydroxyproline (H-Hyp-OH), H-Hyp(tBu)-OH, H-Hyp(Bzl)-OH, H-3,4-dehydro-Pro-OH, 4-keto-proline, α-Me-Pro-OH, and H-4-fluoro-Pro-OH.

Each Parallel Connector Unit or subunit thereof can be independently selected from the group consisting of ornithine and derivatives thereof. Illustrative of examples of ornithine and derivatives thereof include but are not limited to: ornithine (Orn), N-alkyl-ornithine, H-Orn(Boc)-OH, H-Orn(Z)—OH, H-α-difluoro-Me-Orn-OH (Eflornitine), and H-Orn(Alloc)-OH.

Each Parallel Connector Unit or subunit thereof can be independently selected from the group consisting of penicillamine and derivatives thereof. Illustrative of examples of penicillamine and derivatives thereof include but are not limited to: penicillamine, H-penicillamine(Acm)-OH (H-β, β-dimethylcys(Acm)-OH) and N-alkyl-penicillamine.

Each Parallel Connector Unit or subunit thereof can be independently selected from the group consisting of β-alanine derivatives. Illustrative of examples of β-alanine derivatives include but are not limited to: dehydro-alanine.

Each Parallel Connector Unit or subunit thereof can be independently selected from the group consisting of aminoalkanoic derivatives. Illustrative of examples of an aminoalkanoic derivatives include but are not limited to: 4-(neopentyloxysulfonyl)-aminobutyric acid, piperidylacetic acid, 3-aminopropionic acid, and 3-amino-3-(3-pyridyl)-propionic acid.

Each Parallel Connector Unit or subunit thereof can be independently selected from the group consisting of aminoalkynoic acid and derivatives thereof. Illustrative of examples of an aminoalkynoic acid and derivatives thereof include but are not limited to: N-alkylaminoalkynoic acid, 6-amino-4-hexynoic acid, 6-(Boc-amino)-4-hexynoic acid.

Each Parallel Connector Unit or subunit thereof can be independently selected from the group consisting of aminoalkanedioic acid and derivatives thereof. Illustrative of examples of an aminoalkanedioic acid and derivatives thereof include but are not limited to: N-alkylaminoalkanedioic acid, 2-aminohexanedioic acid, 2-aminoheptanedioic acid, 2-aminooctanedioic acid (H-Asu-OH).

Each Parallel Connector Unit or subunit thereof can be independently selected from the group consisting of aminoheterocyclo-alkanoic acid and derivatives thereof. Illustrative of examples of an amino-heterocyclo-alkanoic acid and derivatives thereof include but are not limited to: N-alkylamino-heterocyclo-alkanoic acids, 4-amino-1-methyl-1H-imidazol-2-carboxylic acid, 4-amino-1-methyl-1H-pyrrole-2-carboxylic acid, 4-amino-piperidine-4-carboxylic acid (H-Pip-OH; 1-protected or not), 3-amino-3-(3-pyridyl)-propionic acid.

Each Parallel Connector Unit or subunit thereof can be independently selected from the group consisting of citrulline and derivatives thereof. Illustrative of examples of citrulline and derivatives thereof include but are not limited to: citrulline (cit), N-alkyl-citrulline, thiocitrulline, S-methyl-thiocitrulline, and homocitrulline.

Illustrative of examples of statine and derivatives thereof include but are not limited to: statine, N-alkyl-statine, cyclohexylstatine, and phenylstatine.

Each Parallel Connector Unit or subunit thereof can be independently selected from the group consisting of diaminoalkanoic acid and derivatives thereof. Illustrative of examples of diaminoalkanoic acid (Dab) and derivatives thereof include but are not limited to: N-alkyl-diaminoalkanoic acids, N,N-dialkylamino-alkanoic acids, α,γ-di-aminobutyric acid (H-Dab-OH), H-Dab(Alloc)-OH, H-Dab(Boc)-OH, H-Dab(Z)—OH, α,β-diaminopropionic acid and its side-chain protected versions.

An exemplary $L^P$ unit or subunit thereof, lysine or cysteine or pencillamine, is shown below. The wavy line indicates attachment sites to PEG, the Releasable Assembly Unit (directly or via a Branching Unit or Drug Attachment Unit) and to the Stretcher Unit (directly or via a Branching Unit or Drug Attachment Unit). L and D isomers of the amino acids are suitable for use herein.

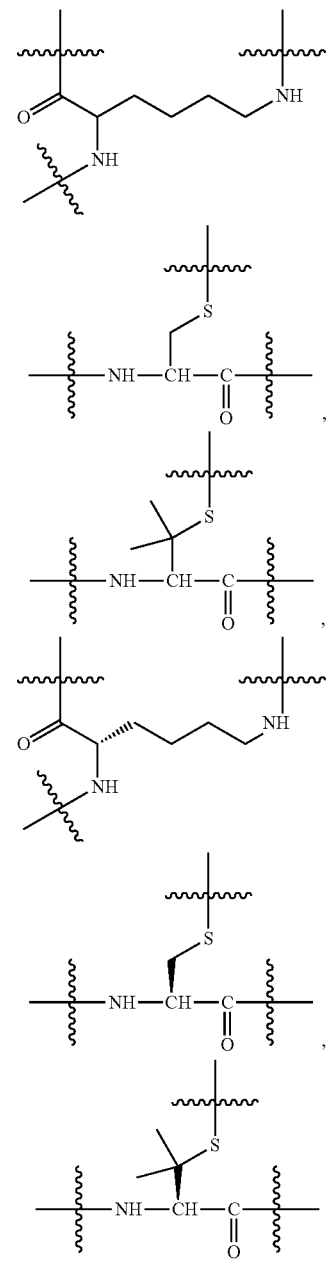

An exemplary Ligand-Drug Conjugate or Drug-Linker Compound having lysine as the $L^P$ unit is shown below wherein Z, L, X, D, PEG, Z', p, and PEG are as described herein. L and D isomers of the amino acids are suitable for use herein.

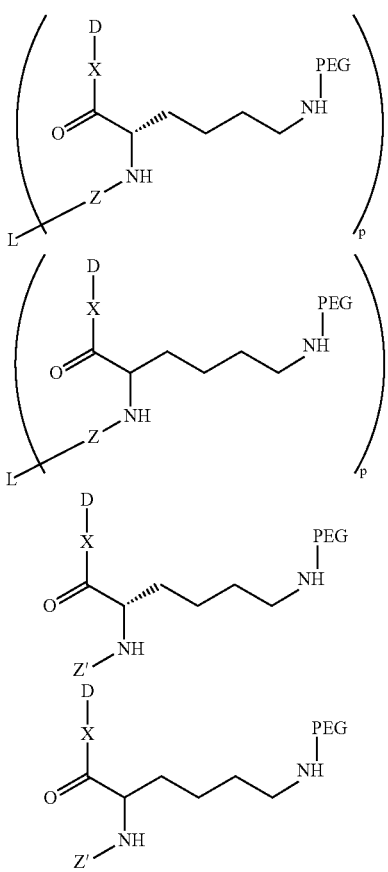

An exemplary Ligand-Drug Conjugate having cysteine or pencillamine as the $L^P$ unit is shown below wherein Z, L, X, D, Z', PEG, and p are as described herein. L and D isomers of the amino acids are suitable for use herein.

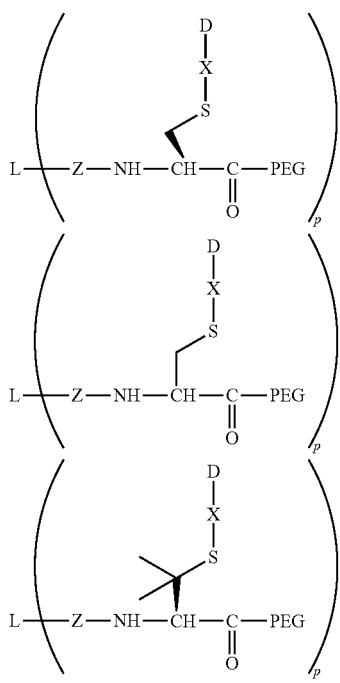

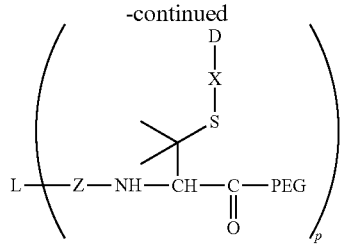

It will be understood that in for certain compounds of the present invention (e.g., Intermediate Linker Compounds and Ligand-Linker Compounds), the Parallel Connector Unit is capable of forming a covalent attachment to -X-D but is not yet connected to -X-D, and the Parallel Connector Unit will not yet be fully assembled into a Ligand-Drug Conjugate, and as such, will comprise a functional group that is reactive to a group present on the Releasable Assembly Unit. An exemplary Parallel Connector Unit having a functional group for attachment is as follows:

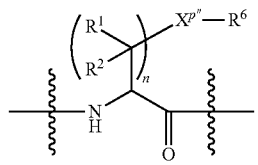

wherein,
the subscript n is from 1 to 4;
$X^{p''}$ is selected from the group consisting of —O—, —NR—, —S—, —C(=O)—, and —S(=O)—; and
$R^1$ and $R^2$ are independently selected from the group consisting of H, $C_{1-3}$ alkyl, phenyl, or $C_2$-$C_5$ heterocycle;
$R^6$ is a protecting group, H, —$C_{1-3}$ alkyl, or —OH,
wherein the wavy lines indicate covalent attachment within the remainder of a Intermediate Linker Compound or Ligand-Linker Compound.

Particularly preferred reactive functional groups that provide $X^{p''}$ are sulfhydryl groups to form disulfide bonds or thioether bonds. The functional group can be protected by a protecting group. $L^P$ can be a thiol-containing group (e.g., thiol-containing amino acid) and, as such, $L^{P'}$ can be a protected thiol containing amino acid, such as a protected cysteine as shown below. Although the L-isomer of cysteine is depicted in the representation below, the D-isomer of cysteine is suitable. Additionally, the t-butylthiol protecting group can be replaced by any other suitable thiol protecting group. Thiol protecting groups include t-butyl sulfide, n-butyl sulfide, n-propyl sulfide, methyl sulfide, phenyl sulfide, thiopyridyl, isopropyl sulfide, ethyl sulfide, and cysteinyl.

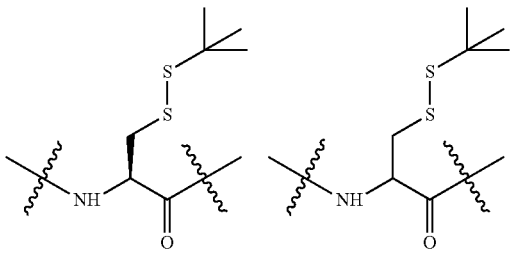 [SMILES: *N[C@@H](CSSC(C)(C)C)C(*)=O ; *NC(CSSC(C)(C)C)C(*)=O]

$L^{P'}$ can be a dipeptide comprising a protected thiol containing amino acid, such a protected cysteine-alanine dipeptide as shown below:

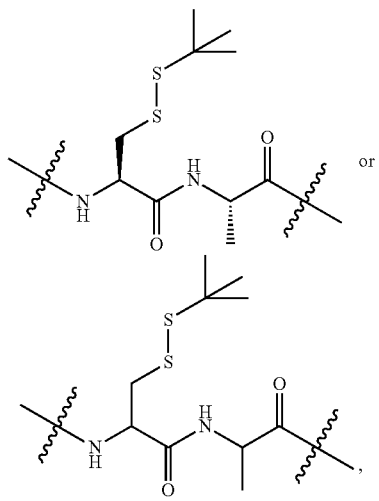

wherein the wavy lines indicate covalent attachment of $L^{P'}$ within the remainder of a Linker Intermediate Compound In preferred embodiments, the $L^P$ unit is selected to minimize or not contribute to the addition of hydrophobicity to drug-linker moieties of the Ligand-Drug Conjugates.

In preferred aspects of the present invention the $L^P$ unit has a mass of no more than about 500 daltons, no more than about 200 daltons, from about 10 to about 500 daltons, or from about 10 to about 200 daltons.

At the termini of the Ligand-Drug Conjugates are the Ligand Units, the Drug Units and the PEG Units.

Ligand Units:

In some embodiments of the invention, a Ligand Unit is present. The Ligand unit (L-) is a targeting agent that specifically binds to a target moiety. The Ligand can specifically bind to a cell component (a Cell Binding Agent) or to other target molecules of interest. The Ligand unit acts to target and present the Drug unit to the particular target cell population with which the Ligand unit interacts. Ligands include, but are not limited to, proteins, polypeptides and peptides. Suitable Ligand units include, for example, antibodies, e.g., full-length antibodies and antigen binding fragments thereof, interferons, lymphokines, hormones, growth factors and colony-stimulating factors, vitamins, nutrient-transport molecules (such as, but not limited to, transferrin), or any other cell binding molecule or substance. The ligand can be, for example, a non-antibody protein targeting agent. Alternatively, the ligand can be, for example, an antibody. Preferred ligands are larger molecular weight proteins, e.g., ligands having a molecular weight of at least about 80 Kd.

A Ligand unit can form a bond to a Stretcher unit. The Ligand Unit has to have the requisite number of attachment sites for the drug-linker, whether they be naturally occurring or non-naturally occurring (e.g, engineered). For example, in order for the value of the subscript p to be from 6 to 14, the Ligand Unit has to be capable of forming a bond with from 6 to 14 Ligand Units. The attachment sites can be naturally-occurring or engineered into the Ligand. A Ligand unit can form a bond to the Stretcher unit of the Linker unit via a reactive or activatable heteroatom or a heteroatom-containing functional group of the Ligand. Reactive or activatable heteroatoms or a heteroatom-containing functional group that may be present on a Ligand unit include sulfur (in one embodiment, from a sulfhydryl group of a Ligand), C=O or (in one embodiment, from a carbonyl, carboxyl or hydroxyl group of a Ligand) and nitrogen (in one embodiment, from a primary or secondary amino group of a Ligand). Those heteroatoms can be present on the Ligand in the Ligand's natural state, for example a naturally-occurring antibody, or can be introduced into the Ligand via chemical modification or biological engineering.

In one embodiment, a Ligand unit has a sulfhydryl group and the Ligand unit bonds to the Linker unit via the sulfhydryl group's sulfur atom.

In another embodiment, the Ligand has lysine residues that can react with activated esters (such esters include, but are not limited to, N-hydroxysuccinimide, pentafluorophenyl, and p-nitrophenyl esters) of the Stretcher unit of the Linker unit and thus form an amide bond consisting of the nitrogen atom of the Ligand unit and the C=O group of the Linker unit.

In yet another aspect, the Ligand unit has one or more lysine residues that can be chemically modified to introduce one or more sulfhydryl groups. The Ligand unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the Ligand unit can have one or more carbohydrate groups that can be chemically modified to have one or more sulfhydryl groups. The Ligand unit bonds to the Linker unit's the Stretcher Unit via the sulfhydryl group's sulfur atom.

In yet another embodiment, the Ligand unit can have one or more carbohydrate groups that can be oxidized to provide an aldehyde (—CHO) group (see, e.g., Laguzza, et al., 1989, *J. Med. Chem.* 32(3):548-55). The corresponding aldehyde can form a bond with a reactive site on a Stretcher Unit. Reactive sites on a Stretcher Unit that can react with a carbonyl group on a Ligand include, but are not limited to, hydrazine and hydroxylamine. Other protocols for the modification of proteins for the attachment or association of Drug units are described in Coligan et al., *Current Protocols in Protein Science*, vol. 2, John Wiley & Sons (2002) (incorporated herein by reference).

A Ligand Unit forms a bond with the reactive group on the Stretcher Unit. A variety of reactive groups are useful and will depend on the nature of the Ligand Unit. The reactive group can be a maleimide which is present on the Stretcher Unit (prior to attachment to L) and covalent attachment of L to the Stretcher Unit is accomplished through a sulfhydryl group of the Ligand Unit to form a thio-substituted succinimide. The sulfhydryl group can be present on the Ligand in the Ligand's natural state, for example a naturally-occurring residue, or can be introduced into the Ligand via chemical modification.

In still another embodiment, the Ligand is an antibody and the sulfhydryl group is generated by reduction of an interchain disulfide. Accordingly, in some embodiments, the Linker unit is conjugated to a cysteine residue of the reduced interchain disulfides.

In yet another embodiment, the Ligand is an antibody and the sulfhydryl group is chemically introduced into the antibody, for example by introduction of a cysteine residue. Accordingly, in some embodiments, the Stretcher Unit is conjugated to an introduced cysteine residue.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker to undergo an elimination reaction and for the drug linker to be transferred from the ligand of a bioconjugate to an alternative reactive thiol present in the milieu of the bioconjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are not susceptible to the elimination reaction (e.g., positions 239 according to the EU index as set forth in Kabat) in addition to other sites.

When the conjugates comprise non-immunoreactive protein, polypeptide, or peptide Ligands instead of an antibody, useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred ligands are antibodies, including intact antibodies. In fact, in any of the embodiments described herein, the Ligand Unit can be an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immuno-specifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, tribodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some aspects, the antibody will specifically bind CD19, CD20, CD30, CD33, CD70, alpha-v-beta-6, Liv-1 or Lewis Y antigen.

The anti-CD30 antibody can be, for example, the chimeric AC10 antibody, brentuximab. The anti-CD30 antibody can have a heavy chain variable region having the amino acid sequence set forth in SEQ ID NO:1, a light chain variable region having the amino acid sequence set forth in SEQ ID NO:2, a human gamma I constant region having the amino acid sequence set forth in SEQ ID NO:7 and a human kappa constant region having the amino acid sequence set forth in SEQ ID NO:8.

The anti-CD30 antibody can be, for example, a humanized AC10 antibody. The anti-CD30 antibody can have a heavy chain variable region having the amino acid sequence set forth in SEQ ID NO:9, a light chain variable region having the amino acid sequence set forth in SEQ ID NO:10. The antibody can further comprise a human gamma I constant region having the amino acid sequence set forth in SEQ ID NO:7 optionally have a serine to cysteine substitution at position 239 (according to the EU index) and a human kappa constant region having the amino acid sequence set forth in SEQ ID NO:8.

The anti-CD70 antibody can be, for example, a humanized antibody (see, e.g., US 2009/0148942). In an exemplary embodiment, the anti-CD70 antibody has a heavy chain variable region having the amino acid sequence set forth in SEQ ID NO:3, and a light chain variable region having the amino acid sequence set forth in SEQ ID NO:4.

The anti-CD19 antibody can be, for example, a humanized antibody (see, e.g., US 2009/0136526 incorporated by reference herein in its entirety and for all purposes). In an exemplary embodiment, the hBU12 antibody has a heavy chain variable region having the amino acid sequence set forth in SEQ ID NO:5, and a light chain variable region having the amino acid sequence set forth in SEQ ID NO:6.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes).

Exemplary attachment to the Ligand is via thioether linkages. The thioether linkages can be via interchain disulfide bonds, introduced cysteines resides, and combinations thereof.

Drug Units:

The effects of the present invention will be more pronounced in embodiments wherein the drugs are hydrophobic in nature. Accordingly, the drugs of the present invention are preferably hydrophobic in nature.

The Drug unit (D) can be a cytotoxic, cytostatic or immunosuppressive drug, also referred to herein as a cytotoxic, cytostatic or immunosuppressive agent. The Drug unit has an atom that can form a bond with the Releasable Assembly Unit (X). In some embodiments, the Drug unit D has a nitrogen atom that can form a bond with the Releasable Assembly Unit (X). In other embodiments, the Drug unit D has a carboxylic acid that can form a bond with the Releasable Assembly Unit (X). In other embodiments, the Drug unit D has a sulfhydryl group that can form a bond with the Releasable Assembly Unit X. In still other embodiments, the Drug unit D has a hydroxyl group or ketone or alcohol that can form a bond with the Releasable Assembly Unit X.

Useful classes of cytotoxic or immunosuppressive agents include, for example, antitubulin agents, DNA minor groove binders, DNA replication inhibitors, alkylating agents, antibiotics, antifolates, antimetabolites, chemotherapy sensitizers, topoisomerase inhibitors, *vinca* alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids, taxanes, benzodiazepines or benzodiazepine containing drugs (e.g., pyrrolo[1,4]-benzodiazepines (PBDs), indolinobenzodiazepines, and oxazolidinobenzodiazepines) and *vinca* alkaloids. Select benzodiazepine containing drugs are described in WO 2010/091150, WO 2012/112708, WO 2007/085930, and WO 2011/023883.

In certain embodiments, the cytotoxic agent is maytansine or a maytansinoid (e.g., DM1, DM4) another group of anti-tubulin agents. (ImmunoGen, Inc.; see also Chari et al., 1992, Cancer Res. 52:127-131 and U.S. Pat. No. 8,163,888).

In some embodiments, the Drug is a benzodiazepine (including benzodiazepine containing drugs e.g., pyrrolo[1,4]benzodiazepines (PBDs), indolinobenzodiazepines, and oxazolidinobenzodiazepines).

PBDs are of the general structure:

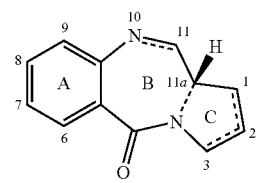

but can differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position, which is the electrophilic centre responsible for alkylating DNA. All of the known natural products have an (S)-orientation at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumour agents. The biological activity of these molecules can be potentiated by, for example, joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand crosslink which is thought to be mainly responsible for their biological activity.

The Drug unit can be, for example, an auristatin or a non-auristatin drug having a hydrophobicity comparable to $R^5$ is selected from the group consisting of H and methyl;

or $R^4$ and $R^5$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle and n is selected from the group consisting of 2, 3, 4, 5 and 6;

$R^6$ is selected from the group consisting of H and $C_1$-$C_8$ alkyl;

$R^7$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from the group consisting of H, OH, $C_1$-$C_8$ alkyl, $C_3$-$C_8$ carbocycle and O—($C_1$-$C_8$ alkyl);

$R^9$ is selected from the group consisting of H and $C_1$-$C_8$ alkyl;

$R^{18}$ is selected from the group consisting of —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle).

MMAE conjugated via its N terminus is shown below:

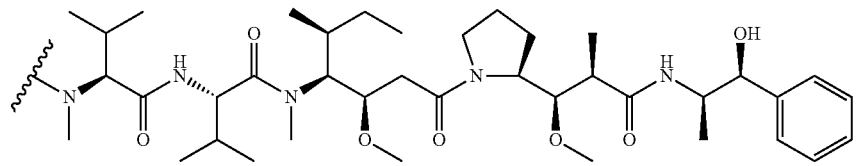

or greater than monomethyl auristatin E. In some aspects, the drug is MMAE or an auristatin having a hydrophobicity comparable to or greater than monomethyl auristatin E. The auristatin drug can be covalently attached to the Releasable Assembly unit, for example, via its N or C terminus. MMAE has a SlogP value of 2.59. In some aspects, drugs to be used in the present invention will have a SlogP value of 1.5 or greater, 2.0 or greater, or 2.5 or greater. In some aspects, drugs to be used in the present invention will have a SlogP value from (a) about 1.5, about 2, or 2.5 to about 7, (b) about 1.5, about 2, or 2.5 to about 6, (c) about 1.5, about 2 or about 2.5 to about 5, (d) about 1.5, about 2, or 2.5 to about 4, or (e) about 1.5, about 2 or about 2.5 to about 3.

The drug unit can have Formula $D_E$ below wherein attachment to the Releasable Assembly unit is via the N terminus:

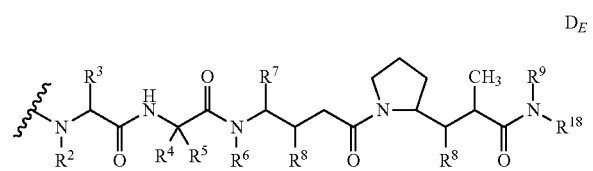

$D_E$ wherein, independently at each location:

$R^2$ is selected from the group consisting of H and $C_1$-$C_8$ alkyl;

$R^3$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

In some embodiments, the Drug unit is a *vinca* compound, a camptothecin or a anthracyclin cytotoxic compound. Example structures of those drug units when present in a X-D moiety are described herein for drug-linker intermediates.

There are a number of different assays that can be used for determining whether a Ligand-Drug Conjugate exerts a cytostatic or cytotoxic effect on a cell line. In one example for determining whether a Ligand-Drug Conjugate exerts a cytostatic or cytotoxic effect on a cell line, a thymidine incorporation assay is used. For example, cells at a density of 5,000 cells/well of a 96-well plated is cultured for a 72-hour period and exposed to 0.5 µCi of ³H-thymidine during the final 8 hours of the 72-hour period, and the incorporation of ³H-thymidine into cells of the culture is measured in the presence and absence of Ligand-Drug Conjugate. The Ligand-Drug Conjugate has a cytostatic or cytotoxic effect on the cell line if the cells of the culture have reduced ³H-thymidine incorporation compared to cells of the same cell line cultured under the same conditions but not contacted with the Ligand-Drug Conjugate.

In another example, for determining whether a Ligand-Drug Conjugate exerts a cytostatic or cytotoxic effect on a cell line, cell viability is measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12). Preferred Ligand-Drug Conjugates include those with an $IC_{50}$ value (defined as the mAB concentration that gives 50% cell kill) of less than 1000 ng/ml, preferably less than 500 ng/ml, more preferably less than 100 ng/ml, even most preferably less than 50 or even less than 10 ng/ml on the cell line.

General procedures for linking a drug to linkers are known in the art. See, for example, U.S. Pat. Nos. 8,163,888, 7,659,241, 7,498,298, U.S. Publication No. US20110256157 and International Application Nos. WO2011023883, and WO2005112919.

Polyethylene Glycol Unit (PEG)

Polydisperse PEGS, monodisperse PEGS and discrete PEGs can be used to make the Compounds of the present invention. Polydisperse PEGs are a heterogenous mixture of sizes and molecular weights whereas monodisperse PEGs are typically purified from heterogenous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains. The polyethylene glycol chains can be linked together, for example, in a linear, branched or star shaped configuration. Typically, at least one of the PEG chains is derivatized at one end for covalent attachment to the Parallel Connector Unit. Exemplary attachments to the Parallel Connector Unit are by means of non-conditionally cleavable linkages or via conditionally cleavable linkages. Exemplary attachments are via amide linkage, ether linkages, ester linkages, hydrazone linkages, oxime linkages, disulfide linkages, peptide linkages or triazole linkages. In some aspects, attachment to $L^P$ is by means of a non-conditionally cleavable linkage. In some aspects, attachment to $L^P$ is not via an ester linkage, hydrazone linkage, oxime linkage, or disulfide linkage. In some aspects, attachment to $L^P$ is not via a hydrazone linkage.

A conditionally cleavable linkage refers to a linkage that is not substantially sensitive to cleavage while circulating in the plasma but is sensitive to cleavage in an intracellular or intratumoral environment. A non-conditionally cleavable linkage is one that is not substantially sensitive to cleavage in any biological environment. Chemical hydrolysis of a hydrazone, reduction of a disulfide, and enzymatic cleavage of a peptide bond or glycosidic linkage are examples of conditionally cleavable linkages.

The PEG Unit will be directly attached to the Ligand-Drug Conjugate (or Intermediate thereof) at the Parallel Connector Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit of the PEG Unit. By untethered, it is meant that the PEG Unit will not be attached at that untethered site to a Drug Unit, to a Ligand Unit, or to a linking component linking a Drug Unit and/or a Ligand Unit. For those embodiments wherein the PEG Unit comprises more than one PEG chain, the multiple PEG chains may be the same or different chemical moieties (e.g., PEGs of different molecular weight or number of subunits). The multiple PEG chains are attached to the Parallel Connector Unit at a single attachment site. The skilled artisan will understand that the PEG Unit in addition to comprising repeating polyethylene glycol subunits may also contain non-PEG material (e.g., to facilitate coupling of multiple PEG chains to each other or to facilitate coupling to the Parallel Connector Unit). Non-PEG material refers to the atoms in the PEG Unit that are not part of the repeating —$CH_2CH_2O$-subunits. In embodiments provided herein, the PEG Unit can comprise two monomeric PEG chains linked to each other via non-PEG elements. In other embodiments provided herein, the PEG Unit can comprise two linear PEG chains attached to a central core that is attached to the Parallel Connector Unit (i.e., the PEG unit itself is branched).

There are a number of PEG attachment methods available to those skilled in the art, [see, e.g., Goodson, et al. (1990) Bio/Technology 8:343 (PEGylation of interleukin-2 at its glycosylation site after site-directed mutagenesis); EP 0 401 384 (coupling PEG to G-CSF); Malik, et al., (1992) Exp. Hematol. 20:1028-1035 (PEGylation of GM-CSF using tresyl chloride); ACT Pub. No. WO 90/12874 (PEGylation of erythropoietin containing a recombinantly introduced cysteine residue using a cysteine-specific mPEG derivative); U.S. Pat. No. 5,757,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal .alpha.-carbon of a peptide); Veronese et al., (1985) Appl. Biochem. Bioechnol 11:141-142 (PEGylation of an N-terminal α-carbon of a peptide with PEG-nitrophenylcarbonate ("PEG-NPC") or PEG-trichlorophenylcarbonate); and Veronese (2001) Biomaterials 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) Methods Enzymol. 184:160; Rose, et al. (1991) Bioconjugate Chem. 2:154; and Gaertner, et al. (1994) J. Biol. Chem. 269:7224].

In some embodiments, PEG molecules may be attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), $mPEG_2$-succinimidyl succinate ($mPEG_2$-SS); mPEG-succinimidyl carbonate (mPEG-SC), $mPEG_2$-succinimidyl carbonate ($mPEG_2$-SC); mPEG-imidate, mPEG-para-nitrophenylcarbonate (mPEG-NPC), mPEG-imidate; $mPEG_2$-para-nitrophenylcarbonate ($mPEG_2$-NPC); mPEG-succinimidyl propionate (mPEG-SPA); $mPEG_2$-succinimidyl propionate (mPEG, -SPA); mPEG-N-hydroxy-succinimide (mPEG-NHS); $mPEG_2$-N-hydroxy-succinimide ($mPEG_2$-NHS); mPEG-cyanuric chloride; $mPEG_2$-cyanuric chloride; $mPEG_2$-Lysinol-NPC, and $mPEG_2$-Lys-NHS.

Generally, at least one of the PEG chains that make up the PEG Unit is functionalized so that it can attach to the Parallel Connector Unit. Functionalization can be, for example, via an amine, thiol, NHS ester, maleimide, alkyne, azide, carbonyl, or other functional group. The PEG Unit can further comprise non-PEG material (i.e., material not comprised of —CH$_2$CH$_2$O—) to facilitate coupling to the Parallel Connector Unit or to facilitate coupling of two or more PEG chains.

A wide variety of polyethylene glycol (PEG) species can be used, and substantially any suitable reactive PEG reagent can be used. In some embodiments, the reactive PEG reagent will result in formation of a carbamate or amide bond upon attachment to L$^P$. The following PEG reagents are useful in various embodiments: mPEG$_2$-NHS, mPEG$_2$-ALD, multi-Arm PEG, mPEG(MAL)$_2$, mPEG$_2$(MAL), mPEG-NH$_2$, mPEG-SPA, mPEG-SBA, mPEG-thioesters, mPEG-Double Esters, mPEG-BTC, mPEG-ButyrALD, mPEG-ACET, heterofunctional PEGs (NH$_2$—PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE™ series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs as selected by those skilled in the art for their particular application and usage.

The addition of the PEG Unit may have two potential impacts upon the pharmacokinetics of the resulting Ligand-Drug Conjugate. The desired impact is the decrease in clearance (and consequent in increase in exposure) that arises from the reduction in non-specific interactions induced by the exposed hydrophobic elements of the drug-linker. The second impact is undesired impact and is the decrease in volume and rate of distribution that may arise from the increase in the molecular weight of the Ligand-Drug Conjugate. Increasing the number of PEG subunits increases the hydrodynamic radius of a conjugate, resulting in decreased diffusivity. In turn, decreased diffusivity may diminish the ability of the Ligand-Drug Conjugate to penetrate into a tumor (Schmidt and Wittrup, *Mol Cancer Ther* 2009; 8:2861-2871). Because of these two competing pharmacokinetic effects, it is desirable to use a PEG that is sufficiently large to decrease the LDC clearance thus increasing plasma exposure, but not so large as to greatly diminish its diffusivity, which may reduce the ability of the Ligand-Drug Conjugate to reach the intended target cell population. See the examples (e.g., examples 1, 18, and 21) for methodology for selecting an optimal PEG size for a particularly drug-linker.

In one group of embodiments, the PEG Unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. As used herein a subunit when referring to the PEG Unit refers to a polyethylene glycol subunit having the formula

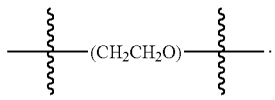

In some such embodiments, the PEG Unit comprises no more than about 72 subunits.

In one group of embodiments, the PEG Unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In preferred embodiments, the PEG Unit comprises a combined total of at least 6 subunits, at least 8, at least 10 subunits, or at least 12 subunits. In some such embodiments, the PEG Unit comprises no more than a combined total of about 72 subunits, preferably no more than a combined total of about 36 subunits.

In another group of embodiments, the PEG Unit comprises a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or from 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit comprises one or more linear PEG chains having a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit is a derivatized linear single PEG chain having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In another group of embodiments, the PEG Unit is a derivatized linear single PEG chain having from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit is a derivatized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

Exemplary linear PEG Units that can be used in any of the embodiments provided herein are as follows:

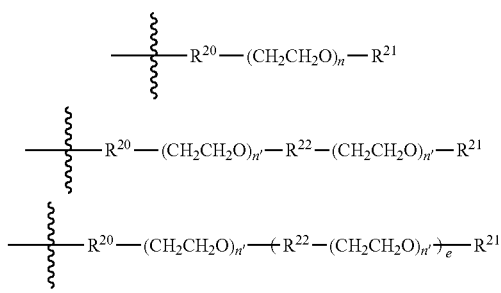

wherein the wavy line indicates site of attachment to the Parallel Connector Unit, $R^{20}$ is a PEG Attachment Unit,
$R^{21}$ is a PEG Capping Unit;
$R^{22}$ is an PEG Coupling Unit (i.e., for coupling multiple PEG subunit chains together)
n is independently selected from 2 to 72 (preferably from 4 to 72, more preferably from 6 to 72, from 8 to 72, from 10 to 72, from 12 to 72 or from 6 to 24);
e is 2 to 5 each n' is independently selected from 1 to 72. In preferred embodiments, there are at least 6, preferably at least 8, at least 10, or at least 12 PEG subunits in the PEG Unit. In some embodiments, there are no more than 72 or 36 PEG subunits in the PEG Unit.

In preferred embodiments, n is 8 or about 8, 12 or about 12, 24 or about 24.

The PEG Attachment Unit is part of the PEG Unit and acts to link the PEG Unit to the Parallel Connector Unit. In this regard, the Parallel Connector Unit has a functional group that forms a bond with the PEG Unit. Functional groups for attachment of the PEG Unit to the Parallel Connector Unit include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG unit can be attached to the Parallel Connector Unit, for example, via disulfide, thioether, hydrazone, oxime, peptide, ester, sulfonamide, carbamate, or amide bonds Typically, the PEG Attachment Unit is a product of the cycloaddition, addition, addition/elimination or substitution reaction that occurs when attaching the PEG Unit to the Parallel Connector Unit.

The PEG Coupling Unit is part of the PEG Unit and is non-PEG material that acts to connect two or more chains of repeating $CH_2CH_2O$— subunits. In exemplary embodiments, the PEG coupling Unit $R^{22}$ is —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$alkyl-S—, or —$C_{2-10}$ alkyl-NH—.

In exemplary embodiments, the PEG Attachment Unit $R^{20}$ is —C(O)—, —O—, —S—, —S(O)—, —NH—, —C(O)O—, —C(O)$C_{1-10}$alkyl, —C(O)$C_{1-10}$alkyl-O—, —C(O)$C_{1-10}$alkyl-CO$_2$—, —C(O)$C_{1-10}$alkyl-NH—, —C(O)$C_{1-10}$alkyl-S—, —C(O)$C_{1-10}$alkyl-C(O)—NH—, —C(O)$C_{1-10}$alkyl-NH—C(O)—, —$C_{1-10}$alkyl, —$C_{1-10}$alkyl-O—, —$C_{1-10}$alkyl-CO$_2$—, —$C_{1-10}$alkyl-NH—, —$C_{1-10}$alkyl-S—, —$C_{1-10}$alkyl-C(O)—NH—, —$C_{1-10}$alkyl-NH—C(O)—, —CH$_2$CH$_2$SO$_2$—$C_{1-10}$alkyl-, —CH$_2$C(O)—$C_{1-10}$ alkyl-, =N—(O or N)—$C_{1-10}$alkyl-O—, =N—(O or N)—$C_{1-10}$alkyl-NH—, =N—(O or N)—$C_{1-10}$alkyl-CO$_2$—, =N—(O or N)—$C_{1-10}$alkyl-S—,

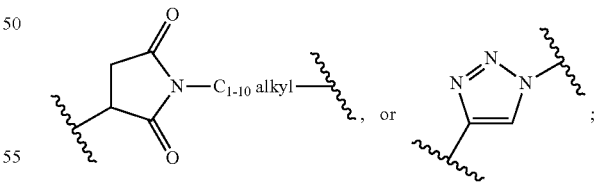

each $R^{21}$ is independently —$C_{1-10}$ alkyl, —$C_{2-10}$ alkyl-CO$_2$H, —$C_{2-10}$ alkyl-OH, —$C_{2-10}$ alkyl-NH$_2$, $C_{2-10}$ alkyl-NH($C_{1-3}$ alkyl), or $C_{2-10}$ alkyl-N($C_{1-3}$ alkyl)$_2$; and each $R^{22}$ is independently —$C_{1-10}$ alkyl-C(O)—NH—, —$C_{1-10}$alkyl-NH—C(O)—, —$C_{2-10}$ alkyl-NH—, —$C_{2-10}$ alkyl-O—, —$C_{1-10}$ alkyl-S—, or —$C_{2-10}$ alkyl-NH—.

In some embodiments, $R^{20}$ is —NH—, —C(=O)—, triazole-linked groups, or —S—, or maleimido-linked groups such as

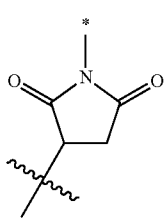 [SMILES: *C1CC(=O)N(C)C1=O]

wherein the wavy line indicates the site of attachment to the Parallel Connector Unit and the asterisk indicates the site of attachment within the PEG Unit. In some such aspects, $R^{21}$ is $C_{1-10}$ alkyl, —$C_{2-10}$ alkyl-$CO_2H$, —$C_{2-10}$ alkyl-OH, or —$C_{2-10}$alkyl-$NH_2$.

Illustrative linear PEG Units that can be used in any of the embodiments provided herein are as follows:

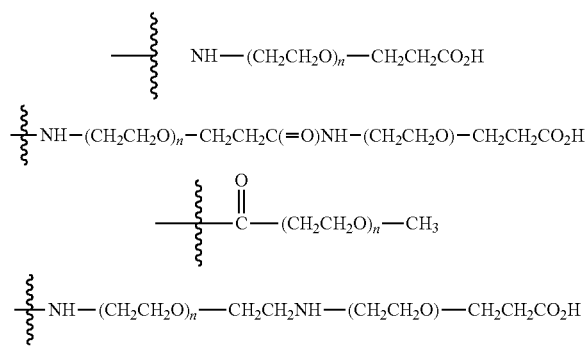

wherein the wavy line indicates site of attachment to the Parallel Connector Unit, and each n is independently selected from 4 to 72, 6 to 72, 8 to 72, 10 to 72, 12 to 72, 6 to 24, or 8 to 24. In some aspects, n is about 8, about 12, or about 24.

As described herein, the PEG unit is selected such that it improves clearance of the resultant Ligand-Drug Conjugate but does not significantly impact the ability of the Conjugate to penetrate into the tumor. In embodiments wherein the Drug Unit and Releasable Assembly Unit of the Ligand-Drug Conjugate has a hydrophobicity comparable to that of a maleimido glucuronide MMAE drug-linker (as shown in the examples), the PEG unit to be selected for use will preferably have from 8 subunits to about 24 subunits, more preferably about 12 subunits. In embodiments wherein the Drug Unit and Releasable Assembly Unit of the Conjugate has a hydrophobicity greater than that of a maleimido glucuronide MMAE drug-linker, a PEG unit with more subunits can be selected. The methodology shown in the examples section can be used to identify the ideal number of subunits for a particular drug-linker.

In preferred embodiments of the prevent invention the PEG Unit is from about 300 daltons to about 5 kilodaltons; from about 300 daltons, to about 4 kilodaltons; from about 300 daltons, to about 3 kilodaltons; from about 300 daltons, to about 2 kilodaltons; or from about 300 daltons, to about 1 kilodalton. In some such aspects, the PEG Unit has at least 6 subunits or at least 8, 10 or 12 subunits. In some such aspects, the PEG Unit has at least 6 subunits or at least 8, 10 or 12 subunits but no more than 72 subunits, preferably no more than 36 subunits.

In preferred embodiments of the prevent invention, apart from the PEG Unit, there are no other PEG subunits present in the drug-linker (i.e., no PEG subunits in any of the other components of the Conjugates and Linkers provided herein). In other aspects of the present invention, apart from the PEG Unit, there are no more than 8, no more than 7, no more than 6, no more than 5, no more than 4, no more than 3, no more than 2 or no more than 1 other polyethylene glycol subunits present in the drug-linker (i.e., no more than 8, 7, 6, 5, 4, 3, 2, or 1 other polyethylene glycol subunits in other components of the Conjugates and Linkers provided herein.) Components include the Stretcher Unit, Parallel Connector Unit, Drug Unit, Branching Unit, and Releasable Assembly Unit.

It will be appreciated that when referring to PEG subunits, and depending on context, the number of subunits can represent an average number, e.g., when referring to a population of Ligand-Drug Conjugates or Intermediate Compounds, and using polydisperse PEGs.

The Stretcher Unit:

The Stretcher unit (—Z—) acts to link the Ligand unit to the Parallel Connector Unit. In this regard, a Stretcher Unit has a functional group that can form a bond with a functional group of a Ligand unit. The Stretcher Unit also has a functional group that can form a bond with a functional group of either the optional Branching Unit, or the Parallel Connector Unit. In the Ligand-Drug Conjugate and Intermediates having more than one Drug Unit per PEG Unit, the Stretcher Unit will have a functional group that can form a bond with a functional group of a Ligand unit and a functional group that can form a bond with a Branching Unit, Parallel Connector Unit, or Drug Attachment Unit. Useful functional groups that can be present on a Ligand unit, either naturally or via chemical manipulation include, but are not limited to, sulfhydryl (—SH), amino, hydroxyl, carboxy, the anomeric hydroxyl group of a carbohydrate, and carboxyl. In one aspect, the Ligand unit's functional groups are sulfhydryl and amino. The Stretcher Unit can comprise for example, a maleimide group, an aldehyde, a ketone, a carbonyl, or a haloacetamide for attachment to the Ligand Unit.

In some aspects, the Stretcher Unit of a Drug-Linker compound or Intermediate Linker compound has an electrophilic group that is reactive to a nucleophilic group present on a Ligand Unit (e.g., an antibody). Useful nucleophilic groups on a Ligand include but are not limited to, sulfhydryl, hydroxyl and amino groups. The heteroatom of the nucleophilic group of a Ligand is reactive to an electrophilic group on a Stretcher Unit and forms a covalent bond to the Stretcher Unit. Useful electrophilic groups include, but are not limited to, maleimide and haloacetamide groups. For an antibody as the Ligand the electrophilic group provides a convenient site for antibody attachment for those antibodies having an accessible nucleophilic group.

In another embodiment, a Stretcher Unit has a reactive site which has a nucleophilic group that is reactive to an electrophilic group present on a Ligand Unit (e.g., an antibody). Useful electrophilic groups on a Ligand include, but are not limited to, aldehyde and ketone and carbonyl groups. The heteroatom of a nucleophilic group of a Stretcher Unit can react with an electrophilic group on a Ligand and form a covalent bond to the antibody. Useful nucleophilic groups on a Stretcher Unit include, but are not limited to, hydrazide, hydroxylamine, amino, hydrazine, thiosemicarbazone, hydrazine carboxylate, and arylhydrazide. For an antibody as the Ligand the electrophilic group on an antibody provides a convenient site for attachment to a nucleophillic Stretcher Unit.

In some aspects, the conjugates can be prepared using a section of the Stretcher Unit having a reactive site for binding to the Parallel Connector Unit and introducing another section of the Stretcher Unit having a reactive site for a Ligand Unit. In one aspect, a Stretcher Unit has a reactive site which has an electrophilic group that is reactive with a nucleophilic group present on a Ligand Unit, such as an antibody. The electrophilic group provides a convenient site for Ligand (e.g., antibody) attachment. Useful nucleophilic groups on an antibody include but are not limited to, sulfhydryl, hydroxyl and amino groups. The heteroatom of the nucleophilic group of an antibody is reactive to an electrophilic group on a Stretcher Unit and forms a covalent bond to a Stretcher Unit. Useful electrophilic groups include, but are not limited to, maleimide and haloacetamide groups and NHS esters.

In another embodiment, a Stretcher Unit has a reactive site which has a nucleophilic group that is reactive with an electrophilic group present on a Ligand Unit. The electrophilic group on a Ligand Unit (e.g., antibody) provides a convenient site for attachment to a Stretcher Unit. Useful electrophilic groups on an antibody include, but are not limited to, aldehyde and ketone carbonyl groups. The heteroatom of a nucleophilic group of a Stretcher Unit can react with an electrophilic group on an antibody and form a covalent bond to the antibody. Useful nucleophilic groups on a Stretcher Unit include, but are not limited to, hydrazide, oxime, amino, hydrazine, thiosemicarbazone, hydrazine carboxylate, and arylhydrazide.

In some embodiments, the Stretcher unit forms a bond with a sulfur atom of the Ligand unit via a maleimide group of the Stretcher Unit. The sulfur atom can be derived from a sulfhydryl group of a Ligand unit. Representative Stretcher Units of this embodiment include those within the square brackets of Formulas XVa and XVb, wherein the wavy line indicates attachment within the Ligand-Drug Conjugate or Intermediates thereof and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$ alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—. Any of the $R^{17}$ substituents can be substituted or nonsubstituted. In some aspects, the $R^{17}$ substituents are unsubstituted. In some aspects, the $R^{17}$ substituents are optionally substituted. In some aspects, the $R^{17}$ groups are optionally substituted by a basic unit, e.g —$(CH_2)_xNH_2$, —$(CH_2)_xNHR^a$, and —$(CH_2)_xNR^a{}_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. It is to be understood that even where not denoted expressly, p is 1 to 14.

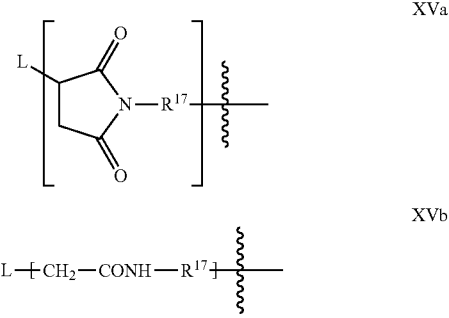

An illustrative Stretcher unit is that of Formula XVa wherein $R^{17}$ is —$C_2$-$C_5$ alkylene-C(=O)— wherein the alkylene is optionally substituted by a basic unit, e.g —$(CH_2)_xNH_2$, —$(CH_2)_xNHR^a$, and —$(CH_2)_xNR^a{}_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. Exemplary embodiments are as follows:

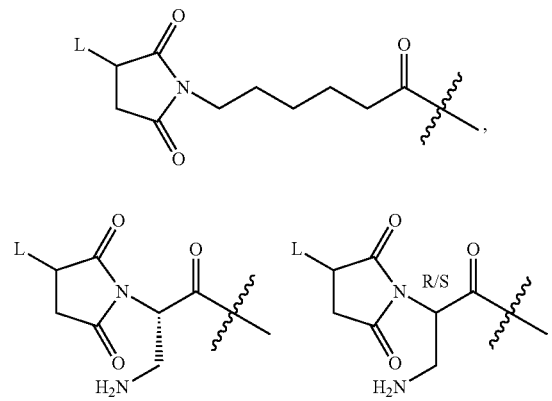

It will be understood that the substituted succinimide may exist in a hydrolyzed form as shown below:

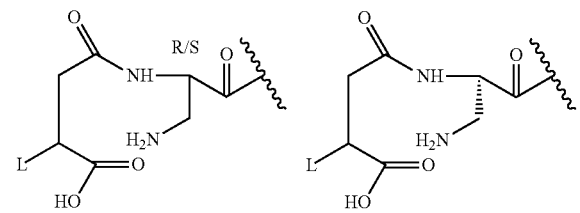

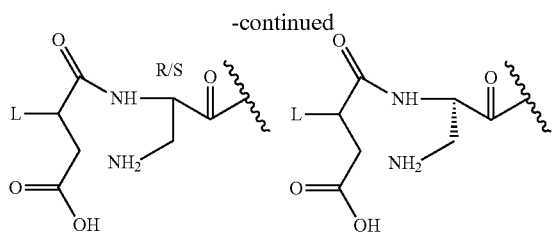

Illustrative Stretcher Units prior to conjugation to the Ligand, include the following:

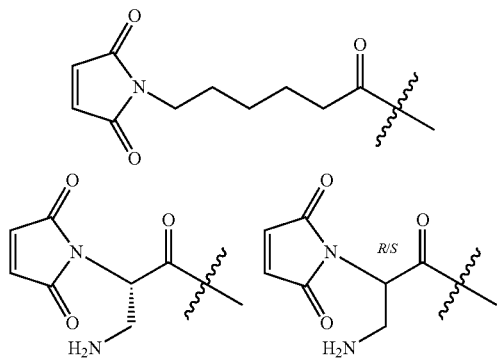

It will be understood that the amino group of the Stretcher Unit may be suitably protected by a amino protecting group during synthesis, e.g., an acid labile protecting group (e.g, BOC).

Still another illustrative Stretcher unit is that of Formula XVb wherein $R^{17}$ is —$(CH_2)_5$—:

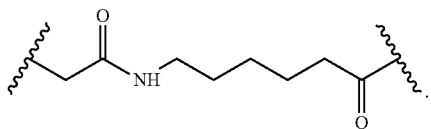 [SMILES: *CC(=O)NCCCCCC(*)=O]

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula XVI, wherein the wavy line indicates attachment within the Ligand-Drug Conjugate or Intermediates thereof and $R^{17}$ is as described above for Formula XVa and XVb.

XVI

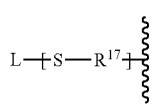

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas XVIIa, XVIIb, and XVIIc wherein the wavy line indicates attachment within the within the Ligand-Drug Conjugate or intermediates thereof and $R^{17}$ is as described above for Formula XVa and XVb.

XVIIa

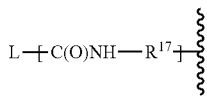

XVIIb

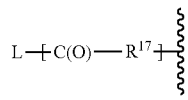

XVIIc

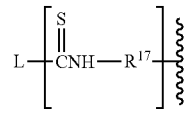

In yet another embodiment, the reactive group of the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. (1991) Bioconjugate Chem. 2:133-41. Representative Stretcher units of this embodiment are depicted within the square brackets of Formulas XVIIIa, XVIIIb, and XVIIIc, wherein the wavy line indicates attachment within the Ligand-Drug Conjugate or Intermediates thereof and $R^{17}$ is as described above for Formula XVa and XVb.

XVIIIa

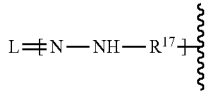

XVIIIb

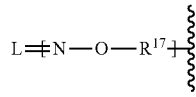

XVIIIc

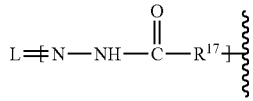

In some embodiments of the prevent invention, it will be desirable to extend the length of the Stretcher Unit. Accordingly, a Stretcher Unit can comprise additional components. For example a Stretcher Unit can include those within the square brackets of Formulas XVa1,

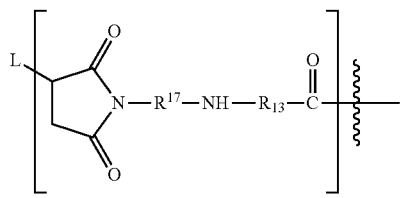

XVa1 wherein the wavy line indicates attachment to the remainder of the Ligand-Drug Conjugate or Intermediates thereof;

$R^{17}$ is as described above, preferably $R^{17}$ is —$C_2$-$C_5$ alkylene-C(=O)— wherein the alkylene is optionally substituted by a basic unit, e.g —$(CH_2)_x NH_2$, —$(CH_2)_x NHR^a$, and —$(CH_2)_x NR^a{}_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group; and $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In preferred embodiments $R^{13}$ is —$C_1$-$C_6$ alkylene-.

In preferred aspects of the prevent invention the Stretcher Unit has a mass of no more than about 1000 daltons, no more than about 500 daltons, no more than about 200 daltons, from about 30, 50 or 100 daltons to about 1000 daltons, from about 30, 50 or 100 daltons to about 500 daltons, or from about 30, 50 or 100 daltons to about 200 daltons.

Optional Branching Unit (A)

The Branching Unit is included in the Ligand-Drug Conjugates in instances where it is desirable to add additional drugs to the drug-linker and, ultimately, to the Ligand. The Branching Unit is capable of forming a covalent bond with two to four Parallel Connector Units, with two to four Drug Attachment Units, or with two to four -X-D Units. As such, the Branching Unit allows for the attachment of multiple

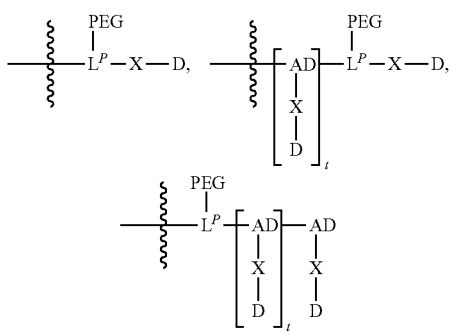

moieties in structures such as

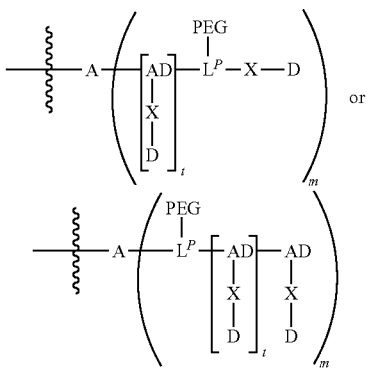

in instances where m is greater than one. The skilled artisan will appreciate that the Branching Unit is designed in such a way to allow branching within the linker. In order to act as a Branching Unit, the Branching Unit has at least a first, second and third attachment site for attachment within the Ligand-Drug Conjugate or Intermediates thereof. In other words, the Branching Unit must be at least trifunctional. In embodiments wherein m is 3 of 4, the Branching Unit will have four or five sites for covalent attachment within the Ligand-Drug Conjugate or Intermediates thereof. In some aspects, the Branching Unit is a single unit or has two or more subunits (e.g, 2 to 10, preferably from 2 to 5, e.g., 2, 3, 4, or 5) to provide the requisite number of attachment sites, wherein the Branching Unit or subunits thereof are independently selected natural or non-natural amino acids, amino alcohols, amino aldehydes, or polyamines or combinations thereof. If necessary in order to have the requisite number of attachments, at least one of the amino acids, amino alcohols, amino aldehydes, or polyamines will have a functionalized side chain to provide for attachment sites for the $L^P$ unit, and/or Z unit, and/or AD units and/or X-D moieties. In some aspects, one or more amino acid(s), amino alcohol(s), or amino aldehyde(s) will be non-natural and will be modified to have one or more functionalized side chains for attachment sites. Exemplary functionalized amino acids, amino alcohols, or amino aldehydes include, for example, azido or alkyne functionalized amino acids, amino alcohols, or amino aldehydes (e.g., amino acid, amino alcohol, or amino aldehyde modified to have an azide group or alkyne group for attachment using click chemistry).

Each amino acid, amino alcohol, amino aldehyde or polyamine can be natural or unnatural. Similarly, each amino acid can be a D- or L-isomer. In some embodiments wherein the Branching Unit is capable of connecting two Parallel Connector Units, two X-D Units or two Drug Attachment Units, the Branching Unit, once assembled, has the formula denoted below:

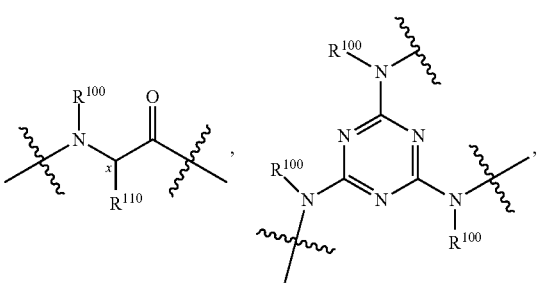

-continued

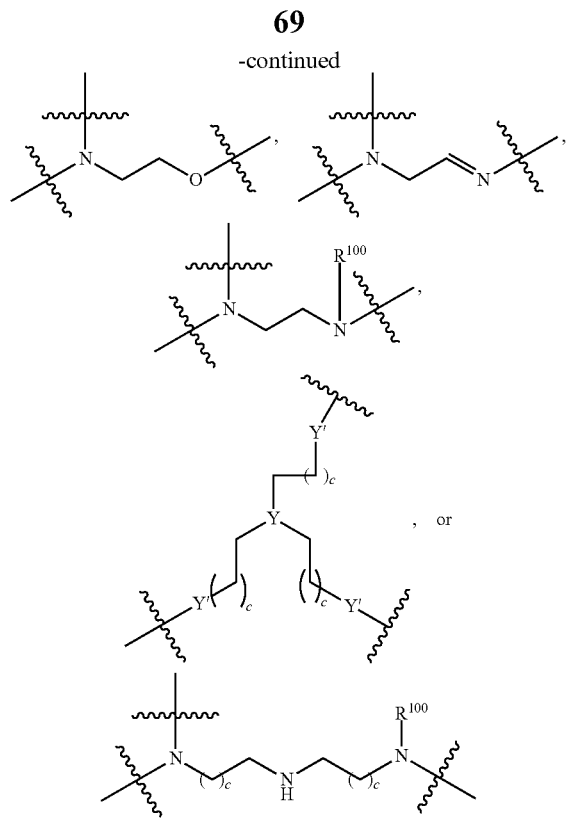

wherein the wavy line indicates two or three of the three attachment sites within the Ligand-Drug Conjugate or Intermediates thereof and wherein $R^{110}$ is

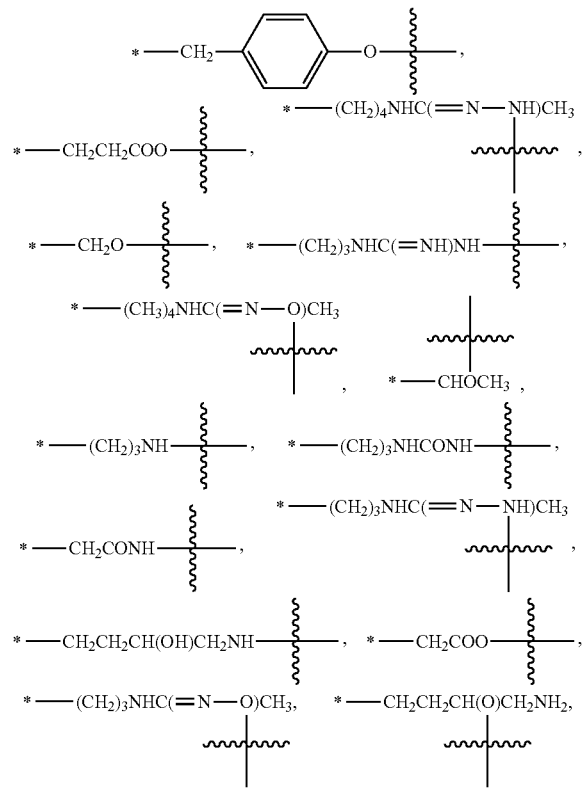

-continued

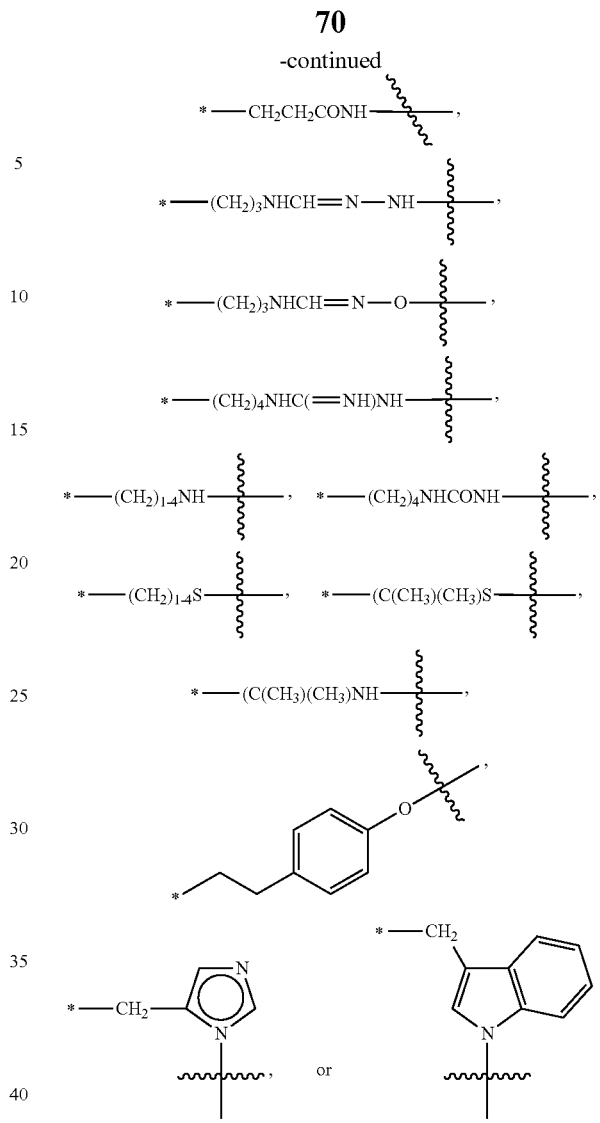

wherein the asterisk indicates attachment to the carbon labeled x and the wavy line indicates one of the three attachment sites of the Branching Unit;

each $R^{100}$ is independently selected from hydrogen or $-C_1-C_3$ alkyl, preferably hydrogen or $CH_3$, Y is independently selected from N or CH, each Y' is independently selected from NH, O, or S, the subscript c is independently an integer ranging from 1 to 10, preferably from 1 to 3.

In preferred embodiments, $R^{110}$ is not

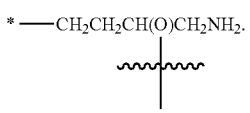

In some embodiments wherein the Branching Unit is capable of connecting to two Parallel Connector Units or two Drug Attachment Units, each Branching Unit in a Ligand-Drug Conjugate or intermediates thereof, once assembled, independently has the formula denoted below:

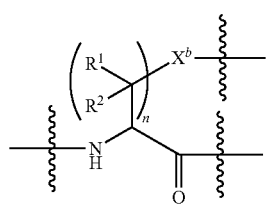

wherein, the subscript n is from 1 to 4;

$X^b$ is selected from the group consisting of —O—, —NR—, —S— —C(=O)—, and —S(=O)—; and $R^1$ and $R^2$ are independently selected from the group consisting of H, $C_{1-3}$ alkyl, phenyl, and $C_2$-$C_5$ heterocycle (preferably H or $C_{1-3}$ alkyl), wherein the wavy line indicates covalent attachment of the Branching Unit within the Ligand-Drug Conjugate or Intermediate thereof.

The amino acid, amino alcohol, amino aldehyde or polyamine of the Branching Unit can be optionally replaced by an optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo as described herein. The optionally substituted heteroalkylene, heterocycle, arylene or carbocyclo will have functional groups for attachment within a Ligand-Drug Conjugate or intermediates thereof.

Optional substituents include (=O), —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3$, —PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, —C$_1$-C$_{20}$ alkyl, —C$_6$-C$_{20}$ aryl, —C$_3$-C$_{14}$ heterocycle, a protecting group or a prodrug moiety. Preferred optional substituents are (=O), —X, —R, —OR, —SR, and —NR$_2$.

An exemplary Branching Unit is lysine as shown below wherein the wavy line and asterisk indicate covalent linkage within the Ligand-Drug Conjugate or Intermediates thereof:

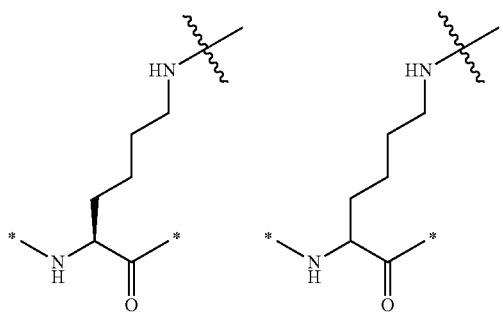 [SMILES: *NCCCC[C@H](NC)C(C)=O ; *NCCCCC(NC)C(C)=O]

It will be appreciated that in the formulas for certain of the Intermediate compounds provided herein, the optional Branching Unit is capable of forming two to four covalent attachments to -X-D moieties but is not yet attached thereto. In such embodiments, the Branching Unit will be in a partially assembled form and, as such, will comprise two or more functional groups that are reactive to groups present on the Releasable Assembly Units of the -X-D moieties. Particularly preferred reactive functional groups include sulfhydryl groups capable of forming disulfide bonds or thioethers.

In preferred aspects of the prevent invention the Branching unit has a mass of no more than about 1000 daltons, no more than about 500 daltons, no more than about 200 daltons, from about 10, 50 or 100 daltons to about 1000 daltons, from about 10, 50 or 100 daltons to about 500 daltons, or from about 10, 50 or 100 daltons to about 200 daltons.

Drug Attachment Unit (AD)

As with the Branching Unit, the Drug Attachment Unit is included in the Ligand-Drug Conjugates in instances where it is desirable to add additional -X-D moieties (i.e., a Releasable Assembly Unit covalently attached to a Drug Unit) to a drug-linker moiety and, ultimately, to the Ligand. A Drug Attachment Unit, depending on placement within the Ligand-Drug Conjugate or intermediates thereof will either have two attachment sites or three attachment sites for linkage to the components of a Ligand-Drug Conjugate or intermediates thereof. The skilled artisan will appreciate that the Drug Attachment Unit can be any group that serves to provide for the attachment of an additional -X-D Unit within a drug-linker moiety and ultimately to a Ligand Unit. In some embodiments, each Drug Attachment Unit is a single unit or has two or more subunits (e.g, 2 to 10, preferably from 2 to 5, e.g., 2, 3, 4, or 5) wherein the Drug Attachment Unit or subunits thereof are independently selected from natural or non-natural amino acids, amino alcohols, amino aldehydes, diamines, or polyamines or combinations thereof. If necessary in order to have the requisite number of attachments, at least one of the amino acids, amino alcohols, amino aldehydes, or polyamines will have a functionalized side chain to provide for attachment sites for the L$^P$ unit, and/or Z unit, and/or AD units and/or X-D moieties. The amino acid(s), amino alcohol(s), or amino aldehyde(s) can be non-natural and can be modified to have one or more functionalized side chains for attachment to the Releasable Assembly Unit. Exemplary functionalized amino acids, amino alcohols, or amino aldehydes include, for example, azido or alkyne functionalized amino acids, amino alcohols, or amino aldehydes (e.g., amino acid, amino alcohol, or amino aldehyde modified to have an azide group or alkyne group for attachment using click chemistry).

In some aspects, wherein an AD unit has three attachment sites, the AD unit, in its assembled form, has the formula denoted below:

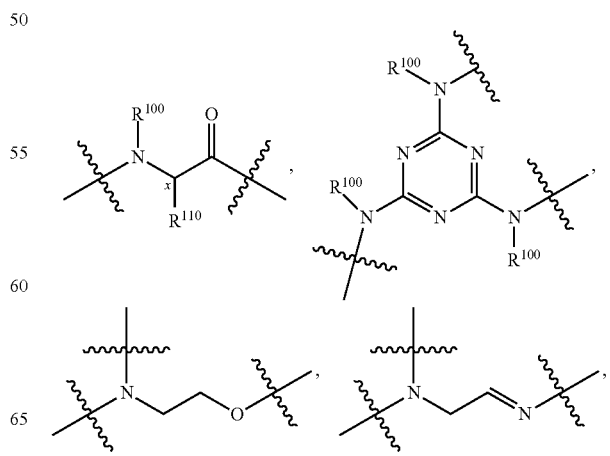

-continued

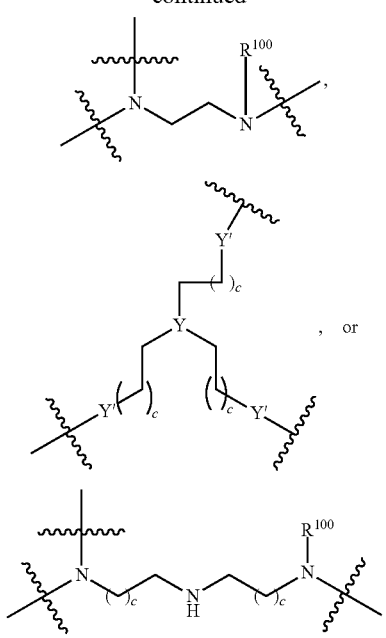

wherein the wavy line indicates two or three of the three AD attachment sites within the Ligand-Drug Conjugate or intermediates thereof and wherein $R^{110}$ is

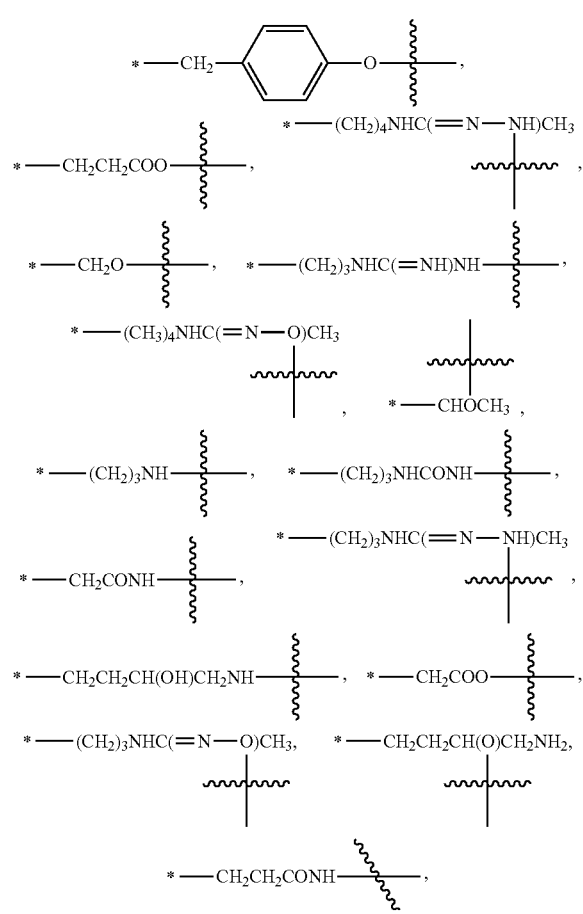

-continued

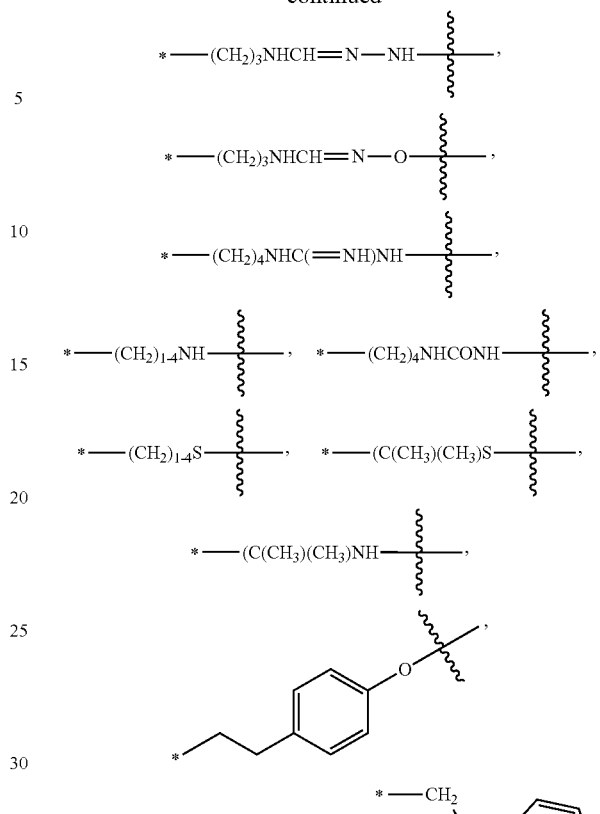

wherein the asterisk indicates attachment to the carbon labeled x and the wavy line indicates one of the three attachment sites;

$R^{100}$ is independently selected from hydrogen or —$C_1$-$C_3$ alkyl, preferably hydrogen or $CH_3$, Y is independently selected from N or CH, Y' is independently selected from NH, O, or S, and the subscript c is independently selected from 1 to 10, preferably 1 to 3.

In preferred aspects, $R^{110}$ is not

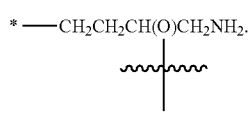

In embodiments wherein an AD Unit has two attachment sites (i.e., a terminal AD Unit) one of the attachment sites shown above can replaced, for example, by H, OH, or a $C_{1-3}$ unsubstituted alkyl group In some embodiments, wherein an AD Unit has three attachment sites, the AD unit, in its assembled form, independently has the formula denoted below:

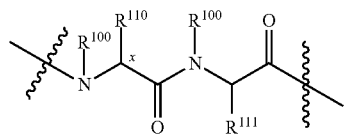

wherein the wavy line indicates the attachment sites within the Ligand-Drug Conjugate or intermediates thereof and wherein x, $R^{100}$ and $R^{110}$ are as previously described immediately above and wherein $R^{111}$ is p-hydroxybenzyl, methyl, isopropyl, isobutyl, sec-butyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-,

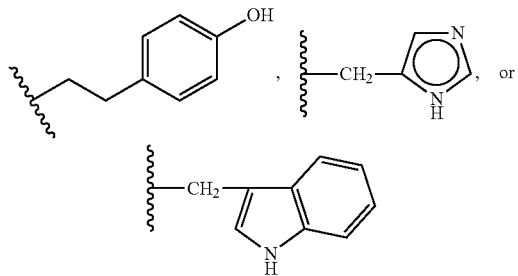

In some embodiments, wherein an AD Unit has three attachment sites, the AD unit is comprised of two or more amino acids. Such an exemplary amino AD Unit is Cysteine-Alanine as shown below wherein the wavy line and asterisk indicates attachment within the Ligand-Drug Conjugate or intermediates thereof:

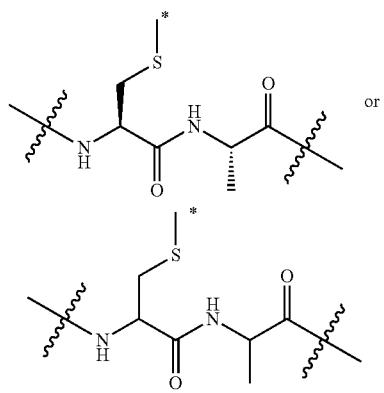

In some embodiments, the asterisk indicates covalent attachment to the Releasable Assembly Unit.

In some embodiments, wherein an AD Unit has two attachment sites, the AD unit is comprised of two or more amino acids. Such an exemplary amino AD Unit is Cysteine-Alanine as shown below wherein the wavy line and asterisk indicates attachment within the Ligand-Drug Conjugate or Intermediates thereof:

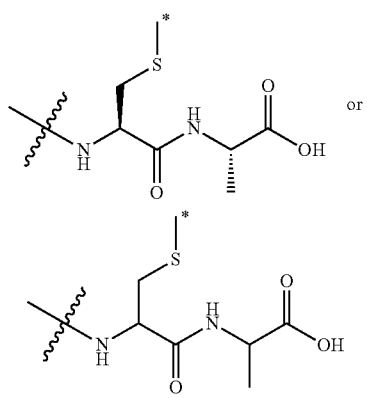

In some embodiments, the asterisk indicates covalent attachment to the Releasable Assembly Unit.

The amino acid, amino alcohol, amino aldehyde or polyamine of the AD Unit can be optionally replaced by an optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo as described herein. The optionally substituted heteroalkylene, heterocycle, arylene or carbocyclo will have functional groups for attachment within a Ligand-Drug Conjugate or intermediates thereof. Optional substituents include (=O), —X, —R, —OR, —SR, —$NR_2$, —$NR_3$, =NR, $CX_3$, CN, OCN, SCN, N=C=O, NCS, NO, $NO_2$, =$N_2$, $N_3$, NRC(=O)R, —C(=O)R, —C(=O)$NR_2$, $SO_3^-$, $SO_3H$, $S(=O)_2R$, —OS(=O)$_2$OR, —S(=O)$_2$NR, —S(=O)R, —OP(=O)(OR)$_2$, —P(=O)(OR)$_2$, $PO^-_3$, $PO_3H_2$, $AsO_2H_2$, C(=O)R, C(=O)X, C(=S)R, $CO_2R$, $CO_2$—, C(=S)OR, C(=O)SR, C(=S)SR, C(=O)$NR_2$, C(=S)$NR_2$, or C(=NR)$NR_2$, where each X is independently a halogen: —F, —Cl, —Br, or —I; and each R is independently —H, —$C_1$ $C_{20}$ alkyl, —$C_6$ $C_{20}$ aryl, —$C_3$ $C_{14}$ heterocycle, a protecting group or a prodrug moiety. Preferred optional substituents are (=O), X, R, OR, SR, and $NR_2$.

A Drug Attachment Unit, can be a straight chain or branched and can be represented by Formula B:

Formula B

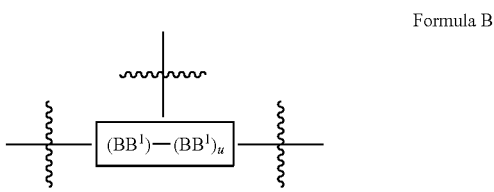

wherein
$BB^1$ is independently selected from an amino acid, optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;

and the subscript u is independently selected from 0 to 4; wherein the wavy line indicates the covalent attachment sites within the Ligand-Drug Conjugate or intermediate thereof. The optionally substituted heteroalkylene, heterocycle, arylene or carbocyclo will have functional groups for attachments between the BB subunits and within a Ligand-Drug Conjugate or intermediates thereof.

In some embodiments at least one instance of $BB^1$ is an amino acid to define a Amino Drug Attachment Unit. The subscript u can be 0, 1, 2, 3, or 4. In some aspects, $BB^1$ is an amino acid and u is 0. In some embodiments, the AD Unit comprises no more than 2 optionally substituted $C_{1-20}$ heteroalkylenes, optionally substituted $C_{3-8}$ heterocyclos, optionally substituted $C_{6-14}$ arylenes, or optionally substituted $C_3$-$C_8$ carbocyclos. In some embodiments, the AD Unit comprises no more than 1 optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo. The optionally substituted heteroalkylene, heterocycle, arylene or carbocyclo will have functional groups for attachment between the BB subunits and within a Ligand-Drug Conjugate or intermediates thereof The amino acid of the Amino Drug Attachment Unit can be an alpha, beta, or gamma amino acid can be natural or non-natural. The amino acid can be a D or L isomer. Attachment within the Amino Drug Attachment Unit or with the other components of the conjugate (or linker) can be, for example, via amino, carboxy, or other functionalities. The optionally substituted heteroalkylene will have functional groups for attachment within the Ligand-Drug Conjugate or intermediates thereof. Methods for the independent activation and reaction of the functional groups are well known in the art.

In any of the embodiments provided herein, an amino acid of a Drug Attachment Unit (including Amino Drug Attachment Unit) can be independently selected from the D or L isomer of a thiol containing amino acid. The thiol containing amino acid can be, for example, cysteine, homocysteine, or penicillamine.

In another embodiment, an amino acid that comprises a Drug Attachment Unit (including Amino Drug Attachment Unit) can be independently selected from the group consisting of the L- or D-isomers of the following amino acids: Alanine (including β-alanine), arginine, aspartic acid, asparagine, cysteine, histidine, glycine, glutamic acid, glutamine phenylalanine, lysine, leucine, methionine, serine, tyrosine, threonine, tryptophan, proline, ornithine, penicillamine, B-alanine, aminoalkynoic acid, aminoalkanedioic acid, heterocyclo-carboxylic acid, citrulline, statine, diaminoalkanoic acid, and derivatives thereof.

Preferred amino acids include cysteine, homocysteine, penicillamine, ornithine, lysine, serine, threonine, glutamine, alanine, aspartic acid, glutamic acid, selenocysteine, proline, glycine, isoleucine, leucine, methionine, valine, and alanine.

It will be understood that in the formulas for certain of the compounds described herein, such as those wherein the Drug Attachment Unit is capable of forming a covalent attachment to -X-D but is not yet connected to -X-D, the Drug Attachment Unit will be in a partially assembled form and, as such, will comprise a functional group that is reactive to a group present on the Releasable Assembly Unit. Particularly preferred reactive functional groups include sulfhydryl groups to form disulfide bonds or thioether bonds. In some aspects, a reactive sulfur atom will be protected by a protecting group. Thiol protecting groups or use in conjugation chemistry are well known in the art, and include, for example, alky thiol (e.g., t-butylthiol, ethanethiol, 2-propanethiol, 2-pyridinethiol) protecting groups, aromatic thiol protecting groups (e.g., 2-pyridinethiol) and acetyl protecting groups.

In preferred aspects of the prevent invention the Drug Attachment Unit has a mass of no more than about 1000 daltons, no more than about 500 daltons, no more than about 200 daltons, from about 10, 50 or 100 daltons to about 1000 daltons, from about 10, 50 or 100 daltons to about 500 daltons, or from about 10, 50 or 100 daltons to about 200 daltons.

Releasable Assembly Unit (X)

The Releasable Assembly Unit (—X—) links the Drug Unit to the remainder of the Ligand-Drug Conjugate. The main function of the Releasable Assembly Unit is to release free drug at the site targeted by the Ligand. In that vein, the Releasable Assembly Unit is capable of forming a cleavable linkage to a drug unit or contains a cleavable linkage to release drug (e.g., upon antigen mediated internalization). In preferred embodiments, release mechanism for the Releasable Assembly Unit is an enzymatic release mechanism or a disulfide elimination mechanism. The recognition site for the enzymatic release mechanism can be, for example, a peptide cleavage site or a sugar cleavage site (e.g., glucuronide cleavage site).

A Releasable Assembly Unit can comprise from 1 to 3 components, a Cleavable Unit ($Q^{CL}$) an optional Spacer Unit ($Q^{SP}$), and an optional Covalent Attachment Unit ($Q^{CO}$). The Spacer Unit when present acts to link the Cleavable Unit and the Drug Unit. Accordingly, in embodiments wherein the Spacer Unit is present, the Spacer Unit will be directly linked to the Drug Unit and the Cleavable Unit will be linked to the Drug Unit via the Spacer Unit. In embodiments wherein the Spacer Unit is absent, the Cleavable Unit will be directly linked to the Drug Unit.

Accordingly, the Releasable Assembly Unit can be represented by the formula below wherein $Q^{CO}$ is a Covalent Attachment Unit, $Q^{SP}$ is a Spacer Unit, and $Q^{CL}$ is a Cleavable Unit. The Covalent Attachment Unit can present or absent and the Spacer Unit can be present or absent. The asterisk indicates the site of covalent attachment to the Drug Unit and the wavy line indicates covalent attachment within the Ligand-Drug Conjugate or intermediate thereof (to $L^P$, A, or AD as the case may be):

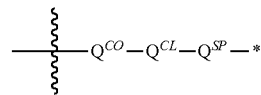

In embodiments wherein the Spacer Unit is absent and the Covalent Attachment Unit is present, -X-D can be represented by formula XIX wherein the wavy line adjacent to the Covalent Attachment Unit indicates covalent attachment to the remainder of the linker (to $L^P$, A, or AD as the case may be).

XIX

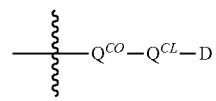

In embodiments wherein the Covalent Attachment Unit is absent and the Spacer Unit is absent, -X-D can be represented by formula XX wherein the wavy line adjacent to the Cleavable Unit indicates covalent attachment to the remainder of the linker (to $L^P$, A, or AD as the case may be):

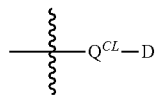
XX

In embodiments wherein the Spacer Unit is present and the Covalent Attachment Unit is present, -X-D can be represented by formula XXI wherein the wavy line adjacent to the Covalent Attachment Unit indicates covalent attachment to the remainder of the linker (to $L^P$, A, or AD as the case may be):

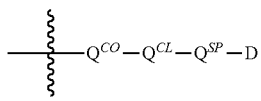
XXI

In embodiments wherein the Spacer Unit is present and the Covalent Attachment Unit is absent, -X-D can be represented by formula XXII wherein the wavy line adjacent to the Cleavable Unit or Spacer Unit indicates covalent attachment to the remainder of the linker ($L^P$, A, or AD as the case may be).

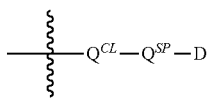
XXII

One of skill in the art will understand that any of the definitions above for -X-D (formulas XIX-XXIV) can be used in any of the formulas and embodiments provided herein, and any of their selected embodiments. Each X, D, and each $Q^{CO}$, $Q^{CL}$, or $Q^{SP}$ Unit can be the same or different.

In preferred aspects of the prevent invention, the Releasable Assembly Unit has a mass of no more than about 5000 daltons, no more than about 4000 daltons, no more than about 3000 daltons, no more than about 2000 daltons, no more than about 1000 daltons, no more than about 800 daltons, or no more than about 500 daltons. In some aspects, the Releasable Assembly Unit has a mass of from about 100 daltons, or from about 200 daltons, or from about 300 daltons to about 5000 daltons, from about 100 daltons, or from about 200 daltons, or from about 300 daltons to about 4000 daltons, from about 100 daltons, or from about 200 daltons, or from about 300 daltons to about 3000 daltons, from about 100 daltons, or from about 200 daltons, or from about 300 daltons to about 2000 daltons, from about 100 daltons, or from about 200 daltons, or from about 300 daltons to about 1000 daltons, from about 100 daltons, or from about 200 daltons, or from about 300 daltons to about 800 daltons, or from about 100 daltons, or from about 200 daltons, or from about 300 daltons to about 500 daltons.

One of skill in the art will understand that the components of the Intermediate Linker or Drug-Linker Compounds can be linked in the same manner as the Ligand-Drug Conjugates wherein the Ligand Unit is lacking.

Cleavable Unit ($Q^{CL}$)

The Cleavable Unit is the only component of the Releasable Assembly Unit that must be present. In some aspects, the Cleavable Unit forms a cleavable bond with the Drug unit. In some aspects, the Cleavable Unit forms a cleavable bond with the Spacer Unit. In some aspects, the cleavable bond is within the Cleavable Unit but allows for release of free drug (e.g., by a 1,6-elimination reaction following cleavage). Functional groups for forming cleavable bonds can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds.

The nature of the Cleavable Unit can vary widely. For example, cleavable linkers include disulfide containing linkers that are cleavable through disulfide exchange, acid-labile linkers that are cleavable at acidic pH, and linkers that are cleavable by hydrolases (e.g., peptidases, esterases, and glucuronidases).

The structure and sequence of the Cleavable Unit can be such that the unit is cleaved by the action of enzymes present at the target site. In other aspects, the Cleavable Unit can be cleavable by other mechanisms. The Cleavable Unit can comprise one or multiple cleavage sites.

In some embodiments, the Cleavable Unit will comprise one amino acid or one or more sequences of amino acids. The Cleavable Unit can comprise, for example, a monopeptide, a dipeptide, tripeptide, tetrapeptide, pentapeptide, hexapeptide, heptapeptide, octapeptide, nonapeptide, decapeptide, undecapeptide or dodecapeptide unit.

Each amino acid of a Cleavable Unit can be natural or unnatural and/or a D- or L-isomer provided of course that there is a cleavable bond. In some embodiments, the Cleavable Unit will comprise only natural amino acids. In some embodiments, the Cleavable unit will comprise 1 to 12 amino acids in contiguous sequence.

In some embodiments, each amino acid of a Cleavable Unit is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, β-alanine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, and selenocysteine. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, and valine. In some embodiments, each amino acid is selected from the proteinogenic or the non-proteinogenic amino acids.

In another embodiment, each amino acid of a Cleavable Unit is independently selected from the group consisting of the following L-(natural) amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In another embodiment, each amino acid of a Cleavable Unit is independently selected from the group consisting of the following D-isomers of these natural amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In some embodiments, the bond between the Cleavable Unit and the Drug unit or Spacer Unit can be enzymatically cleaved by one or more enzymes, including a tumor-associated protease, to liberate the Drug unit (-D), which in one embodiment is protonated in vivo upon release to provide a Drug (D).

Useful Cleavable Units can be designed and optimized in their selectivity for enzymatic cleavage by a particular enzyme, for example, a tumor-associated protease. In one embodiment, a linkage (or bond) between the Cleavable unit and the Drug unit or Spacer unit is that which cleavage is catalyzed by cathepsin B, C and D, or a plasmin protease.

In certain embodiments, the Cleavable Unit can comprise only natural amino acids. In other embodiments, the Cleavable Unit can comprise only non-natural amino acids. In some embodiments, the Cleavable Unit can comprise a natural amino acid linked to a non-natural amino acid. In some embodiments, the Cleavable unit can comprise a natural amino acid linked to a D-isomer of a natural amino acid.

An exemplary Cleavable Unit is the dipeptide -Val-Cit-, -Phe-Lys- or -Val-Ala.

In some embodiments, the Cleavable Unit will comprises a peptide and will comprise from 1 to 12 amino acids. In some such embodiments, the peptide will be conjugated directly to the Drug unit and the Spacer Unit will be absent. In some such embodiments, the peptide will be a dipeptide.

In some embodiments, the Cleavable Unit—CU— will be represented by -(-AM-)$_{1-12}$-, or (-AM-AM-)$_{1-6}$ wherein AM is at each occurrence independently selected from natural or non-natural amino acids. In one aspect, AM is at each occurrence independently selected from natural amino acids. One of skill in the art would appreciate that amino acids are typically linked to the Drug unit or Spacer unit through functional units present in the amino acid, e.g., its carboxylic acid or amino termini.

In other aspects, the Cleavable Unit will comprise a sugar cleavage site. In some such embodiments, the Cleaveable Unit comprises a sugar moiety (Su) linked via an oxygen glycosidic bond to a self-immolative group. In such aspects, the self-immolative group is considered to be part of the Cleavable Unit, $Q^{CL}$. The "self-immolative group" is a tri-functional chemical moiety that is capable of covalently linking together three spaced chemical moieties (i.e., the sugar moiety (via a glycosidic bond), a Drug unit (directly or indirectly via the Spacer Unit $Q^{SP}$), and a $L^P$ unit, A Unit or AD Unit (directly or indirectly via a Covalent Attachment Unit $Q^{CO}$). The glycosidic bond will be one that can be cleaved at the target site to initiate a self-immolative reaction sequence that leads to a release of the drug.

Accordingly, the Cleavable Unit can comprise a sugar moiety (Su) linked via a glycoside bond (—O'—) to a self-immolative group (K) of the formula:

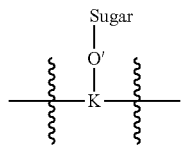

wherein the self-immolative group K forms a covalent bond with the Drug Unit (directly or indirectly via the Spacer Unit) and a covalent bond with $L^P$, AD, or A (directly or indirectly via a Covalent Attachment Unit), as the case may be.

The Cleavable Unit can be, for example, represented by the formula:

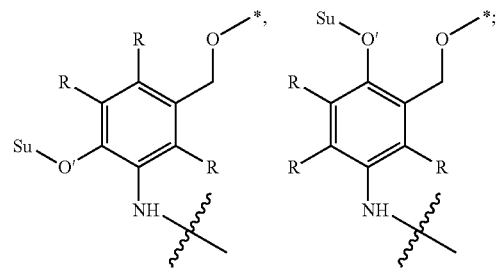

wherein Su is a Sugar moiety, —O'— represents an oxygen glycosidic bond; each R is independently hydrogen, a halogen, —CN, or —NO$_2$; and wherein the wavy line indicates attachment to $L^P$, AD or A (either directly or indirectly through the Covalent Attachment Unit) and the asterisk indicates attachment to the Drug Unit (either directly or indirectly via the Spacer Unit—the Spacer Unit, when present, can be, for example —C(=O)—).

In some such embodiments, the sugar cleavage site is recognized by beta-glucuronidase and the Cleavable Unit comprises a Glucuronide Unit. The Glucuronide Unit can comprise glucuronic acid linked via a glycoside bond (—O'—) to a self-immolative group (K) of the formula:

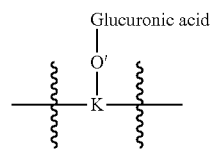

wherein the self-immolative group K forms a covalent bond with the Drug Unit (directly or indirectly via the Spacer Unit) and a covalent bond with $L^P$, AD, or A (directly or indirectly via a Covalent Attachment Unit), as the case may be.

The Glucuronide Unit can be, for example, represented by the formula:

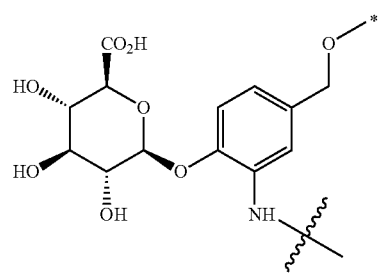 [SMILES: *Nc1cc(COC)ccc1O[C@@H]1O[C@H](C(=O)O)[C@@H](O)[C@H](O)[C@H]1O]

wherein the wavy line indicates covalent attachment to the $L^P$, AD or A (either directly or indirectly through Covalent Attachment Unit) and the asterisk indicates covalent attachment to the Drug Unit (either directly or indirectly via the Spacer Unit)

In some embodiments the Cleavable Unit comprises a sugar cleavage site, -X-D is represented by the following formula:

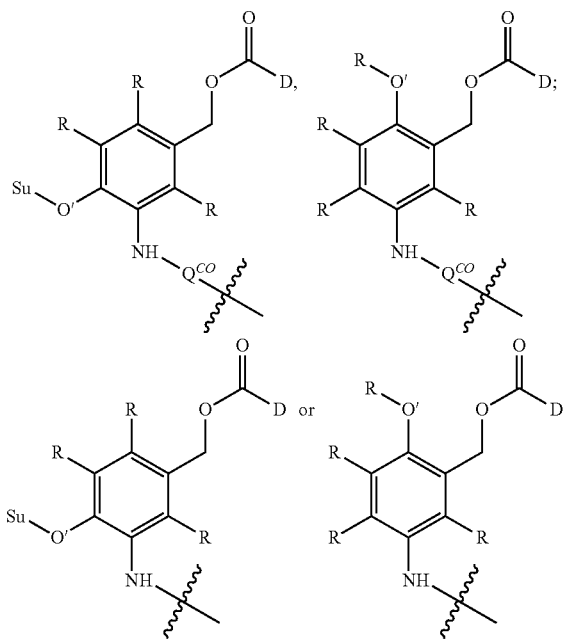

wherein Su is a Sugar moiety, —O'— represents an oxygen glycosidic bond; each R is independently hydrogen or a halogen, —CN, —NO$_2$ or other electron withdrawing group, Q$^{CO}$ is a Covalent Attachment Unit; wherein the wavy bond indicates covalent attachment to remainder of the linker unit (L$^P$, A or AD as the case may be).

When the Cleavable Unit comprises a Glucuronide Unit, -X-D can be, for example, represented by the following formula:

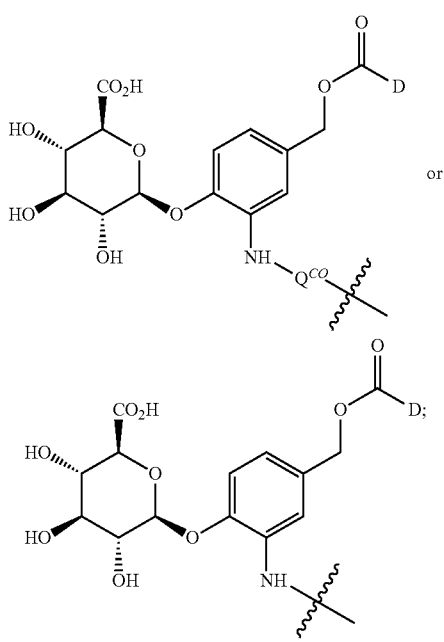

wherein the wavy bond indicates covalent attachment to the remainder of the linker unit (L$^P$, A or AD as the case may be); and Q$^{CO}$ is a Covalent Attachment Unit.

In some other embodiments, the Cleavable unit itself will comprise a sulfur atom that is capable of forming a bond with a sulfur atom of a Spacer Unit or Drug unit to form a disulfide or hindered disulfide. Cleavage occurs between the two sulfur atoms of the disulfide. In some such embodiments, one of the sulfur atoms is cleaved from the Drug unit and, provided there is no further release mechanism, the other sulfur atom remains attached to the Drug Unit and becomes part of the Drug Unit.

A variety of disulfide linkers are known in the art and can adapted for use in the present invention, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate), SMPT (N-succinimidyl-oxycarbonyl-alpha-methyl-alpha-(2-pyridyl-dithio) toluene), and SPP (N-succinimidyl 4-(2-pyridyldithio) pentanoate). (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In some embodiments, the Cleavable Unit is pH-sensitive and will comprise, for example, an acid-labile linker that is hydrolyzable in the lysosome (e.g., a hydrazone, semicarbazone, thiosemicarbazone, cis-aconitic amide, orthoester, acetal, or ketal group) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome.

In some embodiments, the Cleavable unit will be conjugated directly to the Drug unit and the Cleavable unit will be linked to the Drug unit via a cleavable peptide, or disulfide bond.

Spacer Unit (Q$^{SP}$)

The Spacer Unit, when present, acts to link the Drug Unit to the Cleavable Unit. The Spacer Unit, is of two general types: self-immolative and non self-immolative. A non self-immolative unit is one in which part or all of the Spacer Unit remains bound to the Drug Unit after cleavage, and may either be further degraded or spontaneously decompose to produce 'free drug' or may become part of the Drug Unit itself. Examples of a non-self-immolative unit include, but are not limited to a glycine-glycine unit and a single glycine unit (both depicted in Scheme A) (infra). When a Ligand-Drug Conjugate containing a glycine-glycine unit or a single glycine unit undergoes enzymatic cleavage via a tumor-cell associated-protease, a cancer-cell-associated protease or a lymphocyte-associated protease, a glycine-glycine-Drug unit or a glycine-Drug unit is cleaved from the conjugate. In one embodiment, an independent hydrolysis reaction takes place within the target cell, cleaving the glycine-Drug unit bond and liberating the Drug.

Scheme A

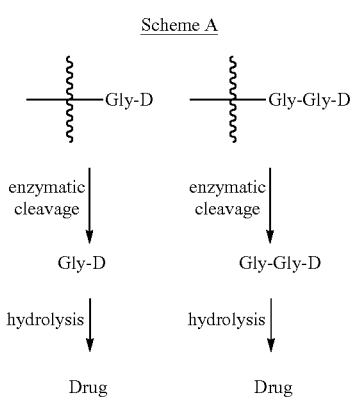

In one embodiment, a non self-immolative unit is -Gly-Gly-. In another embodiment, a non self-immolative unit is -Gly-.

In another embodiment, the Spacer Unit comprises a p-aminobenzyl alcohol (PAB) unit (see Schemes B and C, infra) wherein the phenylene portion is substituted with $Q_m$ wherein Q is —$C_1$-$C_8$ alkyl, —O—($C_1$-$C_8$ alkyl), or other electron donating group or -halogen, -nitro, -cyano or other electron withdrawing group; and m is an integer ranging from 0-4.

Alternatively, a conjugate containing a self-immolative Spacer unit can release -D without the need for a separate hydrolysis step. In some aspects, the Stretcher Unit comprises a PAB group that is linked to a peptide Cleavable Unit via the amino nitrogen atom of the PAB group, and connected directly to the Drug Unit via a carbonate, carbamate or ether group. The PAB group and adjacent carbonyl make up the Spacer Unit. Without being bound by any particular theory or mechanism, Scheme B depicts a possible mechanism of Drug release of a PAB group which is attached directly to -D via a carbamate or carbonate group espoused by Toki et al, 2002, *J Org. Chem.* 67:1866-1872.

Scheme B

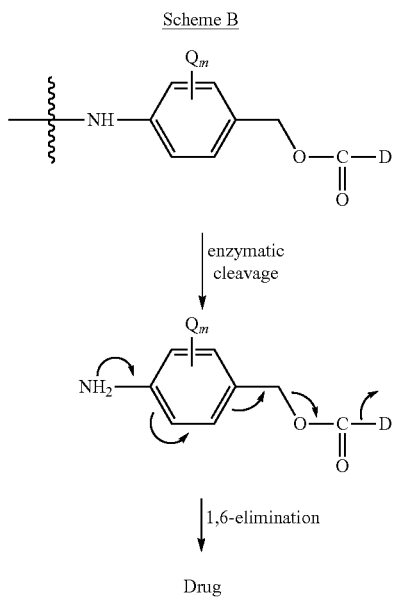

wherein Q is —$C_1$-$C_8$ alkyl, —O—($C_1$-$C_8$ alkyl), -halogen, -nitro or -cyano; and m is an integer ranging from 0-4.

Without being bound by any particular theory or mechanism, Scheme C depicts a possible mechanism of Drug release of a PAB group which is attached directly to -D via an ether or amine linkage.

Scheme C

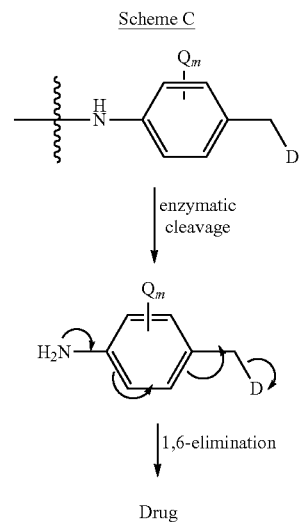

wherein Q is —$C_1$-$C_8$ alkyl, —O—($C_1$-$C_8$ alkyl), -halogen, -nitro or -cyano; and m is an integer ranging from 0-4.

Without being bound by any particular theory or mechanism, Scheme D depicts a possible mechanism of Drug release of a PAB group of a Glucuronide Unit which is attached directly to -D via a carbonyl.

Scheme D

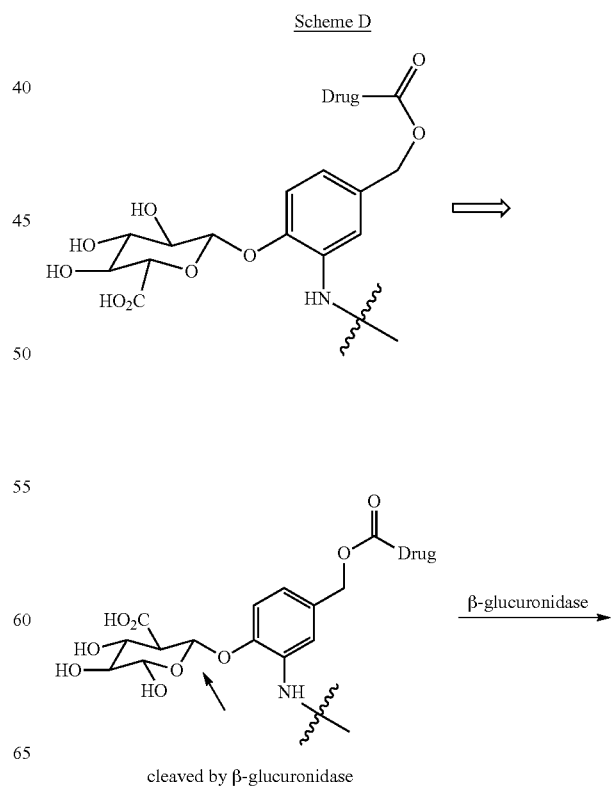

cleaved by β-glucuronidase

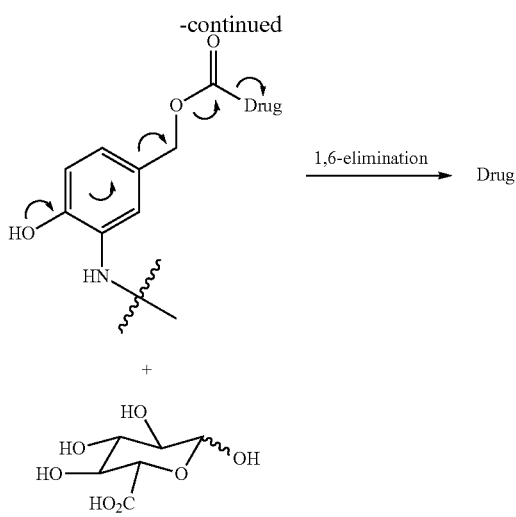

1,6-elimination → Drug

Other examples of self-immolative units include, those comprising aromatic compounds that are electronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) and 2-aminophenylpropionic acid amides (see, e.g., Amsberry et al., 1990, *J. Org. Chem.* 55:5867). Elimination of amine-containing drugs that are substituted at the α-position of glycine (see, e.g., Kingsbury et al., 1984, *J. Med. Chem.* 27:1447) are also examples of self-immolative spacer useful in Exemplary Conjugates.

In preferred embodiments of the prevent invention, the Spacer Unit is comprised of 1, 2, or 3 self-immolative or non-self immolative groups.

In preferred embodiments of the prevent invention the Spacer Unit has a mass of no more than about 1000 daltons, no more than about 500 daltons, no more than about 400 daltons, no more than about 300 daltons, or from about 10, 50 or 100 to about 1000 daltons, from about 10, 50 or 100 to about 500 daltons, from about 10, 50 or 100 daltons to about 400 daltons, from about 10, 50 or 100 daltons to about 300 daltons or from about 10, 50 or 100 daltons to about 200 daltons.

Covalent Attachment Unit ($Q^{CO}$)

The Covalent Attachment Unit, when present, extends the framework of the Releasable Linker Assembly Unit to provide more distance between $L^P$ and the Drug unit. In this regard, the Covalent Attachment Unit has a functional group that can form a bond with a functional group of the optional Branching Unit A or $L^P$ or the Drug Attachment Unit AD at one terminus and a functional group that can form a bond with a functional group of a Cleavable Unit on the other termini. In some aspects, exemplary bonds are by means of non-conditionally cleavable linkages.

The skilled artisan will appreciate that the Covalent Attachment Unit can be any group or moiety that serves to provide for attachment of the Cleavable Unit to the remainder of the molecule. In some aspects, the Covalent Attachment Unit prior to assembly will have two functional groups capable of forming a bond and attaching to components of the Ligand-Drug Conjugate or Intermediate thereof. The skilled practitioner will understand that the Covalent Attachment Unit, prior to assembly, may have more than two functional groups; however, for the purposes of the present invention, will only be attached via two of the functional groups to components of the Ligand-Drug Conjugate or Intermediate thereof. The Covalent Attachment Unit can be of one or more (e.g., 1-10, preferably, 1, 2, 3, or 4) natural or non-natural amino acids, amino alcohols, amino aldehydes, diamines, or natural or non-natural amino acid, amino alcohol, amino aldehyde, or diamine. In some aspects, the Covalent Attachment Unit is a natural or non-natural amino acid, amino alcohol, amino aldehyde, or diamine. Exemplary amino acids capable of acting as Covalent Attachment Units include β-alanine.

In some embodiments, the Covalent Attachment Unit has the formula denoted below:

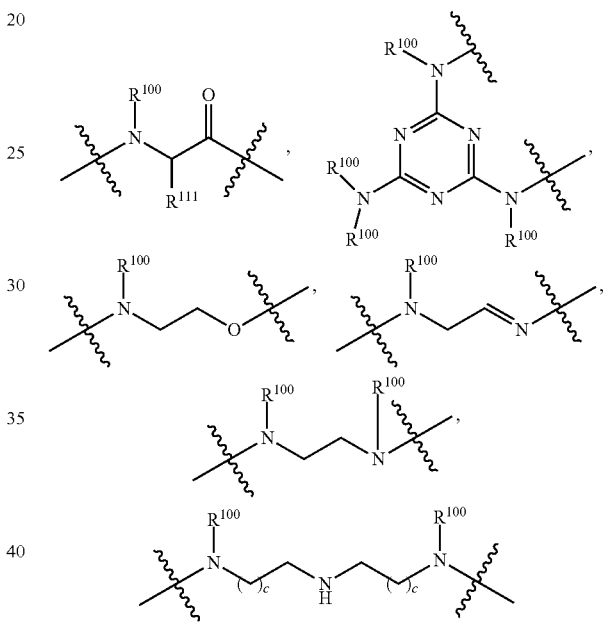

wherein $R^{111}$ is p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-,

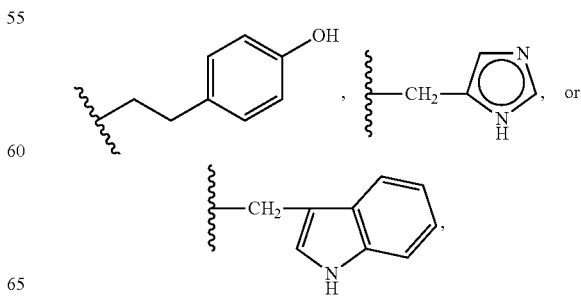

each $R^{100}$ is independently selected from hydrogen or —$C_1$-$C_3$ alkyl, preferably hydrogen or $CH_3$;
and c is an integer independently selected from 1 to 10, preferably 1 to 3

A representative Covalent Attachment Unit having a carbonyl group for linkage to Cleavable Unit is as follows:

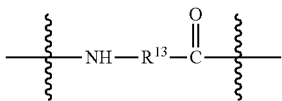

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In preferred embodiments $R^{13}$ is —$C_1$-$C_6$ alkylene.

A representative Covalent Attachment Unit having a carbonyl group for linkage to Cleavable Unit is as follows:

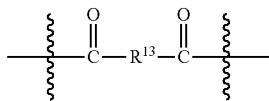

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In preferred embodiments $R^{13}$ is —$C_1$-$C_6$ alkylene.

A representative Covalent Attachment Unit having a NH group for linkage to a Cleavable Unit is as follows:

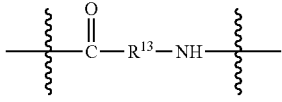

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In preferred embodiments $R^{13}$ is —$C_1$-$C_6$ alkylene.

A representative Covalent Attachment Unit having a NH group for linkage to Cleavable Unit is as follows:

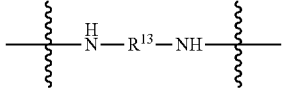

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In preferred embodiments $R^{13}$ is —$C_1$-$C_6$ alkylene.

Selected embodiments of Covalent Attachment Units include the following wherein the wavy line adjacent to the nitrogen indicate covalent attachment to $L^P$ (or AD or A) and the wavy line adjacent to the carbonyl indicates covalent attachment to the Cleavable Unit and m is an integer ranging from 1 to 6, preferably 2 to 6, more preferably 2 to 4.

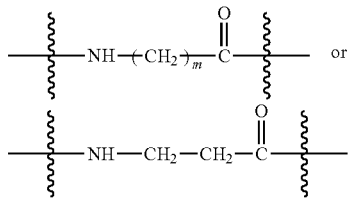

In some aspects, the Covalent Attachment Unit is an optionally substituted $C_{1-8}$ heteroalkylene.

In some aspects, particularly those wherein the Covalent Attachment Unit forms a bond with a sulfur atom of a Parallel Connector Unit, Branching Unit, or Drug Attachment Unit, the Covalent Attachment Unit will form a bond with the sulfur atom via a maleimide group of the Covalent Attachment Unit. Representative Covalent Attachment Units of this embodiment include those within the square brackets of Formulas XXIII and XXIV, wherein the wavy line indicates attachment to the Cleavable Unit as defined herein and the asterisk indicates attachment to the sulfur atom of the Parallel Connector Unit, Branching Unit, or Drug Attachment Unit, and $R^{17'}$ is —$C_1$-$C_{10}$ alkylene-, $C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$ alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—. The $R^{17'}$ substituents can be optionally substituted. In some aspects, the $R^{17'}$ substituents will be unsubstituted. In some aspects, the $R^{17'}$ groups are optionally substituted by a basic unit, e.g —$(CH_2)_xNH_2$, —$(CH_2)_xNHR^a$, and —$(CH_2)_xNR^a_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group.

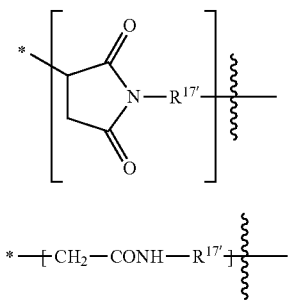

XXIII

XXIV

An illustrative Covalent Attachment Unit is that of Formula XXIII wherein $R^{17'}$ is —$C_2$-$C_5$ alkylene-$C(=O)$— wherein the alkylene is optionally substituted by a basic unit, e.g —$(CH_2)_xNH_2$, —$(CH_2)_xNHR^a$, and —$(CH_2)_xNR^a{}_2$, wherein x is an integer ranging from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. Exemplary embodiments are as follows:

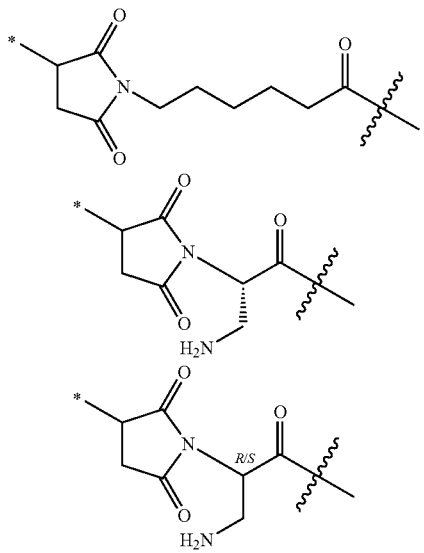

It will be understood that the substituted succinimide depicted above may exist in hydrolyzed form (i.e., a water molecule is added across one and not both of the carbonyl-nitrogen bonds).

It will be understood that the amino group of the Stretcher Unit may be protected by an amino protecting group, e.g., an acid labile protecting group (e.g, BOC).

In preferred aspects of the prevent invention, the Covalent Attachment Unit has a mass of no more than about 1000 daltons, no more than about 500 daltons, no more than about 400 daltons, no more than about 300 daltons, from about 10, 50 or 100 daltons to about 500 daltons, from about 10, 50 or 100 daltons to about 500 daltons, from about 10, 50 or 100 daltons to about 400 daltons, from about 10, 50 or 100 daltons to about 300 daltons or from about 10, 50 or 100 daltons to about 200 daltons.

PEGylated Conjugation Scaffolds

As will be appreciated by the skilled artisan, the size of the PEG Unit to be selected for use in the present invention will be dependent on the hydrophobicity of the drug and the linker components of its drug-linker moiety prior to addition of the PEG Unit. The Intermediate Compounds of Formulas DD, X, XI, or XII can act as PEGylated conjugation scaffolds that can be used to screen for combinations of drugs and PEG Units that result in ADCs having improved PK Parameters and/or minimal aggregation. The PEGylated conjugation scaffolds enable a platform for optimization of the number of PEG subunits for a given drug-linker.

The PEGylated Conjugation Scaffolds are specifically designed to allow for parallel conjugation of varying drug and PEG moieties to examine the ability of PEG to mask the hydrophobicity and improve the PK parameters for a broad range of conventional drug-linkers (i.e., drug-linkers the do not contain a parallel connected PEG Unit according to the present invention). It is preferable to select a PEG Unit of sufficient size that will mask the hydrophobicity of the drug-linker but will not be too big as to negatively impact the ability of the Ligand-Drug Conjugate to diffuse to the targeted site or to enter the targeted cells and release drug.

In particularly preferred embodiments, the conventional drug-linkers to be used for the PEG optimization are those that have a reactive group for conjugating to a thiol group of and antibody, e.g., maleimido-containing drug-linkers and a Releasable Assembly unit X cleavable by a protease. Accordingly, exemplary X-D Units having a Releasable Assembly unit X cleavable by a protease for use with the conjugation scaffolds include the following wherein D is any Drug Unit as described herein:

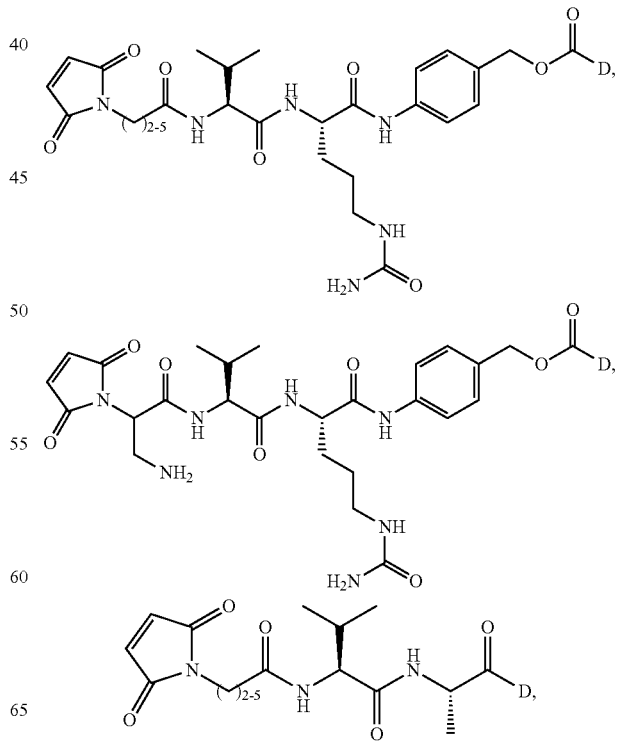

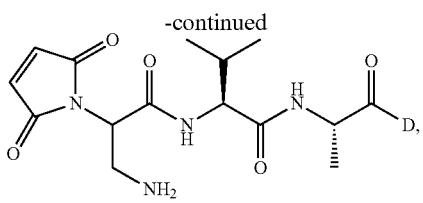

and

In other particularly preferred embodiments, the conventional drug-linkers to be used for the PEG optimization are those that have a reactive group for conjugating to a thiol group of and antibody, e.g., maleimido-containing drug-linkers and a Releasable Assembly unit X cleavable by a glycosidase. Accordingly, exemplary X-D Units having a Releasable Assembly unit X cleavable by a glycosidase for use with the conjugation scaffolds include the following wherein D is any Drug Unit as described herein:

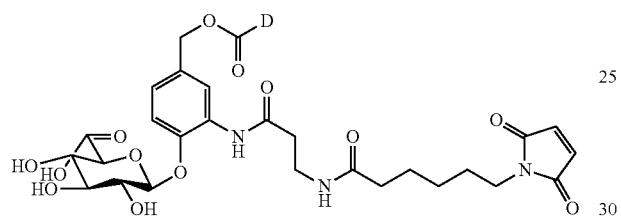

In embodiments where the drug-linkers to be used for the PEG optimization are those that have a reactive group for conjugating to a thiol accepting group such as a maleimide moiety, the conjugation scaffold will have a protected thiol-containing residue that when uprotected is capable of covalent attachment to the thiol-accepting group of the drug-linker. The protected thiol-containing residue can be a component of the Parallel Connector Unit (or Branchaing Unit or Drug Attachment Unit). An exemplary PEGylated conjugate scaffold is of formula DD wherein the $L^{P'}$ Unit comprises an amino acid having the following formula:

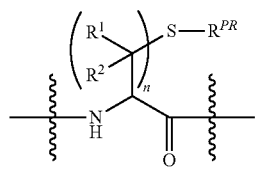

wherein,
the subscript n is an integer ranging from 1 to 4;
$R^1$ and $R^2$ are independently selected from the group consisting of H, $C_{1-3}$ alkyl, phenyl, or $C_2$-$C_5$ heterocycle (preferably hydrogen, methyl, ethyl, or propyl); and
$R^{PR}$ is a suitable thiol-protecting group.

An exemplary PEGylated conjugate scaffold is of formula DD wherein the $L^{P'}$ Unit comprises protected cysteine, homocysteine, or penicillamine. The D or L isomers of the amino acids are suitable. An exemplary amino acid for use as the $L^{P'}$ Unit is cysteine as shown below with t-butylthio as the suitable protecting group.

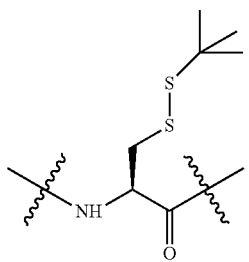 [SMILES: *N[C@@H](CSSC(C)(C)C)C(*)=O]

Exemplary PEGylated conjugation scaffolds in a suitably protected Ligand-Linker Intermediate compound include the following:

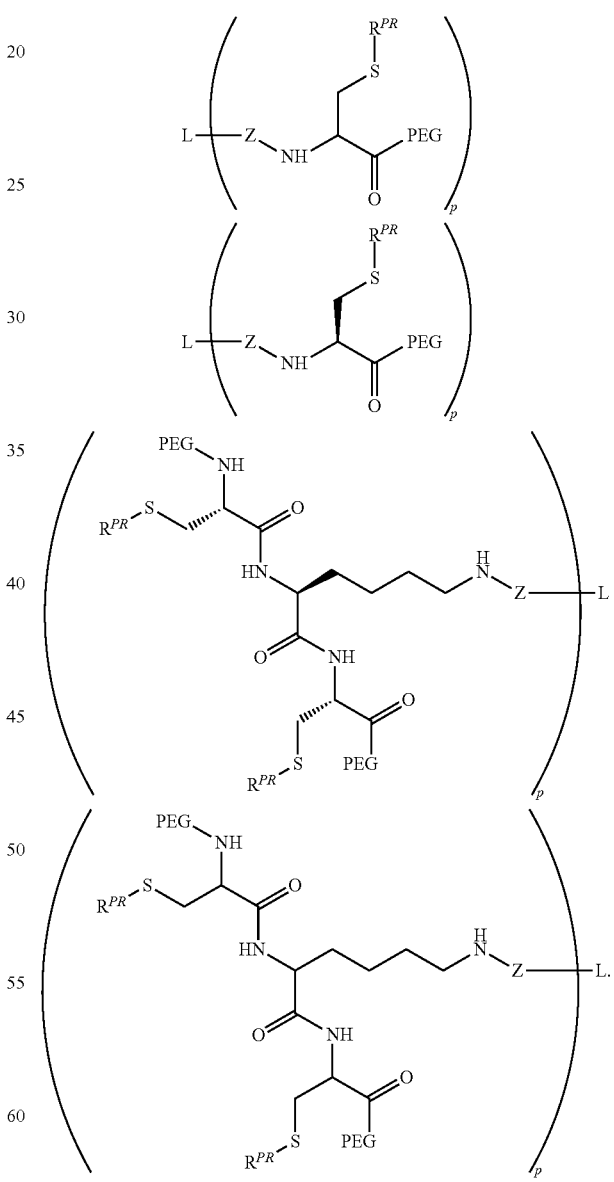

Other Exemplary PEGylated conjugation scaffolds in a suitably protected Ligand-Linker Intermediate compound include the following:

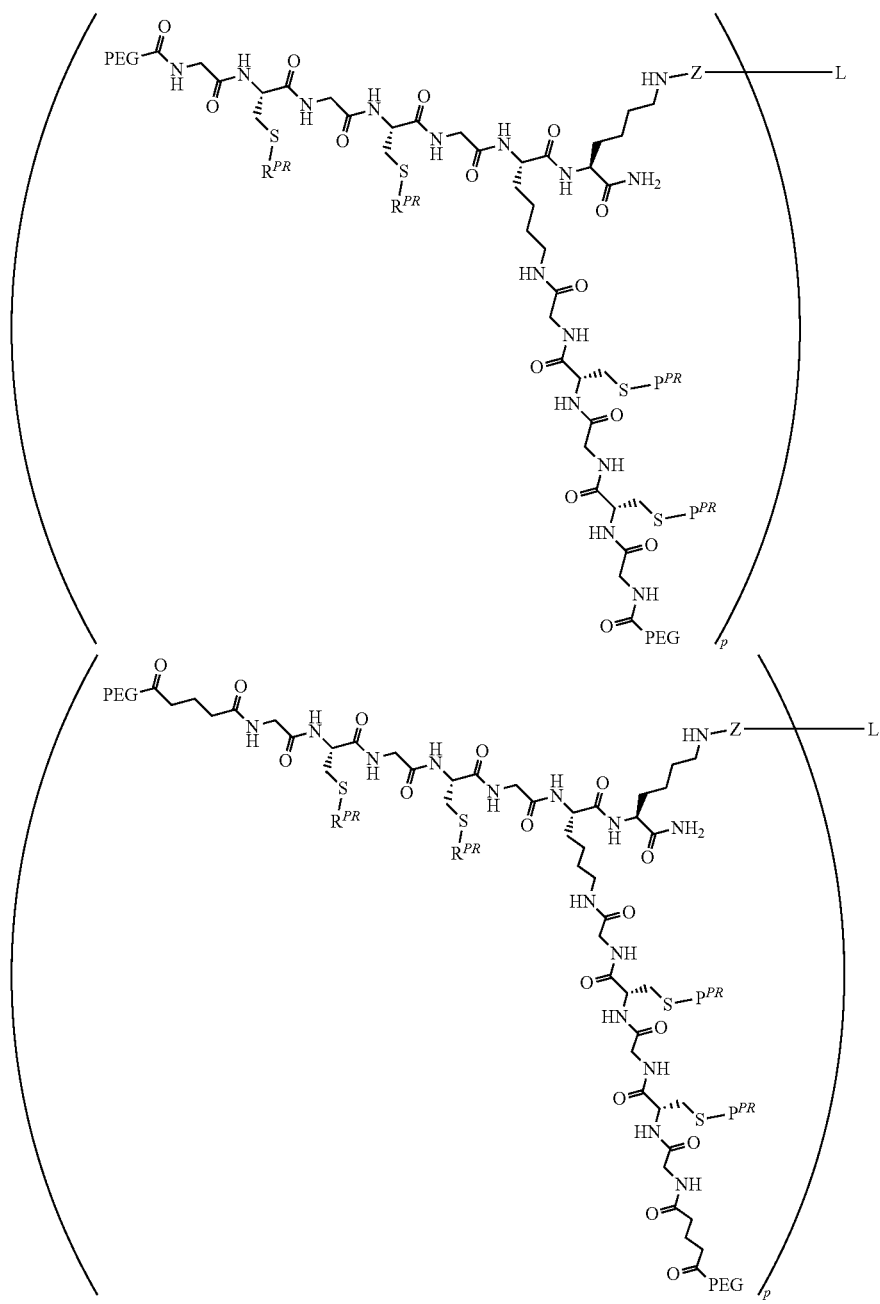
Exemplary PEGylated conjugation scaffolds, after conjugation with drug-linkers, provide Ligand-Drug Conjugates as follows:
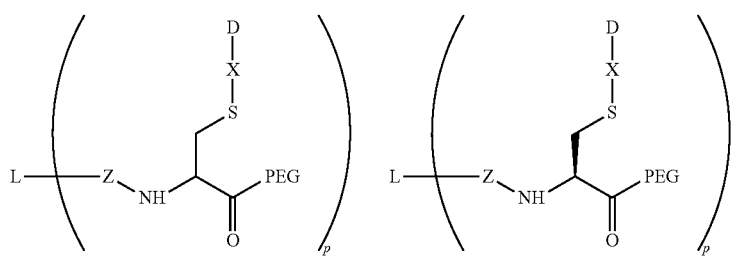

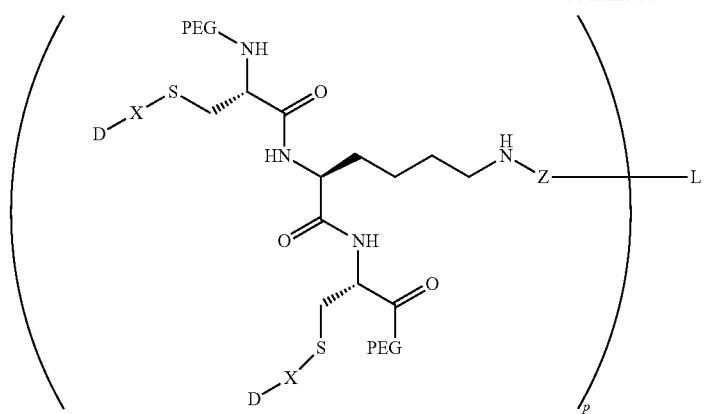
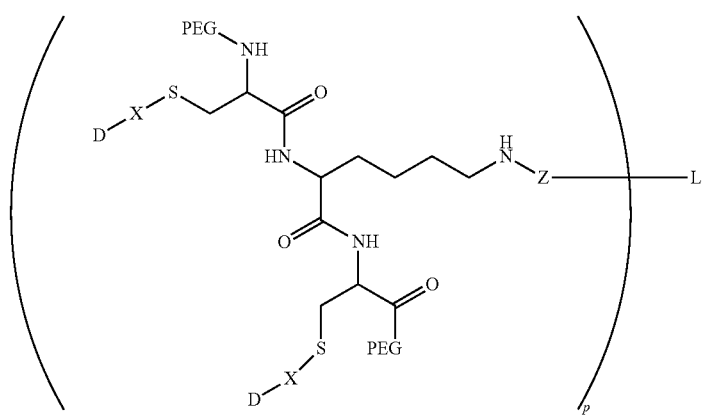
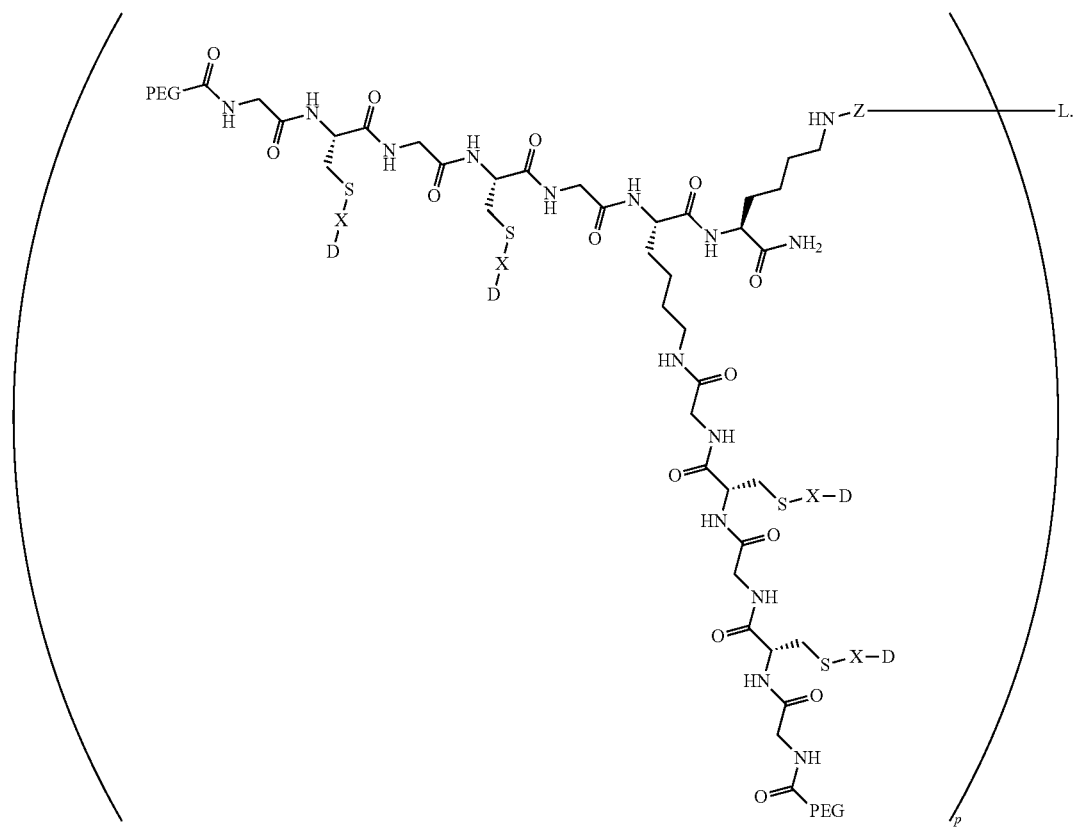

-continued

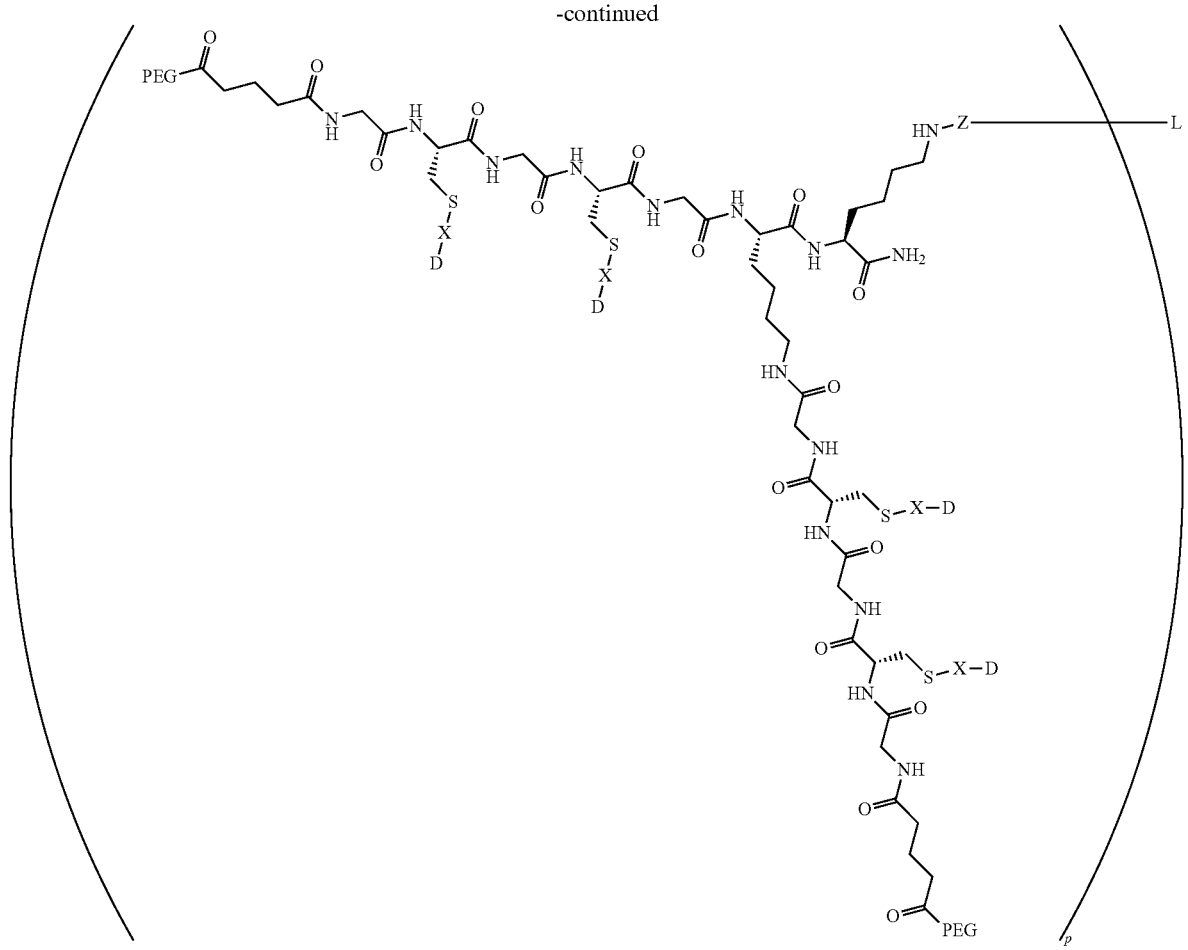

Exemplary Intermediate conjugation scaffolds are of formula (CC) wherein the $L^{P'}$ Unit comprises an amino acid having the following formula:

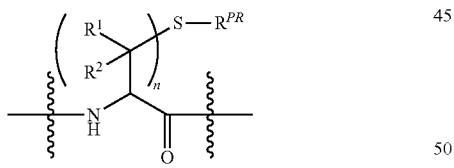

wherein,
the subscript n is an integer ranging from 1 to 4;
$R^1$ and $R^2$ are independently selected from the group consisting of H, $C_{1-3}$ alkyl, phenyl, or $C_2$-$C_5$ heterocycle (preferably hydrogen, methyl, ethyl, or propyl); and
$R^{PR}$ is a suitable thiol-protecting group.

Exemplary intermediate PEGylated conjugate scaffolds in suitably protected Linker Intermediate compounds are shown below:

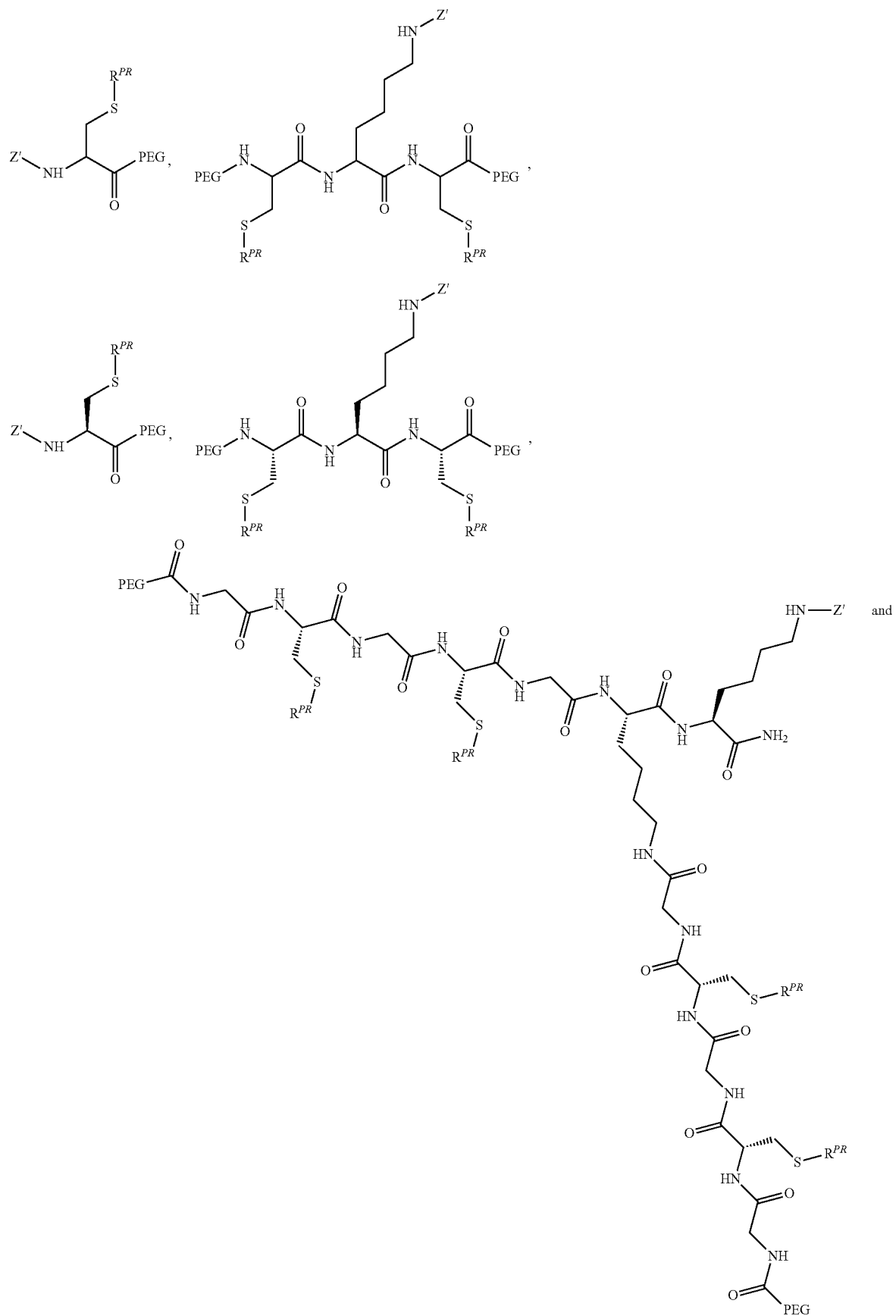

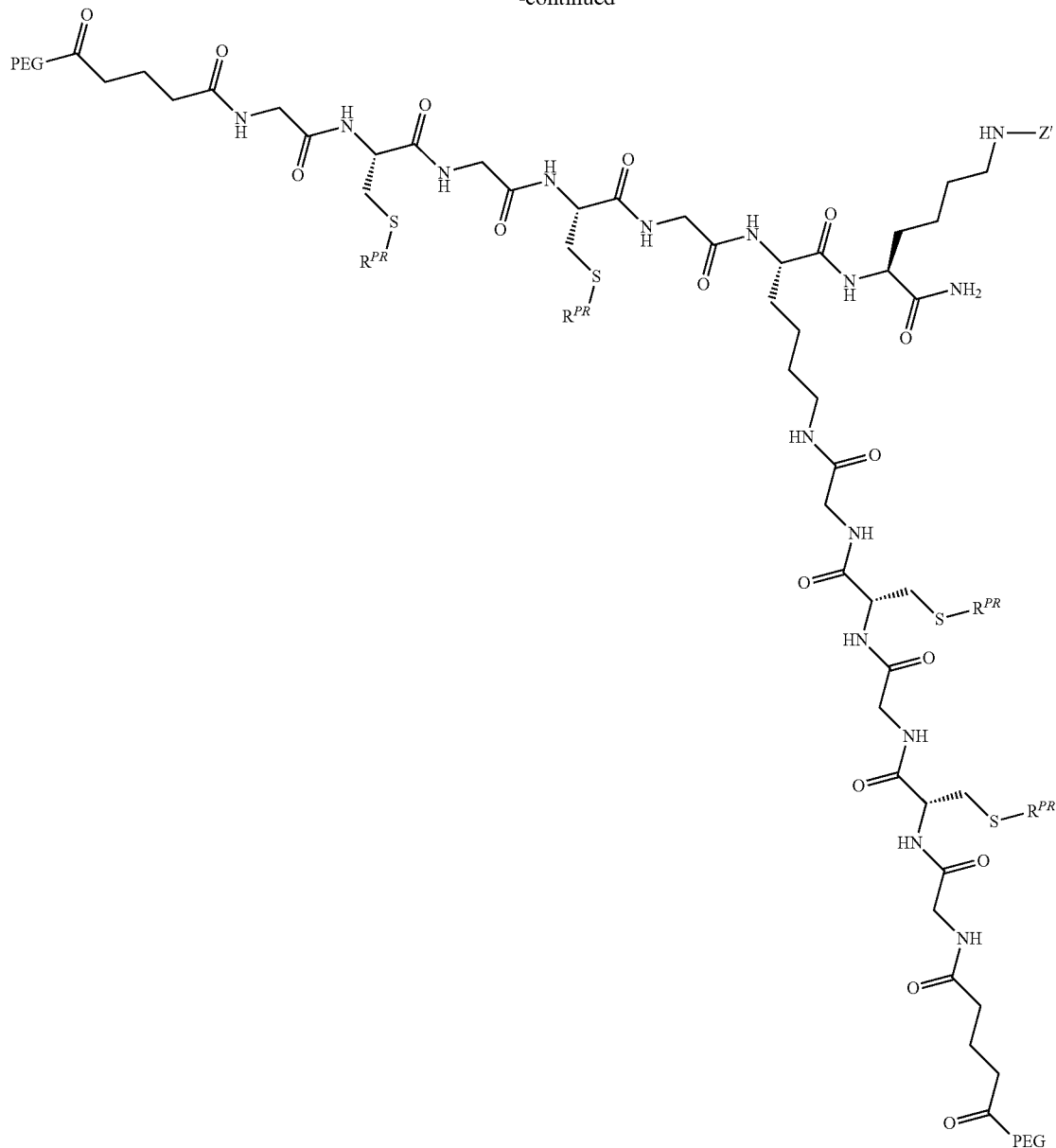

An exemplary PEGylated conjugate scaffold can be of formula XI wherein the $L^{P'}$ Unit and the Drug Attachment Unit AD' each comprises an independently selected amino acid having the following formula:

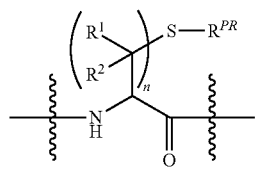

wherein,
the subscript n is a integer ranging from 1 to 4;
R$^1$ and R$^2$ are independently selected from the group consisting of H, C$_{1-3}$ alkyl, phenyl, or C$_2$-C$_5$ heterocycle (preferably hydrogen, methyl, ethyl, or propyl); and
R$^{PR}$ is a suitable thiol-protecting group.

Exemplary PEGylated conjugate scaffolds of Formula XI in a suitably protected Ligand-Linker Intermediate compound are shown below:

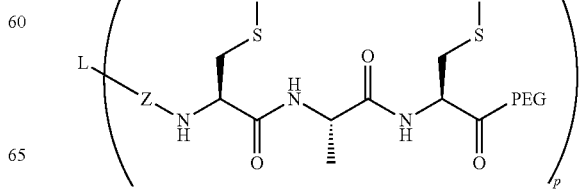

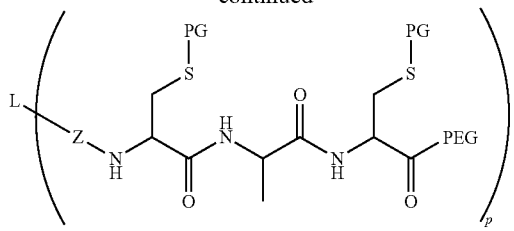

Exemplary PEGylated conjugation scaffolds, after conjugation with drug-linkers provide Ligand-Drug Conjugates of Formula II:

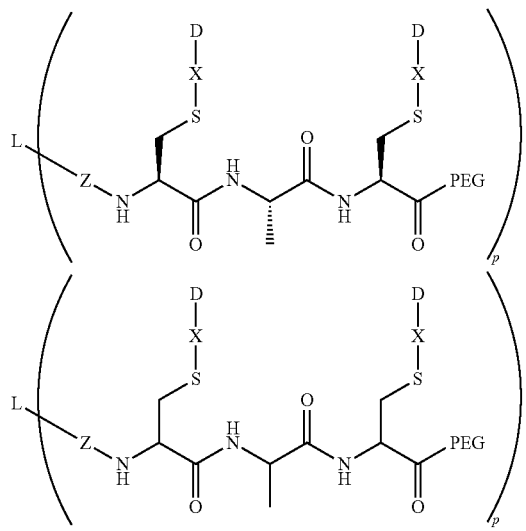

For the PEGylated conjugation scaffolds and intermediates, the Stretcher Unit, Z or Z', PEG, the Ligand, the protecting group $R^{PR}$, and the subscript p is as described in any of the embodiments provided herein. In exemplary aspects, the stretcher unit is a maleimido-containing stretcher unit as described herein. In exemplary embodiments, the PEG unit has the from 6 to 72, 10 to 72, or 12 to 72 subunits and the stretcher unit is a maleimido-containing stretcher unit as described herein and any of the embodiments provided herein for XVa.

Accordingly, the present invention provides methods for selecting a PEG Unit for use in a ligand-drug conjugate, methods comprises the steps of (i) providing a conjugation scaffold having formula (DD) wherein the Parallel Connector Unit comprises a thiol-protected cysteine, (ii) removing the protecting group from the thiol-protected cysteine to form a de-protected conjugation scaffold having a free thiol, (iii) contacting the de-protected conjugation scaffold with a drug-linker having a functional group for covalent attachment with the free thiol under conditions to form a Ligand-Drug Conjugate. The methods can further comprise testing PK parameters of the resultant Ligand-Drug Conjugate (see, for example, example 8 or 21). Also provided are Ligand Drug Conjugates produced by such methods.

Also provided are methods for selecting a PEG Unit for use in a ligand-drug conjugate, methods comprises the steps of (i) providing a conjugation scaffold having formula XI or XII wherein the Parallel Connector Unit and the Drug Attachment Unit(s) comprise a thiol-protected cysteine, (ii) removing the protecting group from the thiol-protected cysteine to form a de-protected conjugation scaffold having a free thiol, (iii) contacting the de-protected conjugation scaffold with a drug-linker having a functional group for covalent attachment with the free thiol under conditions to form a Ligand-Drug Conjugate. The methods can further comprise testing PK parameters of the resultant Ligand-Drug Conjugate (see, for example, example 21). Also provided are Ligand Drug Conjugates produced by such methods.

Drug Loading

Referring generally to the Ligand-Drug Conjugates of formulas I, II, III, and AA, the number of Drug-Linker units per Ligand is represented by p. When referring to individual Ligand-Drug Conjugates in a population of such conjugates, p is an integer representing the number of Drug-Linker molecules per Ligand. When referring to a composition containing multiple conjugates (i.e., a LDC composition), p represents the average number of Drug-Linkers per Ligand and is more typically a non-integer number. In those instances in the experimentals describing LDC compositions comprised of antibody-drug conjugates (ADCs) where reference is made to a drug load of a specified number of Drug Units/antibody (e.g., 8 loads, 16 loads or 32 loads) that value refers to the average drug loading as well as the drug loading of the predominate ADC in the composition, which is dependent on the number of reactive sites on the antibody that will be reacting with a Linker-Drug compound or where applicable with a Ligand intermediate followed by -X-D introduction. In a population of Ligand-Drug Conjugates, there can be an average of from 1 to 14 drug-linkers per ligand, an average of from about 6 to about 14, about 6 to about 12, about 6 to about 10, about 8 to about 14, about 8 to about 12, or about 8 to about 10 Drug-Linker Units per Ligand. Exemplary attachment to the Ligand is via thioether linkages. Exemplary conjugation sites on a Ligand are the thiol of interchain disulfide residues and/or residues introduced into the Ligand such as introduced cysteines. When referring to embodiments wherein the average drug load is about 8, 10, 12, 14, 16, or 32, the value of 8, 10, 12, 14, 16, or 32 typically also refers to the drug loading of the predominate ligand drug conjugate in the composition. Similarly, when referring to embodiments wherein there is an average of from about 8 to about 14, about 8 to about 12, or about 8 to about 10 Drug-Linker Units per Ligand, that value typically also refers to the drug-linker loading of the predominate ADC in the composition.

The average number of Drug-Linker units per Ligand unit in a preparation from a conjugation reaction may be characterized by conventional means such as mass spectroscopy, ELISA assay, HIC and HPLC. The quantitative distribution of Ligand-Linker-Drug conjugates in terms of p may also be determined. In some instances, separation, purification, and characterization of homogeneous Ligand-Drug Conjugates, where p is a certain value from Ligand-Drug Conjugate with other drug loadings may be achieved by means such as reverse phase HPLC or electrophoresis.

Compositions

The present invention provides compositions comprising any of the Ligand-Drug Conjugates described herein. For example, the present invention provides compositions comprising a Ligand-Drug conjugate of formula AA, I, II, or III, and any of their selected embodiments. The variables are as defined herein in any of the embodiments.

When Formulas AA, I, II, or III represent not individual LDC compounds but a LDC composition, (i.e., a composition comprising a population of Ligand Drug Conjugates), the subscript p represents the average number of drug-linker molecules per Ligand molecule (e.g., antibody molecule) in the composition. Similarly, when Formulas DD, X, XI, and XII represent not individual Ligand-Linker Intermediate Compounds but a Ligand Linker Intermediate composition (i.e., a composition comprising a population of Ligand Linker Intermediates compounds), the subscript p represents the average number of linker molecules per Ligand molecule (e.g., antibody) in the composition. It will be understood that the compositions can comprise a collection (or a population) of Ligand-Drug Conjugates having various numbers of drug-linkers attached thereto (e.g., from 1 to 14, 2 to 12, 4 to 12, 6 to 12, 8 to 12) to arrive at an average p value. Alternatively, the composition can comprise a collection (or a population) of Ligand-Drug Conjugates having the same or substantially the same number of drug-linkers attached thereto (from 1 to 14) to arrive at an average p value. The terms collection or population are used synonymously in this context. Within a composition there may be a small percentage of unconjugated antibody that is also reflected in the average p value. For a composition comprising a population of Ligand-Drug Conjugates of the present invention, there can be an average of from 1 to 14 drug-linkers per ligand, an average of from about 6 to about 14, about 6 to about 12, about 6 to about 10, about 8 to about 14, about 8 to about 12, or about 8 to about 10 Drug-Linker Units per Ligand. The use of PEG as taught in the present invention is particularly suitable for Ligand-Drug Conjugates having high drug-loads, e.g., average drug loading of at least about 6, more preferably at least about 8 drug-linkers per ligand wherein each drug-linker has one more -X-D moieties, preferably 1, 2 or 4. Accordingly, the compositions provided herein will preferably have an average drug-linker loading of at least about 8 drug-linker molecules per Ligand in the composition and preferably have about 8, 10, 12, or 16 to about 32 drug units per Ligand unit.

In some aspects, the compositions are pharmaceutical compositions comprising the Ligand-Drug Conjugates described herein and a pharmaceutically acceptable carrier. For example, the present invention provides pharmaceutical compositions comprising a conjugate of formula I, II, or III, and any of their selected embodiments. In some aspect, the pharmaceutical composition will be in liquid form. In some aspects, it will be a lyophilized powder.

The compositions, including pharmaceutical compositions, can be provided in purified form. As used herein, "purified" means that when isolated, the isolate contains at least 95%, and in another aspect at least 98%, of Conjugate by weight of the isolate.

Pharmacokinetics

As previously noted, the present inventors have discovered that the pharmacokinetic profile of certain Ligand-Drug Conjugates can be significantly altered by the addition of a PEG Unit. In certain instances, the placement of PEG in a parallel orientation with the Ligand Unit and Drug unit decreases the plasma clearance of the Ligand-Drug Conjugate and increases plasma exposure, which improve upon the desired pharmacological activity of such conjugates. Surprisingly, placement of a PEG Unit in a serial orientation with the Ligand Unit and Drug Unit did not provide the same improvement in pharmacokinetic effects and, in certain instances, actually increased clearance and decreased relative exposure relative to its non-PEGylated counterpart. Until the present invention efforts towards decreasing hydrophobicity through PEGylation of a hydrophobic compound have not taken into consideration orientation effects of the PEG unit.

There are many ways to measure pharmacokinetic parameters of a Ligand-Drug Conjugate. One method is determining the ligand-drug conjugate concentration, i.e., the amount of ligand-drug conjugate in a given volume of plasma or serum at a certain time point. Another method is determining the drug clearance, i.e., the volume of plasma (or serum) cleared of the ligand-drug conjugate per unit time. A third method is determining area under the curve (AUC), i.e., the integral of the concentration-time curve. Concentration, clearance, and AUC can be determined by plotting the serum (or plasma) concentration of total antibody (μg/ml) along the ordinate (Y-axis) against time (days) along the abscissa (X-axis) following administration of agent of interest to a subject. For example, in one method, pharmacokinetic parameters are measured by injecting mice with a dose of (i) unconjugated Ligand, (ii) a Ligand-Drug Conjugate of the present invention, and (iii) a comparison Ligand-Drug Conjugate and collecting blood samples at various time points after injection (e.g., 1, 2, 3, 7, 14, 21, 28, 35, 42, 49, and 56 days) and isolating serum. Serum (or plasma) concentrations can be measured by methods known in the art. For example, serum (or plasma) concentrations can be measured by sandwich ELISA for total Ligand (e.g., antibody) using an appropriate detection mechanism. Serum (or plasma) concentration data for each animal can be analyzed using appropriate software to arrive at values for concentration, drug clearance and AUC at certain time points. In another embodiment, pharmacokinetic data can be generated using radiolabeled conjugates. For example, animals can be dosed with radiolabeled Ligand or Ligand-Drug Conjugate and plasma (or serum) concentrations are measured by liquid scintillation counting. In some embodiments, the animal model used will be a rat model.

In some embodiments, the pharmacokinetic profile of a Ligand-Drug Conjugate of the present invention resembles that of its unconjugated Ligand. Accordingly, provided herein are Ligand-Drug Conjugates having a clearance value within about 3× or within about 2× the clearance value of the unconjugated Ligand and/or an AUC value that is at least 25% or at least 30% of the AUC value of the unconjugated ligand (e.g., see Table 2).

In some embodiments, the pharmacokinetic profile of a Ligand-Drug Conjugate of the present invention is improved as compared to a comparison conjugate. Accordingly, provided herein are Ligand-Drug Conjugates having an improved concentration value, clearance value and/or AUC value as compared to a comparison conjugate (i.e., not having a PEG unit in parallel orientation to a drug-linker moiety). By the term improved clearance value, it is meant that the Ligand-Drug Conjugate has a clearance that is at least 2× or at least 3× better than the clearance value of the comparison conjugate (e.g., a value of 14.2 mL/day/kg as compared to a value of 48.6 or 57.8 mL/day/kg). By the term improved AUC value, it is meant that the Ligand-Drug Conjugate has an AUC value that is at least 2× or at least 3× better than the AUC value of the comparison conjugate (e.g., a value of 229.7 day*μg/ml as compared to a value of 67 or 52 day*μg/ml).

The comparison conjugate can be the same or substantially similar conjugate lacking the PEG Unit, the same or substantially similar conjugate lacking a PEG Unit placed in a parallel orientation but containing a PEG Unit placed in a serial orientation in relation to the Ligand unit and the Drug unit. In some embodiments, the comparison conjugate is a conjugate comprising the same Drug Unit and either having no PEG Unit (i.e., same or substantially similar conjugate lacking the PEG Unit) or having a PEG Unit that is placed in a serial orientation in relation to the Ligand unit and the Drug unit (i.e., same or substantially the same conjugate having a PEG Unit but not placed in a parallel orientation) Generally, the Ligand-Drug Conjugate and comparison conjugate have the same drug loading (average number of drugs per Ligand Unit in the composition).

As used herein, the phrase "same or substantially similar conjugate lacking the PEG Unit" generally refers to a conjugate comprise the same or substantially the same Ligand unit, Drug Unit, and Linker Unit (e.g., Stretcher Unit, and Releasable Assembly Unit) but lacking the Parallel Connector Unit $L^P$ and the PEG Unit. For a comparison conjugate lacking the PEG unit that most closely resembles a Ligand-Drug Conjugate of the present invention, the comparison conjugate will comprise the same Ligand Unit, Drug Unit, Releasable Assembly Unit, Stretcher Unit and Parallel Connector Unit (and AD or A unit if appropriate). The Parallel Connector Unit, however, will not be attached to a PEG unit but will terminate in a functional group, such as for example, an acetyl group (see for example compound 44 in the examples)

As used herein, the phrase "same or substantially the same conjugate lacking a PEG Unit placed in a parallel orientation but containing a PEG Unit placed in a serial orientation in relation to the Ligand unit and the Drug unit" (i.e., i.e., same or substantially the same conjugate having a PEG Unit but not placed in a parallel orientation) generally refers to a conjugate comprising the same or substantially the same Ligand Unit, Drug Unit, and Linker Unit (e.g., Stretcher Unit, and Releasable Assembly Unit) but lacking the Parallel Connector Unit $L^P$ and the PEG Unit attached thereto in parallel configuration and including a PEG Unit in the Linker in a serial orientation with the Ligand Unit and the Drug Unit.

The term "substantially the same" in this context is meant that there may be some minor variations but such variations are primarily for ease of chemical synthesis and attachment of the various components of the conjugate. See the examples section for examples of comparison conjugates having no PEG or a PEG Unit in a serial orientation in comparison to a Conjugate of the present invention having a PEG Unit in a parallel orientation.

Ligand-Drug conjugates which display significantly greater plasma clearance and correspondingly lower plasma exposure relative to the unconjugated Ligand will be benefited by the present invention as they can be modified as described herein to include a PEG Unit. Significantly greater plasma clearance relative to the unconjugated Ligand refers to a clearance value that is greater than 2λ, greater than 3× or greater than 4× the plasma clearance value for the unconjugated Ligand (see, for example Table 2). Lower plasma exposure relative to the unconjugated Ligand refers to an AUC value that is 30% or less, 25% or less, or 20% or less than the AUC of the unconjugated Ligand (see for example Table 2).

In some embodiments, provided herein are Ligand-Drug Conjugate having a clearance value within about 3× or within about 2× as the clearance value of the unconjugated Ligand and/or an AUC value that is at least 25% or at least 30% of the AUC value of the unconjugated ligand.

In some embodiments, a drug to be used as a Drug Unit in the present invention is one that when conjugated to a Ligand as a Ligand Drug Conjugate lacking PEG or comprising PEG in a serial orientation yields a Ligand-Drug Conjugate that displays significantly greater plasma clearance and correspondingly lower plasma exposure relative to the unconjugated Ligand. Significantly greater plasma clearance relative to the unconjugated Ligand refers to a clearance value that is greater than 2λ, greater than 3× or greater than 4× the plasma clearance value for the unconjugated Ligand (see, for example Table 2). Lower plasma exposure relative to the unconjugated Ligand refers to an AUC value that is 30% or less, 25% or less, or 20% or less than the AUC of the unconjugated Ligand (see for example Table 2).

Ligand-Drug-Conjugates having a hydrophobic Drug Unit or hydrophobic drug-linkers will be benefited by the present invention as they can be modified as described herein to include a PEG Unit and may see their pharmacokinetic parameters enhanced by the application of the present invention.

In preferred embodiments, the ligand is an antibody.

Aggregation

The present inventors have also discovered that the aggregation of certain Ligand-Drug Conjugates can be significantly reduced by the addition of a PEG Unit in a parallel orientation to a hydrophobic drug linker moiety.

In some embodiments, a drug to be used in the present invention is one that when conjugated to a Ligand as a Ligand Drug Conjugate lacking PEG or comprising PEG in a serial orientation and having an average of 4, 8 or 16 drugs per ligand yields a ligand-drug conjugate that has aggregation levels as measured by SEC of 4% or greater, 5% or greater, or 10% or greater.

The present invention provides populations of Ligand-Drug Conjugates having an average of 8 drugs per Ligand Unit or greater, 10 drugs per antibody or greater, 12 drugs per antibody or greater, 16 drugs per antibody or greater, or 32 drug per antibody, having an aggregation level of about 1% or about 2% or about 3% (e.g., formula of 1 or II wherein p is 4 or 8, m is 1, s is zero and t is zero; formula II wherein p is 8, m is 2, s is 1 and t is zero)

In preferred aspects, the Ligand Unit is an antibody.

Selected Embodiments

Exemplary -X-D Units of the present invention include the following wherein the wavy line indicates covalent attached to the $L^P$, A, or AD Unit as the case may be:

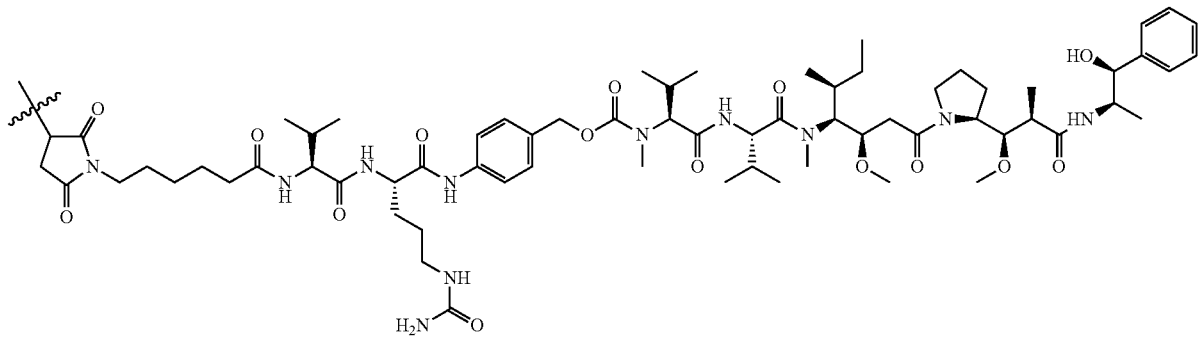

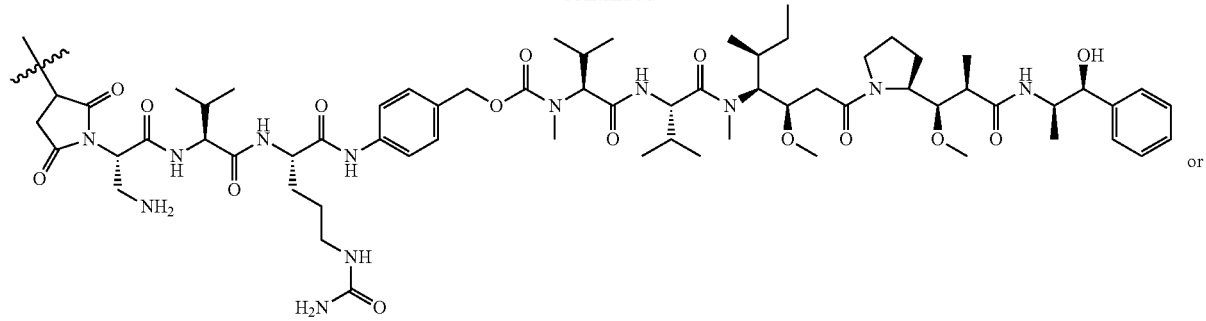
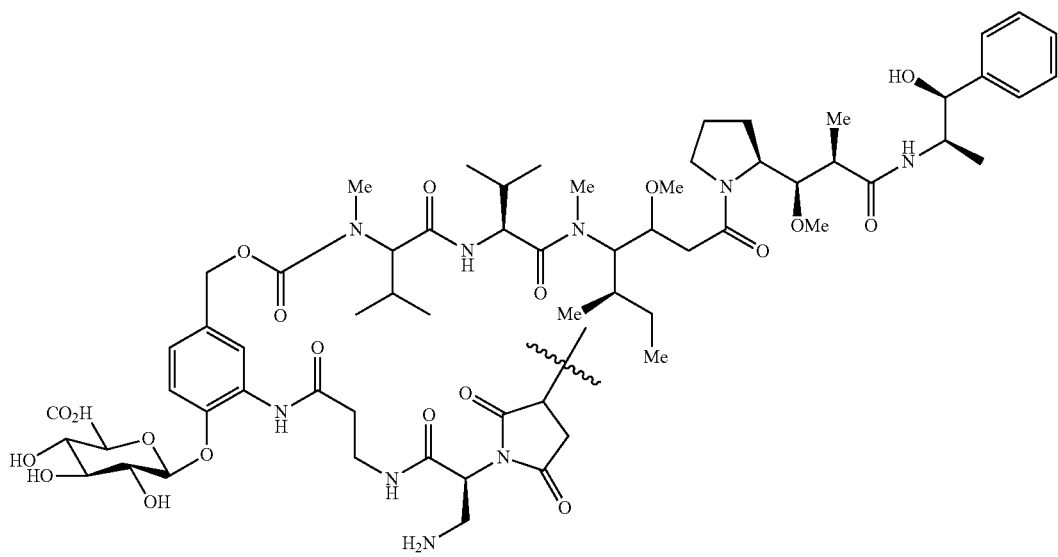
It will be understood that the substituted succinimide depicted above may exist in hydrolyzed form (i.e., a water molecule is added across one and not both of the carbonyl-nitrogen bonds).
Exemplary Drug-Linker Compounds of the present invention include those represented by the following structures:
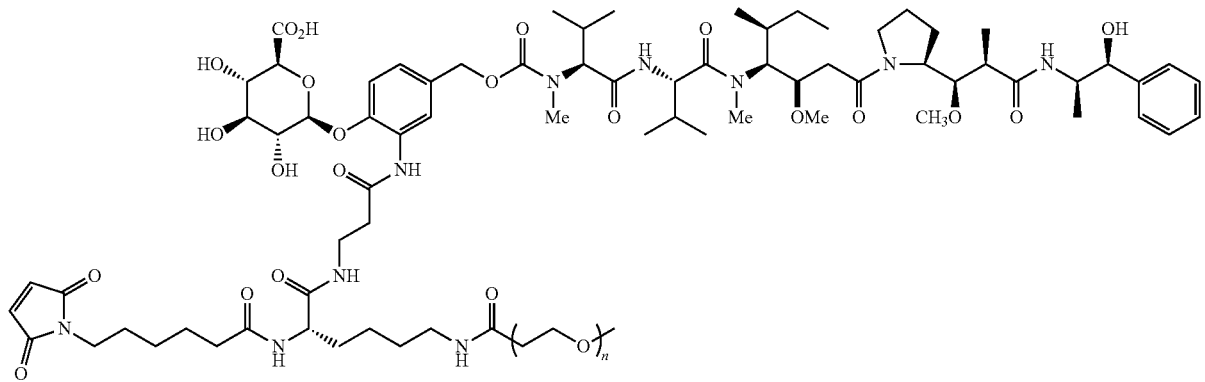

113
-continued
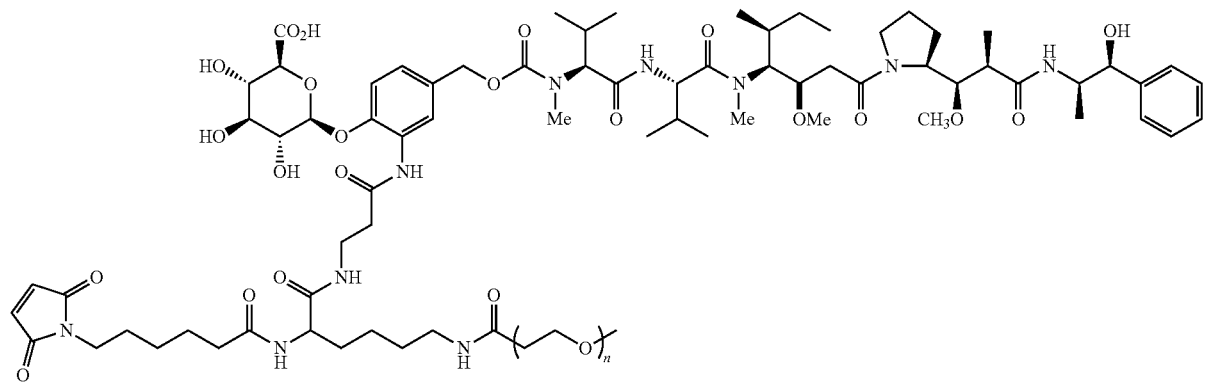
114
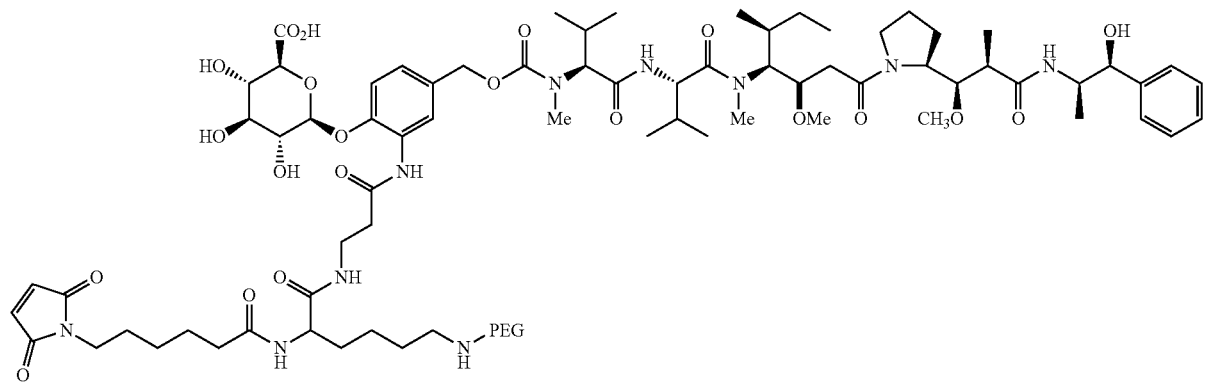
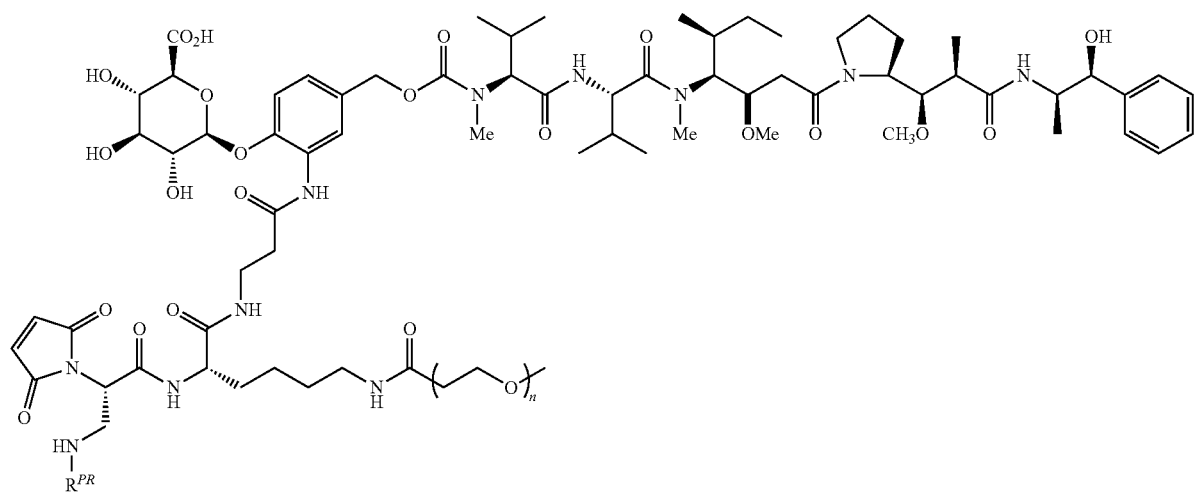

115

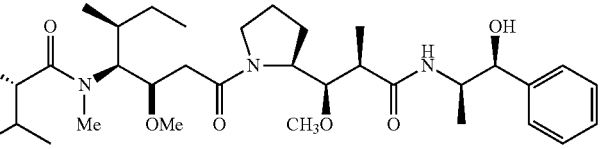

-continued

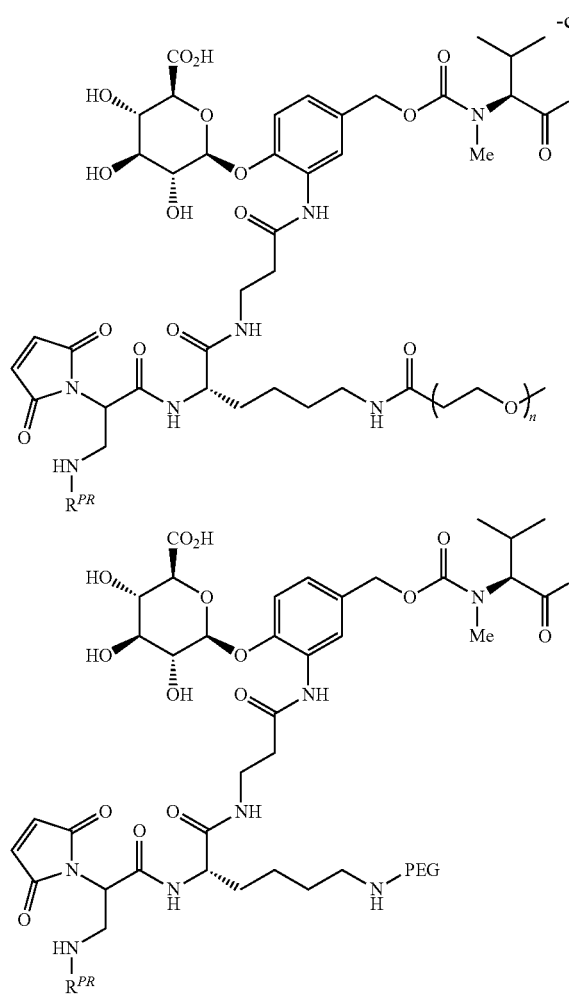

or a pharmaceutically acceptable salt thereof, wherein the PEG unit is as described in any of the embodiments provided herein and can be dispersive or non-dispersive, and n is an integer ranging from 6 to 72, 8 to 72, 10 to 72, 12 to 72, 12 to 38, 12 to 36, 6 to 24, or most preferably 8 to 24 or 12 to 24; $R^{PR}$ is hydrogen or a protecting group, e.g., acid labile protecting group, e.g., BOC. In some embodiments, n is 8, 10, 12 or 24. For a population of Ligand-Drug Conjugates (i.e., an LDC composition) prepared using a dispersive PEG Unit precursor that precursor preferably has a peak average MW corresponding to a PEG Unit having from about 6 to 72, 8 to 72, 10 to 72, 12 to 72, 12 to 38, 12 to 36, 6 to 24, or most preferably 8 to about 24 subunits or from about 12 to about 38 subunits. When PEG is non-dispersive then each LDC of an LDC composition will typically have a PEG Unit that has the same number of PEG subunits (—$OCH_2CH_2$), i.e., same integer value of n. A non-dispersive PEG Unit can, for example, has the structure of

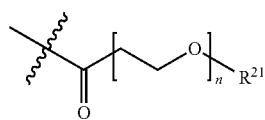

116 wherein $R^{21}$ is a PEG Capping Unit, preferably —$CH_3$ or —$CH_2CH_2CO_2H$, and n is an integer ranging from 8 to 12, 8 to 24 or 12 to 38.

Exemplary Drug-Linker Compounds of the present invention that provide 2× the drug loading include those represented by the following structures

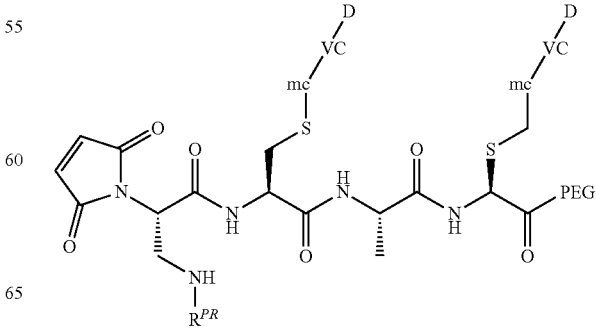

-continued

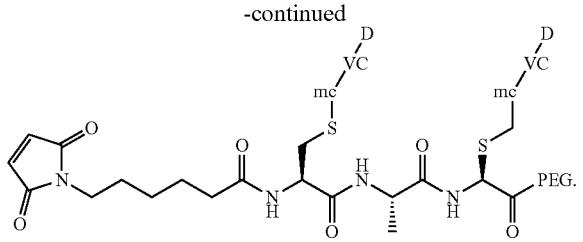

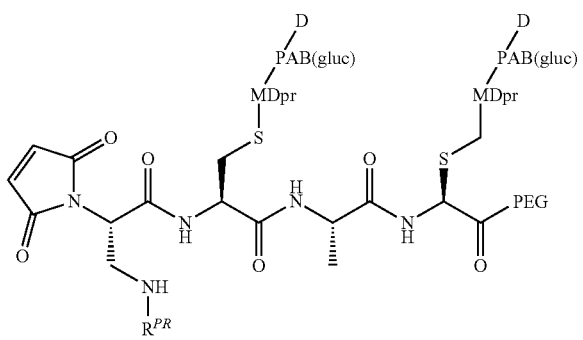

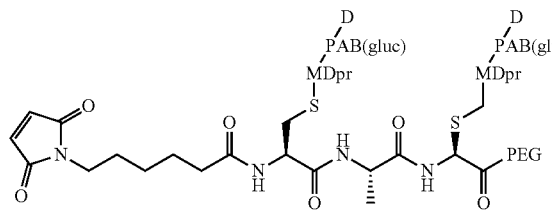

and those structures wherein mc-VC-PAB-D is replaced with mc-VA-PAB-D or mc-VA-D or any other X-D Unit; wherein $R^{PR}$ is hydrogen or a protecting group, e.g., acid labile protecting group, e.g., BOC;
mc-VC-PAB-D has the structure of

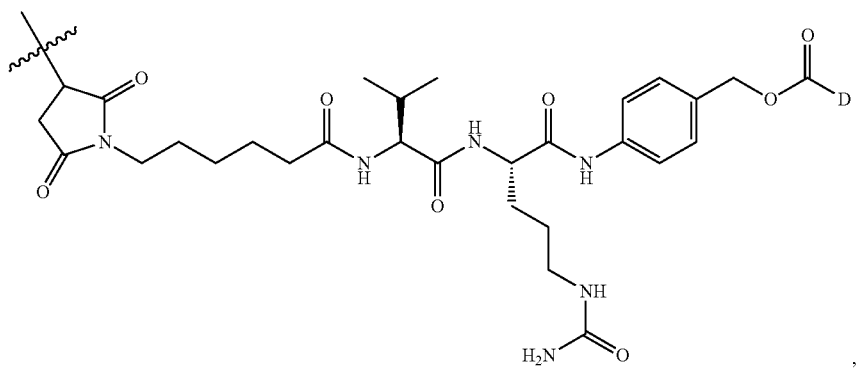 [SMILES: *C1CC(=O)N(CCCCCC(=O)N[C@H](C(=O)N[C@@H](CCCNC(N)=O)C(=O)Nc2ccc(COC([2H])=O)cc2)C(C)C)C1=O]

mc-VA-PAB-D has the structure of

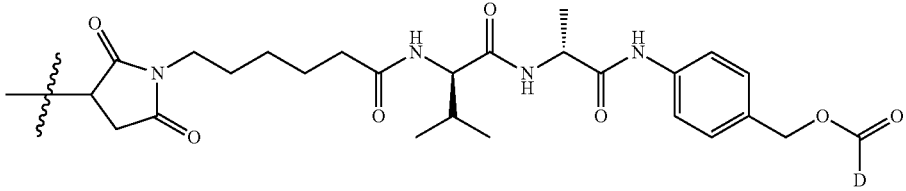 [SMILES: *C1CC(=O)N(CCCCCC(=O)N[C@@H](C(=O)N[C@H](C)C(=O)Nc2ccc(COC([2H])=O)cc2)C(C)C)C1=O]

mc-VA-D has the structure of

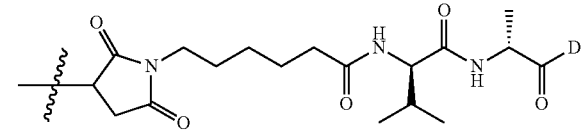 [SMILES: *C1CC(=O)N(CCCCCC(=O)N[C@@H](C(=O)N[C@H](C)C([2H])=O)C(C)C)C1=O]

and

MDpr-PAB(gluc)-D has the structure of

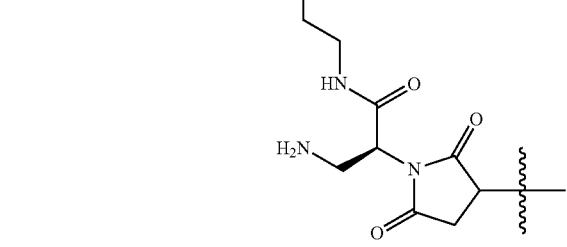

wherein mc-VC-PAB-D, mc-VA-PAB-D, mc-VA-D, and MDpr-PAB(gluc)-D are exemplary -X-D moieties bonded to a PEGylated scaffold, and wherein the wavy line indicates covalent bonding of the succinimide ring of mc or MDpr to the sulfur of the PEGylated scaffold;

and PEG is as described in any of the embodiments provided herein and can be dispersive when describing a population of LDCs prepared using a dispersive PEG Unit precursor, wherein the dispersive PEG Unit precursor preferably has a peak average MW corresponding to a PEG unit having n from about 8 to about 24 subunits or from about 12 to about 38 subunits or is non-dispersive (as defined by a PEG unit having an integer value of n wherein each LDC of an LDC composition will have a PEG Unit that has the same integer value of n). In some embodiments a non-dispersive PEG Unit has the structure of

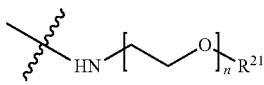

wherein $R^{21}$ is a PEG Capping Unit, preferably —CH$_3$ or —CH$_2$CH$_2$CO$_2$H, the wavy line indicates covalent bonding of the PEG unit to the PEGylated scaffold and n is an integer ranging from 8 to 24 or from 12 to 38.

In some embodiments, an mc moiety in mc-VC-PAB-D, mc-VA-D, and mc-VA-PAB-D, wherein the mc moiety has the structure of

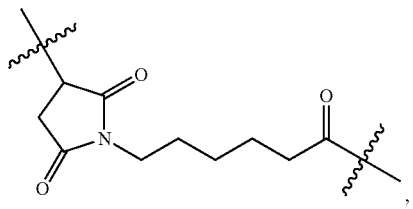 [SMILES: *C(=O)CCCCCN1C(=O)CC(*)C1=O]

wherein the wavy line to the succinimide moiety indicates covalent bonding to the PEGylated scaffold and the wavy line to the carbonyl indicates covalent bonding to the remainder of -X-D, in any of the above structures where that mc moiety is present is replaced with the MDpr moiety, which has the structure of

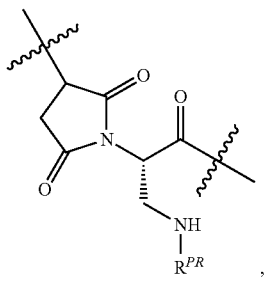

wherein $R^{PR}$ is hydrogen or a protecting group, to provide MDpr-VC-PAB-D, MDpr-VA-D and MDpr-VA-PAB-D, which are further exemplary -X-D moieties.

It will be understood that the substituted succinimide in MDpr in any one of the MDpr-containing -X-D moieties may exist in hydrolyzed form (i.e., a water molecule is added across one and not both of the carbonyl-nitrogen bonds). An -X-D moiety comprised of mc may also have its succinimide ring in hydrolyzed form.

Other Exemplary Drug-Linker Compounds of the present invention that provide 2× the drug loading include the following

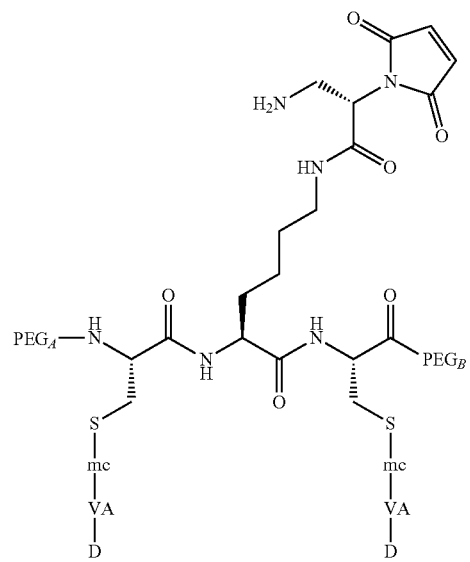

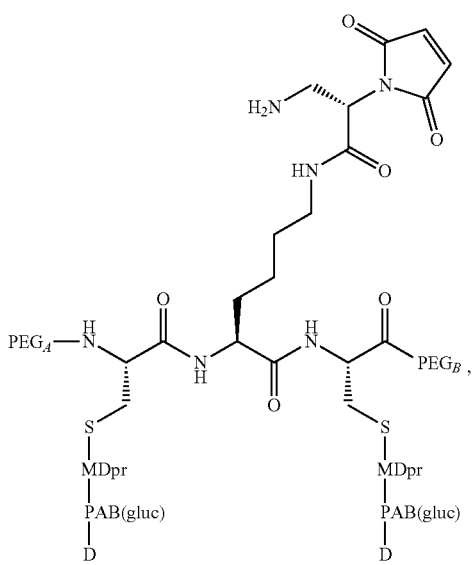

-continued

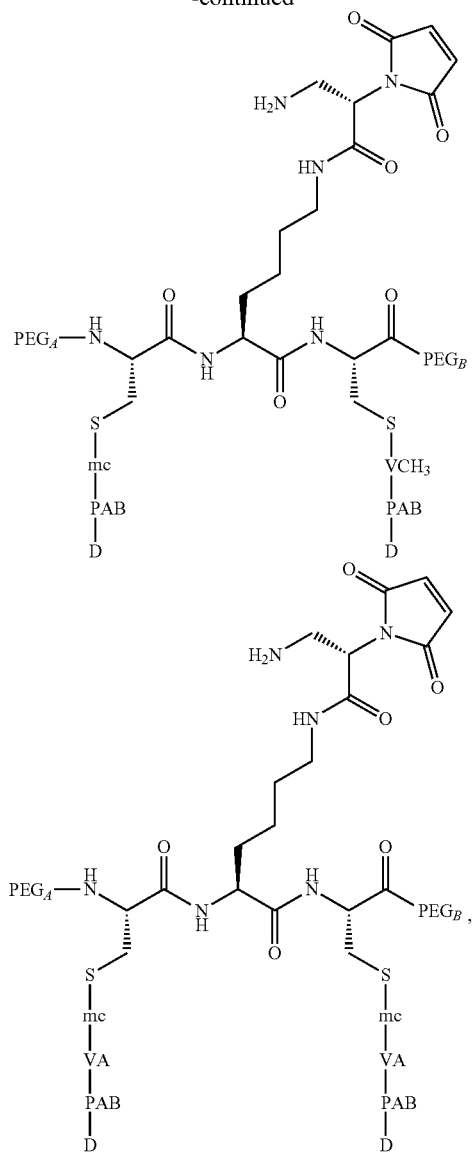

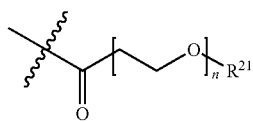

and/or PEG$_B$ is a nondispersive PEG Unit having the structure of

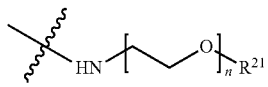

wherein each R$^{21}$ is an independently selected PEG capping unit, an each instance of n independently selected is an integer ranging from 8 to 24 or from 12 to 38. In preferred embodiment one R$^{21}$ is —CH$_3$ and the other is —CH$_2$CH$_2$CO$_2$H.

In some embodiments the mc moiety, which has the structure of

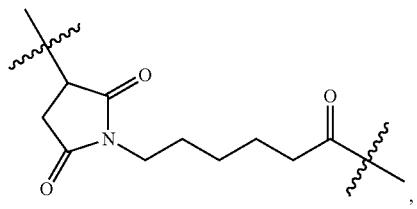 [SMILES: *C(=O)CCCCCN1C(=O)CC(*)C1=O]

in any of the above structures where that moiety is present is replaced with the MDpr moiety, which has the structure of

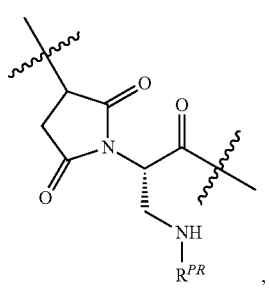

wherein mc-VA-D, mc-VC-PABA-D, mc-VA-PABA-D and MDpr-PAB(gluc)-D are exemplary -X-D moieties as described for the above 2× drug loading structures and wherein PEG$_A$ and PEG$_B$, independently selected, are as described in any of the embodiments for PEG Units provided herein and can be dispersive when referring to a population of ligand-drug conjugates (i.e., an LDC composition) prepared using a dispersive PEG Unit precursor, wherein the dispersive PEG Unit precursor preferably has a peak average MW corresponding to a PEG Unit having n of about 8 to about 24 subunits or of about 12 to about 38 subunits, or PEG$_A$ is non-dispersive (i.e., a PEG Unit having a discrete number of PEG subunits identified by an integer value of so that each LDC of an LDC composition comprised of that ADC will have a PEG Unit that has the same integer value of n). In some embodiments PEG$_A$ is a non-dispersive PEG Unit having the structure of wherein R$^{PR}$ is hydrogen or a protecting group, to provide MDpr-VC-PAB-D, MDpr-VA-D and MDpr-VA-PAB-D as -X-D, In other embodiments the MDpr moiety in the above structure where that moiety is present is replaced with the mc moiety to provide mc-PAB(gluc)D as -X-D.

It will be understood that the substituted succinimide in MDpr in any one of the MDpr-containing -X-D moieties may exist in hydrolyzed form (i.e., a water molecule is added across one and not both of the carbonyl-nitrogen bonds). An -X-D moiety comprised of mc may also have its succinimide ring in hydrolyzed form.

Exemplary Drug-Linker Compounds of the present invention that provide 4× the drug loading include the following

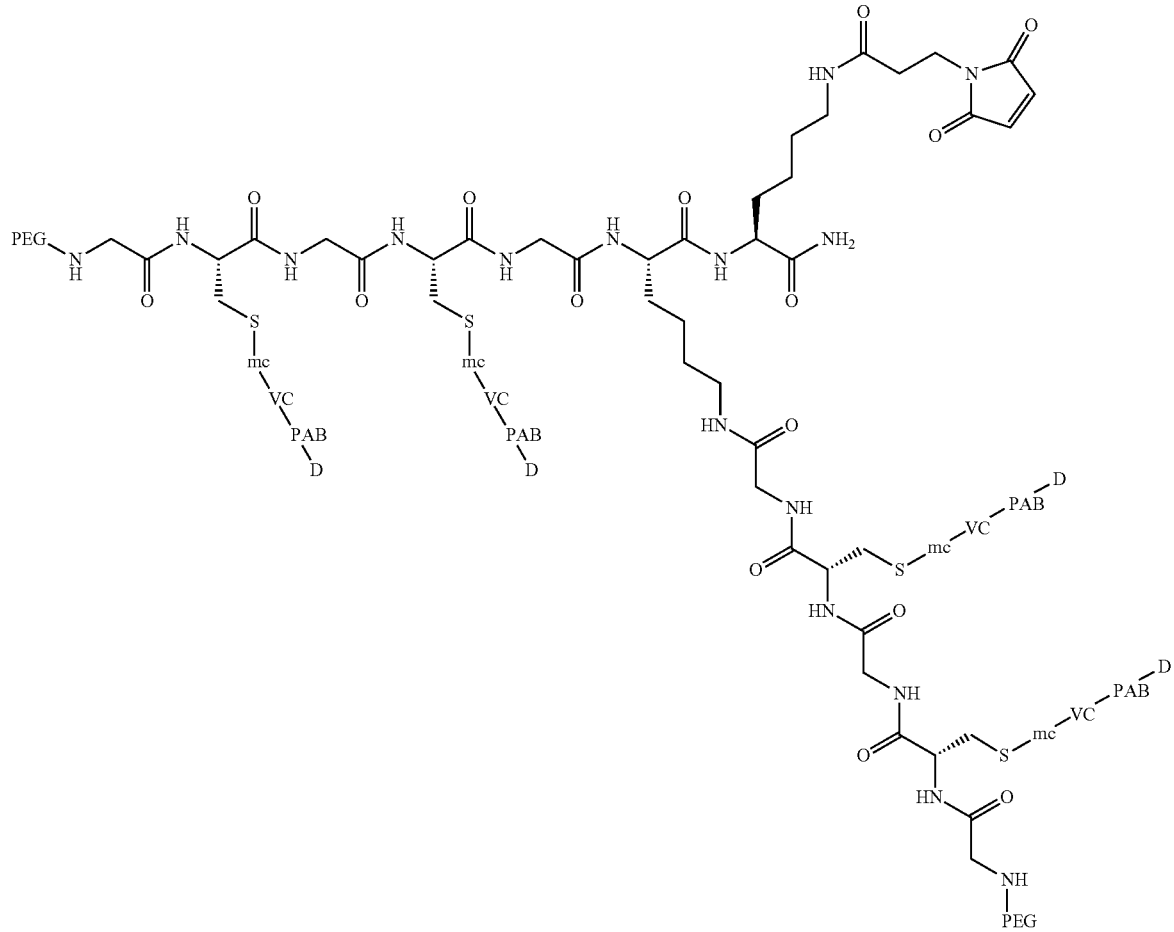

wherein mc-VC-PAB-D is a described for the above 2× drug loading structures; and PEG is as described in any of the embodiments provided herein and can be dispersive when referring to a population of ligand-drug conjugates (i.e., an LDC composition) prepared using a dispersive PEG Unit precursor wherein the dispersive PEG Unit precursor preferably has a peak average MW corresponding to a PEG unit having n of about 8 to about 24 subunits or of about 12 to about 38 subunits, or is non-dispersive (i.e., a PEG Unit having a discrete number of PEG subunits identified by an integer value of so that each LDC of an LDC composition comprised of that ADC will have a PEG Unit that has the same integer value if n). In some embodiments a non-dispersive PEG Unit has the structure of

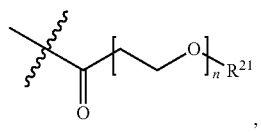
, wherein $R^{21}$ is a PEG Capping Unit, the wavy line indicates covalent bonding to the PEGylated scaffold and n is an integer ranging from 8 to 24 or from 12 to 38. Preferably $R^{21}$ is —$CH_3$ or —$CH_2CH_2CO_2H$.

In some embodiments the mc-VC-PAB-D as the -X-D moiety is replaced with any one of the -X-D moieties described herein including MDpr-VC-PAB-D, mc-VA-PAB-D and MDpr-VA-PAB-D.

It will be understood that the substituted succinimide in MDpr in any one of the MDpr-containing -X-D moieties may exist in hydrolyzed form (i.e., a water molecule is added across one and not both of the carbonyl-nitrogen bonds). An -X-D moiety comprised of mc may also have its succinimide ring in hydrolyzed form.

Other exemplary Drug-Linker Compounds of the present invention that provide 4× the drug loading include the following

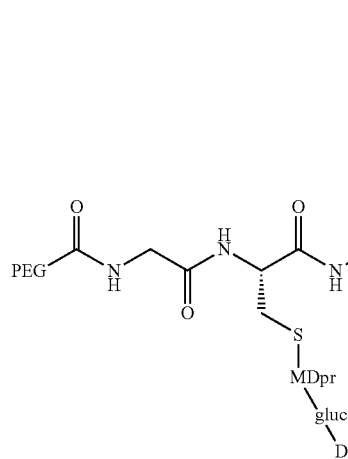
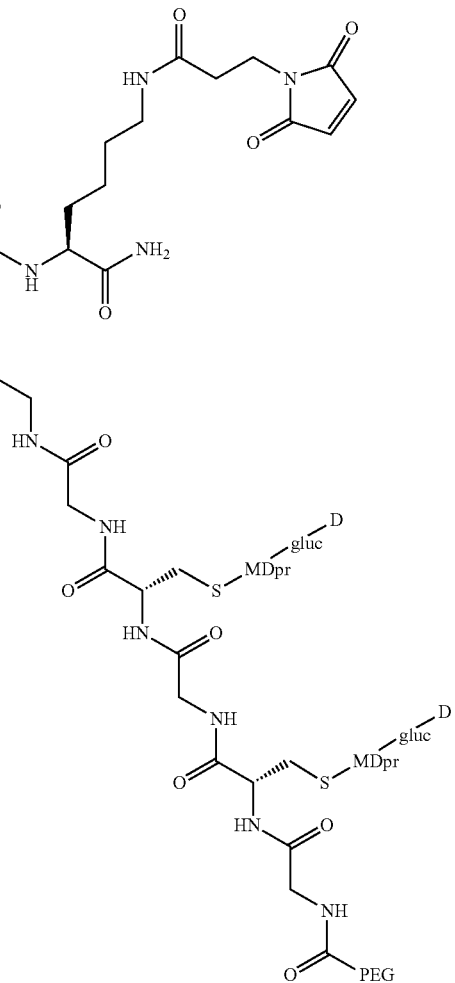

wherein MDpr-PAB(gluc)-D is as described for the above 2× drug loading structures; and PEG is as described in any of the embodiments provided herein and can be dispersive when referring to a population of ligand-drug conjugates (i.e., an LDC composition) prepared using a dispersive PEG Unit precursor wherein the dispersive PEG Unit precursor preferably has a peak average MW corresponding to a PEG unit having n of about 8 to about 24 subunits or of about 12 to about 38 subunits, or $PEG_A$ is non-dispersive (i.e., a PEG Unit having a discrete number of PEG subunits identified by an integer value of so that each LDC of an LDC composition comprised of that ADC will have a PEG Unit that has the same integer value if n). In some embodiments a non-dispersive PEG Unit has the structure of

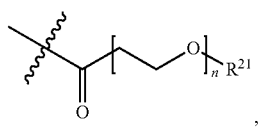

, wherein $R^{21}$ is a PEG Capping Unit, the wavy line indicates covalent bonding to the PEGylated scaffold and n is an integer ranging from 8 to 24 or from 12 to 38. Preferably $R^{21}$ is —$CH_3$ or —$CH_2CH_2CO_2H$.

In some embodiments MDpr-PAB(gluc)-D as the -X-D moiety is replaced with mc-PAB(gluc)-D.

It will be understood that the substituted succinimide in MDpr in any one of the MDpr-containing -X-D moieties may exist in hydrolyzed form (i.e., a water molecule is added across one and not both of the carbonyl-nitrogen bonds). An -X-D moiety comprised of mc may also have its succinimide ring in hydrolyzed form.

Exemplary Ligand-Drug Conjugates of the present invention include those represented by the following structures:
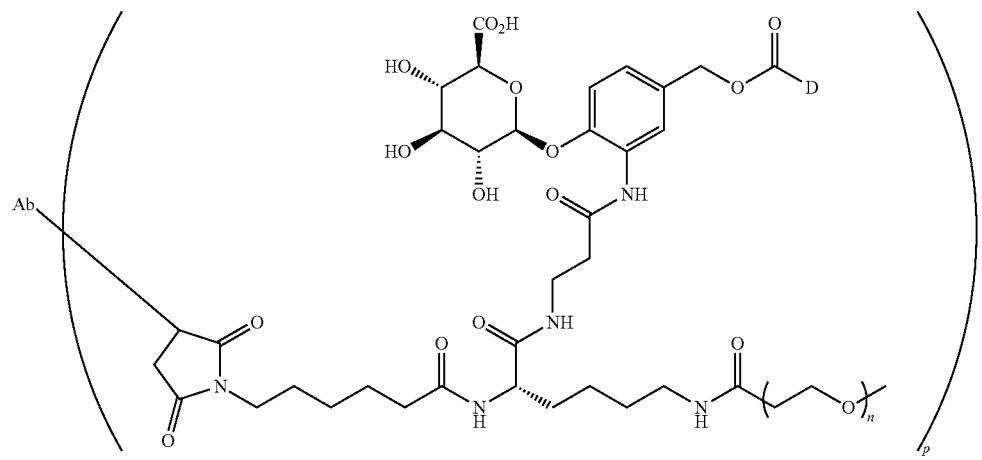
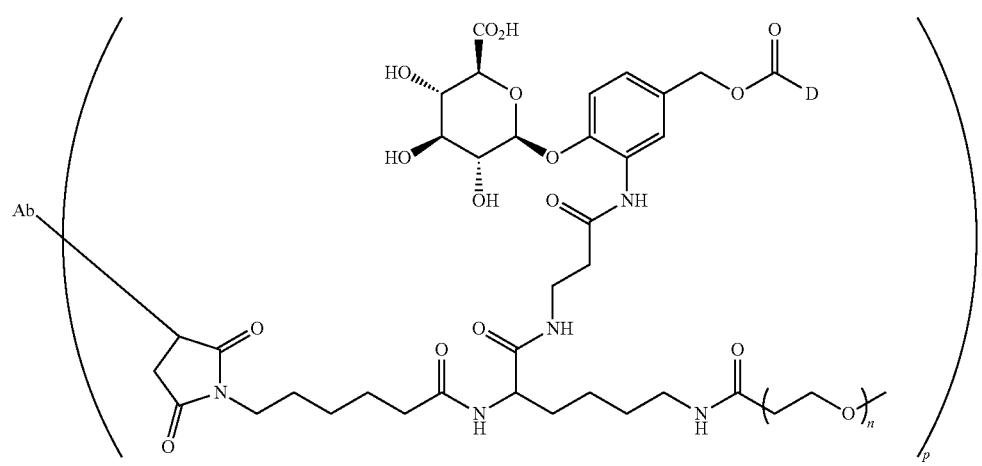
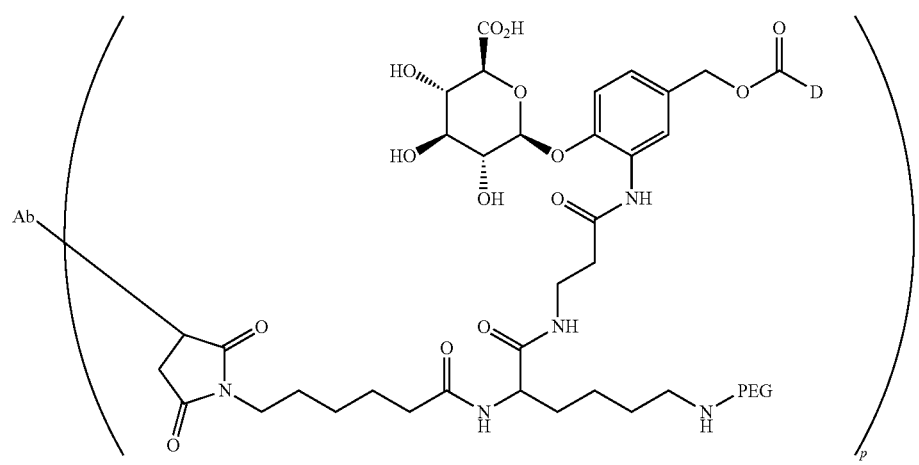

-continued
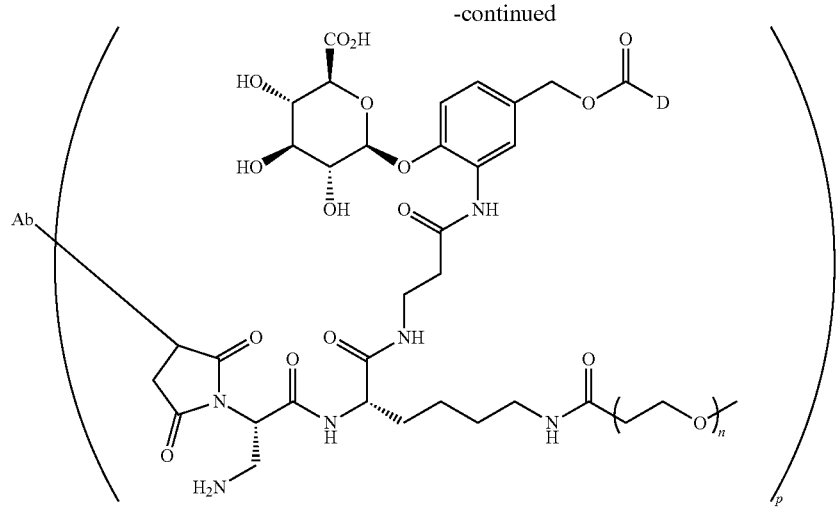
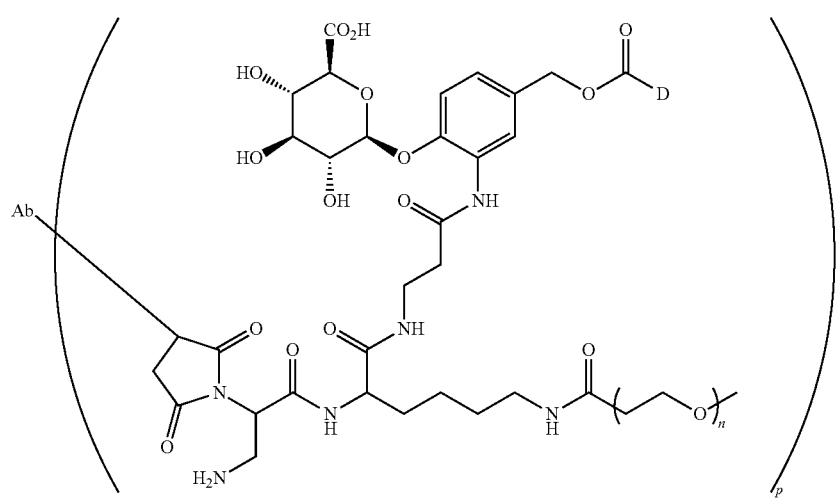
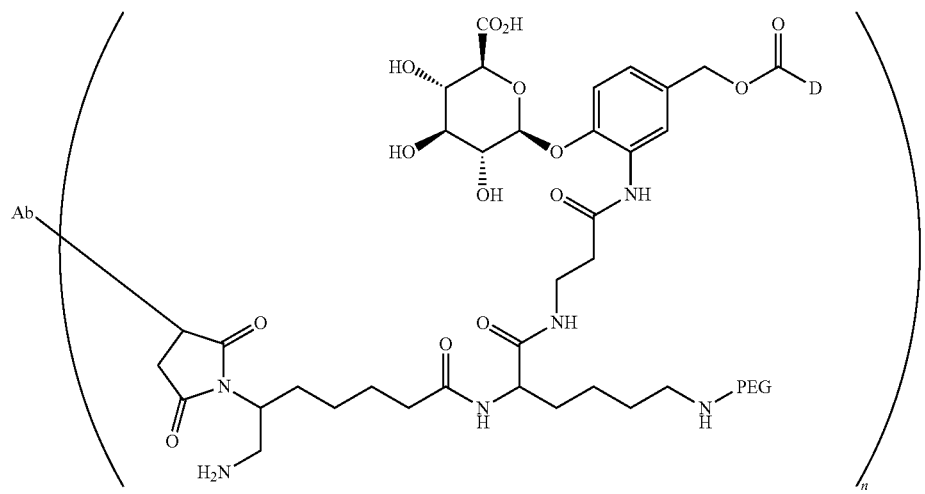

or a pharmaceutically acceptable salt thereof, where p is an integer ranging from 1 to 14, preferably 2 to 12, 6 to 12, 8 to 12, or 8 to 10, Ab is an antibody, preferably a monoclonal antibody, D is a Drug Unit and n is an integer ranging from 6 to 72, 8 to 72, 10 to 72, 12 to 72, 12 to 36 or 38, 6 to 24, or most preferably 8 to 24. PEG is as described in any of the embodiments provided herein for PEG units. It will be understood that an Ab-substituted succinimide may exist in hydrolyzed form (i.e., a water molecule is added across one and not both of the carbonyl-nitrogen bonds), particularly for those antibody-drug conjugates comprised of moieties such as.

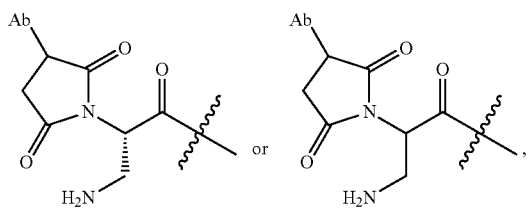

wherein the wavy line indicates covalent binding to the remainder of a drug-ligand moiety of the antibody-drug conjugate.

It will be understood that the above representative structures can also represent compositions in which case p represents the average number of drug-linkers per ligand in the composition. In such embodiments, p is typically not an integer value and can range from 1 to 14, preferably 2 to 12, 6 to 12, 8 to 12, or 8 to 10.

Exemplary Ligand-Drug Conjugates of the present invention that provide 2× the drug loading include those represented by the following structures:

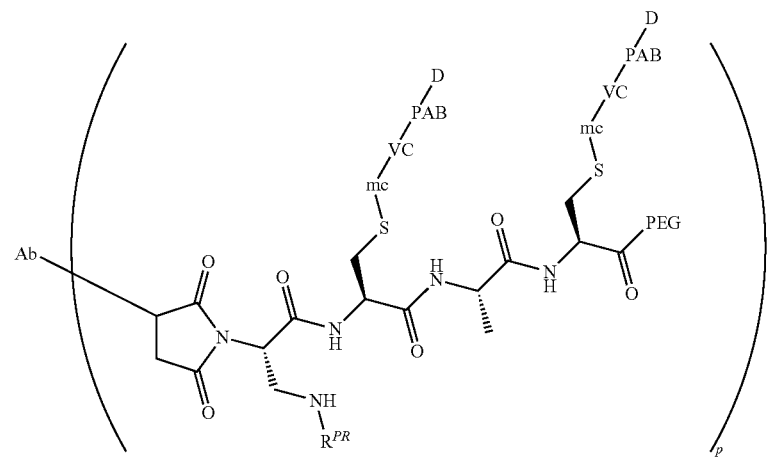

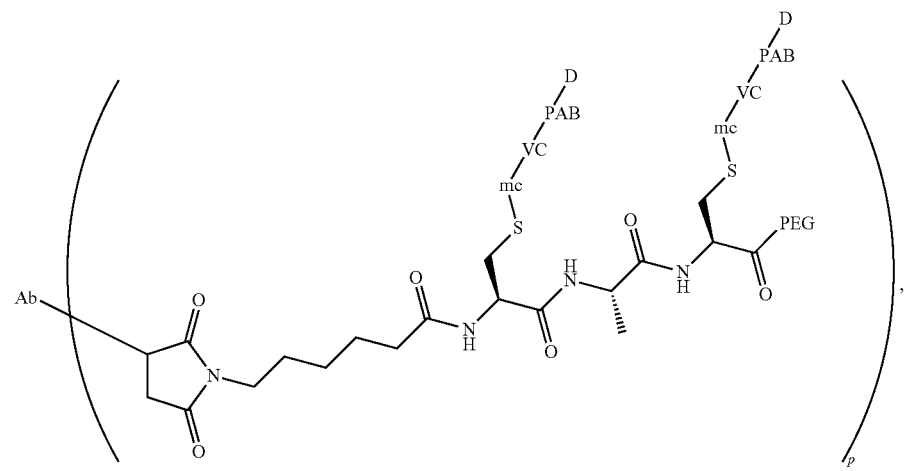

and those structure wherein the -X-D moiety mc-VC-PAB-D is replaced with any one of the -X-D moieties described herein including mc-VA-PAB-D and MDpr-VA-PAB-D

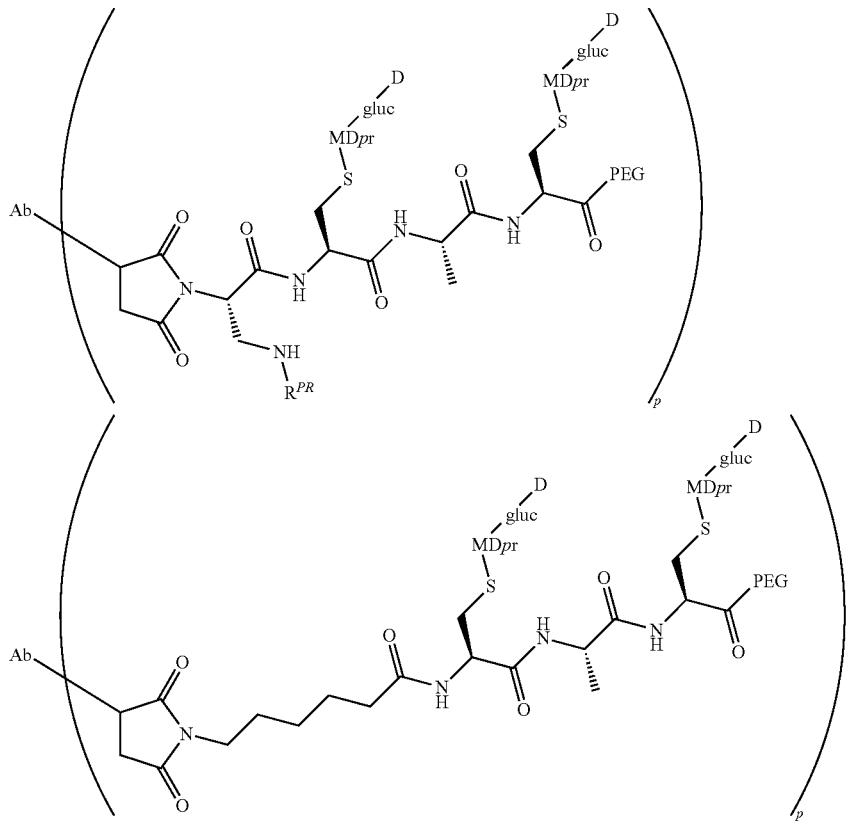

or a pharmaceutically acceptable salt thereof, where p is an integer ranging from 1 to 14, preferably 2 to 12, 6 to 12, 8 to 12, or 8 to 10, Ab is an antibody, preferably a monoclonal antibody, D is a Drug Unit and n is an integer ranging from 6 to 72, 8 to 72, 10 to 72, 12 to 72, 12 to 36 or 38, 6 to 24, or most preferably 8 to 24. PEG is as described in any of the embodiments provided herein for PEG units. It will be understood that the substituted succinimide bonded to Ab or S of the may exist in hydrolyzed form (i.e., a water molecule is added across one and not both of the carbonyl-nitrogen bonds).

It will be understood that the succinimide in a MDpr moiety substituted with Ab or in a -X-D moiety may exist in hydrolyzed form (i.e., a water molecule is added across one and not both of the carbonyl-nitrogen bonds). The succinimide in a mc moiety substituted with Ab or in a -X-D moiety or can also exist in hydrolyzed form.

In any of the embodiments above, the Drug Unit D can be MMAE as follows wherein the wavy line indicates the site of attachment to the remainder of a drug-linker moiety.

In some preferred aspects, including those wherein D is MMAE, p is 6, 7, 8, 9, 10, 11, or 12. In some embodiments, including those wherein D is MMAE, the antibody is conjugated to the linker via a sulfur atom of a cysteine residue of the antibody. The cysteine residue can be, naturally or non-naturally occurring. For example, in some aspects, the cysteine will be from an interchain disulfide. In other aspects, the cysteine residue will be from an introduced cysteine (e.g., cysteine introduced at position 239). In some aspects, the antibody will be attached to the drug-linkers via its interchain disulfides and via introduced cysteines.

In any of the embodiments above, the Drug Unit D can be MMAF as follows wherein the wavy line indicates the site of attachment to the remainder of a drug-linker moiety.

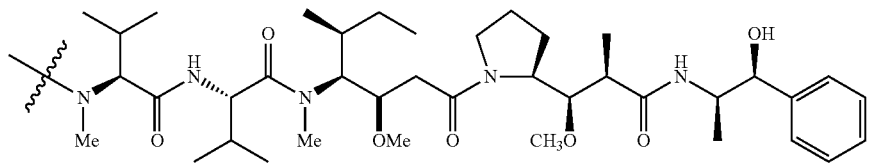

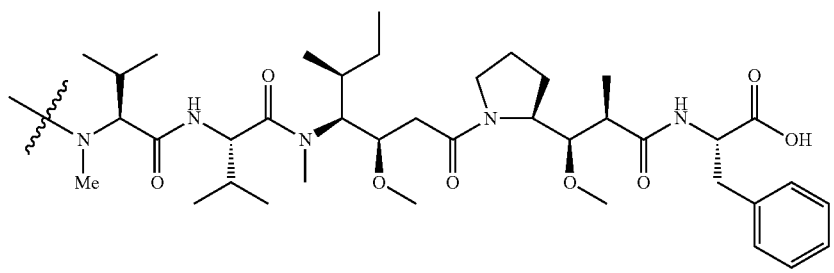 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

In any of the embodiments above, the Drug Unit D can be a camptothecin compound as exemplified for camptothecin itself as follows wherein the wavy line indicates the site of attachment to the remainder of a drug-linker moiety:

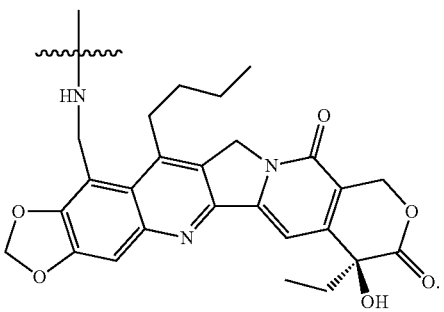 [SMILES: *NCc1c2c(cc3nc4c(c(CCCC)c13)Cn1c-4cc3c(c1=O)COC(=O)[C@]3(O)CC)OCO2]

In any of the embodiments above, the Drug Unit D can be a *vinca* compound as exemplified for vinblastine hydrazide as follows wherein the wavy line indicates the site of attachment to the remainder of a drug-linker moiety:

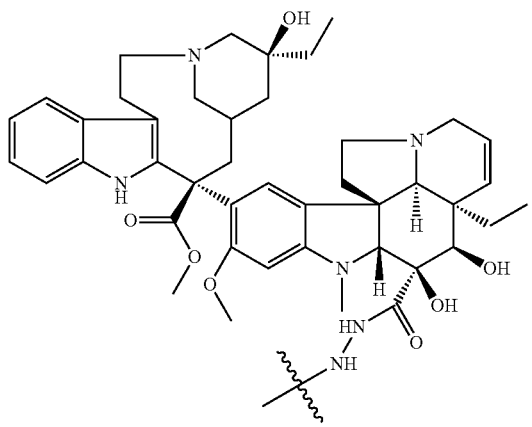

In any of the embodiments above, the Drug Unit D can be a anthracyclin compound as exemplified as follows wherein the wavy line indicates the site of attachment to the remainder of a drug-linker moiety:

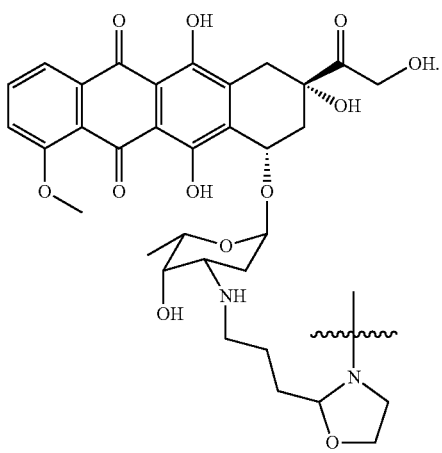 [SMILES: *N1CCOC1CCCNC1CC(O[C@H]2C[C@](O)(C(=O)CO)Cc3c(O)c4c(c(O)c32)C(=O)c2c(OC)cccc2C4=O)OC(C)C1O]

Exemplary PEGylated scaffolds in thiol-protected Linker Intermediate compounds and the corresponding Ligand-Linker compounds of the present invention include the following:

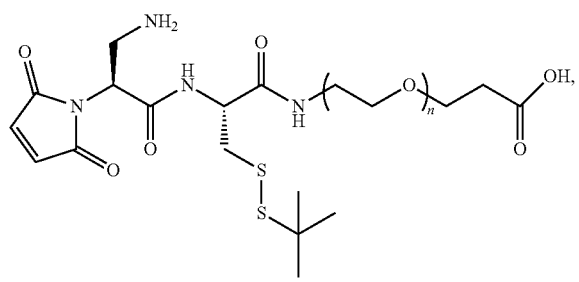
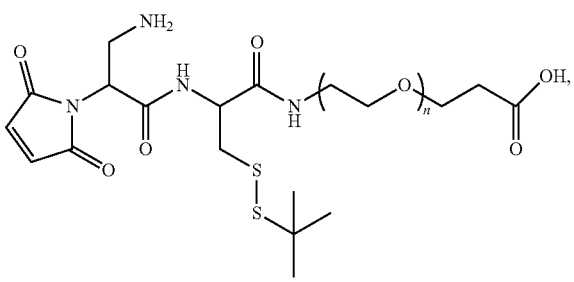

-continued
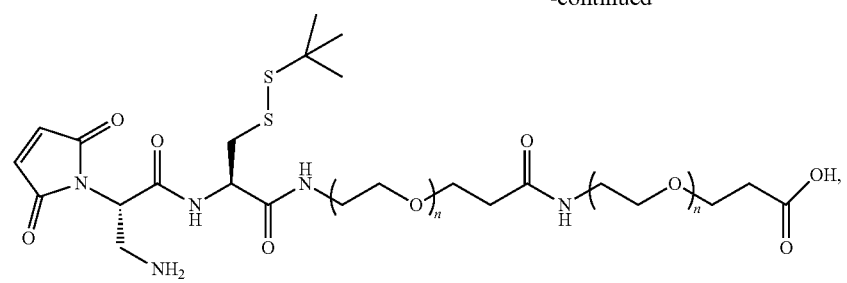
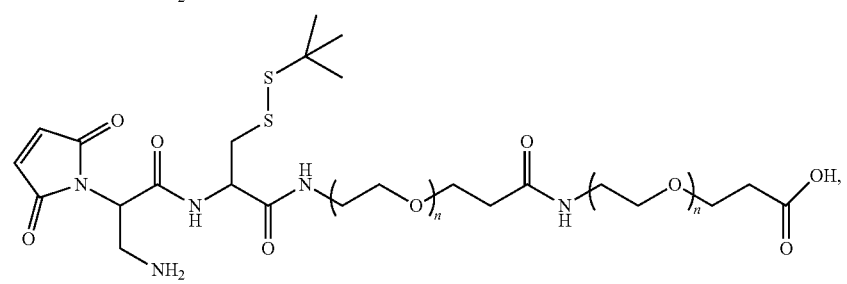
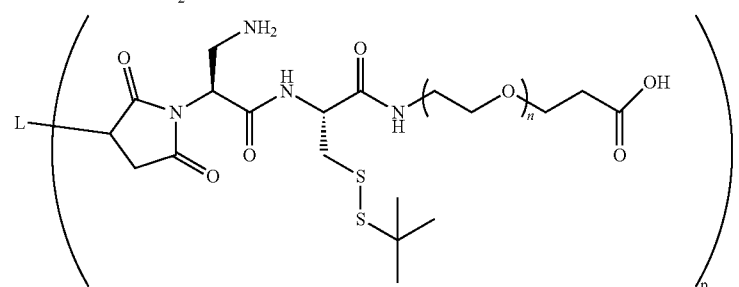
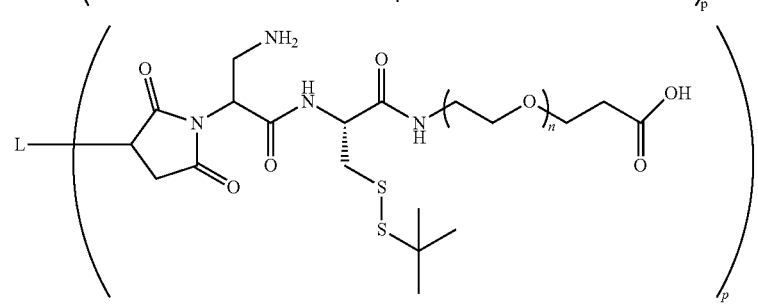
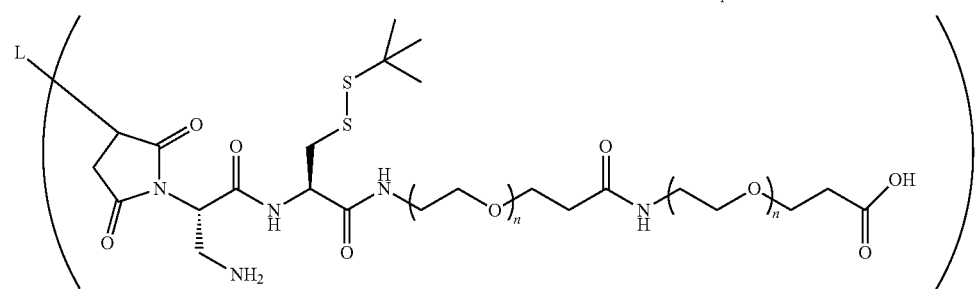
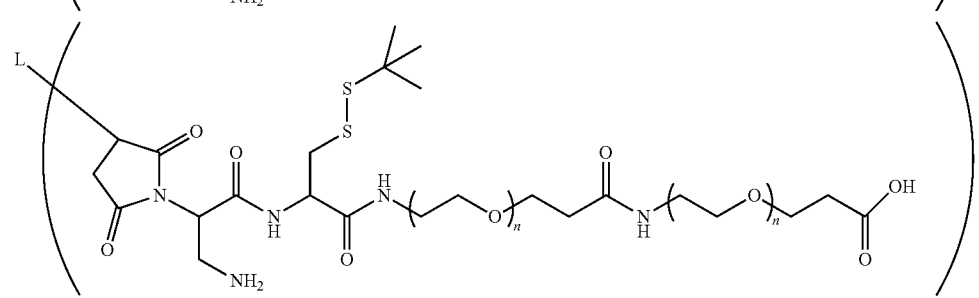

or a pharmaceutically acceptable salt thereof, wherein
n is 2 to 72, preferably 4 to 72 or 8 to 72 or 8 to 24;
p is 1 to 14, preferably about 2 to about 12; and
Ab is an antibody, preferably a monoclonal antibody.

It will be understood in the formulas above that the Ligand-substituted succinimides may exist in their hydrolyzed form (i.e. a water molecule is added across one and not both of the succinimide's C—N bonds). Further, in any of the above embodiments, the t-butylthiol protecting group can be replaced by any other suitable thiol protecting group.

Exemplary multiplexed PEGylated scaffolds as Linker Intermediate compounds and the corresponding Ligand-Linker compounds of the present invention include the following:

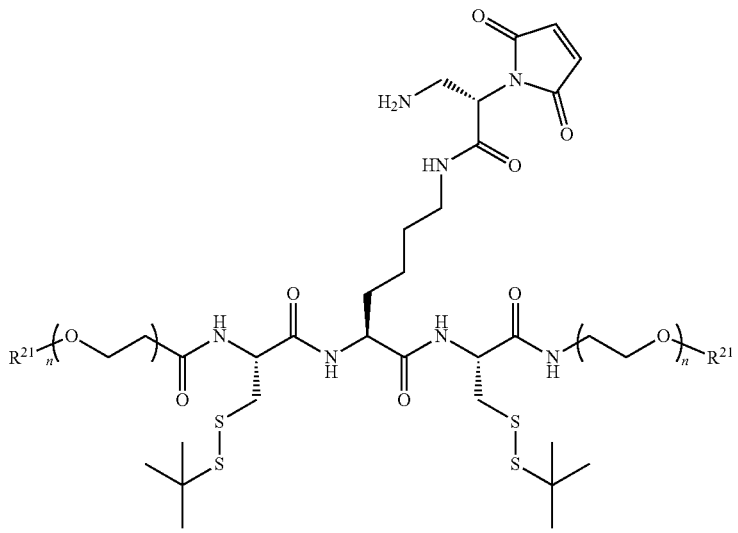

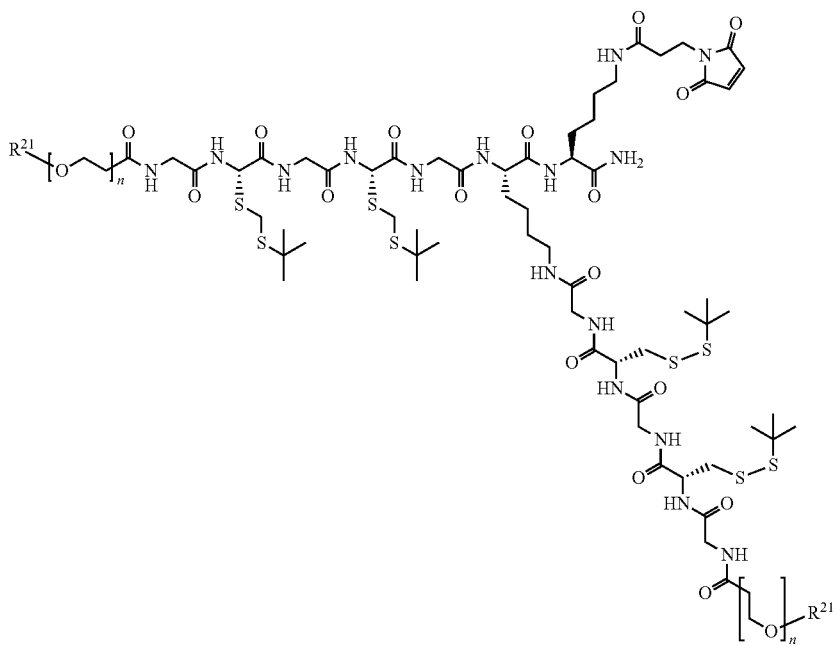

-continued
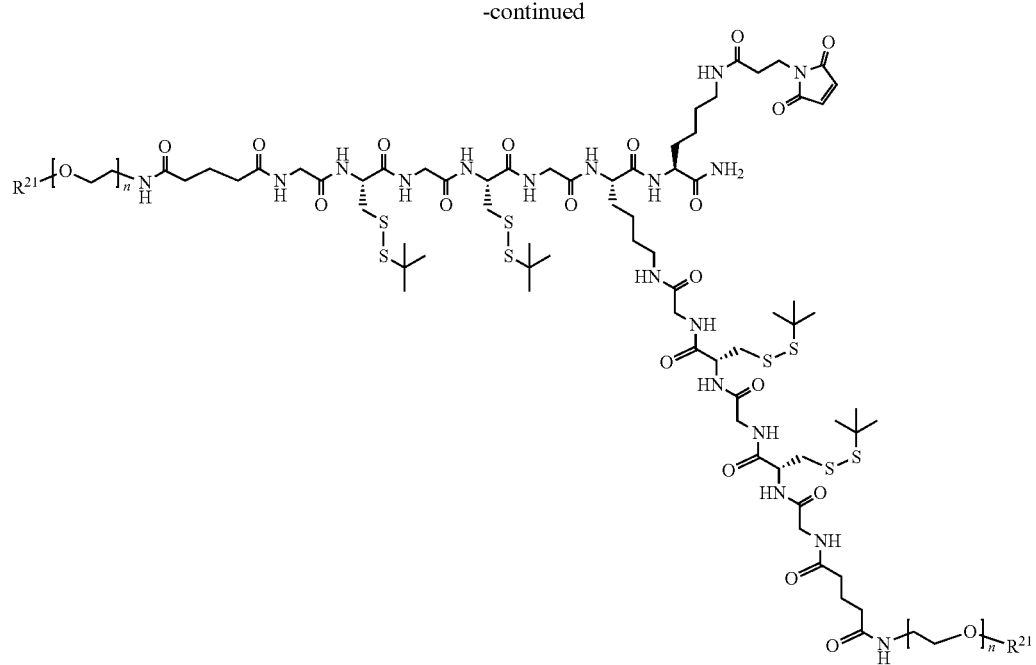
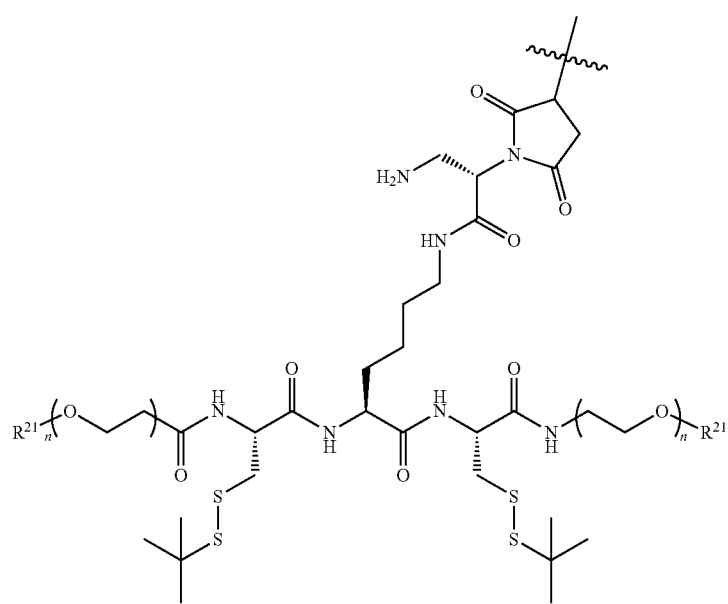

-continued

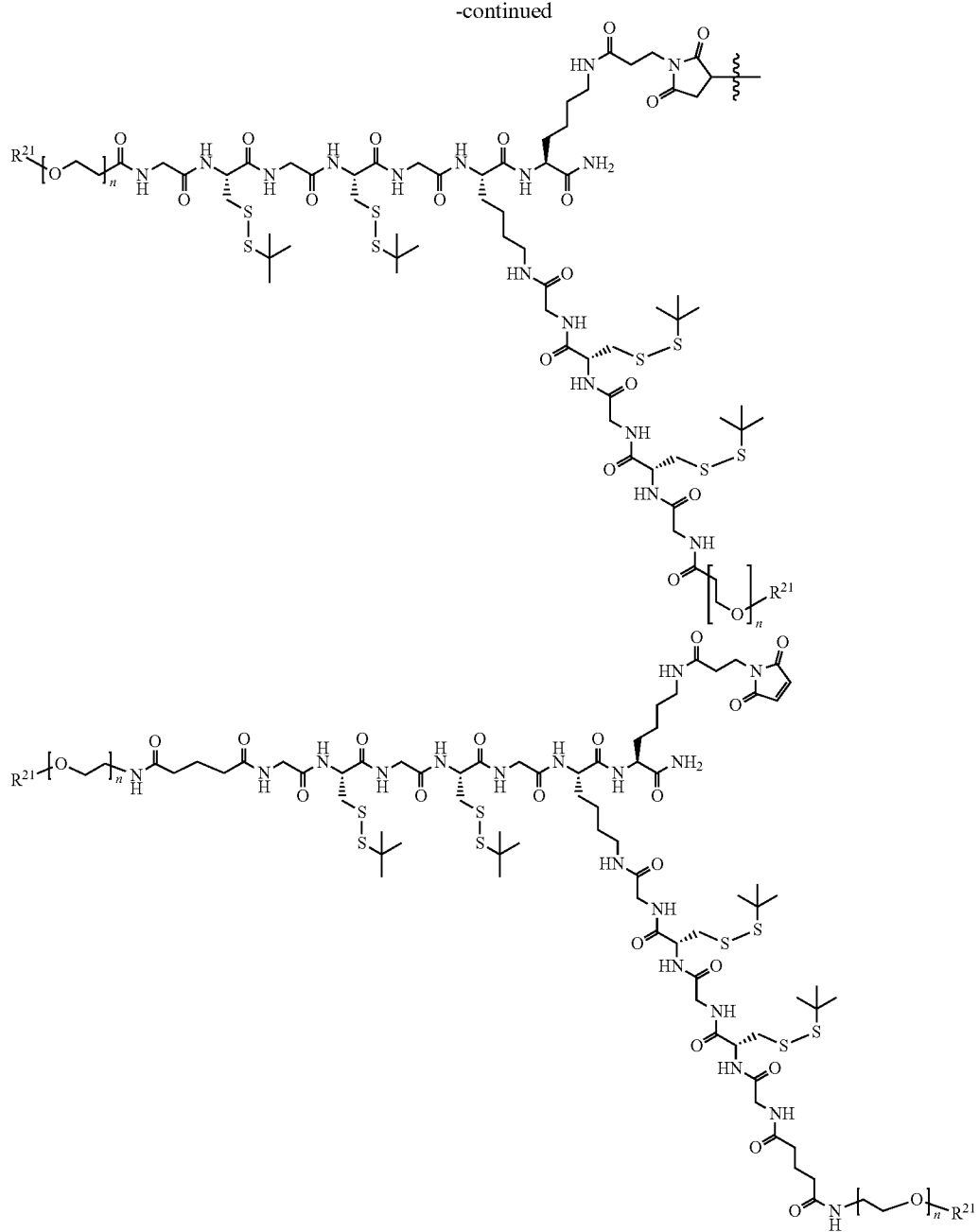

wherein the wavy line indicated covalent attachment to a Ligand Unit, $R^{21}$ are independently selected PEG capping groups, preferably methyl or 3-propionic acid, and n independently ranges from 2 to 72, preferably 4 to 72 or 8 to 72 or 8 to 24 with 24 more preferred. The thiol-protecting group can be replaced by another suitable thiol protecting group.

In some preferred embodiments, p is 6, 7, 8, 9, 10, 11, or 12. In some embodiments, the antibody is conjugated to the linker via a sulfur atom of a cysteine residue of the antibody. The cysteine residue can be, naturally or non-naturally occurring. For example, in some embodiments, the cysteine will be from an interchain disulfide. In other embodiments, the cysteine residue will be from an introduced cysteine (e.g., cysteine introduced at position 239). In some embodiments, the antibody will be attached to the drug-linkers via its interchain disulfides and via introduced cysteines.

In some aspects of the present invention, there are no more than 50, no more than 45, no more than 40, no more than 35, no more than 30, or no more than 25 intervening atoms between the Ligand Unit and the Drug Unit of the Ligand-Drug Conjugates. In some aspects of the present invention, there are no more than 40, no more than 35, no more than 30, or no more than 25 intervening atoms between the Ligand Unit and the Cleavable Unit of the Ligand-Drug Conjugates.

In some embodiments, there are fewer intervening atoms between the Ligand and the Drug Unit of the Ligand-Drug Conjugates than there are atoms in the PEG Unit. In some embodiments, there are fewer intervening atoms between the Ligand and the Cleavable Unit of the Ligand-Drug Conjugates than there are atoms in the PEG Unit.

In some embodiments, there are fewer intervening atoms between the Ligand and the Drug Unit of the Ligand-Drug Conjugates than there are intervening atoms between the distal end of the PEG Unit and the Parallel Connector Unit. In some embodiments, there are fewer intervening atoms between the Ligand and the Cleavable Unit of the Ligand-Drug Conjugates than there are intervening atoms between the distal end of the PEG Unit and the Parallel Connector Unit.

In preferred embodiments of the present invention, the drug is preferably an auristatin (e.g., MMAE or an auristatin having comparable or greater hydrophobicity than MMAE), the releaseable assembly unit comprises a glucuronide unit cleavable by a beta-glucuronidase; and the PEG Unit comprises at least 6, at least 8, at least 10, or at least 12 subunits but no more than 72 subunits, preferably no more than 36 or 24 subunits. In preferred aspects, the PEG Unit will comprise about 8 to about 24 subunits, most preferably about 12 subunits. The other components of the Ligand-Drug Conjugate or Intermediates thereof can be as described in any of the embodiments provided herein.

Preferred compositions of the present invention comprise a population of Ligand-Drug Conjugates wherein the Ligand Unit is an antibody (e.g., an intact antibody) the Drug Unit is an auristatin or non-auristatin (preferably an auristatin, e.g., MMAE or an auristatin having comparable or greater hydrophobicity than MMAE), the releaseable assembly unit comprises a glucuronide unit cleavable by a beta-glucuronidase; the PEG Unit comprises at least 6, at least 8, at least 10, or at least 12 subunits, but no more than 72 subunits, preferably no more than 36 or 24 subunits; and the average number of drug-linker moieties per antibody in the composition is at least 6, or at least about 8. In preferred aspects, the PEG Unit will comprise about 8 to about 24 subunits, most preferably about 12 subunits. The other components of the Ligand-Drug Conjugate can be as described in any of the embodiments provided herein.

Methods of Use

Treatment of Cancer

The Ligand-Drug Conjugates are useful for inhibiting the multiplication of a tumor cell or cancer cell, causing apoptosis in a tumor or cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cancer-cell or a tumor-cell-associated antigen, and the Ligand-Drug Conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, via a cleavable mechanism, the drug is released within the cell. In an alternative embodiment, the Drug or Drug unit is cleaved from the Ligand-Drug Conjugate outside the tumor cell or cancer cell, and the Drug or Drug unit subsequently penetrates the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, Ligand-Drug Conjugates that target a cancer cell antigen present in hematopoietic cancers can be useful treating hematologic malignancies (e.g., anti-CD30, anti-CD70, anti-CD19, anti-CD33 binding Ligand unit (e.g., antibody) can be useful for treating hematologic malignancies). Ligand-Drug Conjugates that target a cancer cell antigen present on solid tumors can be useful treating such solid tumors.

Cancers that can be treated with a Ligand-Drug Conjugate include, but are not limited to, hematopoietic cancers such as, for example, lymphomas (Hodgkin Lymphoma and Non-Hodgkin Lymphomas) and leukemias and solid tumors. Examples of hematopoietic cancers include, follicular lymphoma, anaplastic large cell lymphoma, mantle cell lymphoma, acute myeloblastic leukemia, chronic myelocytic leukemia, chronic lymphocytic leukemia, diffuse large B cell lymphoma, and multiple myeloma. Examples of solid tumors include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Multi-Modality Therapy for Cancer

Cancers, including, but not limited to, a tumor, metastasis, or other disease or disorder characterized by uncontrolled cell growth, can be treated or inhibited by administration of a Ligand-Drug Conjugate.

In other embodiments, methods for treating cancer are provided, including administering to a patient in need thereof an effective amount of a Ligand-Drug Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Ligand-Drug Conjugates can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a Ligand-Drug Conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Treatment of Autoimmune Diseases

The Ligand-Drug Conjugates are useful for killing or inhibiting the replication of a cell that produces an autoimmune disease or for treating an autoimmune disease. The Ligand-Drug Conjugates can be used accordingly in a variety of settings for the treatment of an autoimmune disease in a patient. The Ligand-Drug Conjugates can be used to deliver a drug to a target cell. Without being bound by theory, in one embodiment, the Ligand-Drug Conjugate associates with an antigen on the surface of a target cell, and the Ligand-Drug Conjugate is then taken up inside a target-cell through receptor-mediated endocytosis. Once inside the cell, the Linker unit is cleaved, resulting in release of the Drug or Drug unit. The released Drug is then free to migrate in the cytosol and induce cytotoxic or cytostatic activities. In an alternative embodiment, the Drug is cleaved from the Ligand-Drug Conjugate outside the target cell, and the Drug or Drug unit subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand unit binds to activated lymphocytes that are associated with the autoimmune disease state.

In a further embodiment, the Ligand-Drug Conjugate kills or inhibit the multiplication of cells that produce an autoimmune antibody associated with a particular autoimmune disease.

Particular types of autoimmune diseases that can be treated with the Ligand-Drug Conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); and activated B lymphocyte-related disorders (e.g., systemic lupus erythematosus, Goodpasture's syndrome, rheumatoid arthritis, and type I diabetes).

Multi-Drug Therapy of Autoimmune Diseases

Methods for treating an autoimmune disease are also disclosed including administering to a patient in need thereof an effective amount of a Ligand-Drug Conjugate and another therapeutic agent known for the treatment of an autoimmune disease.

Compositions and Methods of Administration

The present invention provides pharmaceutical compositions comprising the Ligand-Drug Conjugates described herein and a pharmaceutically acceptable carrier. The Ligand-Drug Conjugates can be in any form that allows for the compound to be administered to a patient for treatment of a disorder associated with expression of the antigen to which the Ligand unit binds. For example, the conjugates can be in the form of a liquid or solid. The preferred route of administration is parenteral. Parenteral administration includes subcutaneous injections, intravenous, intramuscular, intrasternal injection or infusion techniques. In one aspect, the compositions are administered parenterally. In one aspect, the conjugates are administered intravenously. Administration can be by any convenient route, for example by infusion or bolus injection Pharmaceutical compositions can be formulated so as to allow a compound to be bioavailable upon administration of the composition to a patient. Compositions can take the form of one or more dosage units, where for example, a tablet can be a single dosage unit.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition can comprise from about 0.01 to about 100 mg of a Ligand-Drug Conjugate per kg of the animal's body weight. In one aspect, the composition can include from about 1 to about 100 mg of a Ligand-Drug Conjugate per kg of the animal's body weight. In another aspect, the amount administered will be in the range from about 0.1 to about 25 mg/kg of body weight of a compound.

Generally, the dosage of a conjugate administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The term "carrier" refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Exemplary Methods

Provided herein are methods of preparing a Drug-Linker compound represented by the structure of formula (IV), (V), or (VI) as described herein, the method comprising step (a): contacting an Intermediate Linker compound represented by the structure of formula VII, VIII or IX as described herein with sufficient amount of X'-D moieties to react with $L^{P'}$ or AD' so as to form a $L^P$-X-D or an AD-X-D moiety for each instance of $L^{P'}$ and AD', wherein -X-D is a Releasable Assembly Unit attached to a Drug Unit; 'and X'-D is a Releasable Assembly Unit precursor attached to a Drug Unit wherein X' is capable of reacting with $L^{P'}$ and/or AD'.

In some aspects, the Drug-Linker so prepared will have the structure represented by formula IVa, IVb, Va, Vb, Vc, VIa or VIb as described herein and the Intermediate Linker compound used in step (a) has the structure represented by formula VIIIa, VIIIb, VIIIc, VIIId, IXa or IXb as described herein.

The method can further comprise the step of (a'): deprotecting a suitably protected Intermediate Linker compound corresponding in structure to formula VIIIa, VIIIb, VIIIc, VIIId, IXa or IXb wherein t is 0 and wherein suitably protected AD' or $L^{P'}$ has the structure of

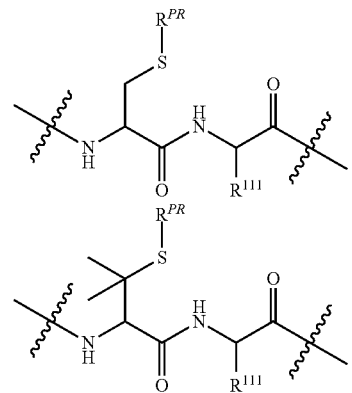

wherein $R^{111}$ is independently selected from hydrogen, p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-

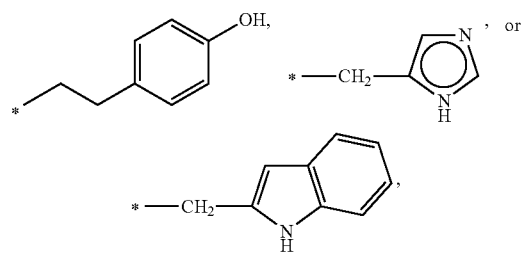

with suitable protection when required, wherein $R^{PR}$ is a suitable thiol protecting group and the wavy line indicates covalent attachment of the suitable protected AD' or $L^{P'}$ moiety within the Intermediate Linker compound;

and in step (a) contacting the resulting deprotected formula VIIIa, VIIIb, VIIIc, VIIId, IXa or IXb product from step (a') with an X'-D moiety wherein X' is comprised of a maleimide moiety capable of reacting with the free thiol group of AD' or $L^{P'}$ to form a thio-substituted succinimide moiety.

Alternatively, the method can further comprise the step of a': deprotecting an Intermediate Linker compound precursor to formula VIIIa, VIIIb, VIIIc, VIIId, IXa or IXb having that structure wherein t is 1 and AD'-AD' or AD'-$L^{P'}$ is suitably protected wherein the suitably protected AD'-AD' or AD'-$L^{P'}$ has the structure of

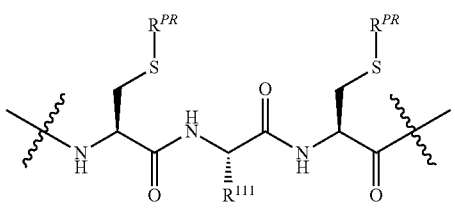

wherein $R^{111}$ is hydrogen or methyl and $R^{PR}$ is a suitable thiol protecting group that is deprotected and the wavy line indicates covalent attachment of the suitable protected AD' moiety within the Intermediate Linker compound; and in step (a) contacting the resulting deprotected formula VIIIa, VIIIb, VIIIc, VIIId, IXa or IXb product from step (a') with an X'-D moiety wherein X' is comprised of a maleimide-containing moiety capable of reacting with the free thiol groups of AD'-AD' or AD'-$L^{P'}$ to form thio-substituted succinimide-containing moieties.

Provided herein are methods of preparing a Ligand-Drug Conjugate represented by the structure of formula I, II or III as described herein, the method comprising steps (a): contacting a Ligand-Linker compound represented by the structure of formula X, XI or XII as described herein with sufficient amount of X'-D moieties to react with $L^{P'}$ or AD' so as to form a $L^P$-X-D or an AD-X-D moiety for each instance of $L^{P'}$ and AD', wherein -X-D is a Releasable Assembly Unit attached to a Drug Unit; and X'-D is a Releasable Assembly Unit precursor attached to a Drug Unit wherein X' is capable of reacting with $L^{P'}$ and/or AD'.

An exemplary Ligand-Drug Conjugate so prepared has the structure represented by formula Ia, Ib, IIa, IIb, IIb, IIIa, or IIIb as described herein and the Ligand-Linker compound has the structure represented by formula XIa, XIb, XIc, XId, XIIa or XIIb as described herein The method can further comprise step a': deprotecting a suitably protected Ligand-Linker compound corresponding in structure to formula X, XI, XII, XIa, XIb, XIc, XId, XIIa or XIIb as described herein wherein t is 0 and wherein suitably protected AD' or $L^{P'}$ has the structure of

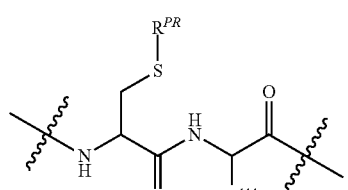

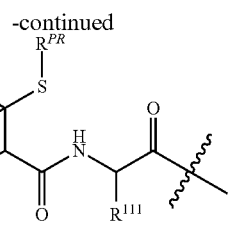

wherein $R^{111}$ is independently selected from hydrogen, p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl- with suitable protection when required,

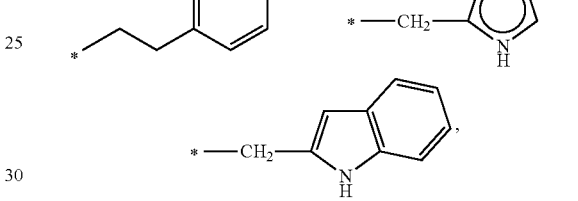

wherein $R^{PR}$ is a suitable thiol protecting group and the wavy line indicates covalent attachment of the suitable protected AD' or $L^{P'}$ moiety within the Intermediate Ligand-Linker compound;

and in step (a) contacting the resulting deprotected formula X, XI, XII, XIa, XIb, XIc, XId, XIIa or XIIb product from step (a') with an X'-D moiety wherein X' is comprised of a maleimide moiety capable of reacting with the free thiol group of AD' or $L^{P'}$ to form a thio-substituted succinimide moiety.

Alternatively, the method can further comprise step (a'): deprotecting a Ligand-Linker compound corresponding in structure to formula XIa, XIb, XIc, XId, XIIa or XIIb wherein t is 1 and AD'-AD' or AD'-$L^{P'}$ is suitably protected wherein the suitably protected AD'-AD' moiety has the structure of

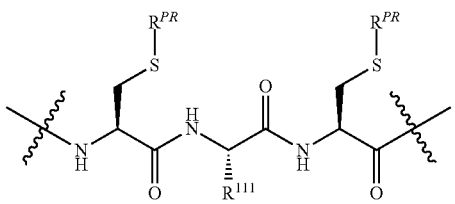

wherein $R^{111}$ is hydrogen or methyl and $R^{PR}$ is a suitable thiol protecting group that is deprotected and the wavy line indicates covalent attachment of the suitable protected AD' moiety within the Intermediate Ligand-Linker compound; and in step (a) contacting the resulting deprotected formula XIa, XIb, XIc, XId, XIIa or XIIb product from step (a') with an X'-D moiety wherein X' is comprised of a maleimide-containing moiety capable of reacting with the free thiol groups of AD'-AD' or AD'-$L^{P'}$ to form thio-substituted succinimide-containing moieties.

An exemplary maleimide moiety capable of reacting with the free thiol(s) resulting from step (a') has the structure of

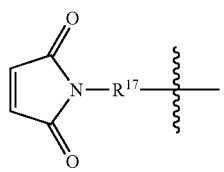

wherein $R^{17}$ is —$(CH_2)_5C(=O)$— and the wavy line indicates attachment within the X'-D moiety or has the structure of:

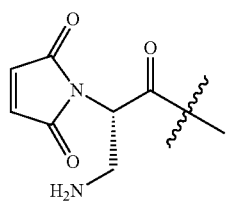 [SMILES: *C(=O)[C@H](CN)N1C(=O)C=CC1=O]

wherein the wavy line indicates attachment within the X'-D moiety and the amino group is optionally protected by an amino protecting group stable under conditions for deprotection of the $R^{PR}$ protected thiol groups.

EXAMPLES

General Information

All commercially available anhydrous solvents were used without further purification. PEG reagents were obtained from Quanta BioDesign (Powell, Ohio). Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Column chromatography was performed on a Biotage Isolera One flash purification system (Charlotte, N.C.). Analytical HPLC was performed on a Varian ProStar 210 solvent delivery system configured with a Varian ProStar 330 PDA detector. Samples were eluted over a C12 Phenomenex Synergi 2.0×150 mm, 4 µm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass mass spectrometer interfaced to an HP Agilent 1100 HPLC instrument equipped with a C12 Phenomenex Synergi 2.0×150 mm, 4 µm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2 Tof mass spectrometer interfaced to a Waters 2695 Separations Module with a Waters 2996 Photodiode Array Detector; the column, mobile phases, gradient, and flow rate were same as for LC-MS system 1.

LC-MS data of antibody-drug conjugates were acquired on a Waters Xevo GS-S QTOF coupled to an Waters Acquity H-Class UPLC system. Samples were chromatographed over an analytical reversed-phase column (Agilent Technologies, PLRP-S, 300Å, 2.1 mm ID×50 mm, 8 µm) at 80° C. and eluted with a linear gradient of 0.01% TFA in acetonitrile from 25% to 65% in 0.05% aqueous TFA over 12.5 minutes, followed by isocratic 65% 0.01% TFA in acetonitrile for 1.5 min at a flow rate of 1 mL/min. Mass spectrometry data for light and heavy chains was acquired in ESI+ mode using a mass range of 500-4000 m/z and were deconvoluted using MaxEnt1 to determine masses of the resulting conjugates.

Preparative HPLC was carried out on a Varian ProStar 210 solvent delivery system configured with a Varian ProStar 330 PDA detector. Products were purified over a C12 Phenomenex Synergi 10.0×250 mm, 4 µm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. Preparative HPLC for compounds in Schemes 3 and 4 was carried out with 0.1% trifluoroacetic acid in both mobile phases, instead of 0.1% formic acid. NMR spectral data were collected on a Varian Mercury 400 MHz spectrometer. Coupling constants (J) are reported in hertz.

Example 1

Synthesis of a Glucuronide-MMAE Drug-Linker Comprising a PEG Unit in a Serial Orientation Scheme 1.

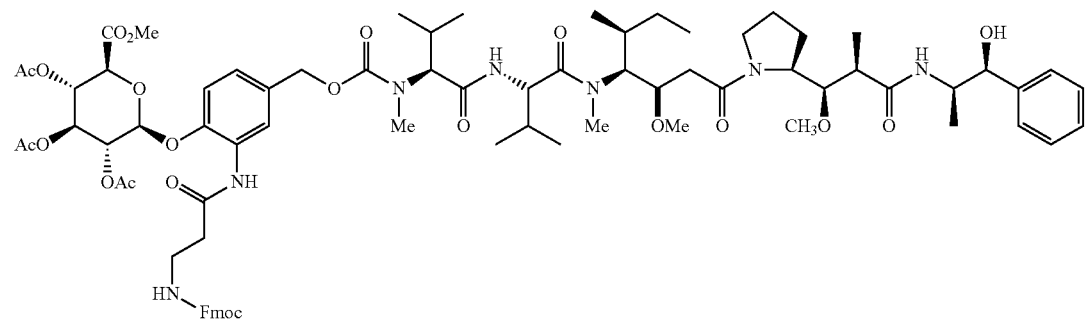

2

LiOH | 87%

-continued

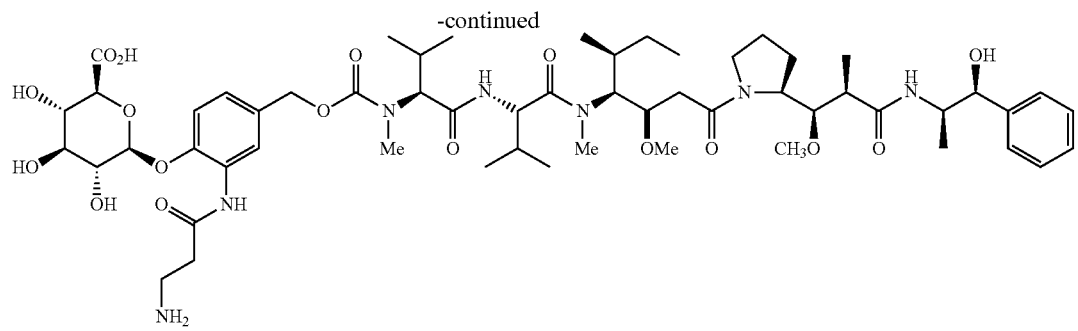

3

Mal—PEG$_{24}$—OSu, DIPEA | 55%

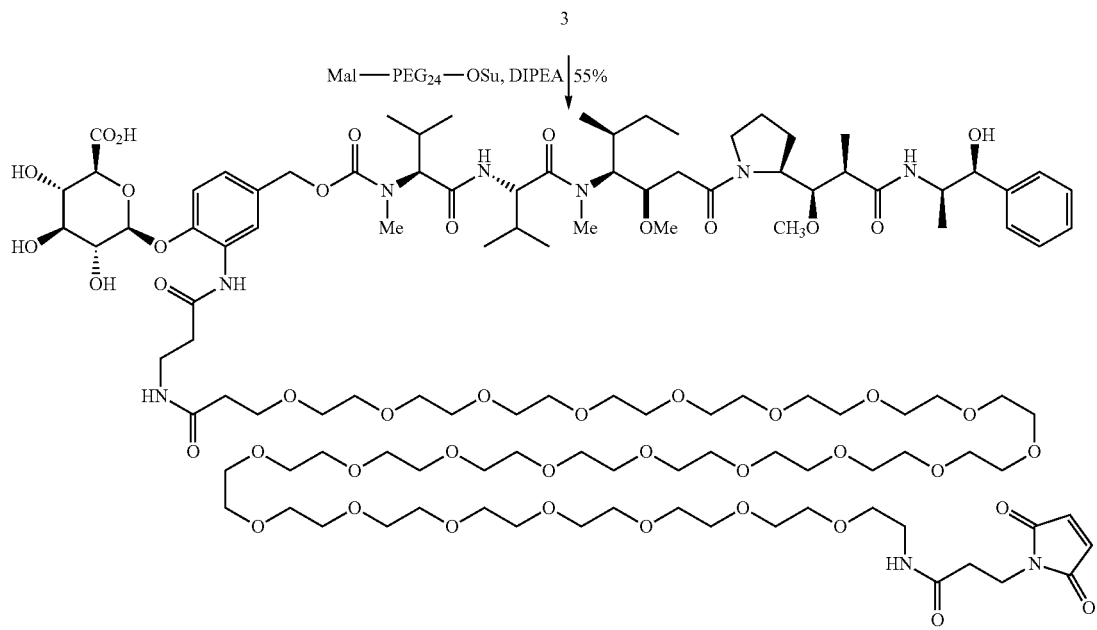

4

(2S,3S,4S,5R,6S)-6-(2-(3-aminopropanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (3)

The synthesis of Compound 2 has been previously described (U.S. patent Publication 2008/0241128), which is incorporated by reference herein. To a flask containing the glucuronide-MMAE intermediate 2 (40 mg, 26.8 μmol) was added 0.9 mL methanol and 0.9 mL tetrahydrofuran. The solution was then cooled in an ice bath and lithium hydroxide monohydrate (6.8 mg, 161 μmol) was added drop wise in as a solution in 0.9 mL water. The reaction was then stirred on ice for 1.5 h, at which time LC/MS revealed complete conversion to product. Glacial acetic acid (9.2 μL, 161 μmol) was then added and the reaction was concentrated to dryness. Preparative HPLC afforded the fully deprotected glucuronide-MMAE linker intermediate 3 (26 mg, 87%) as an oily residue. Analytical HPLC (0.1% formic acid): $t_R$ 9.3 min. LC-MS system 1: $t_R$ 11.10 min, m/z (ES$^+$) found 1130.48 (M+H)$^+$, m/z (ES$^-$) found 1128.63 (M−H)$^-$.

(2S,3S,4S,5R,6S)-6-(4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-2-(1-(2,5-dioxo-2,5-dihydro-1H-pyrrol-1-yl)-3,79-dioxo-7,10,13,16,19,22,25,28,31,34,37,40,43,46,49,52,55,58,61,64,67,70,73,76-tetracosaoxa-4,80-diazatrioctacontanamido)phenoxy)-3,4,5-trihydroxytetrahydro-2H-pyran-2-carboxylic acid (4)

To a flask containing the deprotected glucuronide-MMAE intermediate 3 (26 mg, 23 μmol) dissolved in anhydrous DMF (0.94 mL) was added maleimido-PEG24-NHS ester (32 mg, 23 μmol) as a solution in dimethylacetamide (200 mg/mL). Diisopropylethylamine (20 μL, 115 μmol) was added and the reaction was stirred under nitrogen at an ambient temperature for 6 h, at which time LC/MS revealed conversion to the desired product. The reaction was purified by preparative HPLC to provide the linear maleimido-PEG24-glucuronide-MMAE linker 4 (31 mg, 55%) as an oily residue. $^1$H NMR (CD$_3$OD) δ (ppm) 0.92 (m, 16H), 1.15 (m, 6H), 1.42 (m, 2H), 1.60 (m, 2H), 1.91 (m, 4H), 2.20 (m, 3H), 2.48 (m, 6H), 2.66 (m, 3H), 2.96 (m, 4H), 3.10 (s, 2H), 3.27 (s, 2H), 3.31 (s, 8H), 3.38 (m, 5H), 3.44 (m, 2H), 3.57 (m, 6H), 3.62 (m, 79H), 3.77 (m, 5H), 3.87 (t, J=9.6 Hz, 2H), 4.05 (m, 1H), 4.21 (m, 3H), 4.53 (m, 2H), 4.61 (m, 2H), 4.80 (m, 2H), 5.14 (m, 3H), 6.82 (s, 2H), 7.10 (m, 2H), 7.21 (m, 2H), 7.35 (m, 2H), 7.39 (m, 2H), 7.74 (d, J=8.8 Hz, 1H), 7.94 (m, 2H), 8.10 (m, 1H), 8.27 (m, 2H). Analytical HPLC (0.1% formic acid): $t_R$ 9.9 min. LC-MS system 1: $t_R$ 11.94 min, m/z (ES$^+$) found 1205.34 (M+2H)$^{2+}$. LC-MS system 2: $t_R$ 10.38 min, m/z (ES$^+$) found 2410.3225 (M+H)$^+$.
Example 2
Synthesis of a Glucuronide-MMAE Drug-Linker Comprising a PEG Unit in a Parallel Orientation
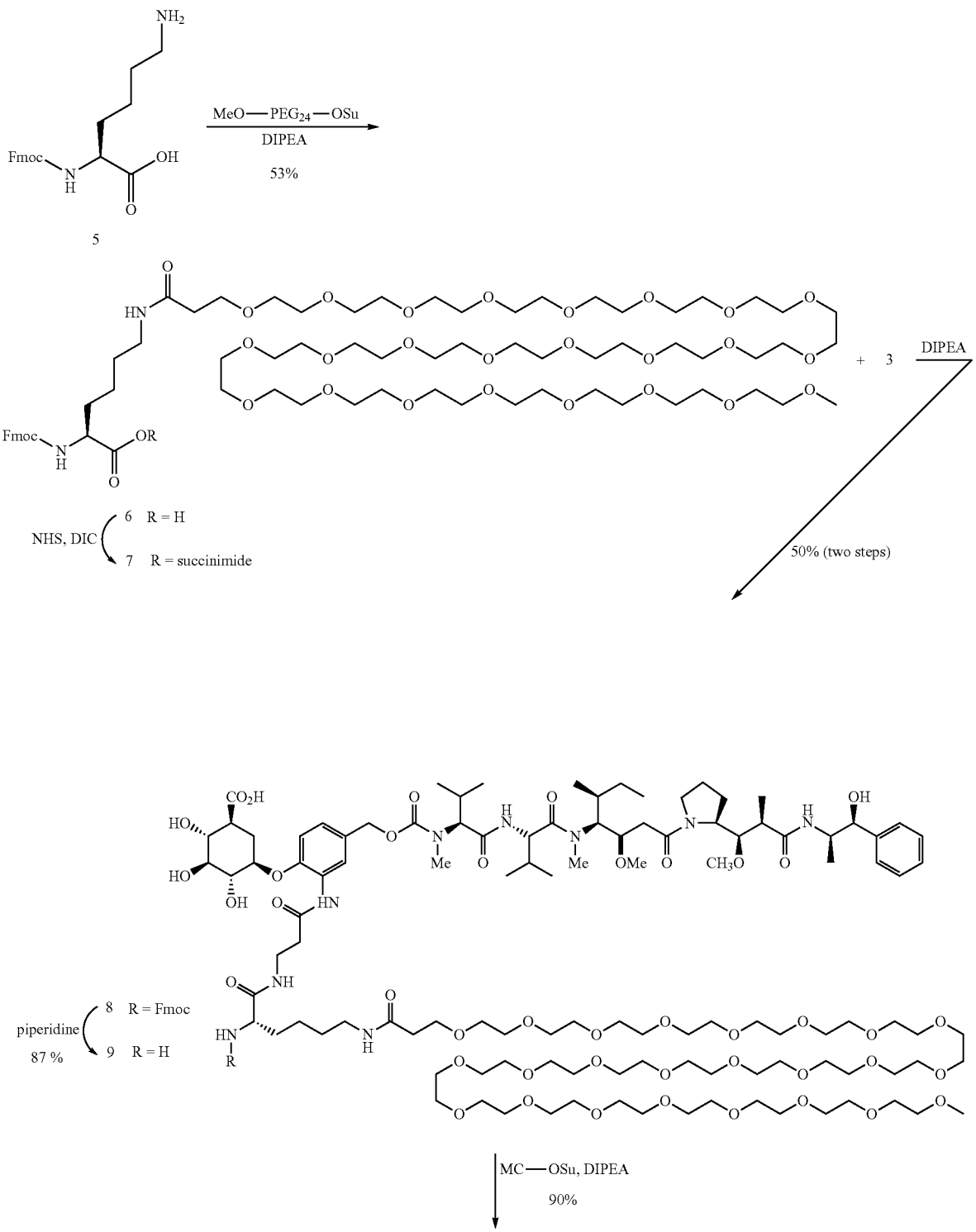

-continued

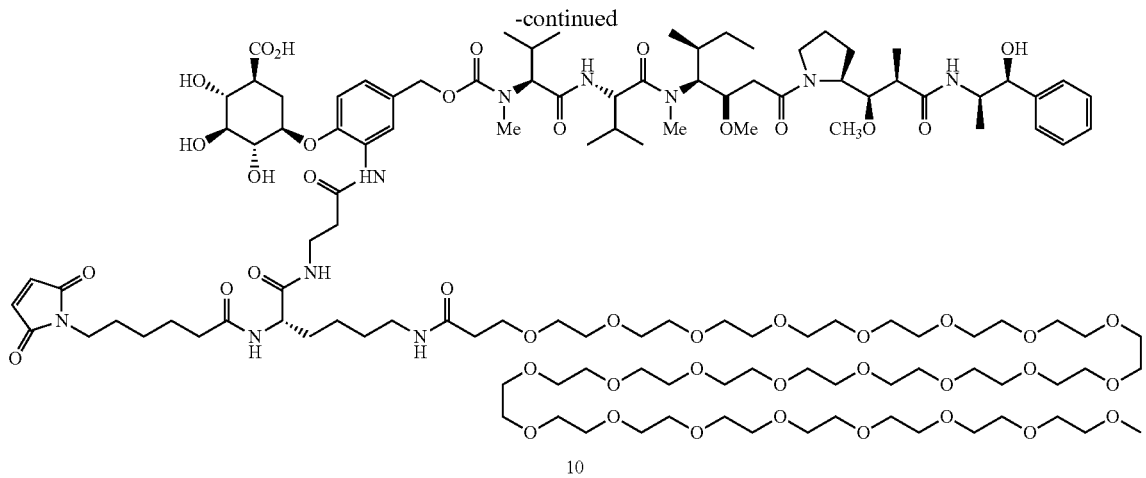

10

(S)-80-((((9H-fluoren-9-yl)methoxy)carbonyl) amino)-74-oxo-2,5,8,11,14,17,20,23,26,29,32,35,38, 41,44,47,50,53,56,59,62,65,68,71-tetracosaoxa-75-azahenoctacontan-81-oic acid (6)

To a flask containing $N_\alpha$-Fmoc-lysine 5 (30 mg, 81.5 µmol) was added 1.6 mL anhydrous dichloromethane, followed by methoxy-PEG24-OSu (100 mg, 81.5 µmol). DIPEA (71 µL, 408 µmol) was then added and the reaction was stirred under nitrogen at room temperature and followed by TLC and LC/MS. After 2 h, LC/MS revealed conversion to product. The reaction solution was diluted in dichloromethane and loaded directly on 1 mm chromatotron plate for purification. The plate was eluted with dichloromethane with increasing amounts of methanol (0% to 15%) to provide the desired product 6 (63 mg, 53%). TLC: $R_f$=0.17, 10% MeOH in $CH_2Cl_2$. $^1H$ NMR ($CDCl_3$) δ (ppm) 1.48 (m, 6H), 2.47 (m, 5H), 3.20 (m, 2H), 3.38 (s, 3H), 3.63 (m, 86H), 4.16 (m, 2H), 4.36 (m, 1H), 7.26 (m, 3H), 7.35 (m, 2H), 7.60 (m, 2H), 7.71 (m, 3H). Analytical HPLC (0.1% formic acid): $t_R$ 10.8 min. LC-MS system 1: $t_R$ 11.95 min, m/z ($ES^+$) found 1468.40 $(M+H)^+$, m/z ($ES^-$) found 1466.36 $(M-H)^-$.

(S)-2,5-dioxopyrrolidin-1-yl 80-((((9H-fluoren-9-yl) methoxy)carbonyl)amino)-74-oxo-2,5,8,11,14,17,20, 23,26,29,32,35,38,41,44,47,50,53,56,59,62,65,68,71-tetracosaoxa-75-azahenoctacontan-81-oate (7)

A flask was charged with $N_\alpha$-Fmoc-lysine(PEG24)-OH 6 (63 mg, 43 µmol) and 0.43 mL anhydrous tetrahydrofuran. N-hydroxysuccinimide (5.5 mg, 47 µmol) was added, followed by diisopropylcarbodiimide (7.3 µL, 47 µmol). The reaction was sealed under nitrogen and stirred overnight. After 18 h, additional N-hydroxysuccinimide (5.5 mg, 47 µmol) and diisopropylcarbodiimide (7.3 µL, 47 µmol) were added and stirring continued for an additional 4 hours, at which time LC/MS revealed complete conversion to product. The crude reaction was diluted in dichloromethane and purified by radial chromatography on a 1 mm plate eluted with dichloromethane with increasing amounts of methanol (0% to 10%) to provide the desired activated ester 7 (36 mg). The material was carried forward without further characterization. TLC: $R_f$=0.43, 10% MeOH in $CH_2Cl_2$. Analytical HPLC (0.1% formic acid): $t_R$ 11.4 min. LC-MS system 2: $t_R$ 11.01 min, m/z ($ES^+$) found 1564.8379 $(M+H)^+$.

(2S,3S,4S,5R,6S)-6-(2-((S)-80-((((9H-fluoren-9-yl) methoxy)carbonyl)amino)-74,81-dioxo-2,5,8,11,14, 17,20,23,26,29,32,35,38,41,44,47,50,53,56,59,62,65, 68,71-tetracosaoxa-75,82-diazapentaoctacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (8)

Deprotected glucuronide-MMAE linker intermediate 3 (26 mg, 23 µmol) was dissolved in anhydrous dimethylformamide (0.58 mL) and added to a flask containing Nα-Fmoc-lysine(PEG)-OSu 7 (36 mg, 23 µmol). Diisopropylethylamine (20 µL, 115 µmol) was then added, the reaction was then stirred under nitrogen at room temperature. After 4.5 h, LC-MS revealed conversion to product. The product was purified by preparative HPLC to provide Fmoc-Lys(PEG24)-glucuronide-MMAE intermediate 8 (30 mg, 50% over two steps) as an oily residue. Analytical HPLC (0.1% formic acid): $t_R$ 11.4 min. LC-MS system 1: $t_R$ 12.31 min, m/z ($ES^+$) found 1291.05 $(M+2H)^{2+}$. LC-MS system 2: $t_R$ 11.30 min, m/z ($ES^+$) found 2580.2515 $(M+H)^+$.

(2S,3S,4S,5R,6S)-6-(2-((S)-80-amino-74,81-dioxo-2,5,8,11,14,17,20,23,26,29,32,35,38,41,44,47,50,53, 56,59,62,65,68,71-tetracosaoxa-75,82-diazapentaoctacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (9)

Fmoc-Lys(PEG24)-glucuronide-MMAE intermediate 8 (30 mg, 12 µmol) was dissolved in 0.46 mL anhydrous dimethylformamide, followed by addition of 0.12 mL of piperidine. The reaction was stirred under nitrogen for 3 hours and then concentrated to dryness. The product was purified by preparative HPLC to provide H-Lys(PEG24)-glucuronide-MMAE intermediate 9 (24 mg, 87%) as an oily residue. $^1$H NMR (CDCl$_3$) δ (ppm) 0.92 (m, 14H), 1.14 (m, 6H), 1.42 (m, 5H), 1.79 (m, 8H), 2.22 (m, 3H), 2.42 (t, J=6.4 Hz, 2H), 2.47 (m, 2H), 2.65 (m, 2H), 2.76 (m, 2H), 2.95 (m, 3H), 3.10 (m, 3H), 3.31 (m, 8H), 3.35 (m, 6H), 3.54 (m, 5H), 3.63 (s, 70H), 3.72 (t, J=6.0 Hz, 3H), 3.85 (m, 2H), 4.07 (m, 1H), 4.22 (m, 3H), 4.52 (d, J=7.2 Hz, 1H), 4.61 (d, J=6.4 Hz, 1H), 4.71 (m, 2H), 5.11 (m, 3H), 7.12 (m, 1H), 7.21 (m, 1H), 7.31 (m, 3H), 7.37 (m, 2H), 7.75 (d, J=8.8 Hz, 1H), 7.89 (d, J=8.8 Hz, 1H), 7.95 (d, J=8.8 Hz, 1H), 8.26 (m, 2H). Analytical HPLC (0.1% formic acid): $t_R$ 8.9 min. LC-MS system 1: $t_R$ 11.18 min, m/z (ES$^+$) found 1178.97 (M+2H)$^{2+}$. LC-MS system 2: $t_R$ 9.50 min, m/z (ES$^+$) found 2358.2341 (M+H)$^+$.

(2S,3S,4S,5R,6S)-6-(4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-2-((S)-80-(6-(2,5-dioxo-2,5-dihydro-1H-pyrrol-1-yl)hexanamido)-74,81-dioxo-2,5,8,11,14,17,20,23,26,29,32,35,38,41,44,47,50,53,56,59,62,65,68,71-tetracosaoxa-75,82-diazapentaoctacontanamido)phenoxy)-3,4,5-trihydroxytetrahydro-2H-pyran-2-carboxylic acid (10)

Maleimidocaproic acid NHS ester (4.2 mg, 14 μmol) was dissolved in 0.6 mL anhydrous dimethylformamide and transferred to a flask containing H-Lys(PEG24)-glucuronide-MMAE intermediate 9 (24 mg, 10 μmol). Diisopropylethylamine (10 μL, 58 μmol) was then added, the reaction was then stirred under nitrogen at room temperature overnight. The reaction mixture was purified directly by preparative HPLC to provide MC-Lys(PEG24)-glucuronide-MMAE linker 10 (23 mg, 90%) as an oily residue. $^1$H NMR (CD$_3$OD) δ (ppm) 0.87 (m, 13H), 1.12 (t, J=7.6 Hz, 2H), 1.17 (d, J=6.8 Hz, 2H), 1.24 (m, 2H), 1.48 (m, 9H), 1.80 (m, 5H), 2.19 (m, 4H), 2.42 (t, J=6.4 Hz, 2H), 2.48 (m, 2H), 2.64 (m, 2H), 2.96 (m, 3H), 3.10 (s, 1H), 3.12 (m, 2H), 3.15 (s, 1H), 3.27 (s, 6H), 3.35 (m, 3H), 3.43 (m, 3H), 3.54 (m, 3H), 3.58 (m, 2H), 3.63 (m, 64H), 3.70 (m, 4H), 3.92 (m, 2H), 4.22 (m, 4H), 4.54 (m, 1H), 4.61 (t, J=6.4 Hz, 1H), 4.83 (m, 1H), 5.13 (m, 3H), 6.80 (s, 2H), 7.10 (m, 1H), 7.20 (m, 2H), 7.29 (m, 2H), 7.38 (m, 2H), 7.74 (d, J=8.8 Hz, 1H), 7.90 (m, 3H), 8.08 (s, 1H), 8.26 (m, 2H). Analytical HPLC (0.1% formic acid): $t_R$ 10.6 min. LC-MS system 1: $t_R$ 11.88 min, m/z (ES$^+$) found 1276.23 (M+2H)$^{2+}$. LC-MS system 2: $t_R$ 10.54 min, m/z (ES$^+$) found 2551.2871 (M+H)$^+$.

Example 3

Synthesis of a mDPR (Maleimido-Diaminopropanoic) Glucuronide-MMAE Drug-Linker

Scheme 3a

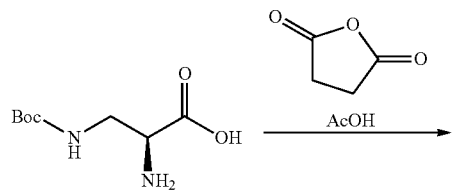

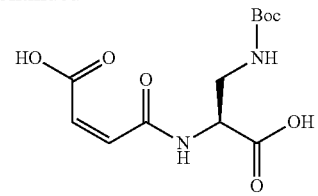

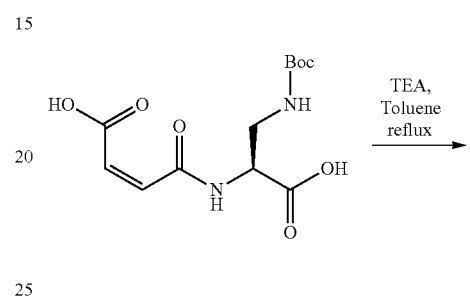

In a 50 ml round bottom flask, H-DPR(boc)-OH and maleic anhydride were dissolved in 4 vol. acetic acid and the solution was stirred at room temperature for 3 hours. The reaction mixture was concentrated to an oil on the rotovap, and the product was precipitated by adding ~10 ml dichloromethane. The precipitate was collected by vacuum filtration, washed with dichloromethane, and dried overnight in the vacuum oven.

Maleyl-DPR(boc)-OH was suspended in toluene (3 ml) and triethylamine (224 uL) over molecular sieves in a 50 ml round bottom flask equipped with a condenser. DMA (~150 uL) was added to aid solubility. The solution was heated to 125° C. and refluxed for 4 hours after which the reaction was shown to be complete by LCMS. The reaction mixture was concentrated to dryness on the rotovap, redissolved in DMSO and purified by preparative HPLC. The product was isolated as a white powder.

Scheme 3b.
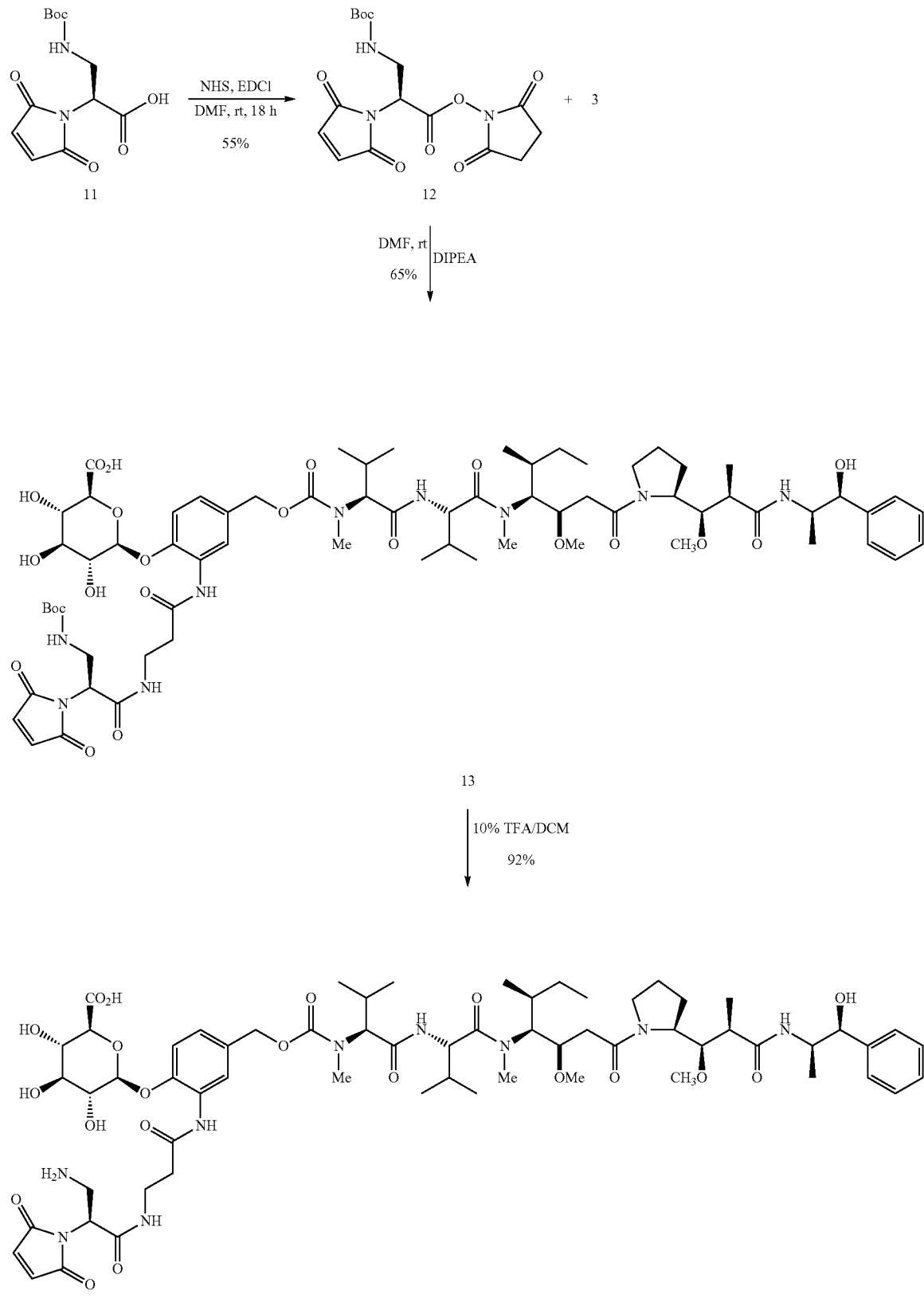

(S)-2,5-dioxopyrrolidin-1-yl 3-((tert-butoxycarbonyl)amino)-2-(2,5-dioxo-2,5-dihydro-1H-pyrrol-1-yl)propanoate (12)

(S)—$N_\alpha$-maleimido-$N_\beta$-Boc-diaminopropanoic acid 11 (Scheme 3a) (400 mg, 1.4 mmol) was dissolved in 7 mL anhydrous dimethylformamide. N-hydroxysuccinimide (178 mg, 1.5 mmol) was added, followed by 1-ethyl-3-(3-dimethylaminopropyl) carbodiimide (298 mg, 1.5 mmol). The reaction was stirred at room temperature under nitrogen for 3 hours. Aqueous workup was achieved through dilution into 120 mL water; the aqueous layer was then extracted three times with 60 mL ethyl acetate. The combined organic layer was then washed with brine, dried over sodium sulfate, and concentrated to dryness. The product was purified by flash column chromatography, eluting mixtures of hexanes: ethyl acetate (50:50 to 0:100) to provide (S)—$N_\alpha$-maleimido-$N_\beta$-Boc-diaminopropanoic acid NHS ester [MDpr(Boc)-OSu] 12 (297 mg, 55%). LC-MS system 1: $t_R$ 12.23 min, m/z (ES$^+$) found 282.0599 (M+H-Boc group)$^+$. LC-MS system 2: $t_R$ 11.30 min, m/z (ES$^+$) found 2580.2515 (M+H)$^+$.

(2S,3S,4S,5R,6S)-6-(2-(3-((S)-3-((tert-butoxycarbonyl)amino)-2-(2,5-dioxo-2,5-dihydro-1H-pyrrol-1-yl)propanamido)propanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (13)

MDpr(Boc)-OSu 12 (33 mg, 86 μmol) was dissolved in 1.1 mL of anhydrous dimethylformamide and added to a flask containing deprotected glucuronide-MMAE linker intermediate 3 (49 mg, 43 μmol). Diisopropylethylamine (37 μL, 220 μmol) was then added, the reaction was then stirred under nitrogen at room temperature for 30 min. The reaction was quenched with 37 μL glacial acetic acid and purified by preparative HPLC to afford MDpr(Boc)-glucuronide-MMAE intermediate 13 (39 mg, 65%). LC-MS system 2: $t_R$ 11.09 min, m/z (ES$^+$) found 1396.7321 (M+H)$^+$.

(2S,3S,4S,5R,6S)-6-(2-(3-((S)-3-amino-2-(2,5-dioxo-2,5-dihydro-1H-pyrrol-1-yl)propanamido)propanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (14)

A flask containing MDpr(Boc)-glucuronide-MMAE intermediate 13 (18 mg, 13 μmol) was cooled to 0° C. in an ice bath under nitrogen. A solution of 10% trifluoroacetic acid in dichloromethane (1.3 mL) was added dropwise. The reaction was then stirred at 0° C. for 2 h, at which time LC-MS revealed complete Boc deprotection. The reaction was then concentrated to a crude residue and purified by preparative HPLC to provide MDpr-glucuronide-MMAE linker 14 (15 mg, 92%). LC-MS system 2: $t_R$ 9.13 min, m/z (ES$^+$) found 1296.6697 (M+H)$^+$.

Example 4

Synthesis of a mDPR (Maleimido-Diaminopropanoic) Glucuronide-MMAE Drug-Linker Comprising a PEG Unit in a Parallel Orientation Scheme 4.

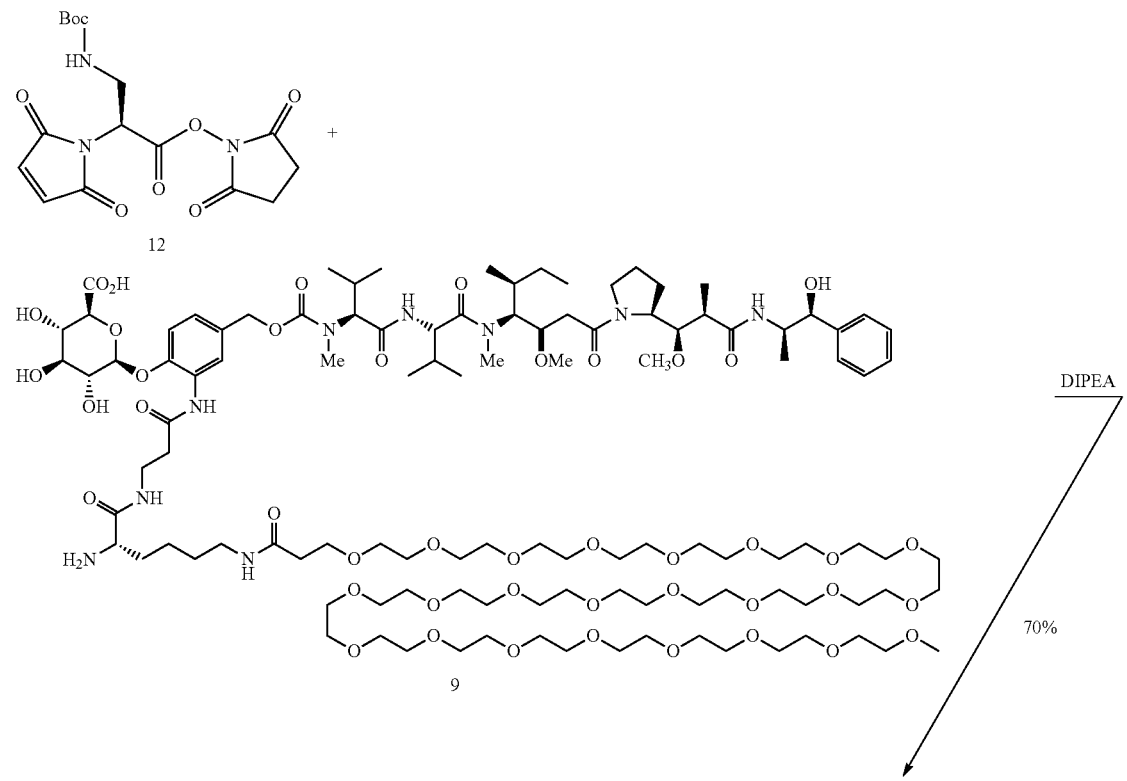

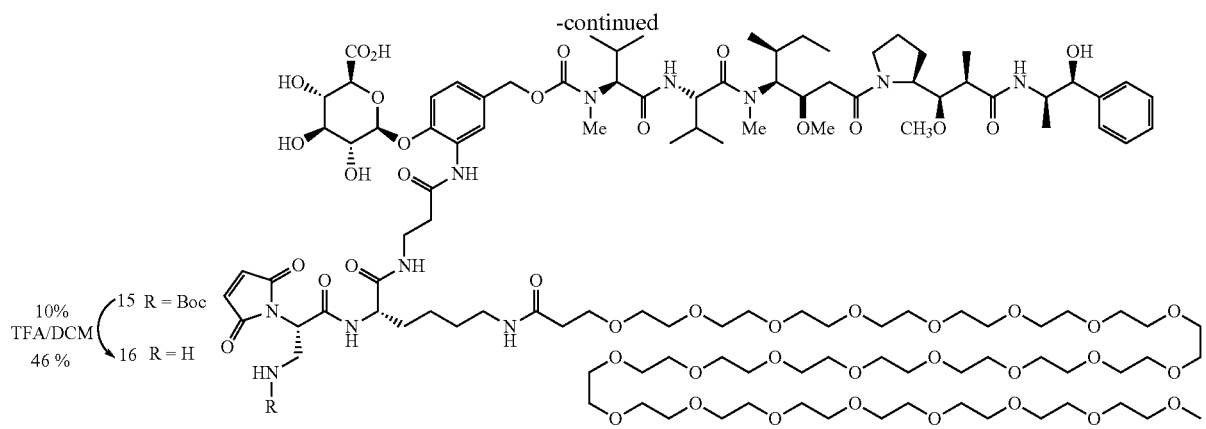

-continued (2S,3S,4S,5R,6S)-6-(2-((S)-80-((S)-3-((tert-butoxy-carbonyl)amino)-2-(2,5-dioxo-2,5-dihydro-1H-pyrrol-1-yl)propanamido)-74,81-dioxo-2,5,8,11,14,17,20,23,26,29,32,35,38,41,44,47,50,53,56,59,62,65,68,71-tetracosaoxa-75,82-diazapentaoctacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (15)

MDpr(Boc)-OSu 12 (33 mg, 86 μmol) was dissolved in 0.66 mL of anhydrous dimethylformamide and added to a flask containing H-Lys(PEG24)-glucuronide-MMAE linker intermediate 9 (135 mg, 57 μmol). Diisopropylethylamine (50 μL, 290 μmol) was then added, the reaction was then stirred under nitrogen at room temperature for 2.5 h. The reaction was quenched with 50 μL glacial acetic acid and purified by preparative HPLC to afford MDpr(Boc)-Lys(PEG24)-glucuronide-MMAE intermediate 15 (86 mg, 58%). LC-MS system 2: $t_R$ 11.71 min, m/z (ES$^+$) found 2624.2004 (M+H)$^+$.

(2S,3S,4S,5R,6S)-6-(2-((S)-80-((S)-3-amino-2-(2,5-dioxo-2,5-dihydro-1H-pyrrol-1-yl)propanamido)-74,81-dioxo-2,5,8,11,14,17,20,23,26,29,32,35,38,41,44,47,50,53,56,59,62,65,68,71-tetracosaoxa-75,82-diazapentaoctacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (16)

A flask containing MDpr(Boc)-Lys(PEG24)-glucuronide-MMAE intermediate 15 (86 mg, 33 umol) was cooled to 0° C. in an ice bath under nitrogen. A solution of 10% trifluoroacetic acid in dichloromethane (3.3 mL) was added dropwise. The reaction was then stirred at 0° C. for 2 h, at which time LC-MS revealed complete Boc deprotection. The reaction was then concentrated to a crude residue and purified by preparative HPLC to provide MDpr-Lys(PEG24)-glucuronide-MMAE linker 16 (38 mg, 46%). LC-MS system 2: $t_R$ 10.54 min, m/z (ES$^+$) found 2524.2256 (M+H)$^+$.

Example 5

Synthesis of a mDPR (Maleimido-Diaminopropanoic) Glucuronide-MMAE Drug-Linker Comprising a PEG12, PEG8, or PEG4-(PEG4)$_3$ Unit in a Parallel Orientation Scheme 5.

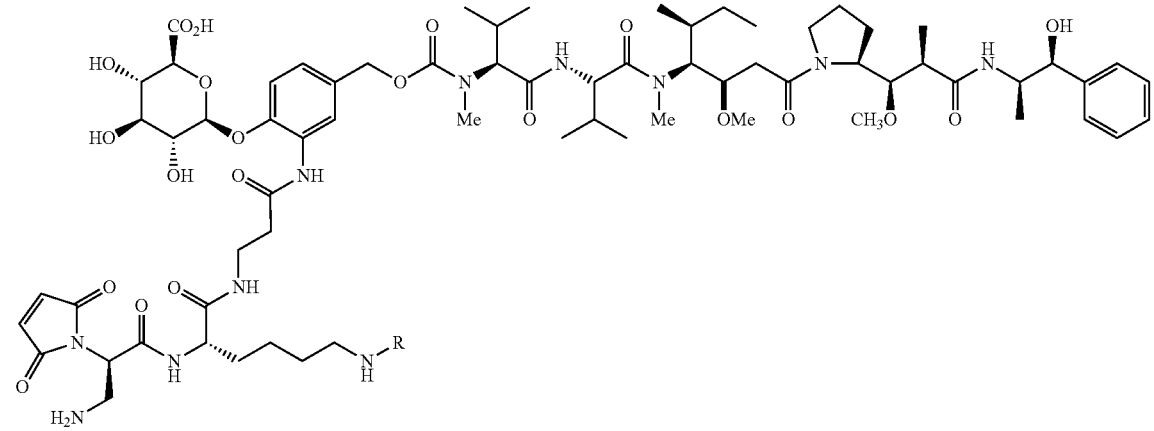

17

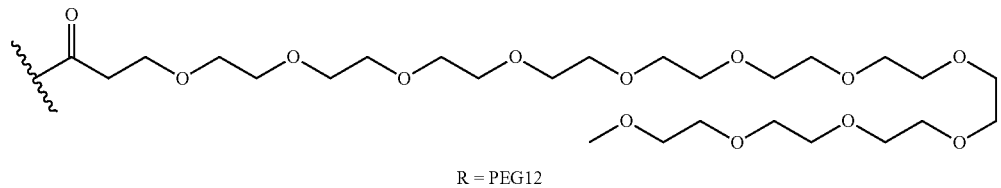

R = PEG12

18

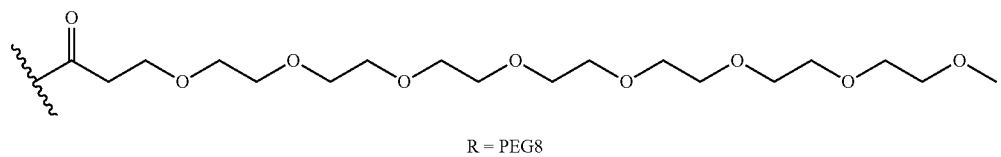

R = PEG8

42

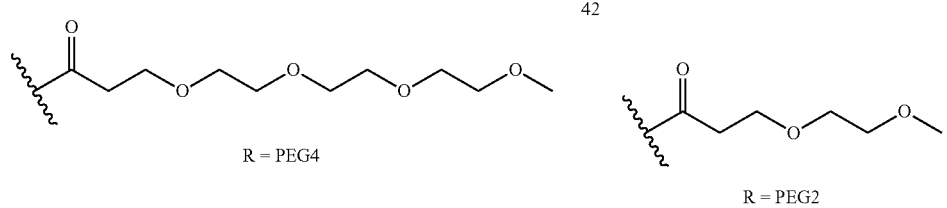

R = PEG4

43

R = PEG2

44

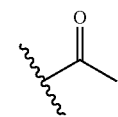

R = Ac (acetyl)

19

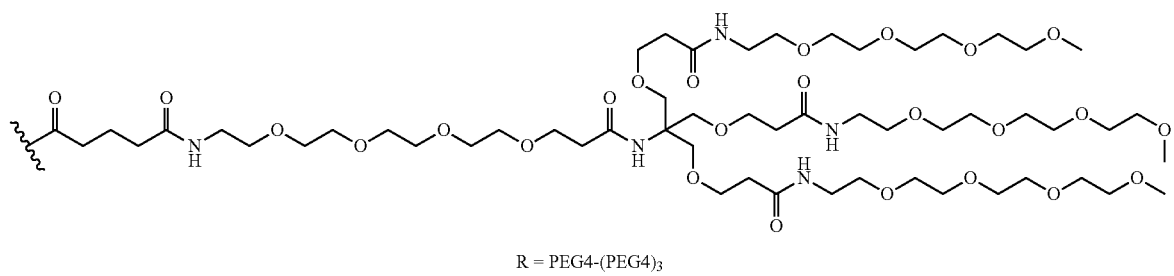

R = PEG4-(PEG4)₃

(2S,3S,4S,5R,6S)-6-(2-((S)-44-((R)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (17)

MDpr-Lys(PEG12)-glucuronide-MMAE linker 17 was prepared in a manner identical to 16, described in schemes 2 and 4. LC-MS system 2: $t_R$ 9.88 min, m/z (ES⁺) found 1996.1001 (M+H)⁺.

(2S,3S,4S,5R,6S)-6-(2-((S)-32-((R)-3-amino-2-(2,5-dioxo-2,5-dihydro-1H-pyrrol-1-yl)propanamido)-26,33-dioxo-2,5,8,11,14,17,20,23-octaoxa-27,34-diazaheptatriacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (18)

MDpr-Lys(PEG8)-glucuronide-MMAE linker 17 was prepared in a manner identical to 16, described in schemes 2 and 4. LC-MS system 2: $t_R$ 10.50 min, m/z (ES⁺) found 1818.8678 (M+H)⁺.

(2S,3S,4S,5R,6S)-6-(2-((S)-48-((R)-3-amino-2-(2,5-dioxo-2,5-dihydro-1H-pyrrol-1-yl)propanamido)-15,22,38,42,49-pentaoxo-20,20-bis(15-oxo-2,5,8,11,18-pentaoxa-14-azanonadecan-19-yl)-2,5,8,11,18,25,28,31,34-nonaoxa-14,21,37,43,50-pentaazatripentacontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (19)

MDpr-Lys(PEG4[PEG4]3)-glucuronide-MMAE linker 19 was prepared in a manner identical to 16, described in schemes 2 and 4. LC-MS system 2: $t_R$ 9.92 min, m/z (ES$^+$) found 2674.3813 (M+H)$^+$.

(2S,3S,4S,5R,6S)-6-(2-((S)-20-((R)-3-amino-2-(2,5-dioxo-2,5-dihydro-1H-pyrrol-1-yl)propanamido)-14,21-dioxo-2,5,8,11-tetraoxa-15,22-diazapentacosanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (42)

MDpr-Lys(PEG4)-glucuronide-MMAE linker 42 was prepared in a manner identical to 16, described in schemes 2 and 4. LC-MS system 2: $t_R$ 10.18 min, m/z (ES$^+$) found 1642.8586 (M+H)$^+$.

(2S,3S,4S,5R,6S)-6-(2-((S)-14-((R)-3-amino-2-(2,5-dioxo-2,5-dihydro-1H-pyrrol-1-yl)propanamido)-8,15-dioxo-2,5-dioxa-9,16-diazanonadecanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (43)

MDpr-Lys(PEG2)-glucuronide-MMAE linker 43 was prepared in a manner identical to 16, described in schemes 2 and 4. LC-MS system 2: $t_R$ 10.10 min, m/z (ES$^+$) found 1554.8093 (M+H)$^+$.

(2S,3S,4S,5R,6S)-6-(2-(3-((S)-6-acetamido-2-((R)-3-amino-2-(2,5-dioxo-2,5-dihydro-1H-pyrrol-1-yl)propanamido)hexanamido)propanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (44)

MDpr-Lys(Ac)-glucuronide-MMAE linker 44 was prepared in a manner identical to 16, described in schemes 2 and 4. LC-MS system 2: $t_R$ 10.38 min, m/z (ES$^+$) found 1466.8109 (M+H)$^+$.

Example 6

Synthesis of a mDPR (Maleimido-Diaminopropanoic) Valine-Citrulline-MMAE Drug-Linker Comprising a PEG Unit in a Parallel Orientation

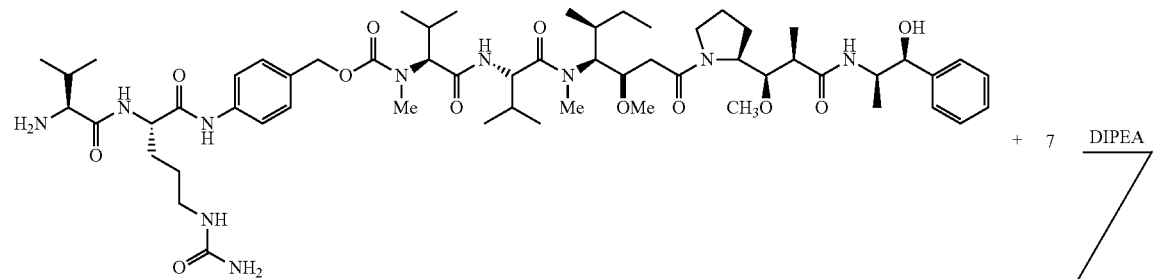

Scheme 6.

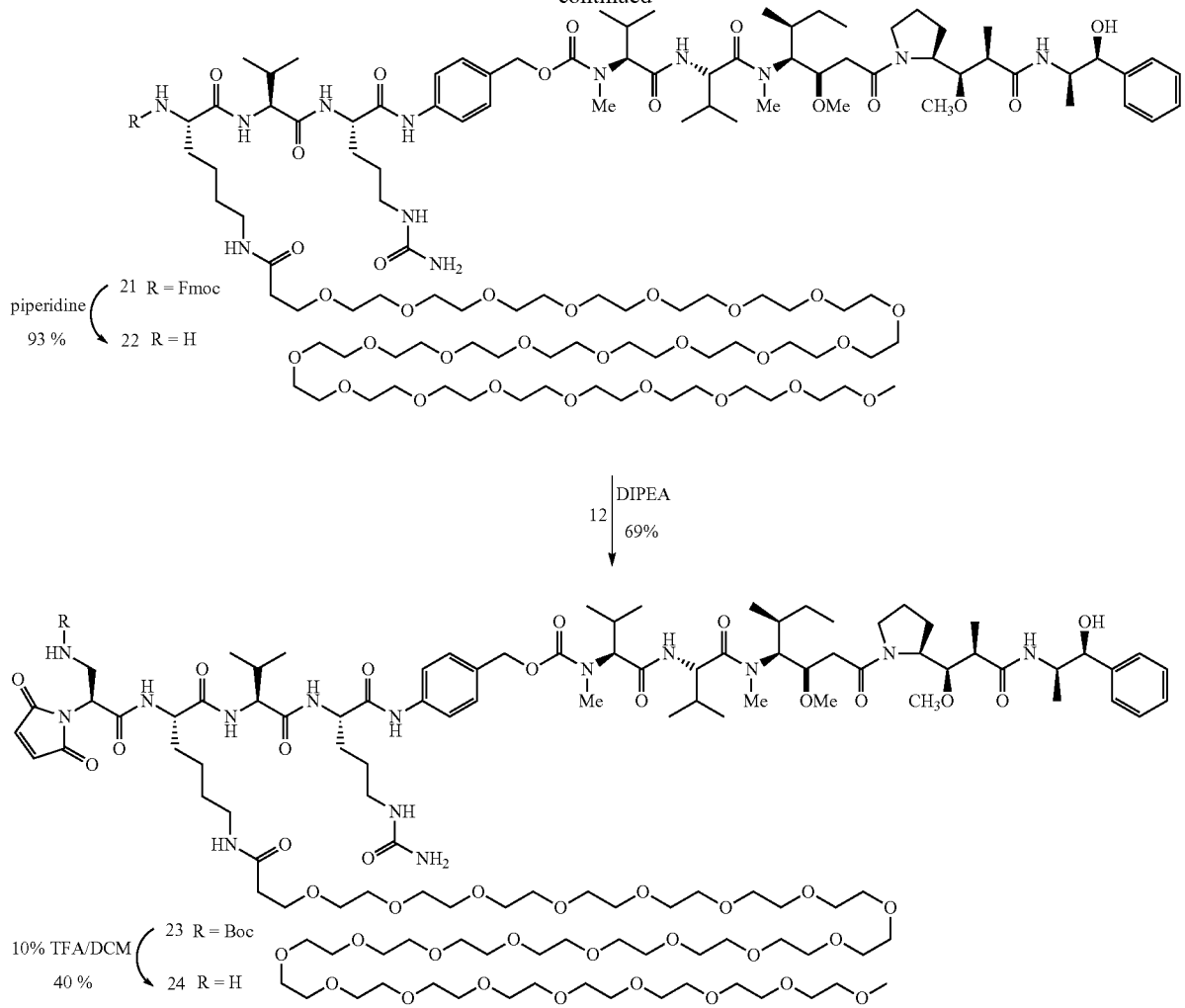

4-((80S,83S,86S)-80-(((((9H-fluoren-9-yl)methoxy)carbonyl)amino)-83-isopropyl-74,81,84-trioxo-86-(3-ureidopropyl)-2,5,8,11,14,17,20,23,26,29,32,35,38,41,44,47,50,53,56,59,62,65,68,71-tetracosaoxa-75,82,85-triazaheptaoctacontanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (21)

ValCit-PAB-MMAE linker (synthesized as described in U.S. Pat. No. 7,659,241) intermediate 20 (16 mg, 14 µmol) was dissolved in anhydrous dimethylformamide (0.28 mL) and added to a flask containing Nα-Fmoc-lysine(PEG)-OSu 7 (25 mg, 17 µmol). Diisopropylethylamine (12 µL, 70 µmol) was then added, the reaction was then stirred under nitrogen at room temperature. After 6 h, LC-MS revealed conversion to product. The product was purified by preparative HPLC to provide Fmoc-Lys(PEG24)-ValCit-PAB-MMAE intermediate 21 (15 mg, 42%) as an oily residue. Analytical HPLC (0.1% formic acid): LC-MS system 2: $t_R$ 11.67 min, m/z (ES$^+$) found 2573.2493 (M+H)$^+$.

4-((80S,83S,86S)-80-amino-83-isopropyl-74,81,84-trioxo-86-(3-ureidopropyl)-2,5,8,11,14,17,20,23,26,29,32,35,38,41,44,47,50,53,56,59,62,65,68,71-tetracosaoxa-75,82,85-triazaheptaoctacontanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (22)

Fmoc-Lys(PEG24)-ValCit-PAB-MMAE intermediate 21 (15 mg, 6 µmol) was dissolved in 0.16 mL anhydrous dimethylformamide, followed by addition of 0.04 mL of piperidine. The reaction was stirred under nitrogen for 1.5 hours and then concentrated to dryness. The product was purified by preparative HPLC to provide H-Lys(PEG24)-ValCit-PAB-MMAE intermediate 22 (13 mg, 93%) as an oily residue. LC-MS system 2: $t_R$ 9.72 min, m/z (ES$^+$) found 2351.1787 (M+H)$^+$.

4-((80S,83S,86S)-80-((S)-3-((tert-butoxycarbonyl)
amino)-2-(2,5-dioxo-2,5-dihydro-1H-pyrrol-1-yl)
propanamido)-83-isopropyl-74,81,84-trioxo-86-(3-
ureidopropyl)-2,5,8,11,14,17,20,23,26,29,32,35,38,
41,44,47,50,53,56,59,62,65,68,71-tetracosaoxa-75,
82,85-triazaheptaoctacontanamido)benzyl ((S)-1-
(((S)-1-(((3R,4S,5S)-1-((S)-2-((1R,2R)-3-(((1S,2R)-
1-hydroxy-1-phenylpropan-2-yl)amino)-1-methoxy-
2-methyl-3-oxopropyl)pyrrolidin-1-yl)-3-methoxy-5-
methyl-1-oxoheptan-4-yl)(methyl)amino)-3-methyl-
1-oxobutan-2-yl)amino)-3-methyl-1-oxobutan-2-yl)
(methyl)carbamate (23)

MDpr(Boc)-OSu 12 (4 mg, 11 μmol) was dissolved in 0.12 mL of anhydrous dimethylformamide and added to a flask containing H-Lys(PEG24)-ValCit-PAB-MMAE linker intermediate 22 (13 mg, 5.5 μmol). Diisopropylethylamine (5 μL, 28 μmol) was then added, the reaction was then stirred under nitrogen at room temperature for 1 h. The reaction was quenched with 5 μL glacial acetic acid and purified by preparative HPLC to afford MDpr(Boc)-Lys(PEG24)-Val-Cit-PAB-MMAE intermediate 23 (10 mg, 69%). LC-MS system 2: $t_R$ 11.25 min, m/z (ES$^+$) found 2617.3203 (M+H)$^+$.

Example 7

ADCs Comprising PEG in a Parallel Orientation Exhibit In Vitro Activity Similar to their Non-PEGylated Counterparts or ADCs Comprising PEG in a Serial Orientation Cells cultured in log-phase growth were seeded for 24 h in 96-well plates containing 150 μL RPMI 1640 supplemented with 20% FBS. Serial dilutions of ADC in cell culture media were prepared at 4× working concentration; 50 μL of each dilution was added to the 96-well plates. Following addition of ADC, the cells were incubated with test articles for 4 d at 37° C. After 96 h, growth inhibition was assessed by Cell Titer Glo (Promega, Madison, Wis.) and luminescence was measured on a plate reader. The IC$_{50}$ value, determined in triplicate, is defined here as the concentration that results in a 50% reduction in cell growth relative to untreated controls.

Compounds 1, 4, and 10 were conjugated via their interchain thiols to the chimeric cAC10 antibody described in U.S. Pat. No. 7,090,843 at an average drug loading of 8 drugs per antibody. Compounds 4 and 10 are described above. Compound 1 is as follows:

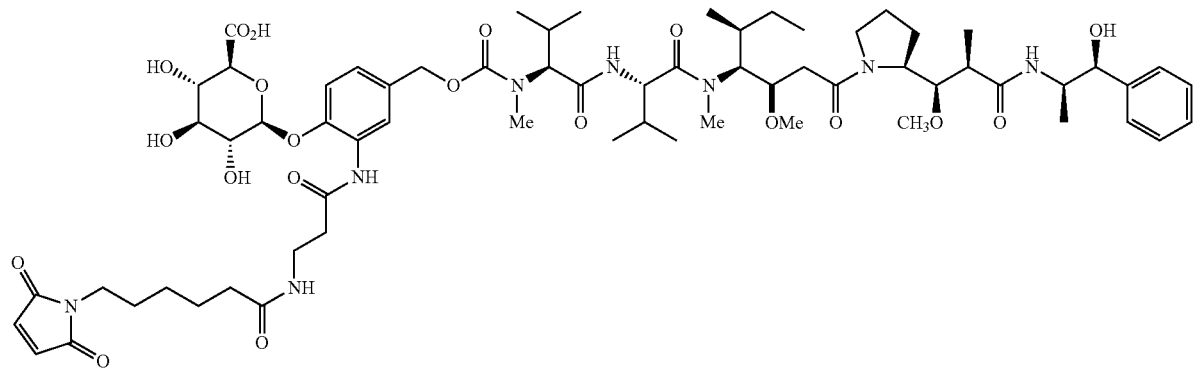

4-((80S,83S,86S)-80-((S)-3-amino-2-(2,5-dioxo-2,5-
dihydro-1H-pyrrol-1-yl)propanamido)-83-isopropyl-
74,81,84-trioxo-86-(3-ureidopropyl)-2,5,8,11,14,17,
20,23,26,29,32,35,38,41,44,47,50,53,56,59,62,65,68,
71-tetracosaoxa-75,82,85-
triazaheptaoctacontanamido)benzyl ((S)-1-(((S)-1-
(((3R,4S,5S)-1-((S)-2-((1R,2R)-3-(((1S,2R)-1-
hydroxy-1-phenylpropan-2-yl)amino)-1-methoxy-2-
methyl-3-oxopropyl)pyrrolidin-1-yl)-3-methoxy-5-
methyl-1-oxoheptan-4-yl)(methyl)amino)-3-methyl-
1-oxobutan-2-yl)amino)-3-methyl-1-oxobutan-2-yl)
(methyl)carbamate (24)

A flask containing MDpr(Boc)-Lys(PEG24)-ValCit-PAB-MMAE intermediate 23 (10 mg, 4 umol) was cooled to 0° C. in an ice bath under nitrogen. A solution of 10% trifluoroacetic acid in dichloromethane (0.4 mL) was added dropwise. The reaction was then stirred at 0° C. for 3 h. The reaction was then concentrated to a crude residue and purified by preparative HPLC to provide MDpr-Lys(PEG24)-ValCit-PAB-MMAE linker 24 (4 mg, 40%). LC-MS system 2: $t_R$ 9.81 min, m/z (ES$^+$) found 2517.2930 (M+H)$^+$.

The in vitro cytotoxic activity of the resultant ADCs was measured against CD30$^+$ and CD30$^-$ cell lines. Neither the addition of PEG nor its configuration had any significant impact on in vitro activity; only negligible differences in ADC potency were observed, and in two cell lines (L540cy and Karpas-299) the activities were essentially identical (Table 1).

TABLE 1

In vitro cytotoxic activity of anti-CD30 ADCs; values represent IC$_{50}$s in ng/mL.

| ADC | drugs/Ab | CD30+ cell lines | | | CD30− |
| | | Karpas 299 | L540cy | L428 | WSU-NHL |
| --- | --- | --- | --- | --- | --- |
| cAC10-1 | 8 | 2.5 | 4.4 | 9 | no effect |
| cAC10-4 | 8 | 1.5 | 4.4 | 34 | no effect |
| cAC10-10 | 8 | 1.7 | 6.6 | 13 | no effect |

Example 8

ADCs Comprising PEG in a Parallel Orientation Exhibit Favorable Pharmacokinetics as Compared to ADCs Comprising PEG in a Serial Orientation Antibody and ADC Radiolabeling-Pharmocokinetic (PK) experiments were performed using radiolabeled antibody or ADC. PK test articles were radiolabeled using the following procedure. To a solution of antibody or ADC in PBS supplemented with an additional 50 mM potassium phosphate (pH 8.0) and 50 mM sodium chloride was added 55 µCi N-succinimidyl propionate, [propionate-2,3-$^3$H]— (Moravek Biochemicals, Cat. No.: MT 919, 80 Ci/mmol, 1 mCi/mL, 9:1 hexane:ethyl acetate solution) per mg of antibody or ADC. The resulting mixture was vortexed and left at room temperature for 2 hours. The mixture was centrifuged at 4,000×g for 5 minutes and the lower aqueous layer was removed and split into Amicon Ultra-15 Centrifugal Filter Units (Millipore, Cat. No.: UFC903024, 30 kDa MWCO). Unconjugated radioactivity was removed by 4 rounds of dilution and centrifugation at 4,000×g. The resulting products were filtered through sterile 0.22 µm Ultrafree-MC Centrifugal Filter Units (Millipore, Cat. No.: UFC30GV0S) and the final antibody or ADC concentration was measured spectrophotometrically. The specific activity (µCi/mg) of each product was determined by liquid scintillation counting.

Pharmacokinetic Experiments—The pharmacokinetic properties of the unconjugated antibody or ADC were examined in several rodent models. In each experiment, 1-3 mg of radiolabeled antibody or ADC per kg of animal weight were injected via the tail vein. Each test article was dosed once in replicate animals. Blood was drawn into K$_2$EDTA tubes via the saphenous vein or by cardiac puncture for terminal bleeds at various time points. Plasma was isolated by centrifugation for 10 minutes at 10,000×g. A 10-20 µL of sample of plasma from each time point was added to 4 mL Ecoscint-A liquid scintillation cocktail (National Diagnostics) and the total radioactivity was measured by liquid scintillation counting. The resulting disintegrations per minute values were converted to µCi and the specific activity of the radiolabeled test articles was used to calculate the concentration of antibody or ADC remaining in the plasma at each time point. Pharmacokinetic parameters (clearance and AUC) were determined from the resulting plasma concentration data. The estimated pharmacokinetic parameters were calculated by non-compartmental analysis in Phoenix WinNonlin v6.3 (Pharsight, Mountain View, Calif.) using the intravenous bolus dose option.

Figure 7:
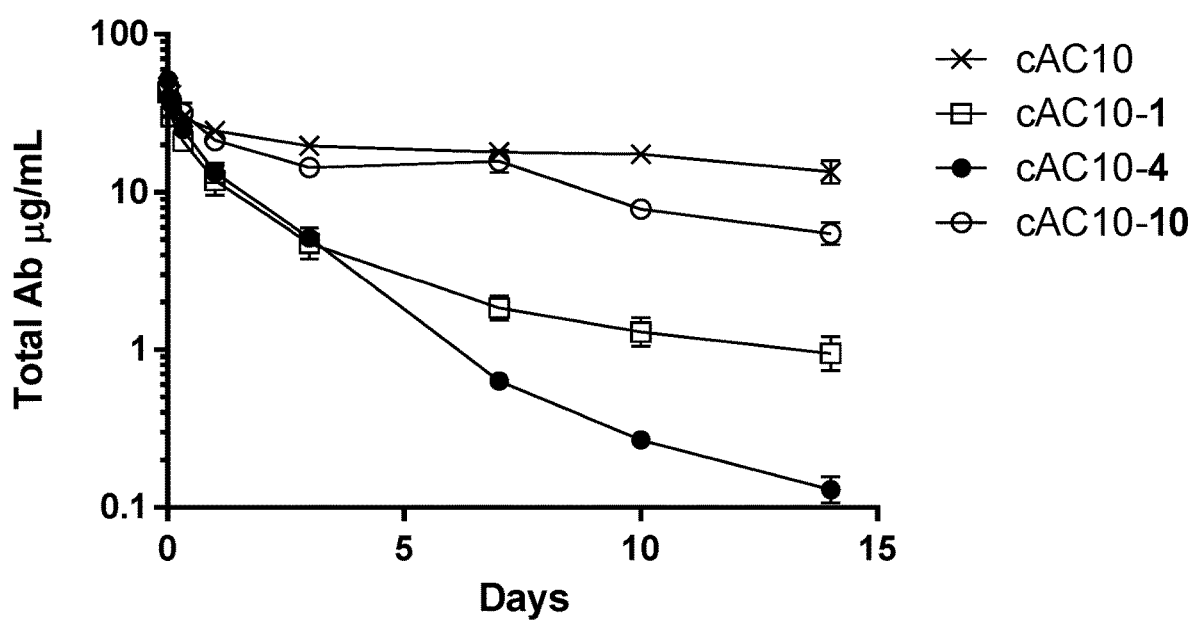
FIG. 7. Pharmokinetic profile (total Ab concentration in μg/mL vs time in days) in rat following a single intavenous 3 mg/Kg dose of unconjugated cAC10 antibody, its non-PEGylated ADC (cAC10-1), Parallel-oriented PEGylated ADC (cAC10-10), and serial-oriented PEGylated ADC (cAC10-4) compositions with average drug loading of 8 drugs/Ab.

Compounds 1, 4, and 10 were conjugated via their interchain thiols to the chimeric cAC10 antibody described in U.S. Pat. No. 7,090,843, which is incorporated by reference herein, at an average drug loading of 8 drugs per antibody. As expected, an ADC prepared with 8 copies of the non-PEGylated drug-linker 1 exhibited very fast clearance and low exposure relative the unconjugated antibody (FIG. 7). Surprisingly, the PEGylated drug-linker 4, utilizing PEG in a serial configuration, yielded an ADC with even faster clearance and lower exposure than the non-PEGylated format. This result was unexpected given the number of examples in the art of ADCs prepared according to this design. In contrast, the ADC prepared with drug-linker 10, utilizing PEG in a parallel configuration, yielded an ADC with considerably slower clearance and greater exposure than the non-PEGylated format (see FIG. 7 and Table 2).

TABLE 2

| Ligand-Drug Conjugate | Clearance (mL/day/kg) | AUC$_{0-inf}$ (day * µg/ml) |
|---|---|---|
| cAC10 | 8.6 | 604.1 |
| cAC10-1 | 48.6 | 67.0 |
| cAC10-4 | 57.8 | 52.0 |
| cAC10-10 | 14.2 | 229.7 |

Alternatively, an ELISA based total antibody (Tab) assay can be used to obtain pharmacokinetic measurements. A 100 µL solution of an anti-human IgG kappa antibody (0.5 mg/mL, Antibody Solutions, Mountain View Calif.) in 0.05M carbonate-bicarbonate buffer (pH 9.6, Sigma Aldrich, St. Louis, Mo.) was added to each well of a 96-well polystyrene plate coated with MaxiSorp™ (Sigma Aldrich, St. Louis, Mo.). The plates were incubated at 4° C. overnight. After incubation, the plate was washed 3 times with PBS containing 0.05% Tween-20 (PBS-T). The wells were then blocked with PBS-T containing 1% bovine serum albumin at room temperature for at least 1 hour. After blocking, the plate was washed 3 times with PBS-T. Concentrated stocks of antibody or ADC standards (40×concentrations) were prepared in rat or mouse plasma in order to generate a standard curve. Plasma samples and standards were then diluted 1:40 in PBS-T. The diluted samples and standards (100 µL) were added to the wells of the ELISA plate and were incubated at room temperature for 1 hour. After incubation, the samples were removed and plate was washed 3 times with PBS-T. A solution of Peroxidase-AffiniPure F(ab')2 Fragment Goat Anti-Human IgG, Fcγ Fragment Specific (Jackson ImmunoResearch Laboratories, Inc., West Grove, Pa.) was diluted 1:30,000 in PBS-T and 100 µL was added to each well. The plate was incubated at room temperature for 1 hour. After incubation, the samples were removed and plate was washed 3 times with PBS-T. A solution of SureBlueTMB Microwell Peroxidase Substrate (KPL, Inc. Gaithersburg, Md.) was added to each well (100 µL). The plate was incubated at room temperature for 11 to 12 minutes and the reactions were quenched with 100 µL 1N HCl. The plates were read at 450 nm on a Molecular Devices Spectromax plate reader.

Example 9

ADCs Comprising PEG in a Parallel Orientation have Improved In Vivo Activity as Compared to ADCs Comprising PEG in a Serial Orientation or ADCs Lacking a PEG Unit In vivo xenograft models—All experiments were conducted in concordance with the Animal Care and Use Committee in a facility fully accredited by the Association for Assessment and Accreditation of Laboratory Animal Care. Efficacy experiments were conducted in xenograft models of Karpas 299 anaplastic large cell lymphoma, L540cy Hodgkin's lymphoma, Ramos Burkitt's lymphoma, and MCF-7 breast cancer. Cell suspensions or tumor fragments were implanted sub-cutaneous in immune-compromised mice. Mice bearing MCF-7 tumors were co-administered a slow-release tablet of 17β-estradiol implanted sub-cutaneously. Mice were randomized to study groups when the average tumor volume reached about 100 mm$^3$. The ADC or controls were dosed ip once. Tumor volume as a function of time was determined using the formula (L×W$^2$)/2. Animals were euthanized when tumor volumes reached 1000 mm$^3$. Mice showing durable regressions were terminated around day 100 post implant.

Figure 2:
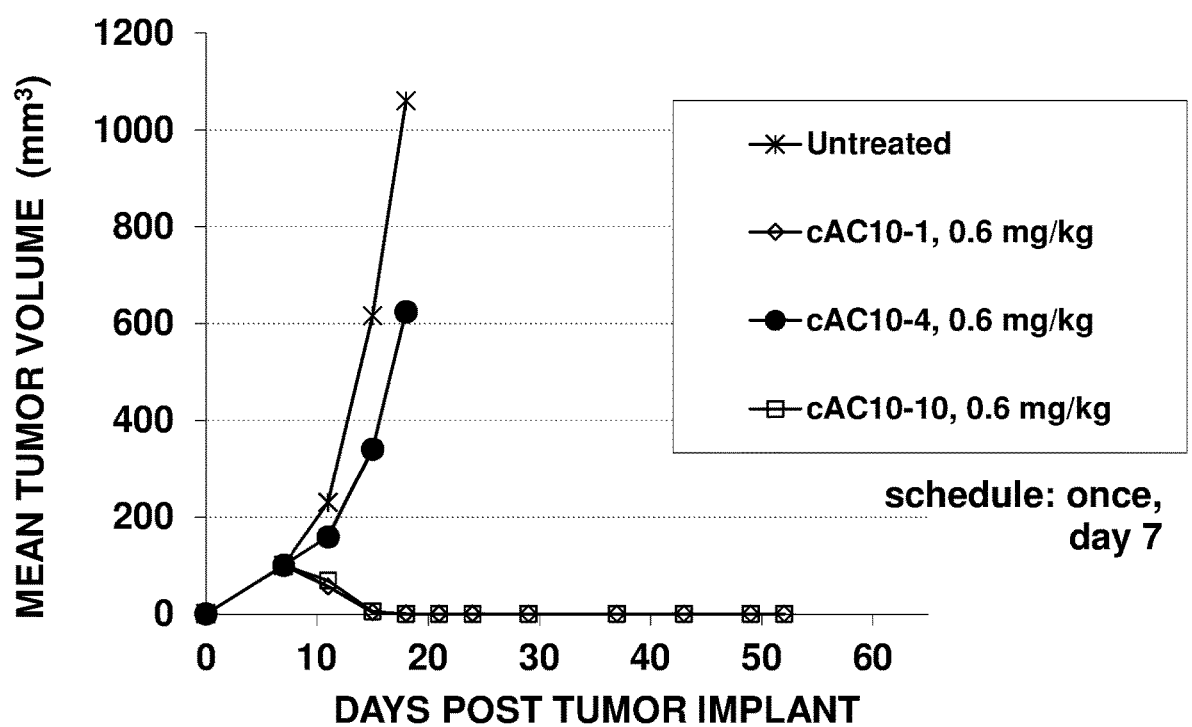
FIG. 2. Mean tumor volume versus days post implant for xenograft Karpas299 model (ALCL) dosed at higher single dose (0.6 mg/kg) with non-PEGylated ADC (cAC10-1), Parallel-oriented PEGylated ADC (cAC10-10), and serial-oriented PEGylated ADC (cAC10-4) compositions with average drug loading of 8 drugs/Ab.
Figure 3:
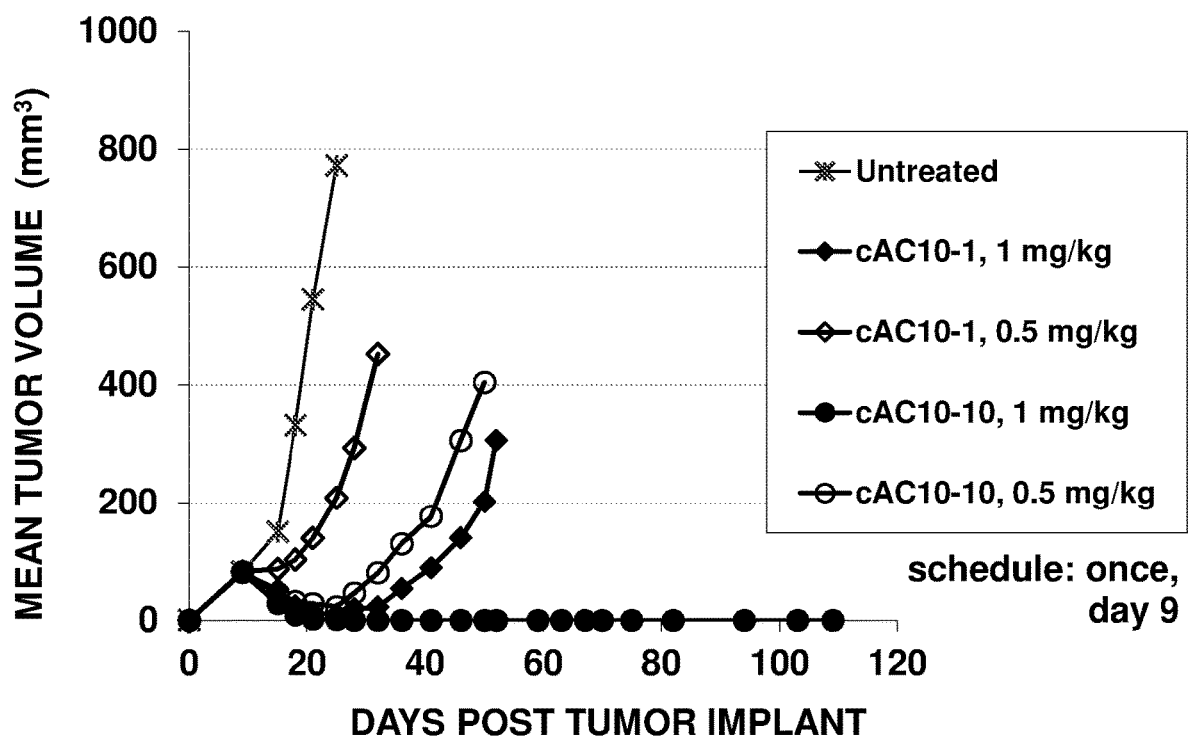
FIG. 3. Mean tumor volume versus days post implant for xenograft L540cy model (Hodgkin Lymphoma) dosed at lower single dose (0.5 mg/kg) with non-PEGylated ADC (cAC10-1), Parallel-oriented PEGylated ADC (cAC10-10), and serial-oriented PEGylated ADC (cAC10-4) compositions.
Figure 4:
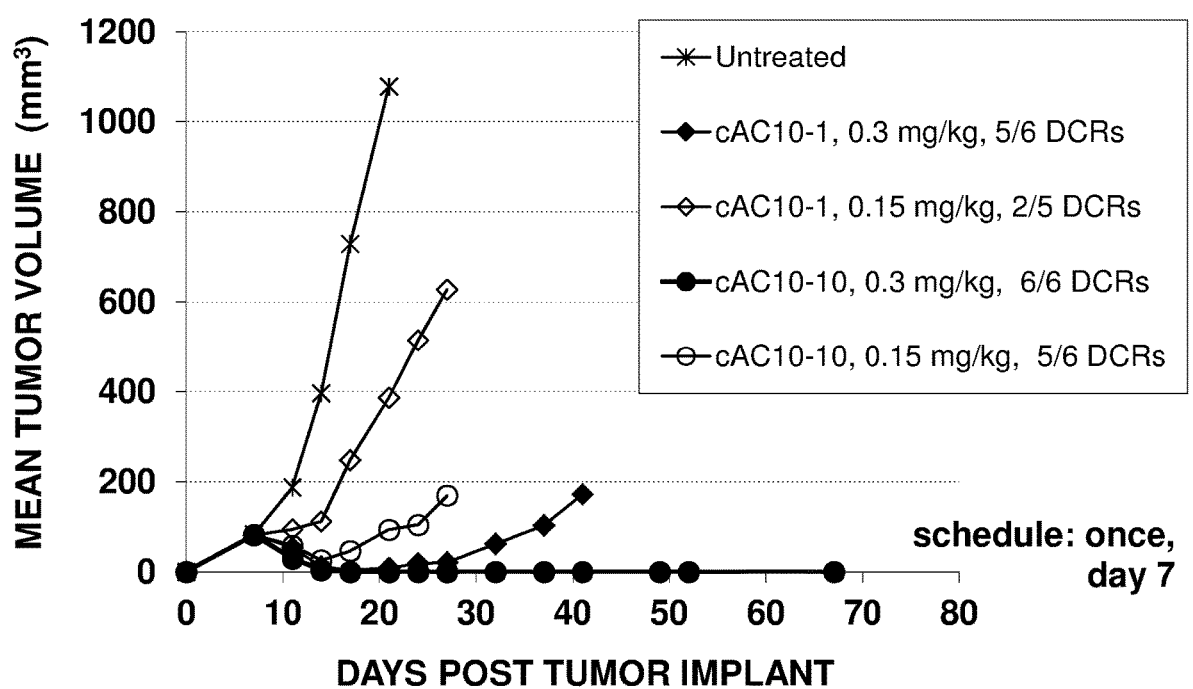
FIG. 4. Mean tumor volume versus days post implant for xenograft Karpas299 model (ALCL) dosed at lower single dose (0.15 mg/kg) with non-PEGylated ADC (cAC10-1), Parallel-oriented PEGylated ADC (cAC10-10), and serial-oriented PEGylated ADC (cAC10-4) compositions with average drug loading of 8 drugs/Ab.

Initial studies were conducted with the L540cy model (FIG. 1) dosed at 2 mg/kg (single dose) of each ADC, and at 0.6 mg/kg (single dose) for the Karpas-299 model (FIG. 2). The plots of tumor volume over time are shown in FIGS. 1 and 2. All drug-linkers were conjugated via their interchain thiols to the chimeric cAC10 antibody described in U.S. Pat. No. 7,090,843, which is incorporated by reference herein, at an average drug loading of 8 drugs per antibody. In both models, the ADCs prepared with 1 (cAC10-mc-PAB(gluc), non-PEGylated) and 10 (PEGylated design in Scheme 2) cured all animals (5/5) in their dose groups, while the ADC prepared with 4 produced no cures, and only modest delays in tumor growth. The diminished activity of cAC10-4 is consistent with its greatly reduced exposure observed in the PK study, shown in FIG. 7. It was suspected that pharmacokinetically-driven differences in activity would also be observed between cAC10-1 and cAC10-10, but that lower doses would be required. Accordingly, studies were repeated with both models at dose levels ½ and ¼ of the dosages used in the initial studies. For L540cy, a dose of 1 mg/kg produced complete cures (6/6) for cAC10-10, and only 2/6 cures for cAC10-1 (FIG. 3). At 0.5 mg/kg, no cures were observed for either group; however, cAC10-10 provided a longer tumor growth delay than cAC10-1 (FIG. 3). At both dose levels, the L540cy antitumor activity for cAC10-10 is greater than for cAC10-1, in line with their respective pharmacokinetic properties. For Karpas-299, a dose of 0.3 mg/kg produced 6/6 cures for cAC10-10 and 5/6 cures for cAC10-1 (FIG. 4). At 0.15 mg/kg, 5/6 cures were observed for cAC10-10 and only 2/6 cures for cAC10-1 (FIG. 4). Thus for Karpas-299, greater antitumor activity was observed at the lowest dose level for cAC10-10, with both ADCs exhibiting high cure rates above this level.

Figure 5:
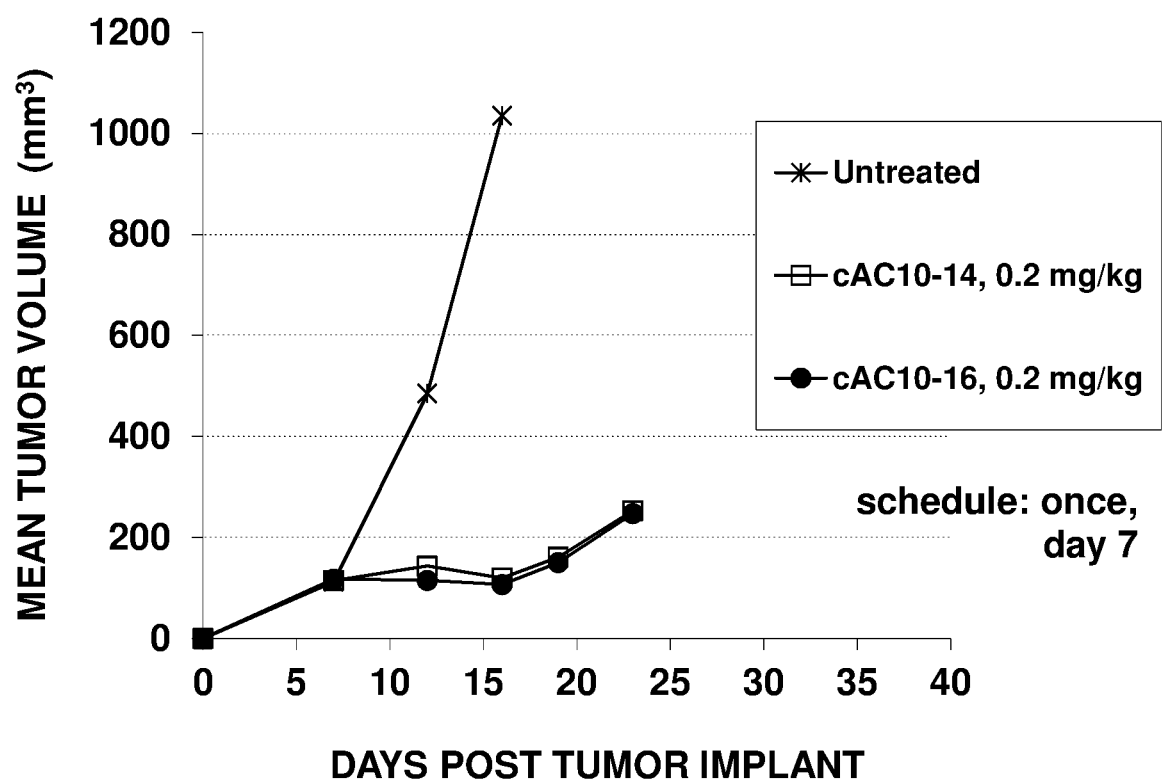
FIG. 5. Mean tumor volume versus days post implant for xenograft Karpas299 model (ALCL) single dosed at 0.2 mg/kg with non-PEGylated ADC, cAC10-[MDpr-PAB(gluc)-MMAE]$_p$ (cAC10-14), and Parallel-oriented PEGylated ADC (cAC10-16) compositions with average drug loading of 8 drugs/Ab (i.e., p is 8).
Figure 6:
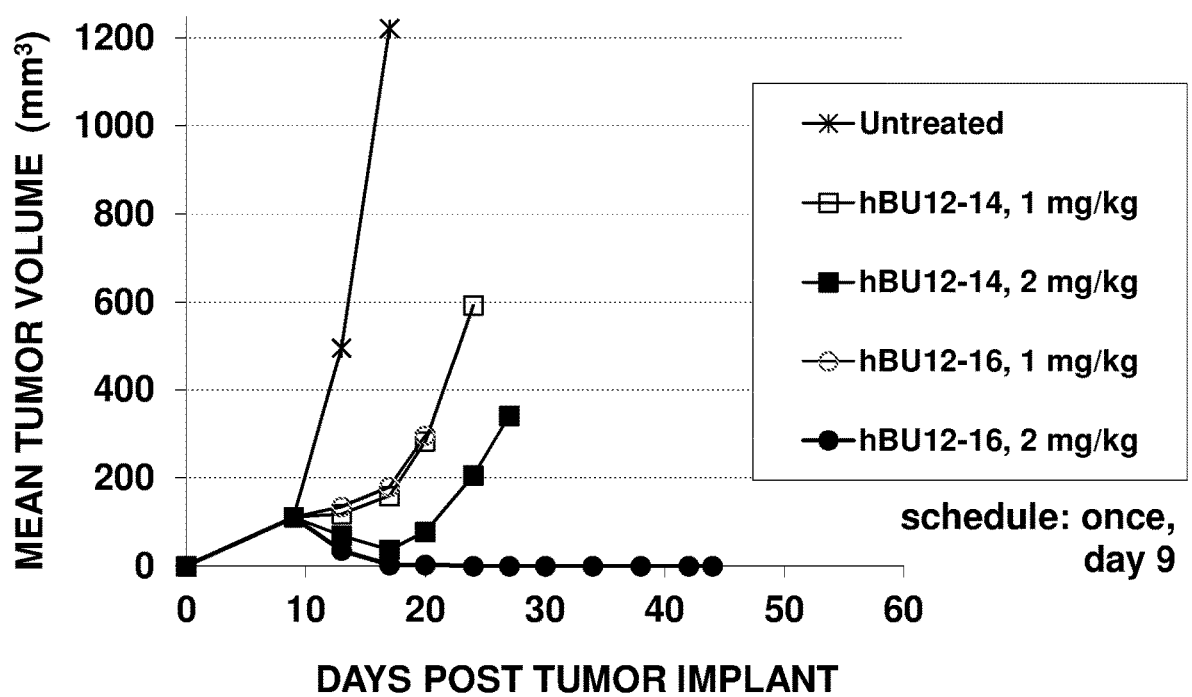
FIG. 6. Mean tumor volume versus days post implant for xenograft Ramos model (Burkitt's Lymphoma) single dosed at 1 mg/kg with non-PEGylated ADC, hBU12-[MDpr-PAB(gluc)-MMAE]$_p$ (hBU12-14), and Parallel-oriented PEGylated ADC (hBU12-16) compositions with average drug loading of 8 drugs/Ab (i.e., p is 8).

Schemes 3 and 4 describe the syntheses of analogs of the non-PEGylated linker 1 and the PEGylated linker 10, respectively, incorporating the Nα-maleimido-diaminopropionic (MDpr) acid group as the point of conjugation. The two linkers were evaluated in the Karpas299 ALCL and Ramos Burkitt's lymphoma models. For Karpas299, cAC10 conjugates of 14 (non-PEGylated) and 16 (parallel PEGylation) were dosed once at 0.2 mg/kg and a similar delay in tumor outgrowth was observed (FIG. 5). In contrast, in the Ramos model, hBU12-16 exerted greater antitumor activity than hBU12-14 at two different doses. Following a single dose of 2 mg/kg, hBU12-16 produced 5/5 cures compared to 0/5 for hBU12-14 (FIG. 6).

Example 10

Synthesis of a mDPR-cys(StBu)-PEG$_{2-36}$-OH conjugation scaffold and a mDPR-cys(StBu)-PEG$_{48-72}$-OH conjugation scaffold

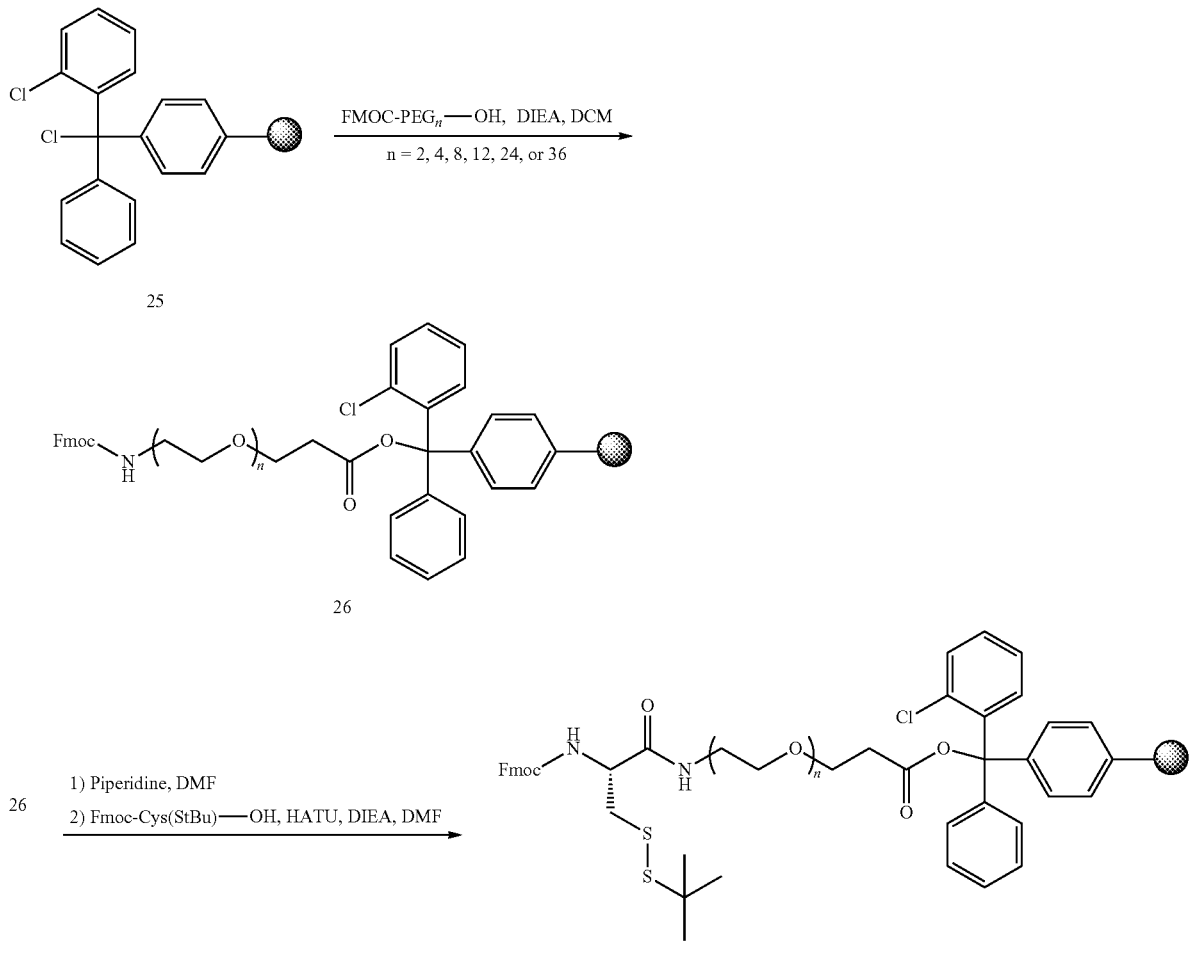

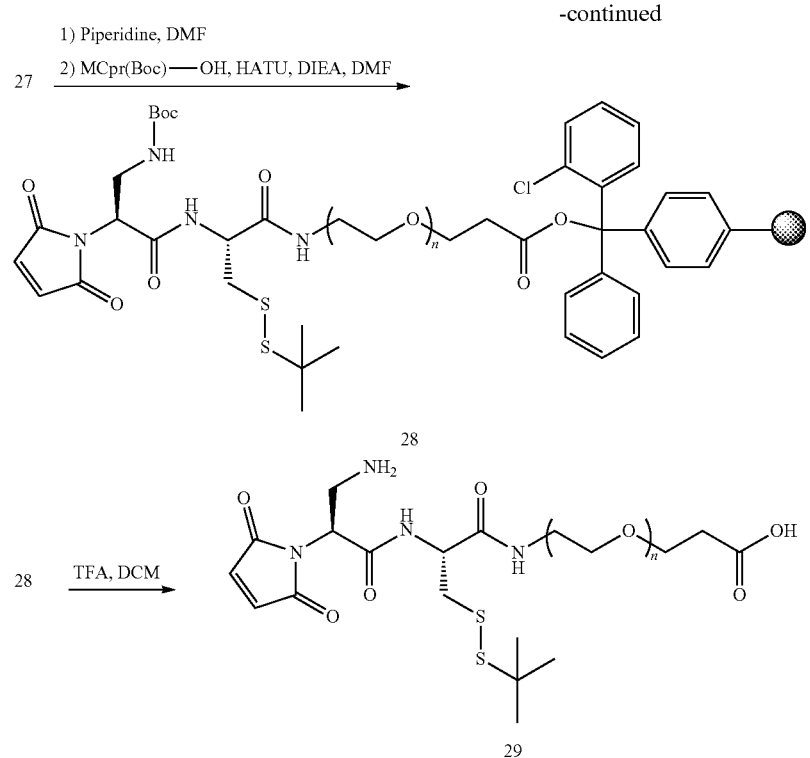
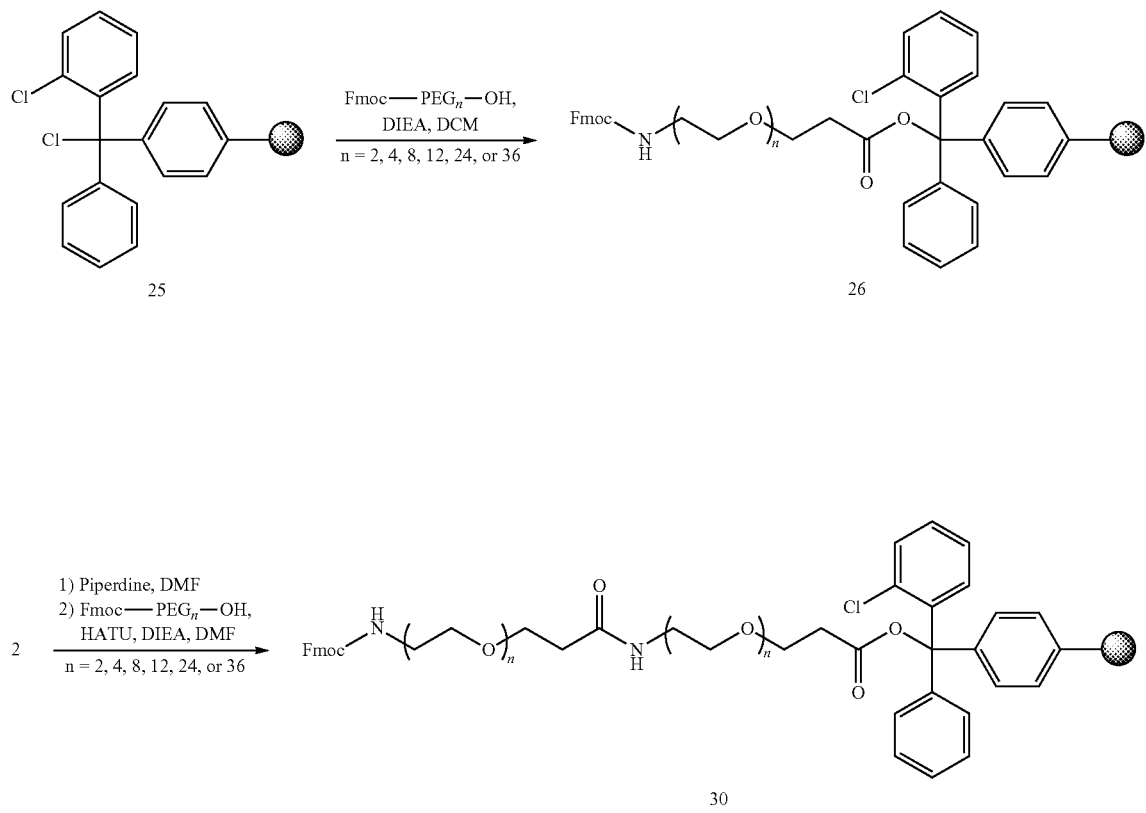
Scheme 8: Synthesis of MDpr-Cys(StBu)-PEG$_{48-72}$-OH

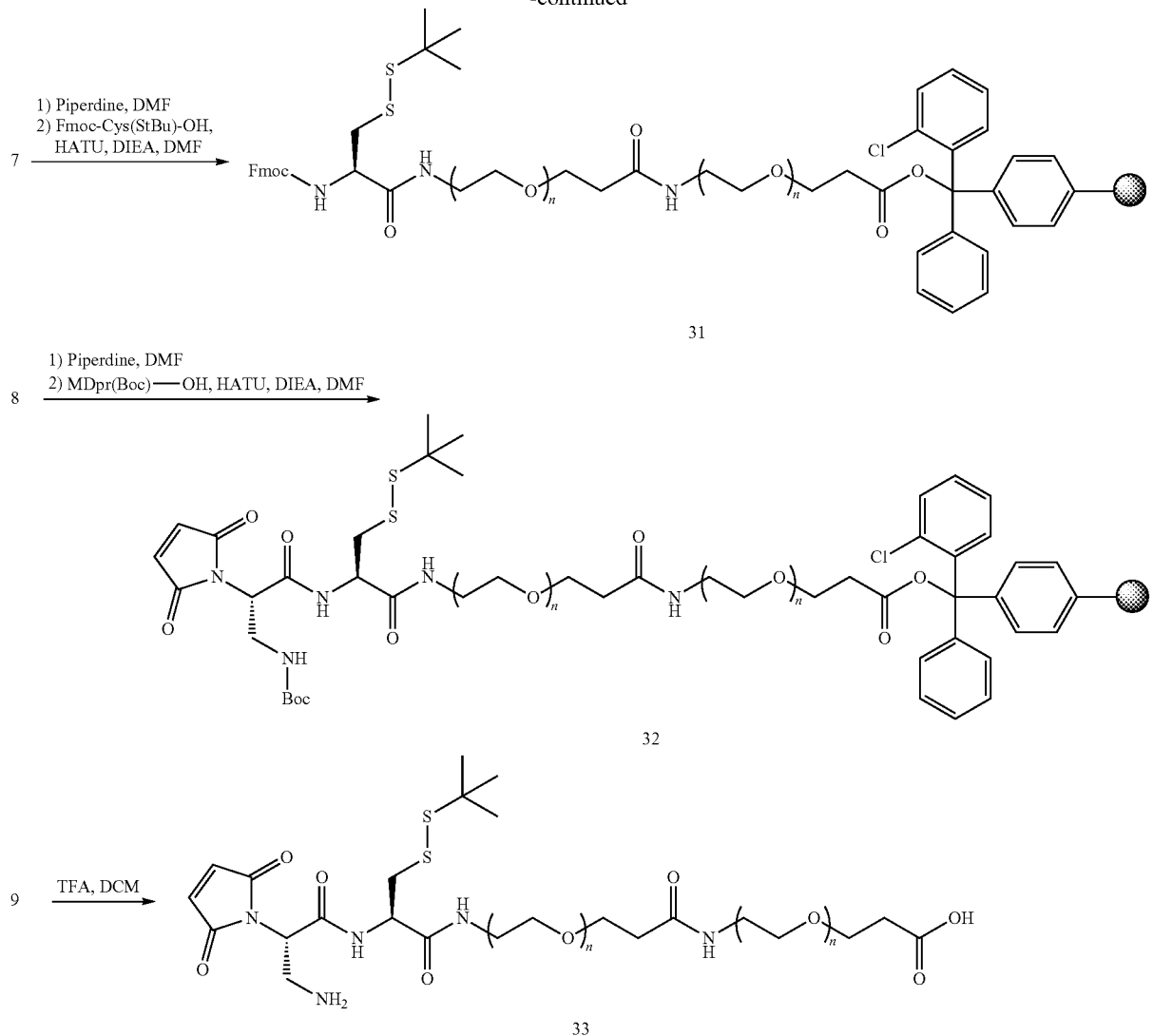

2-Chlorotrityl-Chloride Resin Loading:

A polypropylene syringe fitted with a porous polypropylene disc was loaded with 2-chlorotrityl-chloride resin. A solution of Fmoc-PEG$_n$-OH (1 equiv) and DIEA (1 equiv) in anhydrous DCM (10 mL/gram of resin) was drawn into the syringe. The syringe was capped with a rubber stopper and agitated for 5 min at which point additional DIEA (1.5 equiv) was added. After shaking for an additional 30 min, MeOH (at least 0.8 mL/gram of resin) was drawn into the syringe to quench unreacted resin. After shaking for 5 min, the solution was blown out of the syringe and the resin was washed with DMF (6×5 mL), DCM (6×5 mL), and diethyl ether (6×5 mL). The resin was dried under vacuum.

Rink Amide Resin Loading:

To a solution of an Fmoc protected PEG or amino acid (4 equiv) in anhydrous DMF (10 mL/gram of resin) was added HATU (4 equiv) and DIEA (8 equiv). The solution was agitated for 5 min and drawn into a polypropylene syringe fitted with a porous polypropylene disc loaded with Rink Amide Resin. The reaction mixture was agitated for a minimum of 2 hours and reaction completeness was confirmed by Kaiser test. The resin was washed with DMF (6×5 mL), DCM (6×5 mL), and diethyl ether (6×5 mL) and dried under vacuum.

Fmoc Deprotection:

Fmoc-PEG$_n$-2-chlorotrityl resin in a polypropylene syringe fitted with a porous polypropylene disc was swelled for 30 min with DCM (10 mL/gram of resin). The DCM was blown out and the resin was washed with DMF (6×5 mL). The resin was washed with a solution of 20% piperidine in DMF (3×2 min and 1×60 min) with agitation. Reaction completeness was confirmed by Kaiser test and the resulting Fmoc deprotected resin was washed with DMF (6×5 mL), DCM (6×5 mL), and diethyl ether (6×5 mL) and dried under vacuum.

Amino Acid Coupling:

To a solution of an Fmoc protected PEG acid, amino acid, or MDpr(Boc)-OH (3 equiv) in anhydrous DMF (10 mL/gram of resin) was added HATU (3 equiv) and DIEA (6 equiv). The solution was agitated for 5 min and drawn into the polypropylene syringe containing the Fmoc deprotected aminoacid 2-chlorotrityl-resin. The reaction mixture was agitated for a minimum of 2 hours and reaction completeness was confirmed by Kaiser test. The resin was washed with DMF (6×5 mL), DCM (6×5 mL), and diethyl ether (6×5 mL) and dried under vacuum.

Removal of IvDde Protecting Group:

To remove the IvDde protecting group the peptide resin was washed with a solution of 2% hydrazine in DMF (2×30 min) with agitation. Reaction completeness was confirmed by Kaiser test and the resulting IvDde deprotected resin was washed with DMF (6×5 mL), DCM (6×5 mL), and diethyl ether (6×5 mL) and dried under vacuum.

Peptide-Resin Cleavage:

Final peptides were cleaved from resin by treatment with TFA in DCM (30% v/v for 2-chlorotrityl resin or 95% v/v for Rink amide resin) for 15 min. After cleavage, the solution was left for an additional 60 min to ensure complete removal of the Boc protecting group from the MDpr residue. The resulting solution was evaporated with a stream of nitrogen and the resulting peptides were analyzed by LC-MS. Peptides were either used crude or purified by preparative reversed phase HPLC followed by LC-MS analysis.

Example 11

Conjugation of Pegylated Conjugation Scaffold to Antibody and Drug-Linker

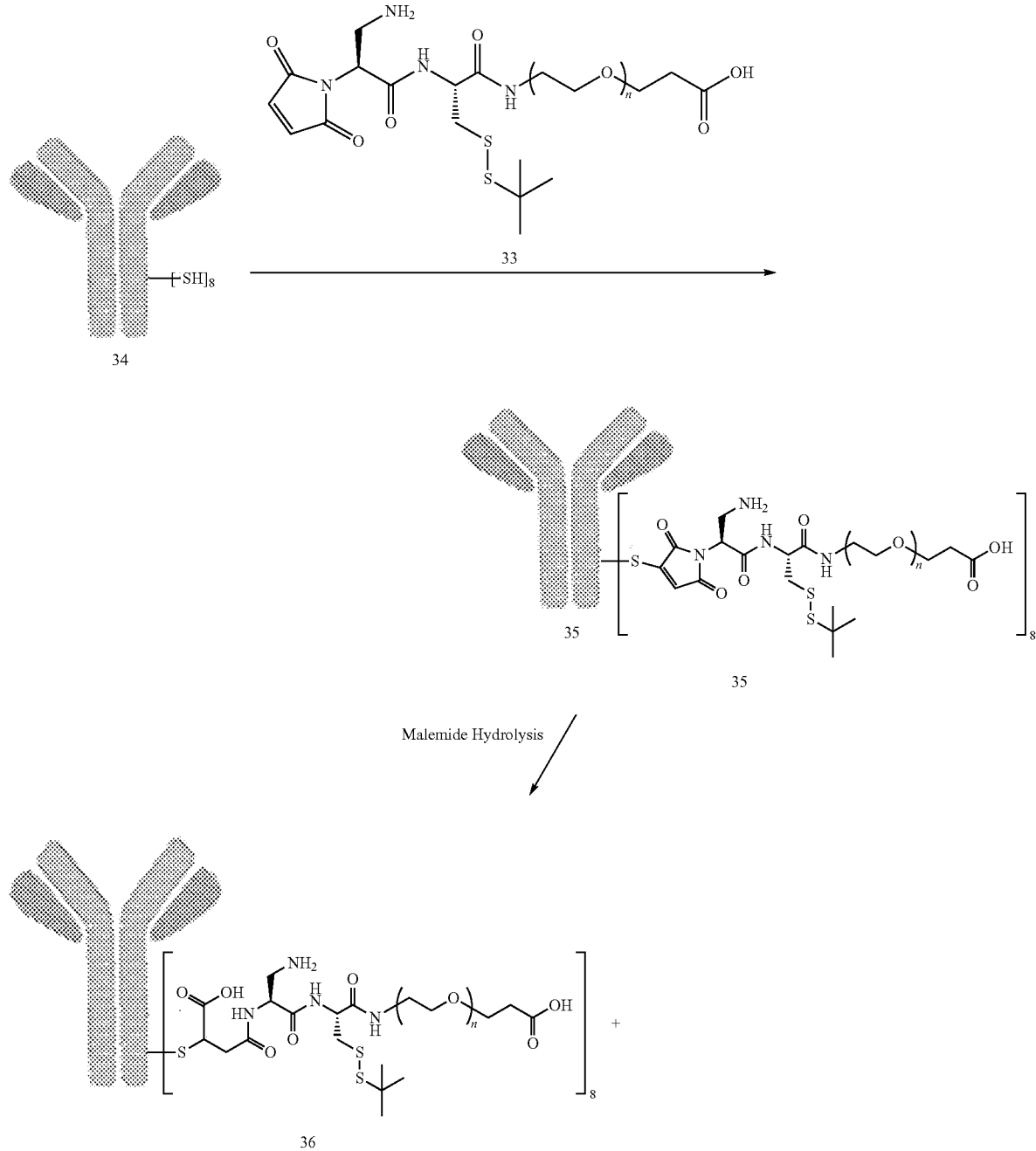

Scheme 9: Conjugation of PEGylated Scaffold to Fully Reduced Antibody Interchain Disulfides

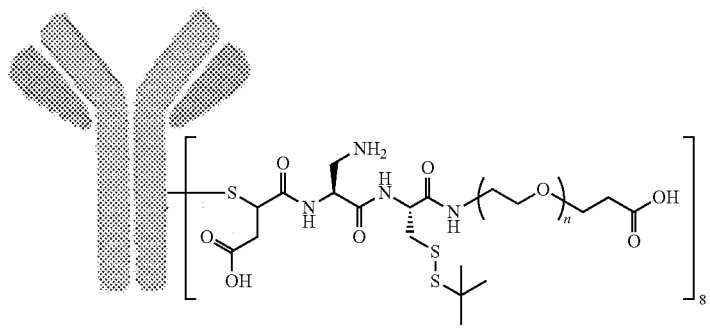
37

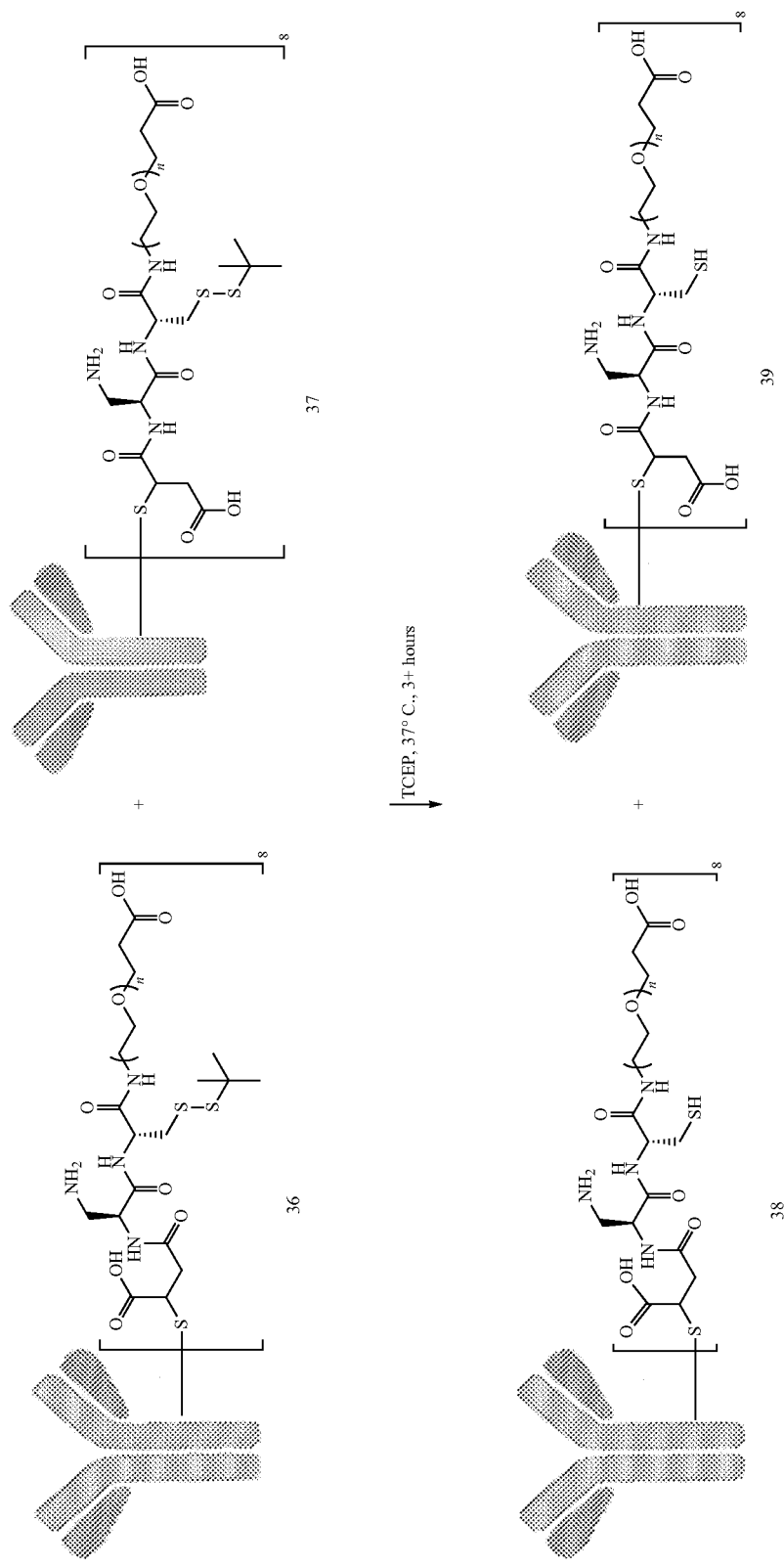
Scheme 10: Deprotection of PEGylated Conjugation Scaffolds

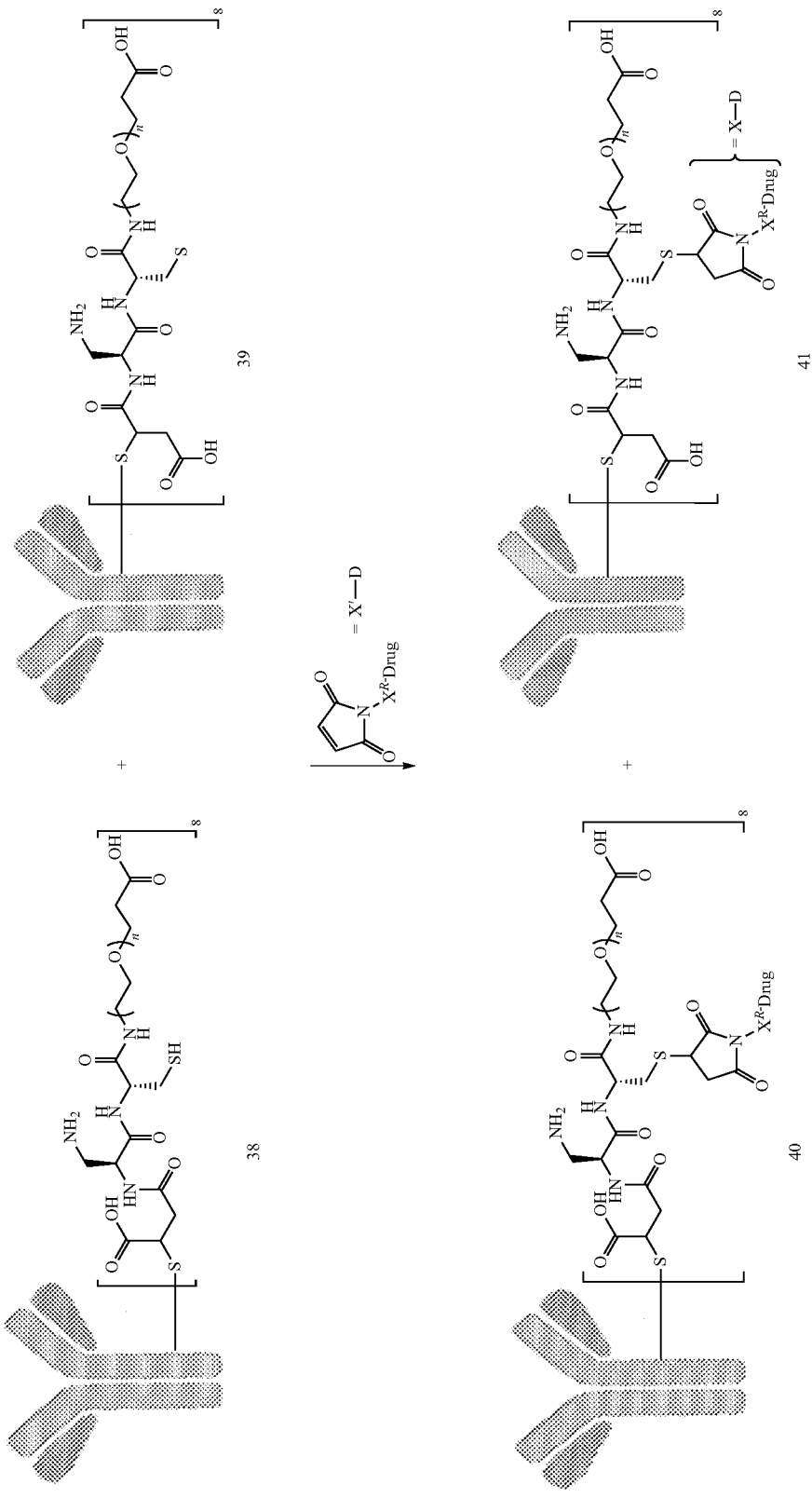
Scheme 11: Drug Conjugation of PEGylated Scaffolds wherein X$^R$ is the remainder of the Releasable Assembly Unit precursor X' in a X'-D moiety or the remainder of the Releasable Assembly unit X in an -X-D moiety.

Full Reduction of Antibody Interchain Disulfide Bonds:

To a solution of antibody at a concentration of approximately 10 mg/mL in PBS containing diethylenetriaminepentaacetic acid (1 mM) and buffered with additional potassium phosphate (100 mM, pH 7.4) was added 12 equivalents of tris(2-carboxyethyl)-phosphine (TCEP). The solution was vortexed and incubated at 37° C. for 1 hour. Complete reduction of interchain disulfide bonds was confirmed by reversed phase chromatography. Additional TCEP was added if reduction was incomplete. After reduction, the antibody solution was desalted into PBS containing 2 mM EDTA by 3 rounds of dilution and centrifugation at 4,000×g through a 30 kDa MWCO filter. The resulting fully reduced antibody (34 was filtered through a sterile 0.22 μm centrifugal filter and used immediately or stored at −80° C.

Conjugation of Maleimide Containing PEGylated Scaffold:

To a solution of fully reduced antibody (34) at a concentration of approximately 10 mg/mL in PBS containing EDTA (2 mM) and buffered with additional potassium phosphate (100 mM, pH 7.4) was added 12 molar equivalents of MDpr-PEG$_n$-OH from a 5-20 mM DMSO stock solution. The resulting solution was left at room temperature for 30 min. Complete conjugation was confirmed by reversed phase chromatography. Additional PEG reagent was added if the conjugation was incomplete. After conjugation, the antibody solution was desalted into PBS by 3 rounds of dilution and centrifugation at 4,000×g through a 30 kDa MWCO filter. The resulting PEGylated antibody solution (36 and 37) was filtered through a sterile 0.22 μm centrifugal filter and used immediately or stored at −80° C.

Removal of t-Butylthiol Protecting Groups from PEGylated Conjugation Scaffold:

To a solution of PEGylated antibody (36 and 37) at concentration of approximately 10 mg/mL in PBS containing diethylenetriaminepentaacetic acid (1 mM) and buffered with additional potassium phosphate (100 mM, pH 7.4) was added 20-30 equivalents TCEP. The solution was vortexed and incubated at 37° C. for 3 hours. The complete removal of t-butylthiol protecting groups was confirmed by reversed phase chromatography. Additional TCEP was added and the incubation at 37° C. was continued if the reduction was incomplete. After reduction, the antibody solution was desalted into PBS containing 2 mM EDTA by 3 rounds of dilution and centrifugation at 4,000×g through a 30 kDa MWCO filter. The resulting deprotected PEGylated antibody solution (38 and 39) was filtered through a sterile 0.22 μm centrifugal filter and used immediately or stored at −80° C.

Conjugation Maleimide Containing Drug Linkers:

To a solution of deprotected PEGylated antibody (38 and 39) at a concentration of approximately 10 mg/mL in PBS containing EDTA (2 mM) and buffered with additional potassium phosphate (100 mM, pH 7.4) was added 12 molar equivalents of a maleimide containing drug-linker from a 5-20 mM DMSO stock solution. The resulting solution was left at room temperature for 30 min. Complete conjugation was confirmed by reversed phase chromatography. Additional drug-linker was added if the conjugation was incomplete. After conjugation, the antibody solution was desalted into PBS by 3 rounds of dilution and centrifugation at 4,000×g through a 30 kDa MWCO filter. The resulting PEGylated antibody-drug conjugate solution (40 and 41) was filtered through a sterile 0.22 μm centrifugal filter, analyzed by size exclusion chromatography (SEC), and stored at −80° C.

Example 12

ADCs Comprising PEG in a Parallel Orientation Exhibited Low Aggregation Levels

SEC Analysis of Conjugates:

Antibody, ADC, of PEGylated ADC samples (50 μg) were diluted to 1 mg/mL in PBS and 30 μL injections were chromatographed over an analytical SEC column (TOSOH TSKgel G3000SW$_{XL}$, 7.8 mm ID×30 cm, 5 μm) on a Waters 2695 HPLC system. Samples were eluted isocratically with 92.5% 25 mM sodium phosphate (pH 6.8), 350 mM NaCl, and 7.5% isopropyl alcohol at a flow rate of 1 mL/min.

Figure 8:
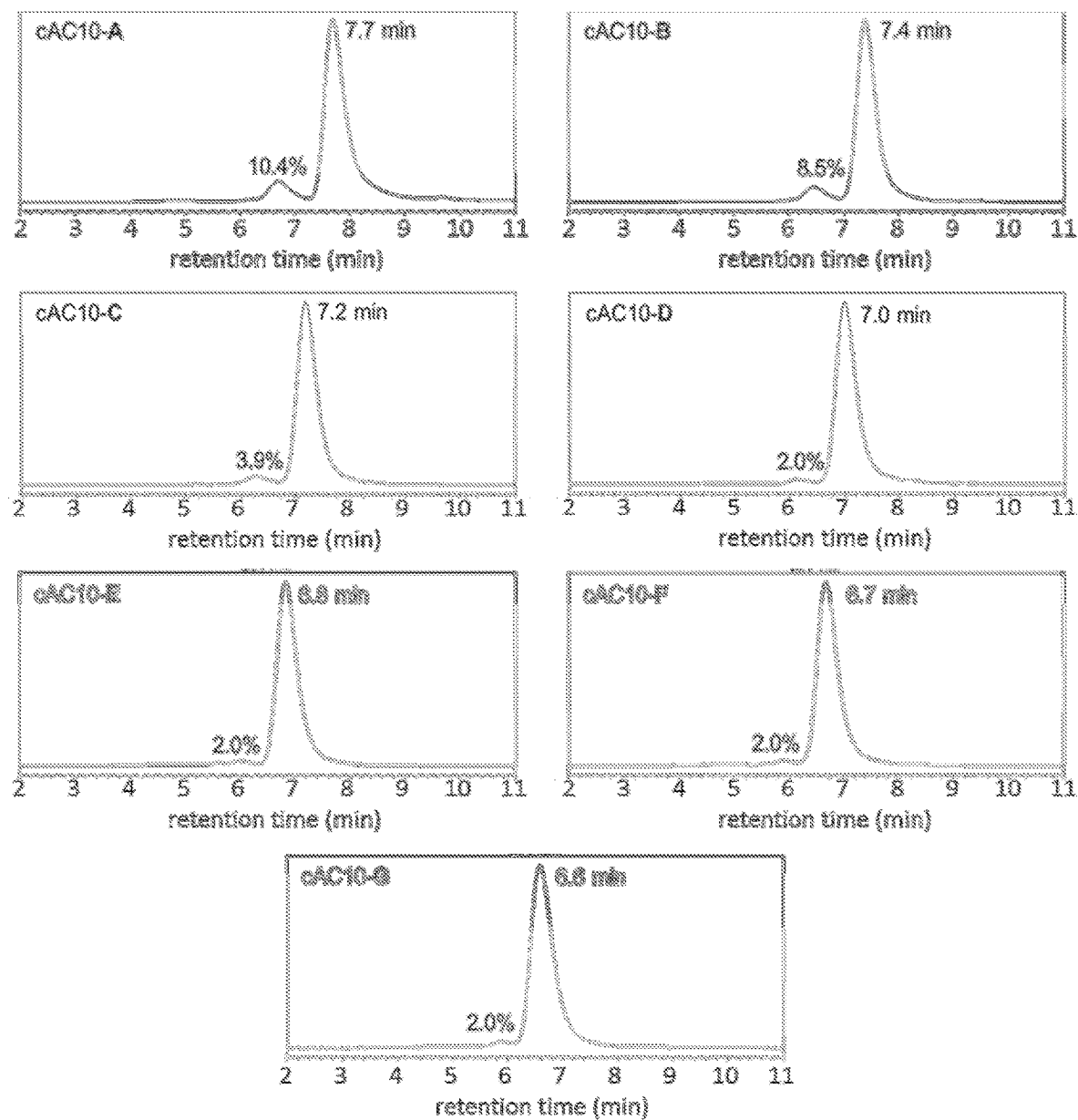
FIG. 8. Size exclusion chromatograms of cAC10 ADCs with 8 drugs/Ab having non-PEGylated drug linkers and parallel-oriented PEGylated drug linker moieties, wherein the drug-linker moiety is MDpr-VC-PABA-MMAE, with PEG units of varing lengths: cAC10-A (non-PEGylated), cAC10-B (PEG$_{12}$), cAC10-C(PEG$_{24}$), cAC10-D (PEG$_{36}$), cAC10-E (PEG$_{12}$+PEG$_{36}$), cAC10-F (PEG$_{24}$+PEG$_{36}$), and cAC10-G (PEG$_{36}$+PEG$_{36}$).

In order to examine the effect of PEG length on ADC aggregation, cAC10-MDpr-vcMMAE ADCs with 8 drugs per antibody were prepared with or without PEGylated conjugations scaffolds assembled using PEG units of varying size. SEC results are shown in FIG. 8. Without inclusion of the PEGylated conjugation scaffold (cAC10-A), ADC aggregation was 10.4%. Adding the PEGylated scaffold generates ADCs with lower aggregation levels. Aggregation decreased with increasing PEG length up to PEG$_{36}$ (cAC10-D), where the aggregate peak was 2.0% of the total signal. In the case of cAC10-MDpr-vcMMAE, PEG units longer than PEG$_{36}$ (cAC10-D -cAC10-G) do not decrease aggregation further.

Structures of Drug-Linkers Included in SEC Study:

The ADCs are conjugated to the antibody via the interchain thiols. The antibody-substituted succinimides may exist in their hydrolyzed forms (i.e., a water molecule is added across one and not both of the succinimide's C—N bonds).

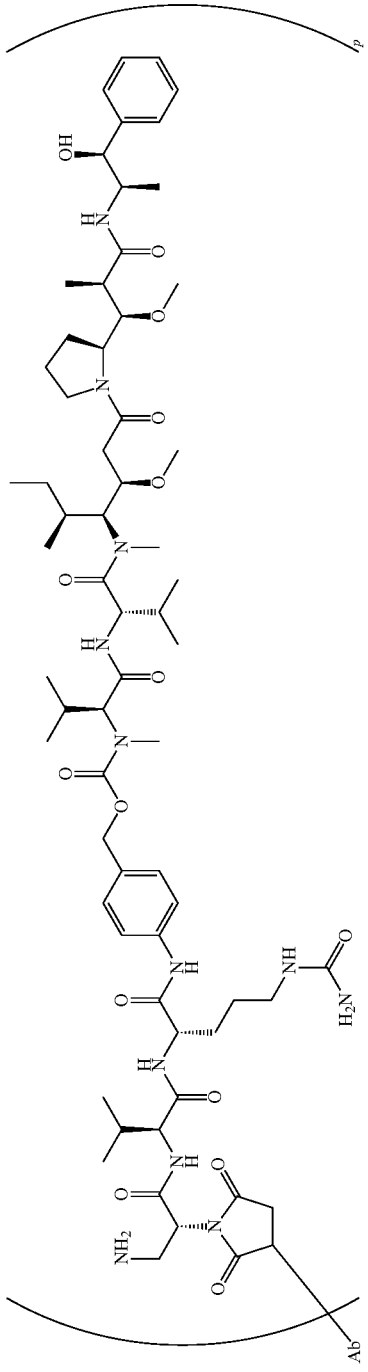
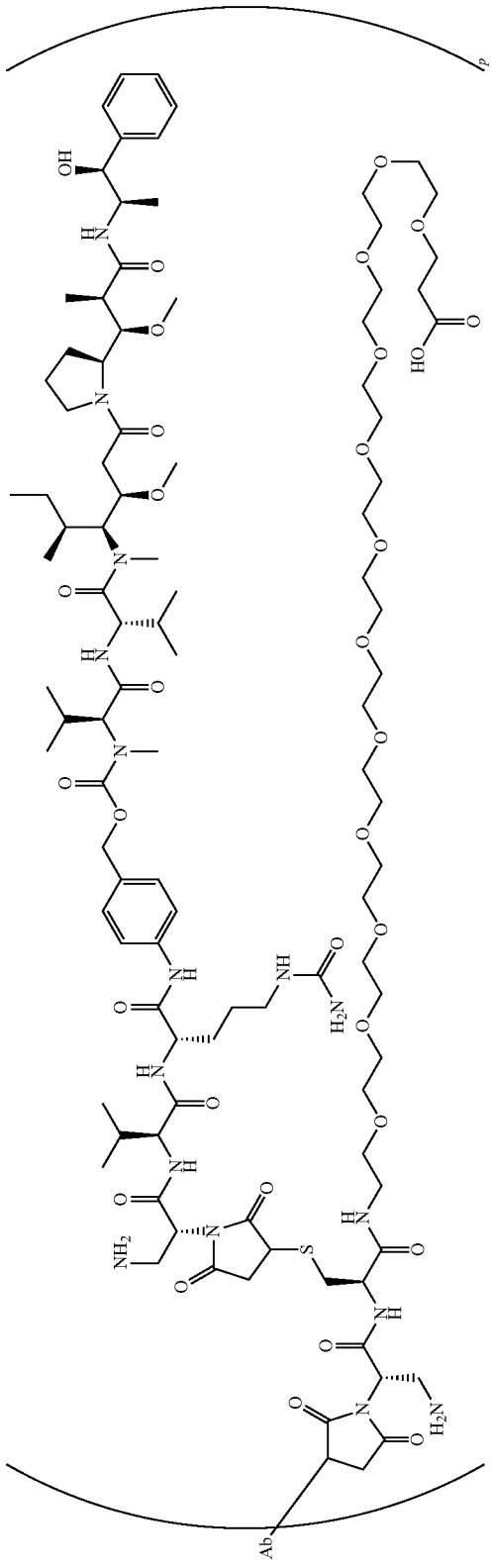

C
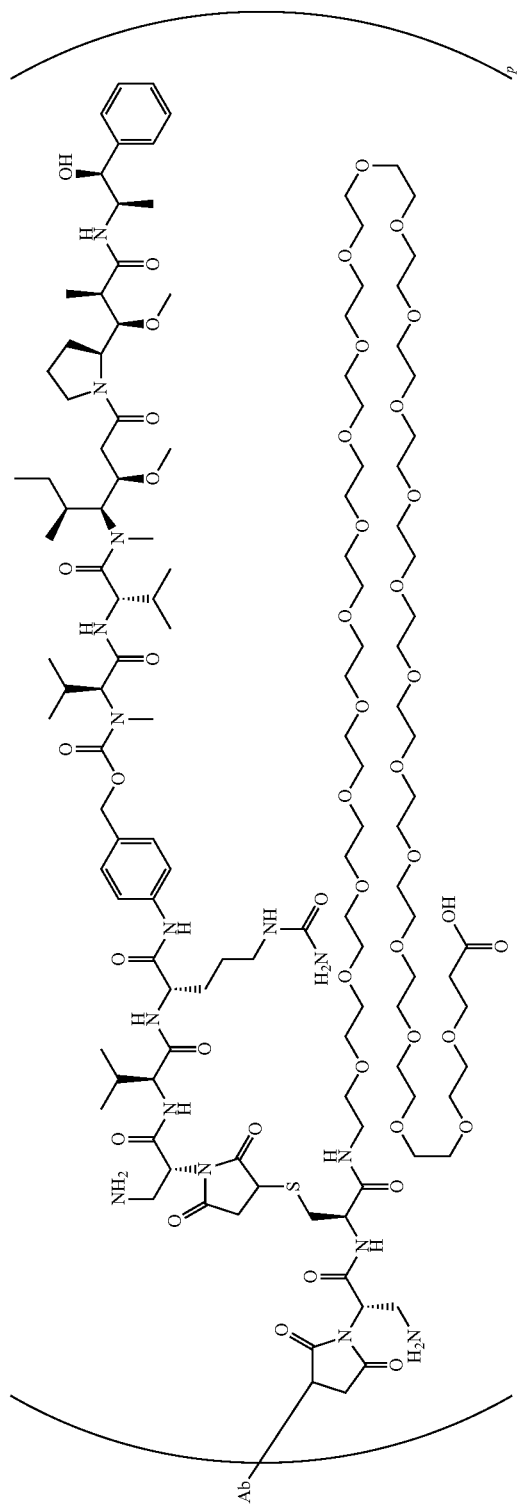
D
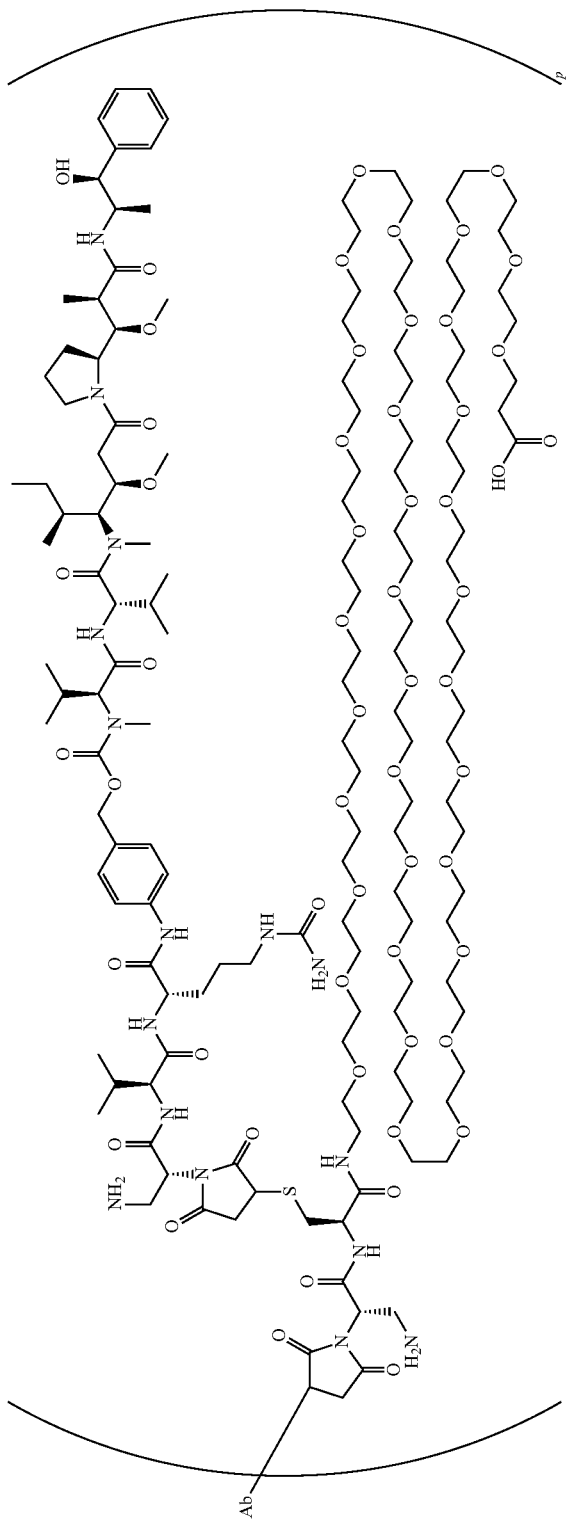

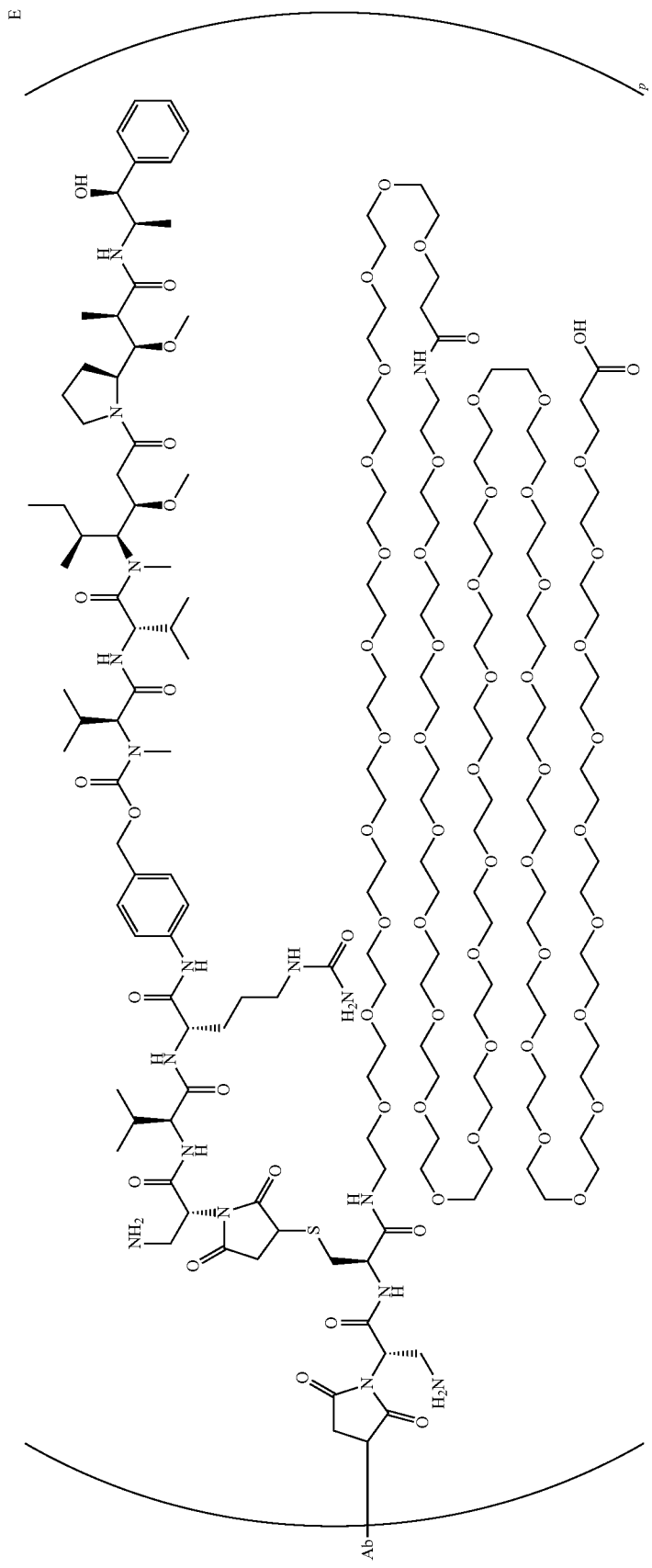

Example 13

ADCs Comprising PEG in a Parallel Orientation Exhibit In Vitro Activity Similar to their Non-Pegylated Counterparts In Vitro Cytotoxicity of ADCs Prepared with PEGylated Conjugation Scaffolds MDpr-vcMMAE-based ADCs directed toward CD30 were prepared with and without the addition of a PEGylated conjugation scaffold. Conjugates of compounds A (non-PEGylated), B ($PEG_{12}$), C ($PEG_{24}$), and D ($PEG_{36}$) were tested against the CD30 positive cell lines, Karpas 299 and L540cy. The inclusion of PEG and the increasing PEG length lead to negligible difference in in vitro cytotoxicity (Table 3). Control ADCs (non-PEGylated and PEGylated) prepared with n-ethylaminomaleimide (NAEM) instead of MDpr-vcMMAE (cAC10-H, cAC10-I, and cAC10-J) showed no activity in this assay indicating that the PEGylated scaffolds are not contributing to in vitro cytotoxicity.

TABLE 3

In vitro cytotoxic activity of anti-CD30 ADCs prepared with PEGylated conjugation scaffolds; values represent $IC_{50}s$ in ng/mL.

| ADC | drugs/Ab | CD30+ cell lines | |
| --- | --- | --- | --- |
| | | Karpas 299 | L540cy |
| cAC10-A | 8 | 1.7 | 5.6 |
| cAC10-B | 8 | 2.2 | 5 |
| cAC10-C | 8 | 4.2 | 5.5 |
| cAC10-D | 8 | 4.3 | 4 |
| cAC10-NAEM | 8 | No Effect | No Effect |
| cAC10-H | 8 | No Effect | No Effect |
| cAC10-I | 8 | No Effect | No Effect |
| cAC10-J | 8 | No Effect | No Effect |

When compared to the non-PEGylated conjugate cAC10-A with 4 drug loading the 8 drug loaded cAC10-A had 2-4× the in vitro cytotoxicity against Karpas 299 and L540cy; however, the 8 loaded ADC did not out perform the 4-loaded ADC in in vivo xenograft models due to more rapid clearance of the 8-loaded ADC (see example 14).

The PEG 24 cAC10 conjugate, cAC10-10 having -X-D of mc-PABA(gluc)-MMAE, which was prepared from the Linker-Drug intermediate of example 2 and has the $PEG_{24}$ unit in parallel orientation (drug/Ab of 8) to the drug, also had greater activity in xenograft models in comparison to the corresponding 8-loaded non-PEGylated ADC (cAC10-1) and the 8-loaded ADC having the $PEG_{24}$ unit in serial orientation (cAC10-4), in which the latter was prepared from the Linker-Drug intermediate of example 1 (see FIGS. 1 and 2).

NAEM Capped Conjugation Scaffolds Used as Controls:

The ADCs are conjugated to the antibody via the interchain thiols. The antibody-substituted succinimides may exist in their hydrolyzed forms (i.e., a water molecule is added across one and not both of the succinimide's C—N bonds).

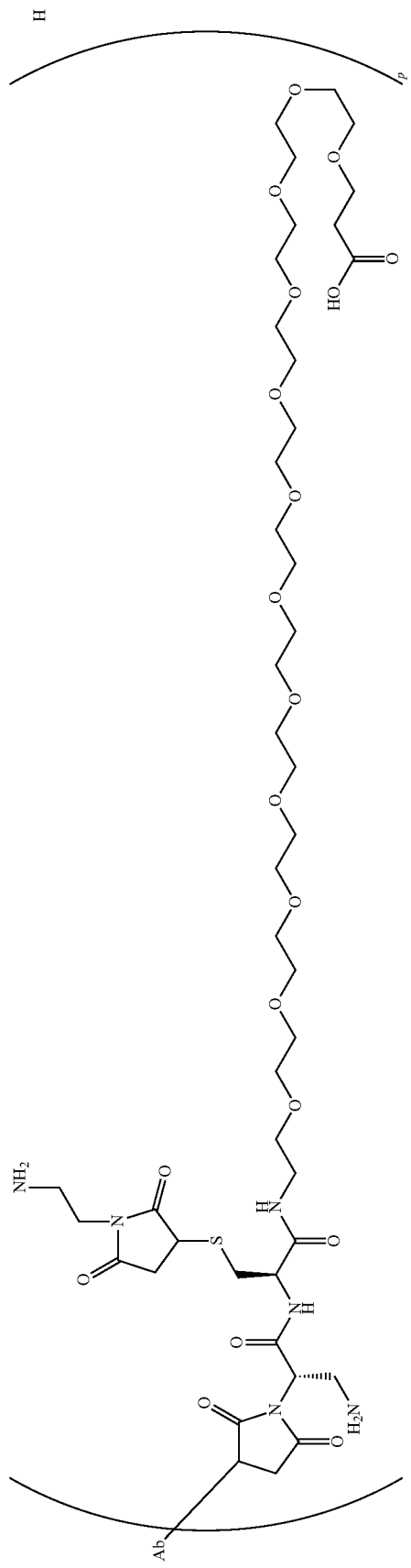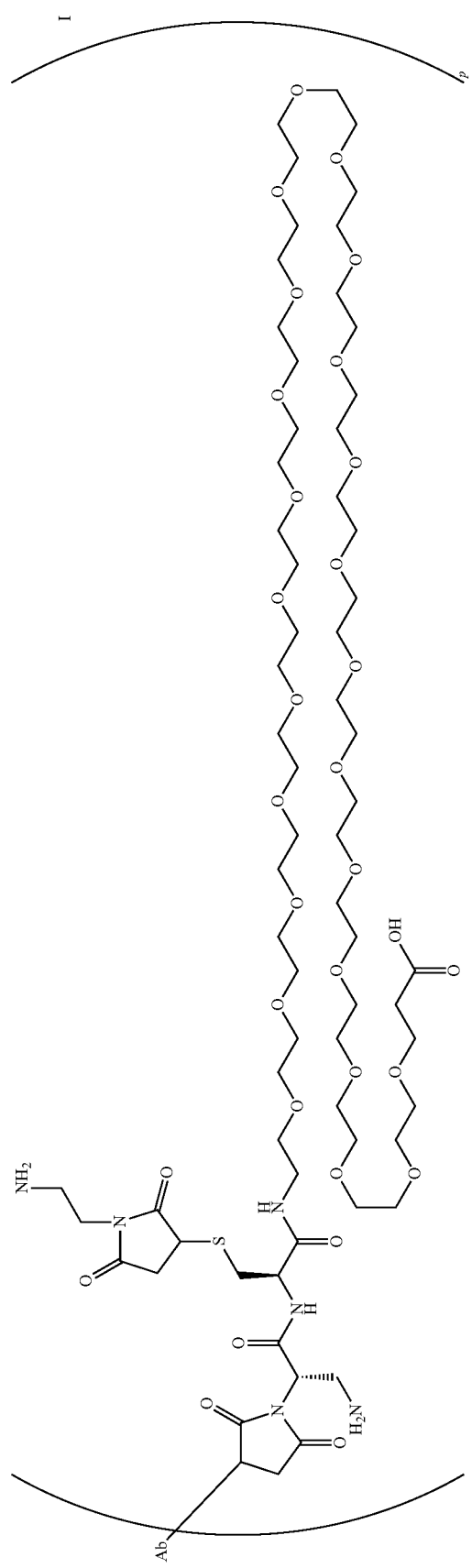

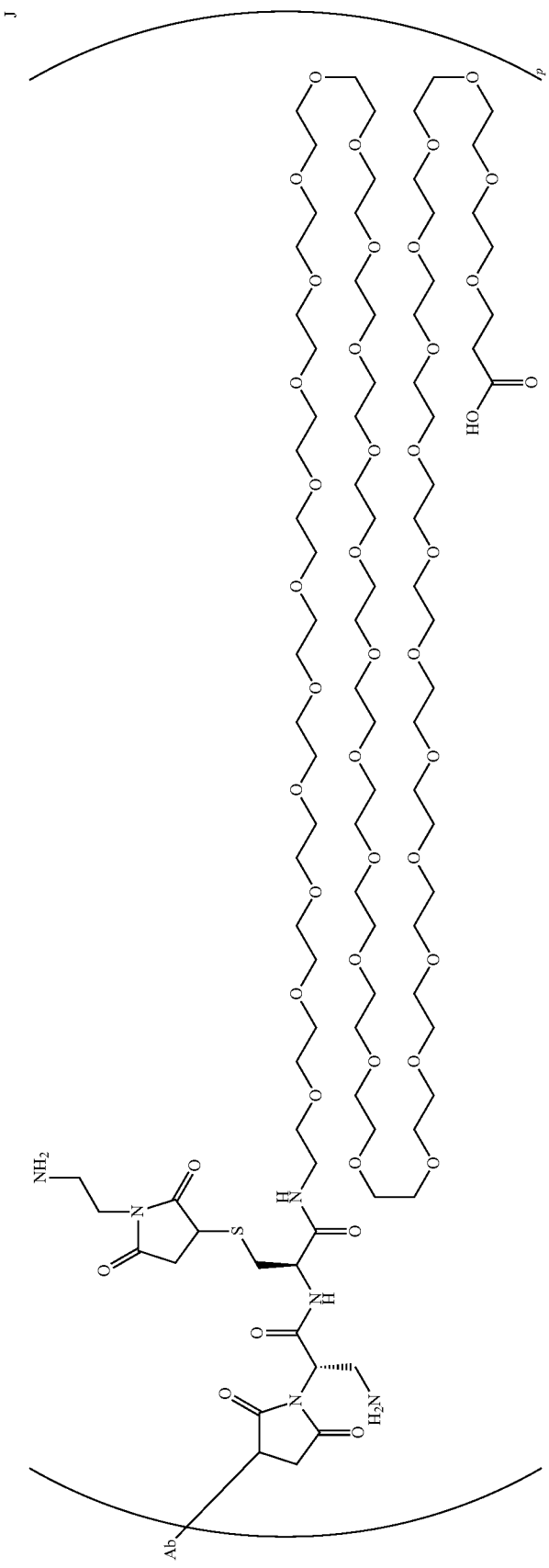

Example 14

Figure 9:
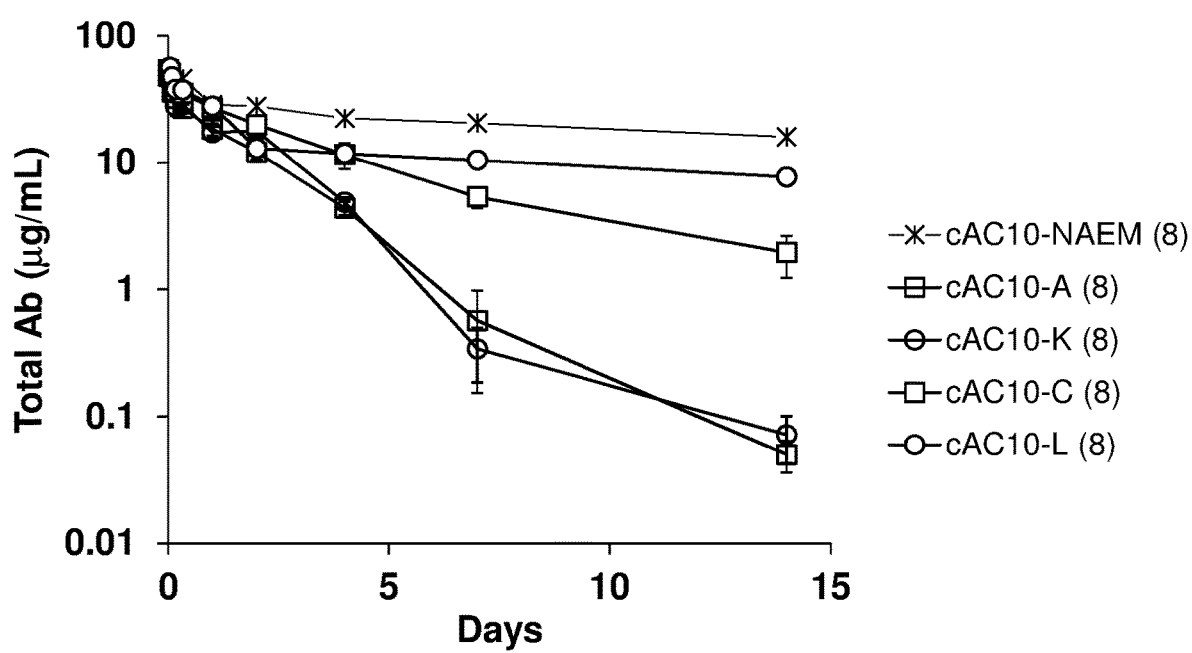
FIG. 9. Pharmokinetic profile (total Ab concentration in μg/mL vs time in days) in rat following a single intavenous 3 mg/Kg dose of cAC10 ADCs with 8 drugs/Ab having non-PEGylated drug linkers, wherein the ADC conjugate is c-AC10-MDpr-VC-PAB-MMAE (cAC10-A) and cAC10-mc-VC-PABA-MMAE (cAC10-K), and parallel oriented PEGylated drug linker moieties wherein the ADC is represented by the structure of cAC10-[MDpr (-X-D)-PEG$_{24}$]$_p$, and -X-D is MDpr-VC-PAB-MMAE (cAC10-C) or mc-VC-PABA-MMAE (cAC10-L) and p is 8 compared to a control conjugates cAC10-NAEM (cAC10-I) having a PEG$_{24}$ scaffold capped using n-ethylaminomaleimide (i.e., no attached drug unit).

ADCs Comprising PEG in a Parallel Orientation Improved Pharmacokinetics as Compared to ADCs Comprising No PEG Mice were dosed with a single iv dose of 3 mg/kg of each ADC loaded at 8 drugs/mAb. As expected, the non-PEGylated ADCs prepared with either mc-vcMMAE (K) or MDpr-vcMMAE (A) cleared from circulation much more rapidly than the control conjugate prepared with NAEM. The corresponding PEGylated ADCs C and L showed improved PK, i.e. slower clearance (FIG. 9).

Additional Compounds Included in Mouse PK—

The ADCs are conjugated to the antibody via the interchain thiols. The antibody substituted succinimides may exist in their hydrolyzed forms (i.e., a water molecule is added across one and not both of the succinimide's C—N bonds).

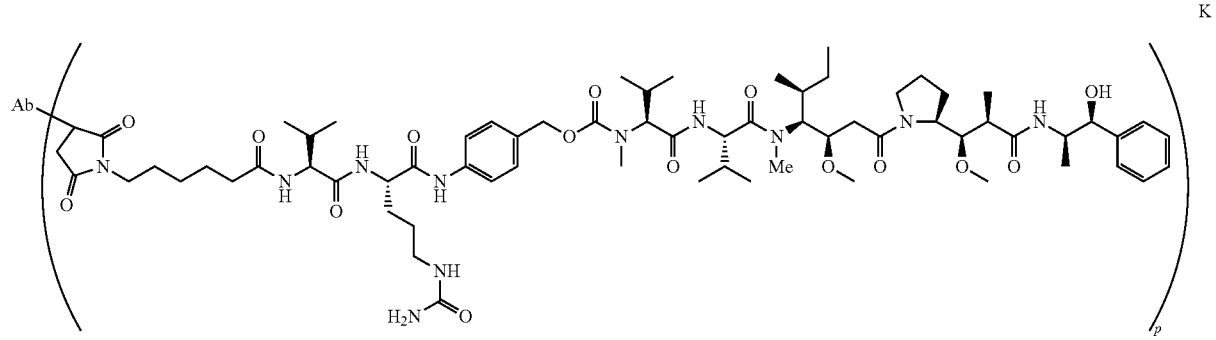

K

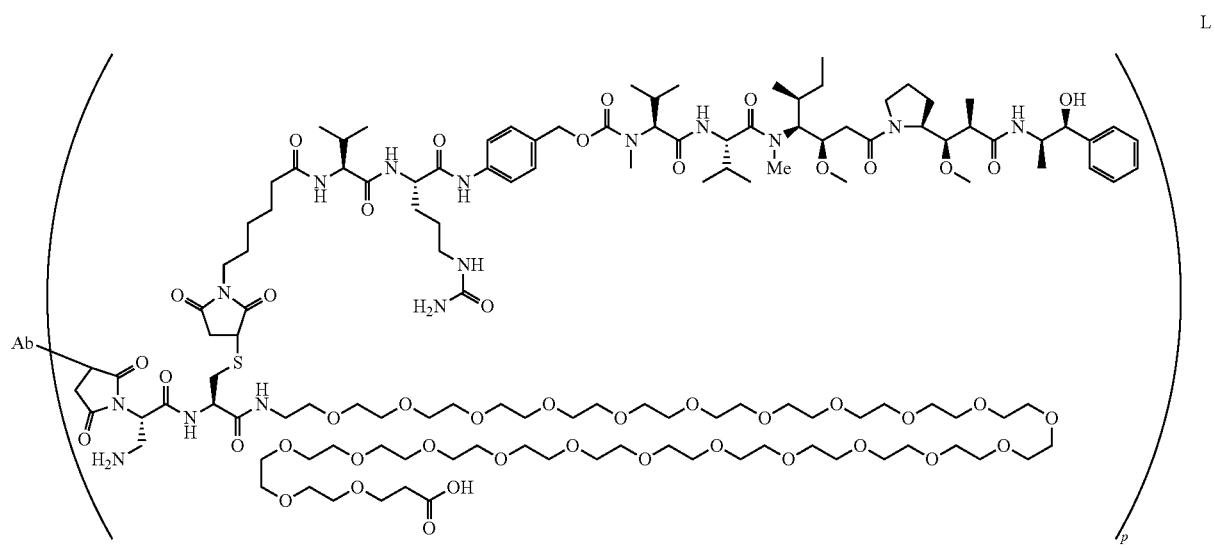

L

Figure 10:
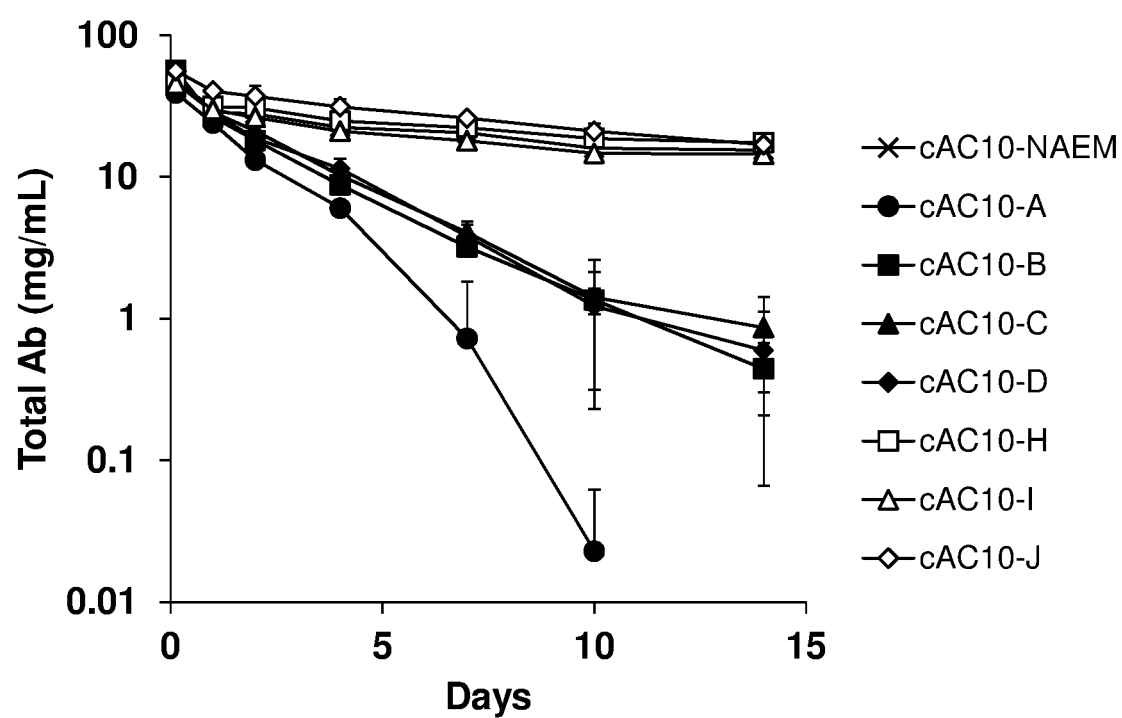
FIG. 10. Pharmokinetic profile (total Ab concentration in μg/mL vs time in days) in rat following a single intavenous 3 mg/Kg dose of cAC10 ADCs with 8 drugs/Ab having non-PEGylated drug linkers, wherein the ADC conjugate is c-AC10-[MDpr-VC-PAB-MMAE]$_p$ (cAC10-A) or parallel-oriented PEGylated drug linker moieties, wherein the ADC is represented by the structure of cAC10-[MDpr (-X-D)-PEG]$_p$, wherein p is 8, -X-D is MDpr-VC-PAB-MMAE and PEG is a PEG Unit having varing lengths: PEG$_{12}$ (cAC10-B), PEG$_{24}$ (cAC10-C), and PEG$_{36}$ (cAC10-D) compared to corresponding control conjugates having a PEG scaffold capped using n-ethylaminomaleimide (i.e., no attached drug unit): PEG$_{12}$ (cAC10-H), PEG$_{24}$ (cAC104), and PEG$_{36}$ (cAC10-J).

In a second experiment, mice were dosed with a single iv dose of 3 mg/kg of each ADC loaded at 8 drugs/mAb. As above (FIG. 9), the ADC prepared with the non-PEGylated MDpr-vcMMAE A showed accelerated clearance from circulation (FIG. 10). The three ADCs prepared with the PEGylated conjugation scaffolds B, C, and D exhibited improved clearance (FIG. 10). In this assay, ADCs prepared with the varying PEG lengths, $PEG_{12}$ (B), $PEG_{24}$ (C), and $PEG_{36}$ (D) showed negligible differences from each other. As anticipated, control conjugates prepared from NAEM capped PEGylation scaffolds (H, I, and J) showed PK closely resembling NAEM capped antibody (FIG. 10).

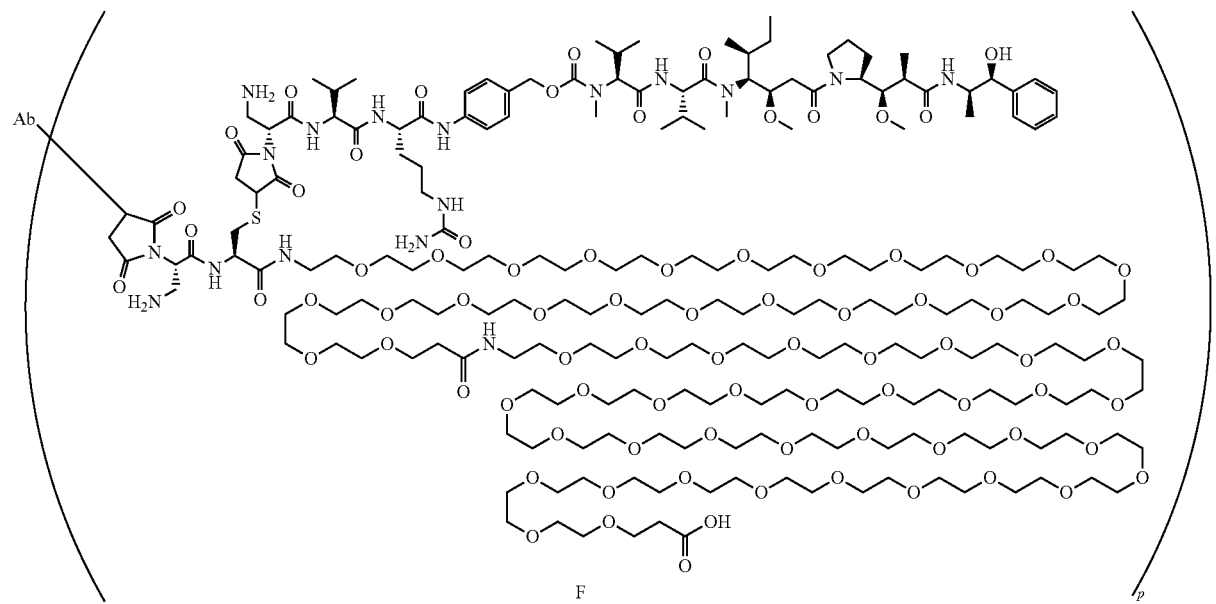

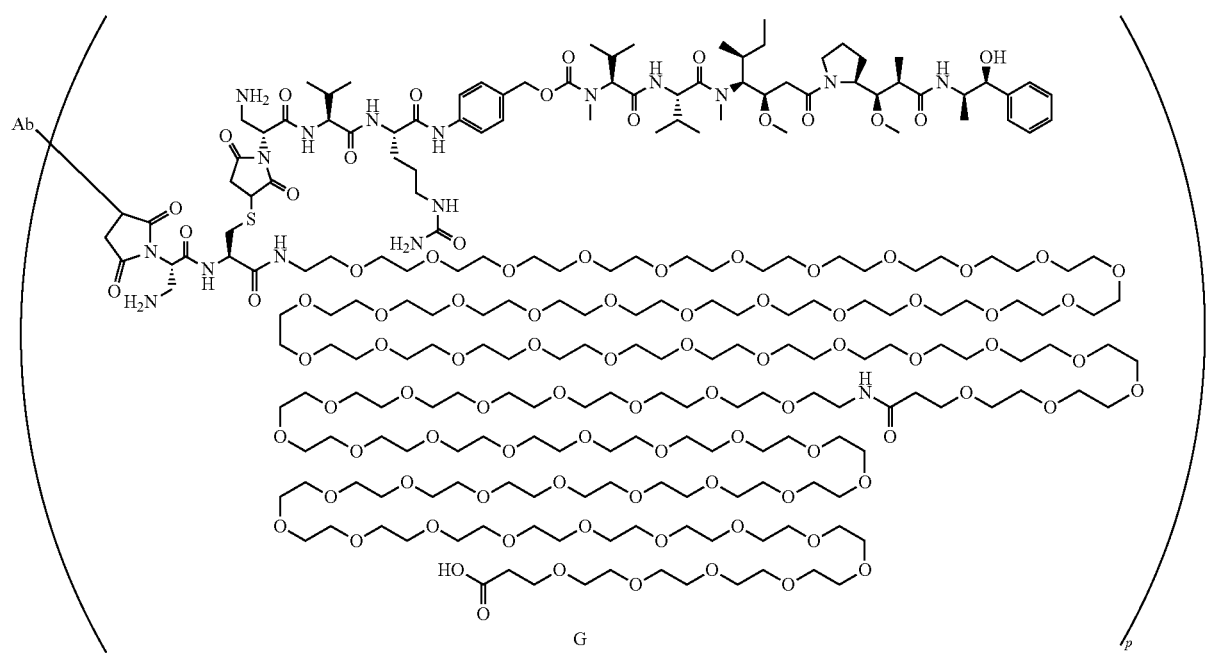

Example 15

Figure 11:
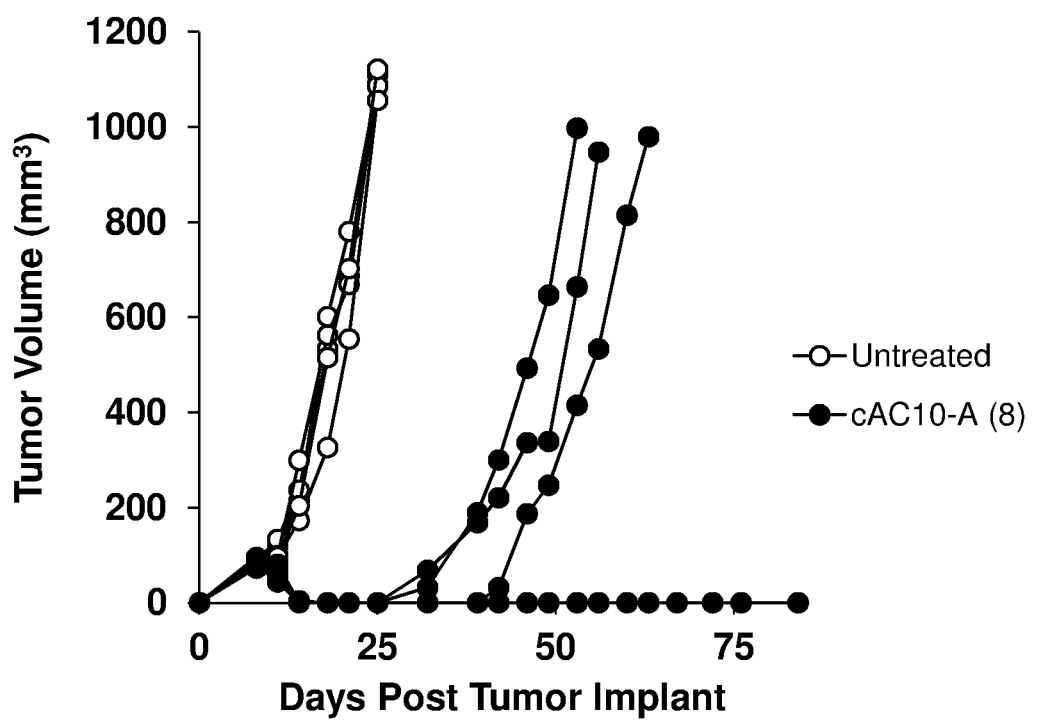
FIG. 11. Tumor volume (mm$^2$) vs. days post tumor transplant in a L540cy xenograft model dosed once intraveneously with 2 mg/Kg of non-PEGylated ADC: c-AC10-[MDpr-VC-PAB-MMAE]$_p$ (cAC10-A), in comparison to untreated animal.
Figure 12:
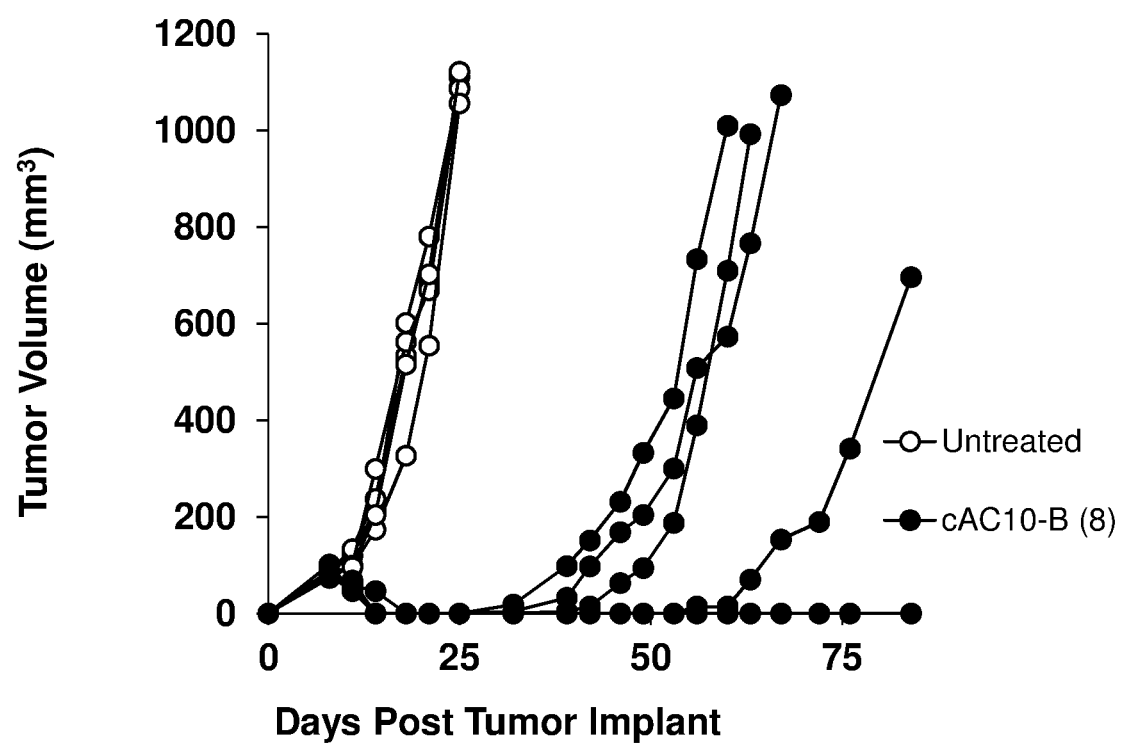
FIG. 12. Tumor volume (mm$^2$) vs. days post tumor transplant in a L540cy xenograft model dosed once intraveneously with 2 mg/Kg of parallel-oriented PEGylated ADC (cAC10-B): cAC10-[MDpr (-X-D)-PEG$_{12}$]$_p$, wherein p is 8 and -X-D is MDpr-VC-PAB-MMAE, in comparison to untreated animal.
Figure 13:
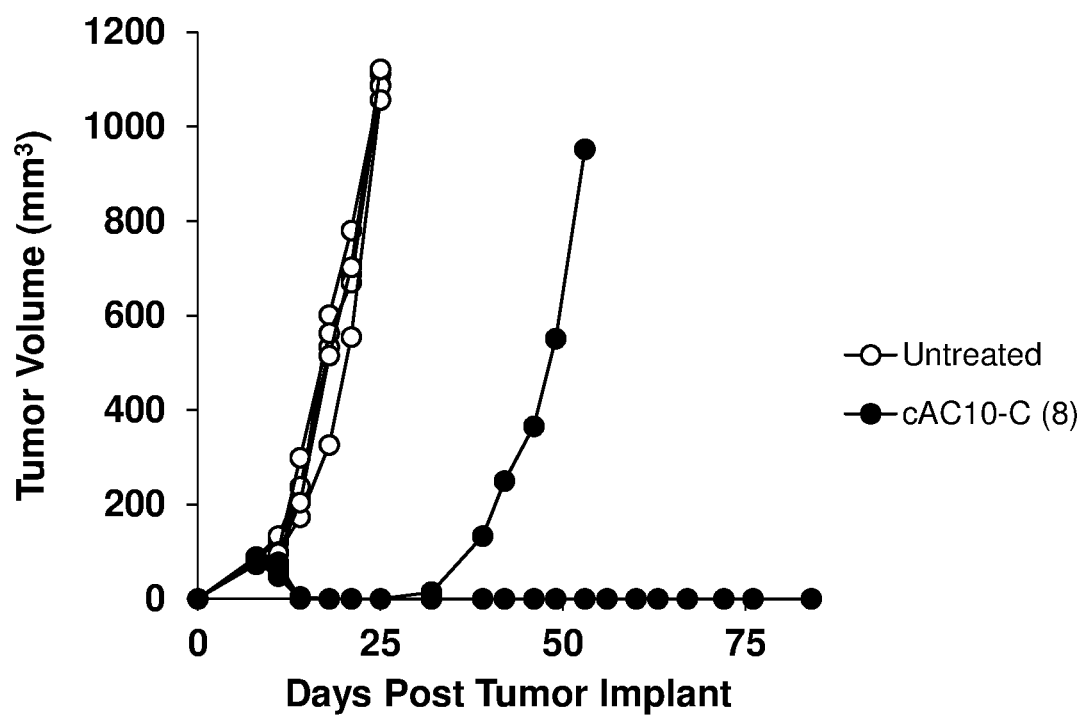
FIG. 13. Tumor volume (mm$^2$) vs. days post tumor transplant in a L540cy xenograft model dosed once intraveneously with 2 mg/Kg of parallel-oriented PEGylated ADC (cAC10-C): cAC10-[MDpr (-X-D)-PEG$_{24}$]$_p$, wherein p is 8 and -X-D is MDpr-VC-PAB-MMAE, in comparison to untreated animal.

ADCs Comprising PEG in a Parallel Orientation Improved Pharmacokinetics as Compared to ADCs Comprising No PEG cAC10-based ADCs prepared with (B, C, and D) and without (A) PEGylated conjugation scaffolds were analyzed in an L540cy xenograft model. Animals were dosed with 2 mg/kg (single dose) of each ADC and tumor volume was measured over time. The tumor volume in untreated animals reached 1,000 mm$^3$ on day 25 of the study. The ADC prepared with the non-PEGylated drug linker (A) cured 2 of 5 mice with a mean time of 57.3 days for tumor volumes to reach 1,000 mm$^3$ in the uncured animals (FIG. 11). The ADC prepared with the PEGylated conjugation scaffold assembled with PEG$_{12}$ (B) showed similar activity to the ADC prepared with A (FIG. 12). In this case 1 of 5 animals was cured and a mean time of 68.5 days was required for tumor volumes to reach 1,000 mm$^3$ in the uncured animals. The ADC prepared with the PEG$_{24}$ containing scaffold (C) showed improvement over A curing 4 of 5 mice with the one remaining tumor reaching 1,000 mm$^3$ on day 53 (FIG. 13).

Figure 14:
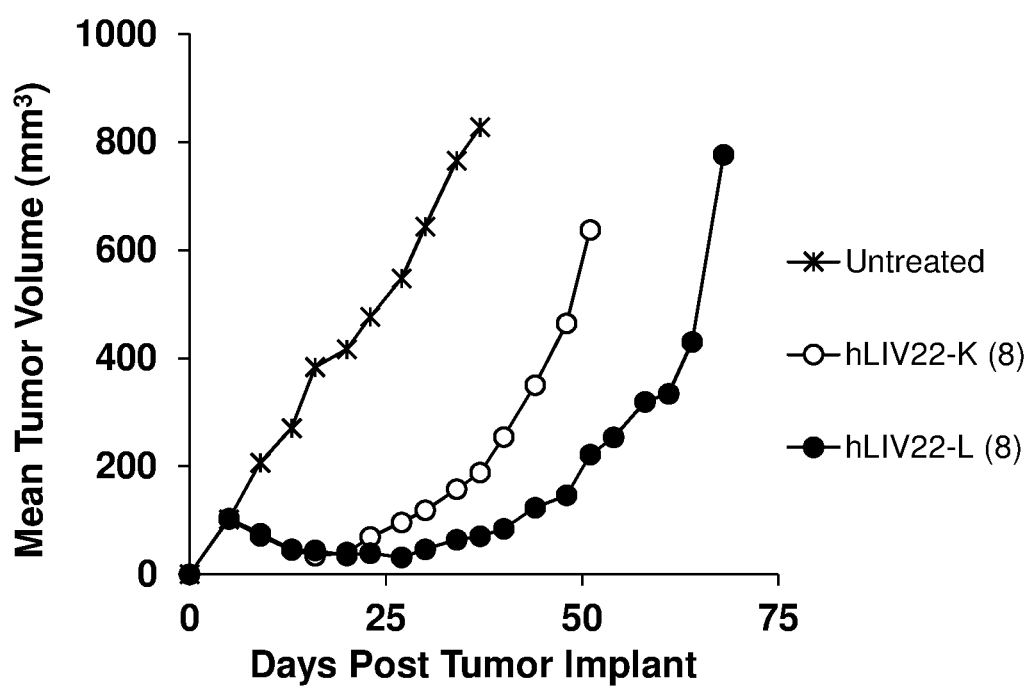
FIG. 14. Mean tumor volume (mm$^2$) vs. days post tumor transplant in a xenograft breast cancer model with non-PEGylated ADC targeting the antigen LIV-1: hLIV22-[mc-VC-PAB-MMAE)]$_p$ or hLIV22-[MDpr (-X-D)-PEG$_{24}$]$_p$ wherein p is 8 and -X-D is mc-VC-PAB-MMAE in comparison to untreated animals.
Figure 15:
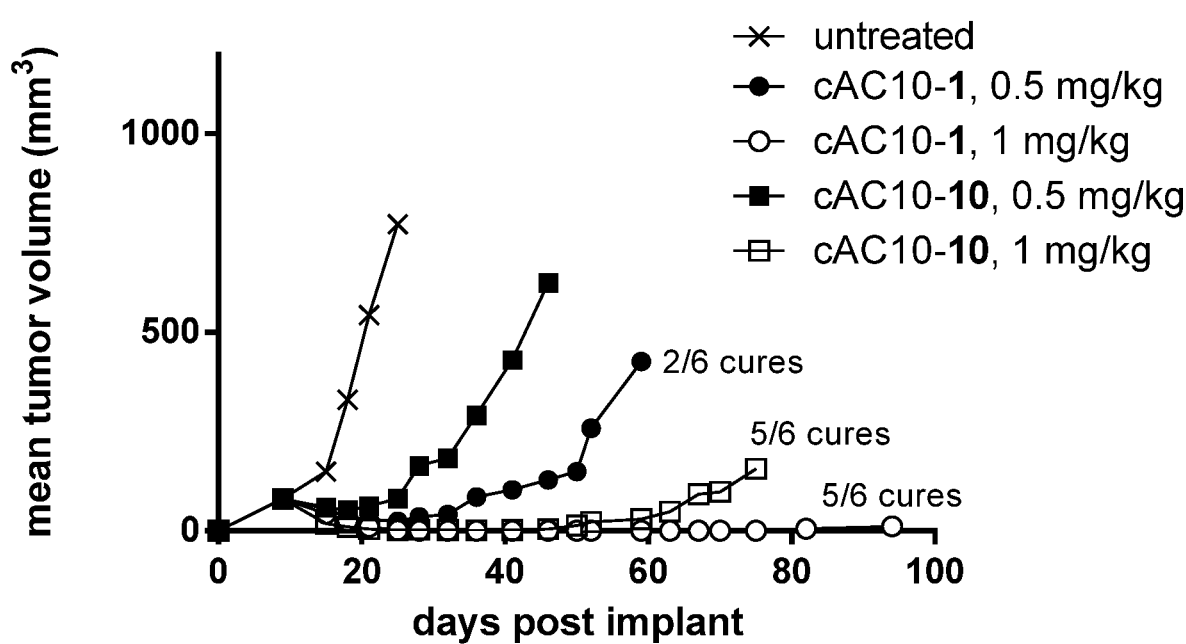
FIG. 15: Mean tumor volume (mm$^2$) vs. days post tumor transplant in a L540cy xenograft model dosed once intraveneously with 1 or 0.5 mg/Kg non-PEGylated ADC: cAC10-[mc-PAB(gluc)-MMAE]$_p$ (cAC10-1) or its corresponding parallel-oriented PEGylated ADC: cAC10-{mc-[PAB(gluc)-MMAE]-PEG$_{24}$}$_p$ (cAC10-10), wherein p is 4, in comparison to untreated animals.

In a second experiment, hLIV22-based ADCs (hLIV22 antibody is described in PCT Publication No. WO 2012/078688, which is incorporated by reference herein) targeting the breast carcinoma antigen, LIV-1, were prepared with mc-vcMMAE with (L) and without the PEG$_{24}$ enabled conjugation scaffold (K). Animals were dosed with 3 mg/kg (single dose) of each ADC. In the untreated arm of the study, the mean time for tumors volumes to reach 1,000 mm$^3$ was 39.2 days. Treatment with hLIV22-K delayed this time to 57.6 days and the PEGylated ADC, hLIV22-L further shifted this mean to 71.4 days (FIG. 14).

Example 16

ADCs Comprising PEG in a Parallel Orientation and 16 Drugs Per Antibody Displayed Less Aggregation as Compared to ADCs Comprising No PEG In order to examine the effect of PEG on aggregation of 16-load ADCs, anti-transferrin receptor conjugates were prepared using MDpr-Glucuronide-Camptothecin as the -X-D Unit. ADCs were prepared as standard 8 loads (8 drugs per antibody) or 16 loads (16 drugs per antibody) with or without inclusion of a PEG Unit. Conjugation was via the interchain disulfides. The PEGylated and the control non-PEGylated Conjugation Scaffolds (PEG Scaffold A and Control Scaffold A, respectively) that were used for preparing 16 drug load ADCs are as follows PEG Scaffold A

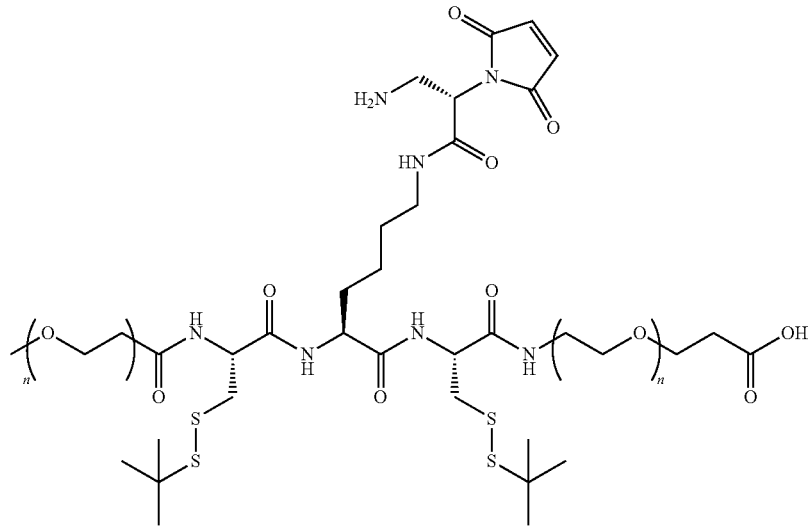

Control Scaffold A

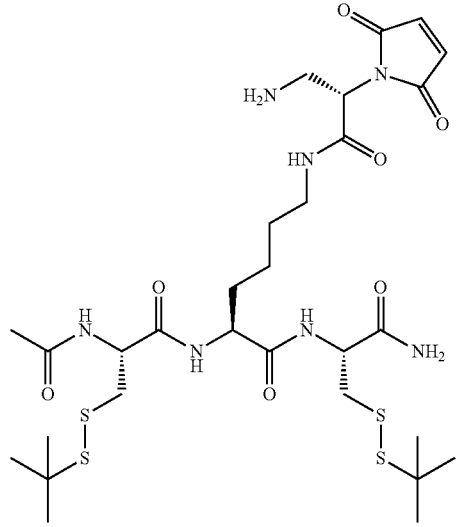

Antibody drug conjugates were prepared from the PEG scaffold A with n=23, which represents an exemplary Ligand Intermediate Compound, and Control Scaffold A as described in Example 11 by (a) contacting the scaffold with an antibody having thiol groups capable of conjugate addition to the scaffold's Maleimide Unit to form antibody-substituted succinimide moieties (b) removing the thiol protecting groups and (c) contacting the resultant product with -X-D moieties wherein X is a Releasable Assembly unit comprised of a Maleimide Unit and a Cleavable Unit wherein the X-D Maleimide units are capable of reacting with the free thiol groups obtained from step (b) by conjugate addition under conditions suitable that converts the Maleimide units of X-D to additional substituted succinimide moieties while avoiding premature hydrolysis the succinimide moieties derived from the scaffold and X-D moieties and (d) hydrolysis of the collective substituted succinimides of the Linker-Drug Compound obtained from step (c) by addition of a water molecule across one and not both of the succinimide's C—N bonds for each of the succinimide moieties introduced from a MDpr moiety as the Maleimide Unit.

PEG Scaffold A is encompassed by

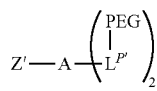

(i.e., Formula VIIIb), wherein Z' is the MDpr-containing moiety, A is the central lysine residue and the two Lp are the flanking cysteine residues.

Another suitably protected scaffold that provides for 16 drug loaded conjugate is PEG Scaffold B whose structure is

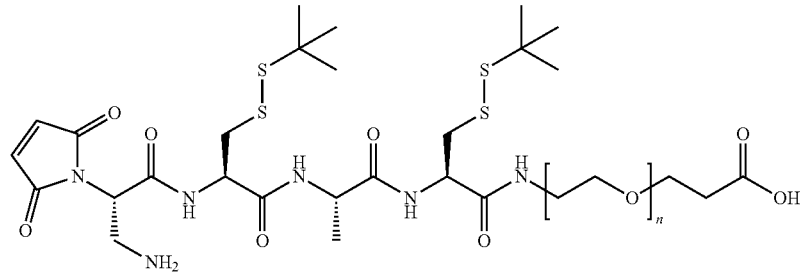

(PEG Scaffold B) wherein n is 36.
PEG Scaffold B is encompassed by

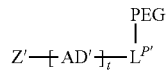

(i.e., Formula VIIId), wherein Z' is the MDpr moiety, t is 1 and AD and $L^P$ are each cysteine residues.

Without inclusion of the PEGylated conjugation scaffold, the aggregation level of the 16 load ADC was 22%. Adding the PEGylated scaffold, which has the PEG Unit in parallel orientation to the Drug Unit lowered the aggregation level to that of the 8 load, i.e., 2% aggregate.

The 8-load and PEGylated 16 load anti-transferrin receptor ADCs (cOKT9) having -X-D of MDpr-PABA(gluc)-Camptothecin were tested against a panel $TfR^+$ cancer cell lines. In most cases, doubling the drug loading increased ADC potency by approximately 2-fold. In several cases, ADC potency increased 3-10 fold or higher, even through drug loading was only increased 2λ. Most notably the 16-load conjugate was active against the colorectal cell line HT-29 (TfR copy number 23K) and the melanoma cell line SK-MEL-5 (TfR copy number 21K), whereas the 8-load conjugate was considered inactive (IC50>1 μM).

Example 17

ADCs Loaded at 4-Drugs Per Antibody with PEG24 in a Parallel Orientation Exhibit Diminished Activity In Vivo Relative to their Non-PEGylated Counterparts When ADC drug loading was reduced to 4 drugs per antibody, conjugates bearing PEGylated glucuronide-MMAE linker 10 were found to have similar PK exposure to non-PEGylated conjugate bearing linker 1. Accordingly, PEGylation did not provide an enhancement in activity in in vivo xenograft models.

Figure 16:
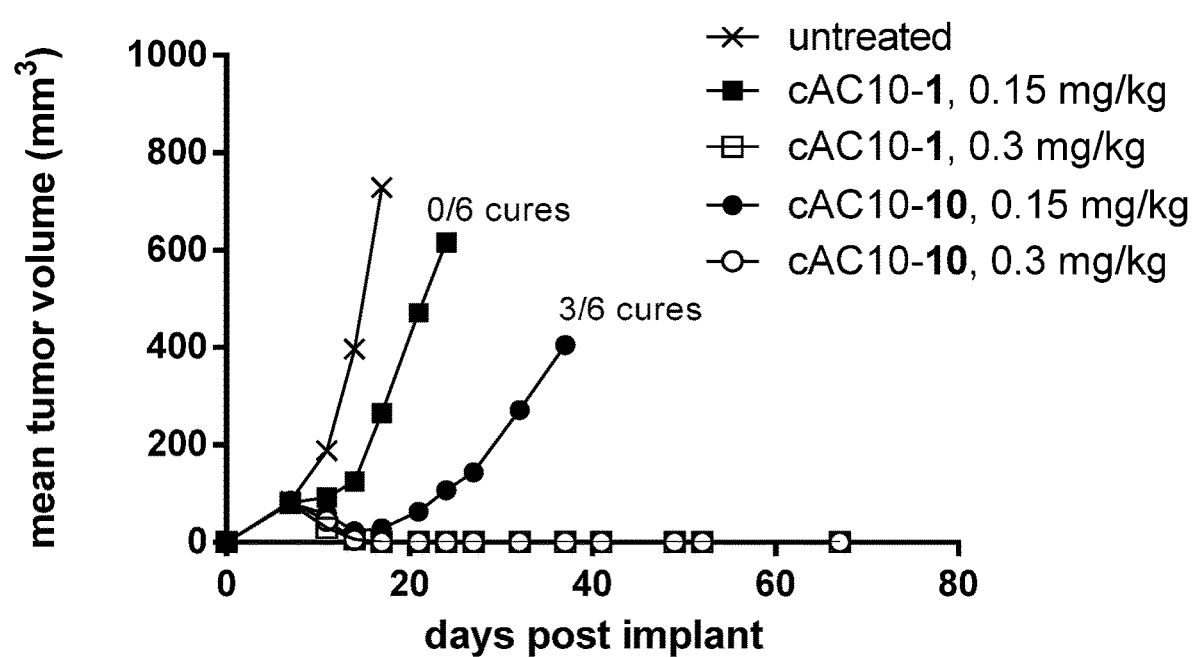
FIG. 16: Mean tumor volume (mm$^2$) vs. days post tumor transplant in a Karpas299 xenograft model dosed once intraveneously with 0.3 or 0.15 mg/Kg non-PEGylated ADC: cAC10-[mc-PAB(gluc)-MMAE]$_p$ (cAC10-1) or its corresponding parallel-oriented PEGylated ADC: cAC10-{mc-[PAB(gluc)-MMAE]-PEG$_{24}$}$_p$ (cAC10-10), wherein p is 4, in comparison to untreated animals.

Anti-CD30 chimeric antibody cAC10 was conjugated with non-PEGylated linker 1 or PEGylated linker 10 at an average loading of 4 drugs/antibody and evaluated in L540cy Hodgkin lymphoma and Karpas 299 anaplastic large cell lymphoma tumor models. For L540cy (FIG. 13), animals were administered a single ip dose of ADC at 0.5 and 1 mg/kg. At the higher dose of 1 mg/kg, both PEGylated (cAC10-10) and non-PEGylated (cAC10-1) were equipotent, providing cures in 5/6 mice. However, at the lower dose of 0.5 mg/kg the non-PEGylated linker (cAC10-1) provided a more prolonged average tumor growth delay with 2/6 mice cured. Whereas, the PEGylated linker (cAC10-10) was less potent, with no mice cured. Analogous results were obtained in the Karpas299 xenograft model (FIG. 16).

These finding suggest that in the absence of conjugate PK enhancement, PEGylation with 24 units of PEG causes a diminutive attenuation of activity in vivo. This may be due to impaired enzymatic drug release or decreased permeability due the increase in conjugate size upon PEGylation.

Example 18

ADCs Loaded with PEGylated Glucuronide Drug Linkers Exhibit In Vivo Activity Consistent with Conjugate PK Properties To determine if there is an optimum PEG size for the glucuronide and MMAE combination, a series of PEGx linkers were prepared and evaluated, spanning non-PEGylated, PEG2, PEG4, PEG8, PEG12, PEG24, and branched PEG4-(PEG4)$_3$. The non-pegylated ADCs cAC10-14 and hBU12-14 of Tables 4 and 5, respectively, are similar in structure to the PEGylated ACDs, but lack an L$^P$ unit, which in the case of the PEGylated scaffolds is a lysine residue.

Initial in vitro work demonstrated a minimal effect of PEG size on activity on most of the cell lines tested. Anti-CD30 and anti-CD19 antibodies, cAC10 and hBU12, respectively, were conjugated at 8-drugs/antibody and evaluated against a panel of lymphoma cell lines. CD30-positive L540cy and L428 Hodgkin lymphoma lines and Karpas 299 anaplastic large cell lymphoma were highly sensitive to all cAC10 conjugates regardless of PEG size as shown in Table 4.

TABLE 4

In vitro cytotoxicity - αCD30 conjugates (IC$_{50}$ in ng/mL)

| ADC$^a$ | PEGx | CD30+ cell lines | | | CD30− |
|---|---|---|---|---|---|
| | | Karpas 299 | L540cy | L428 | RL |
| cAC10-14 | no PEG | 0.3 | 3 | 85 | >1000 |
| cAC10-43 | PEG2 | 0.3 | 2 | 10 | >1000 |
| cAC10-42 | PEG4 | 0.4 | 3 | 16 | >1000 |
| cAC10-18 | PEG8 | 0.3 | 2 | 18 | >1000 |
| cAC10-17 | PEG12 | 0.3 | 2 | 19 | >1000 |
| cAC10-16 | PEG24 | 0.4 | 3 | 8 | >1000 |
| cAC10-19 | PEG4-(PEG4)3 | 0.1 | 1 | 8 | >1000 |

$^a$ADCs loaded at 8 drugs/Ab

Figure 17:
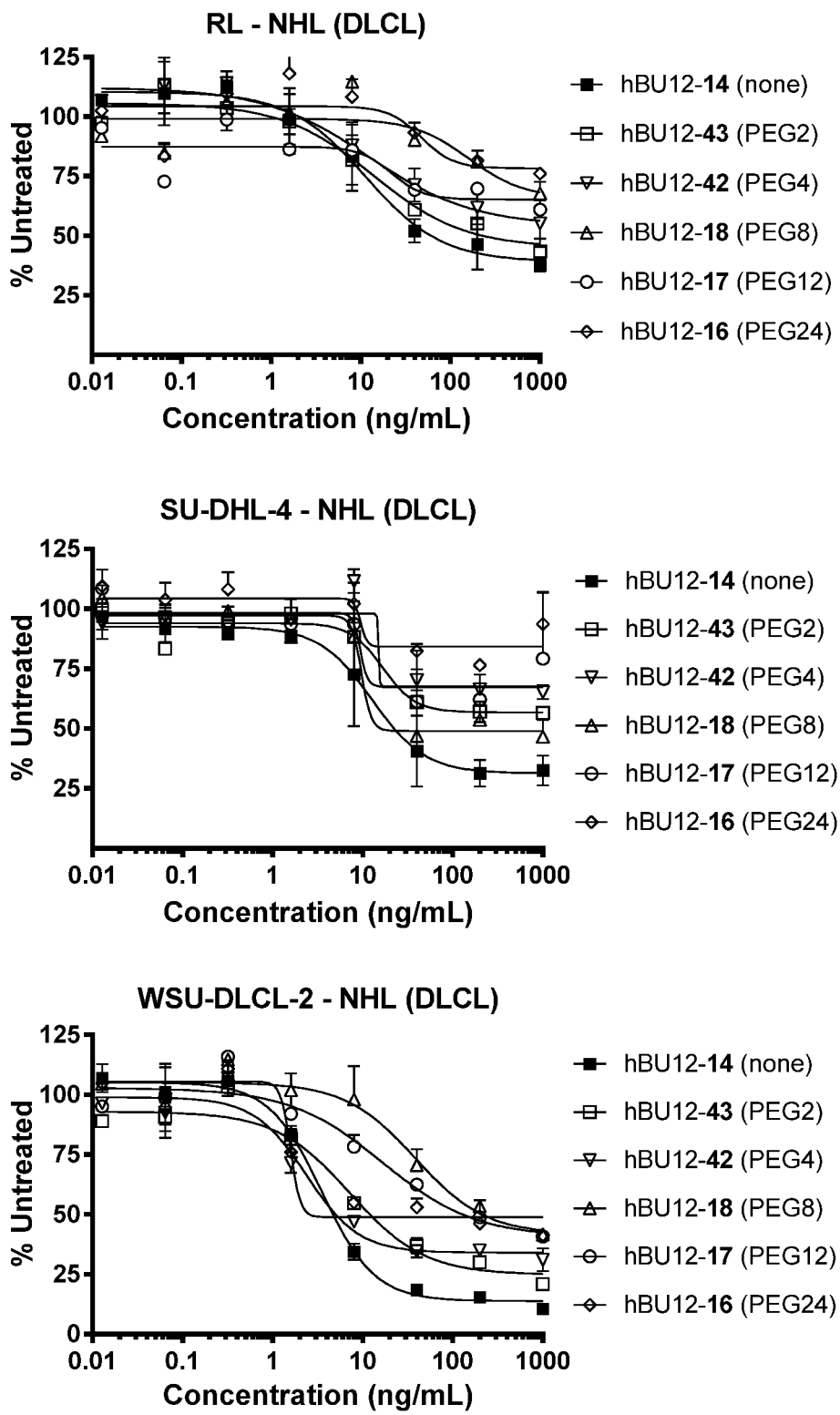
FIG. 17: Dose response curves for 8 drug loaded hBU12 ADCs having PEGylated scaffolds with varing lengths for their PEG Units against a panel of non-Hodgkin lymphoma cell lines with drug-linker represented by the structure of MDpr-L$^p$-(PEG)$_x$(PAB(glu)), wherein L$^p$ is Lysine as the parallel connector unit, wherein x is 0 (hBU12-14) in which the PEG Unit at epsilon amino of lysine replace with acetyl, x is 2 (hBU12-43), 4 (hBU12-42), 8 (hBU12-18), 12 (hBU12-17), 24 (hBU12-16), or is the branched structure of PEG$_4$-(PEG$_4$)$_3$ (hBU12-19).

The activity of hBU12 (anti-CD19) conjugates bearing PEGx-glucuronide-MMAE linkers on a panel of non-Hodgkin lymphoma cell lines were more variable, as shown in Table 5. PEG size had no effect on ADC potency on Ramos Burkitt's lymphoma. However, conjugate potency appeared variable as a function of PEG size in diffuse large B-cell lymphoma cell lines SU-DHL-4, WSU-DLCL-2, and RL. As measured by IC$_{50}$, there did not appear to be a correlation between PEG size and activity. However, closer examination of the dose response curves did reveal an apparent inverse correlation between PEG size and maximal growth inhibition. These data are shown in FIG. 17.

TABLE 5

In vitro cytotoxicity - αCD19 conjugates (IC50 in ng/mL)

| ADC$^a$ | PEGx | CD19+ cell lines | | | | CD19− |
|---|---|---|---|---|---|---|
| | | Ramos | SU-DHL-4 | WSU-DLCL-2 | RL | L540cy |
| hBU12-14 | No PEG | 2 | 22 | 5 | 61 | >1000 |
| hBU12-43 | PEG2 | 2 | >1000 | 12 | 229 | >1000 |
| hBU12-42 | PEG4 | 3 | >1000 | 5 | >1000 | >1000 |
| hBU12-18 | PEG8 | 2 | 16 | 211 | >1000 | >1000 |
| hBU12-17 | PEG12 | 2 | >1000 | 129 | >1000 | >1000 |
| hBU12-16 | PEG24 | 4 | >1000 | 3 | >1000 | >1000 |
| hBU12-19 | PEG4-(PEG4)3 | 2 | >1000 | 247 | >1000 | >1000 |

$^a$ADCs loaded at 8 drugs/Ab

The pharmacokinetic properties of conjugates spanning the PEGx series was assessed as described above. Rats were administered a single intravenous dose of 1 mg/kg conjugate comprised of non-binding humanized IgG (h00) bearing MDpr-PEGx-glucuronide-MMAE linkers loaded at 8 drugs/Ab. Plasma samples were taken at various time points and total circulating antibody was quantified as above. Antibody clearance displayed a direct correlation with PEG size, as shown in FIG. 16. PEGylated conjugates with PEG8, PEG12, and PEG24 displayed clearance properties approximating naked antibody; whereas, shorter PEGs and non-PEGylated counterparts were cleared more rapidly from circulation.

Figure 18:
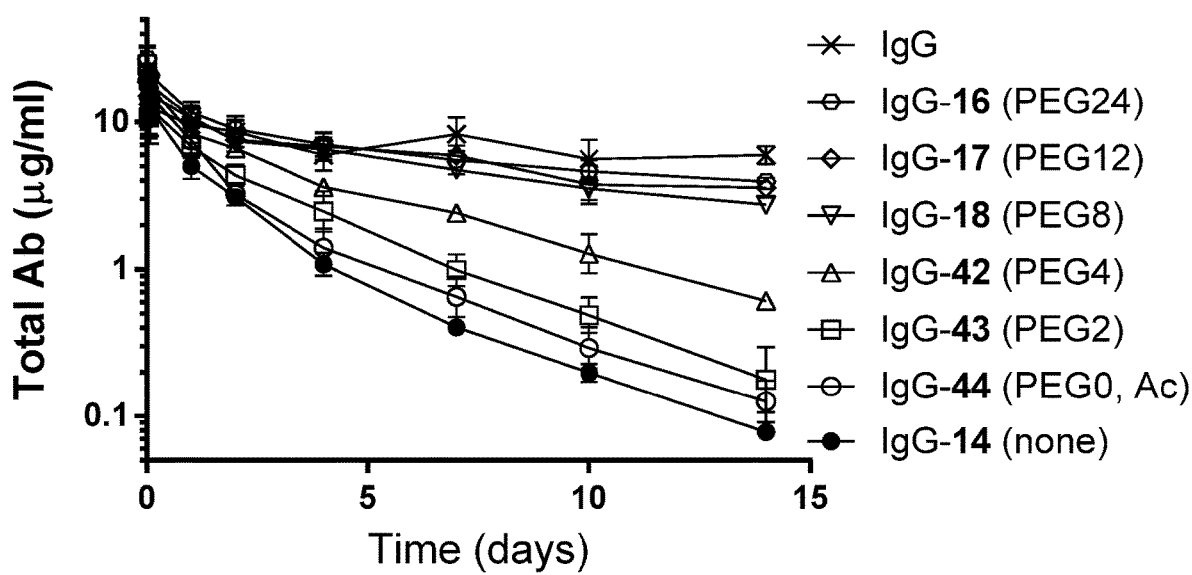
FIG. 18. Pharmokinetic profile (total Ab concentration in μg/mL vs time in days) in rat following a single intaveneous 1 mg/Kg dose of unconjugated non-targeting antibody (h00), its conjugates having PEGylated scaffolds with varing lengths for its PEG Unit with drug-linker represented by the structure of MDpr-L$^p$-(PEG)$_x$(PAB(glu)), wherein L$^p$ is Lysine as the Parallel Connector Unit, wherein x is 0 (h00-14) in which the PEG Unit at epsilon amino of lysine replace with acetyl, x is 2 (h00-43), 4 (h00-42), 8 (h00-18), 12 (h00-17) or 24 (h00-16).
Figure 19:
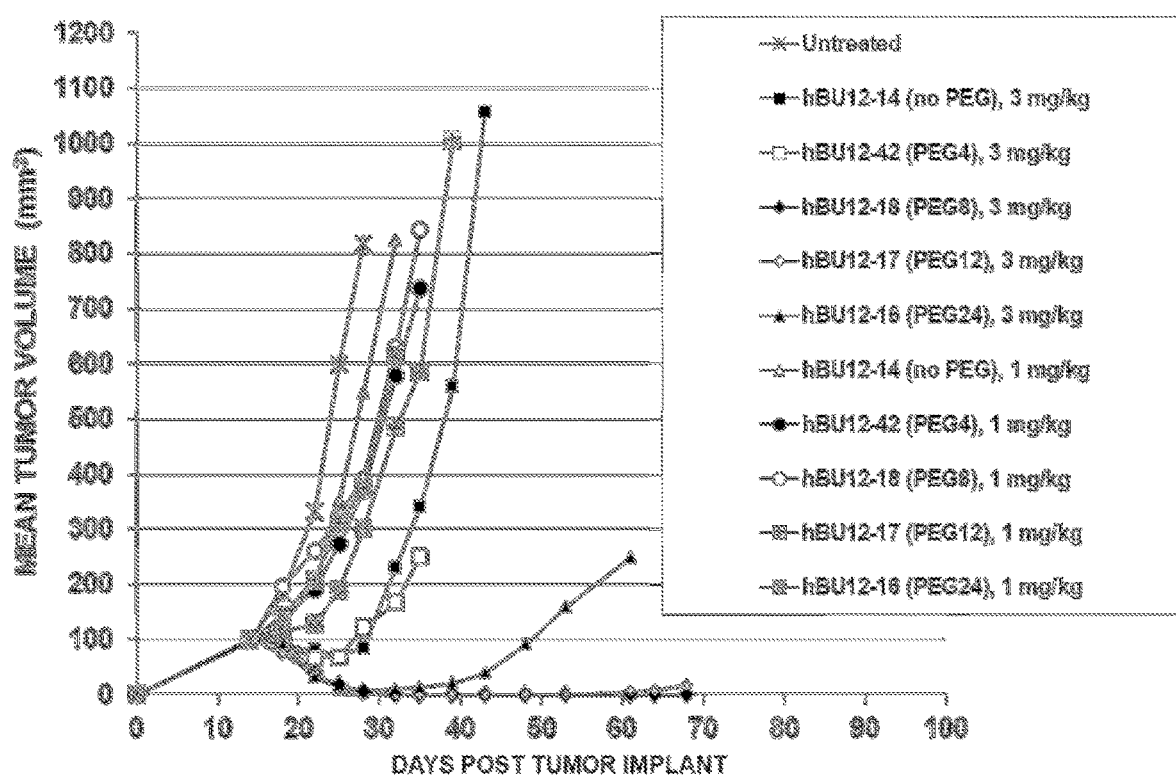
FIG. 19: Mean tumor volume (mm$^2$) vs. days post tumor transplant in a CD19-positive RL diffuse large B-cell lymphoma model after single dose intraveneous administration of 1 or 3 mg/Kg hBU12 ADCs having PEGylated scaffolds with varing lengths for their PEG Units with drug-linker represented by the structure of MDpr-L$^P$-(PEG)$_x$(PAB(gluc)), wherein L$^P$ is Lysine as the Parallel Connector Unit, wherein x is 0 (hBU12-14) in which the PEG Unit at epsilon amino of lysine replace with acetyl, x is 2 (hBU12-43), 4 (hBU12-42), 8 (hBU12-18), 12 (hBU12-17) or 24 (hBU12-16) in comparison to untreated animals.

The PEGx linkers were evaluated in vivo in xenograft models. Studies were carried out in CD19-positive RL diffuse large B-cell lymphoma models and CD30-positive L540cy Hodgkin lymphoma models. Anti-CD19 (hBU12) conjugates spanning linkers with no PEG, PEG4, PEG8, PEG12, and PEG24 were dosed once ip at 1 and 3 mg/kg once the average tumor volume reached 100 mm$^3$; results for the RL model are shown in FIG. 17. At 1 mg/kg, all groups exerted only a modest tumor growth delay and a significant correlation between PEG size and activity was not observed. At the higher dose of 3 mg/kg, the conjugates bearing no PEG and PEG4 achieved a tumor growth delay with tumor outgrowth around day 35. In contrast, conjugates with linkers bearing PEG8, PEG12, and PEG24 achieved complete remissions at 3 mg/kg, with 1/5 mice experience tumor re-growth in the PEG24 group. The enhanced activity at the higher dose of PEG8, PEG12, and PEG24 relative to the PEG4 and non-PEGylated counterparts is consistent with the PK observations in FIG. 18.

Example 19

Figure 20:
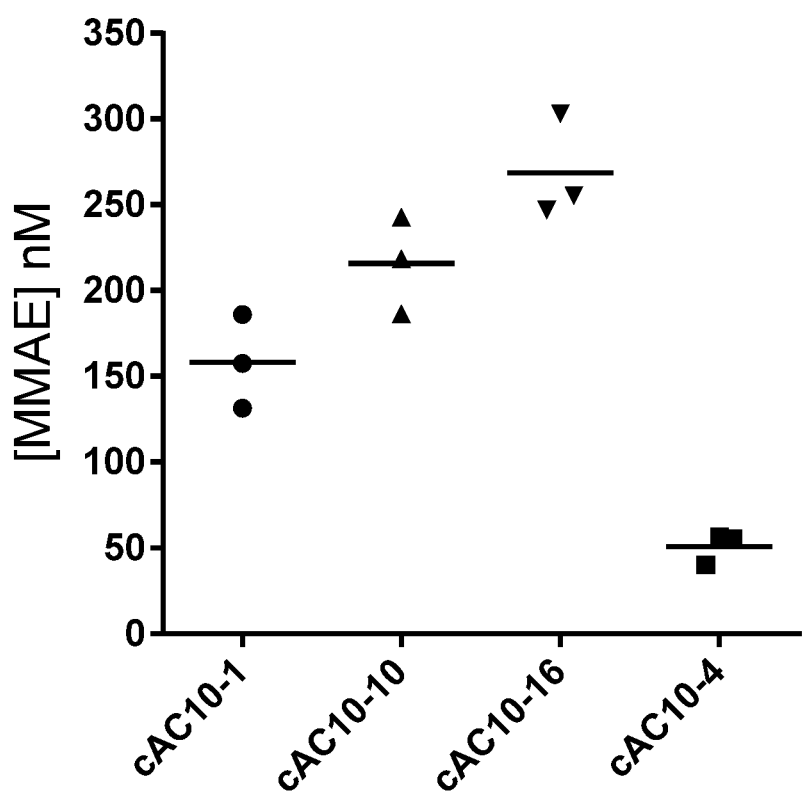
FIG. 20. Drug concentrations (nM) in xenograft tumors of CD30$^+$ L540cy Hodgkin Lymphoma in mice after single dose administration of 1 mg/Kg non-PEGylated ADC, cAC10-[mc-PAB(gluc) MMAE]$_p$, (cAC10-1), Parallel-oriented PEGylated ADCs with drug-linker mc-L$^P$-(PAB(gluc)-MMAE)PEG$_{24}$ (cAC10-10), MDpr-L$^P$-(PAB(gluc)-MMAE)PEG$_{24}$ (cAC10-16), wherein the Parallel Connector Unit L$^P$ is lysine, or serial-oriented PEGylated ADC (cAC10-4), wherein the ADCs have average drug loading of 8.

Intratumoral Delivery of MMAE is Correlated with the PK Properties of the Conjugate Mice bearing CD30-positive L540cy Hodgkin lymphoma tumors around 200 mm$^3$ were administered a single dose at 1 mg/kg of cAC10 conjugates loaded at 8-drugs/Ab with mc-glucuronide-MMAE (linker 1), mc-Lys(PEG24)glucuronide-MMAE (linker 10), maleimido-PEG24-glucuronide-MMAE (linker 4), or MDpr-Lys(PEG24)-glucuronide-MMAE (linker 16). Tumors were harvested 3 days post-dose and the intratumoral concentration was assessed by mass spectrometry. Consistent with conjugate PK, the ADCs with PEG24 in a parallel configuration (linkers 10 and 16) delivered significantly higher MMAE to the tumor, relative to the non-PEGylated conjugate (cAC10-1), as shown in FIG. 20. Furthermore, the conjugates containing PEG24 as a stretcher in series between the maleimide and glucuronide (cAC10-4) delivered 4-fold less MMAE than its counterpart (cAC10-10). Lastly, incorporation of the mDPR maleimide (cAC10-16) further increased delivery of MMAE over the maleimidocaproyl-containing counterpart (cAC10-10).

Example 20

Figure 21:
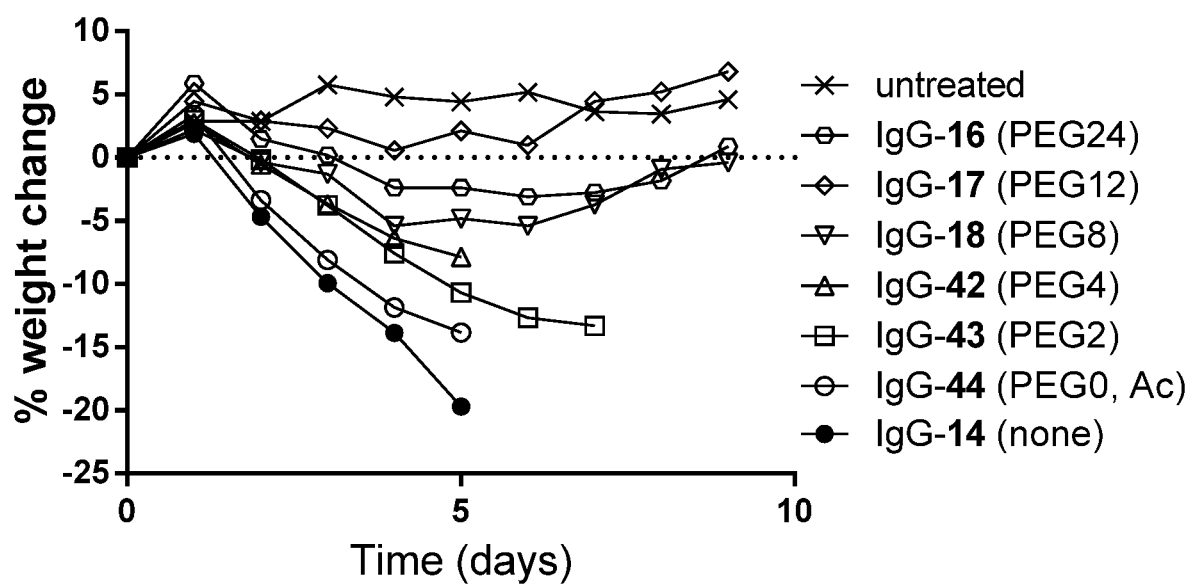
FIG. 21. Tolerability as shown by % weight change over time to a single intaveneous dose of 50 mg/Kg non-targeted control PEGylated Drug conjugates having PEGylated scaffolds with varing lengths for their PEG Units with drug-linker represented by the structure of MDpr-L$^P$-(PEG)$_x$(PAB(gluc)), wherein L$^P$ is Lysine as the Parallel Connector Unit, wherein x is 0 (h00-43) in which the PEG Unit at epsilon amino of lysine replace with acetyl, x is 2 (h00-43), 4 (h00-42), 8 (h00-18), 12 (h00-17) or 24 (h00-16), wherein the ADCs have average drug loading of 8, in comparison to untreated animals.

ADCs Loaded at 8-Drugs Per Antibody with PEGylated Linkers that Maintain Parental Antibody PK are Better Tolerated In Vivo Relative to their Shorter PEG and Non-PEGylated Counterparts Balb/c mice (n=3) were administered a single ip dose of 50 mg/kg of conjugate on day 0. The mice were observed daily for outward signs of morbidity and measured for body mass; animals were euthanized if they lost greater than 20% body mass or were found moribund. Body weight change relative to day 0 is plotted as a function of time in FIG. 21. Plotting was discontinued for each group upon sacrifice of at least one animal. Mice administered conjugates with no PEG (IgG-14 and -44), PEG2 (IgG-43), and PEG4 (IgG-42) exhibited significant weight loss or outward signs of toxicity and were euthanized between days 5 and 7. In contrast, mice receiving conjugates bearing PEG8 (IgG-18), PEG12 (IgG-17), and PEG24 (IgG-16) displayed minimal weight loss and no outward signs of moribundity. These data, in conjunction with the PK profiles in FIG. 18, suggest that the conjugates with decreased PK exposure exert greater acute toxicity.

Example 21

Maximizing PEG Length

Figure 22:
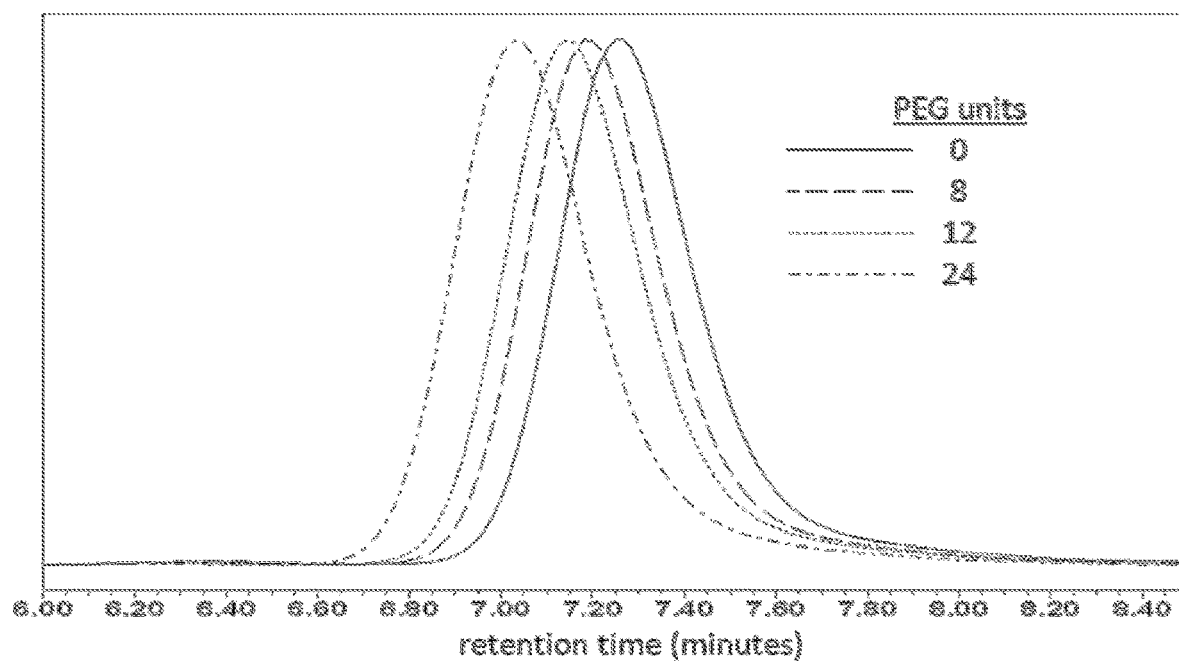
FIG. 22. Size Exclusion Chromatography (SEC) chromatograms for non-targeted control PEGylated Drug conjugates having PEGylated scaffolds with varing lengths for their PEG Units with drug-linker represented by the structure of MDpr-L$^P$-(PEG)$_x$(PAB(gluc)), wherein L$^P$ is Lysine as the Parallel Connector Unit, wherein x is 8 (h00-18), 12 (h00-17) or 24 (h00-16)
Figure 23:
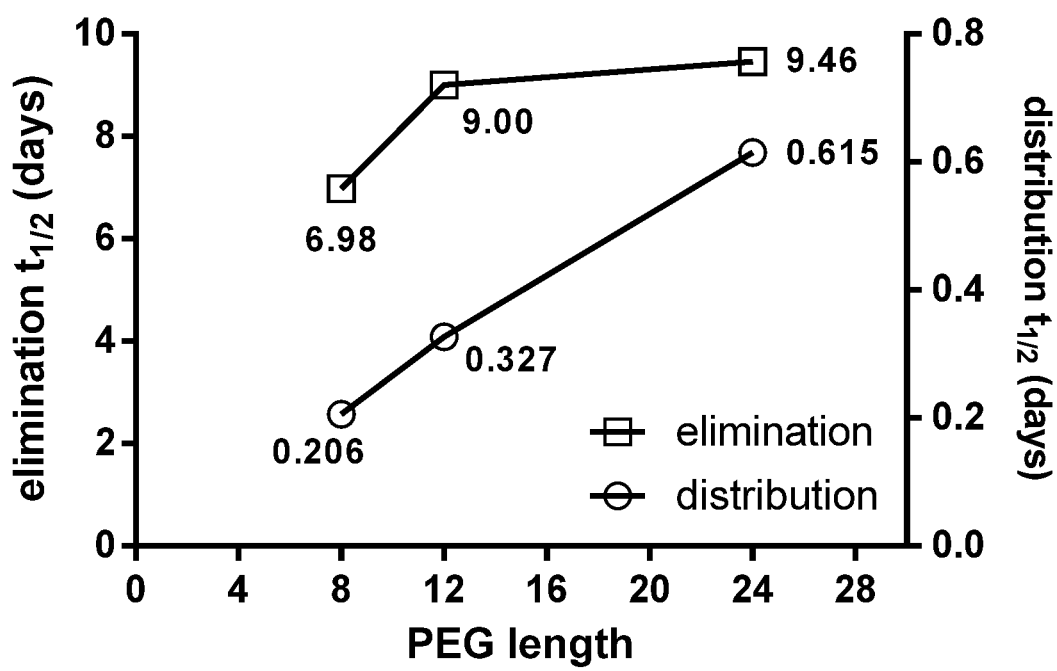
FIG. 23. Elimination half-life and distribution fitted to a two-compartment model for non-targeted control PEGylated Drug conjugates having PEGylated scaffolds with varing lengths for their PEG Units with drug-linker represented by the structure of MDpr-L$^P$-(PEG)$_x$(PAB(gluc)), wherein L$^P$ is Lysine as the Parallel Connector Unit, wherein x is 8 (h00-18), 12 (h00-17) or 24 (h00-16)

As the length of the PEG chain on the drug-linker increases, the overall size and hydrodynamic radius of the conjugate will increase as well. This is illustrated in FIG. 22, which shows analytical size-exclusion chromatography traces of ADCs prepared with drug-linkers 18, 17, and 16, having 8, 12, and 24 PEG units, respectively. From first principles, as the apparent size of the ADC increases, its diffusivity in an in vivo system may be expected to decrease. This may have the undesirable effect of diminishing the rate or extent that an ADC can penetrate into a solid tumor. This decreased diffusivity can also be observed in plasma pharmacokinetics by fitting the data to a two-compartment model which includes rate terms for the distribution and elimination phases. Pharmacokinetic data for ADCs prepared with drug-linkers 18, 17, and 16, (having 8, 12, and 24 PEG units, respectively) was collected for 21 days and fit to a two-compartment model, with the half-lives for the two processes (distribution and elimination) shown in FIG. 23.

It is evident from these data that increasing the PEG chain from 8 to 12 units results in a slowing of the plasma elimination (increase in t1/2 of approximately 2 days), but doubling the PEG from 12 to 24 units has little additional PK improvement. Conversely, the distribution t1/2 increases in a nearly linear fashion over this range, so that doubling the PEG chain from 12 to 24 units nearly doubles the half-time required for distribution into the tissue compartment. These data suggest that 12 PEG units may be the optimal length for this drug-linker, as larger PEGs have the effect of diminishing the distribution rate without significant impact on the elimination rate. This example shows how PK data can be used to select an optimal PEG size for any particular drug-linker.

Example 22

Preparation of Multiplex PEGylated Scaffolds

Schemes 12-14 depict synthesis of multiplex PEGylated scaffolds A and B, which provide ADC having 16 Drug Units/Antibody and of multiplex PEGylated Scaffold C, whose structure immediately follows, using peptide coupling methods described for PEGylated scaffolds providing 4 and 8 Drug units/Antibody.

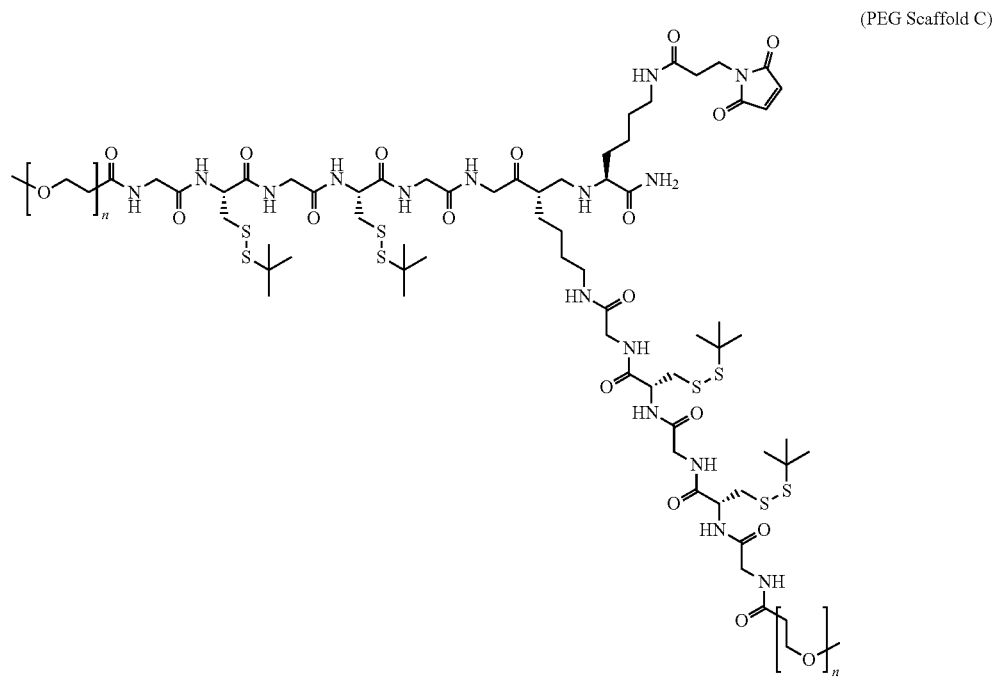

(PEG Scaffold C)

PEG Scaffold C is encompassed by the structure of

VIIIc wherein Z' is the maleimide-containing moiety, A is the branching lysine-lysine residue, t is 1 and each AD and each Lp is a cysteine residue.

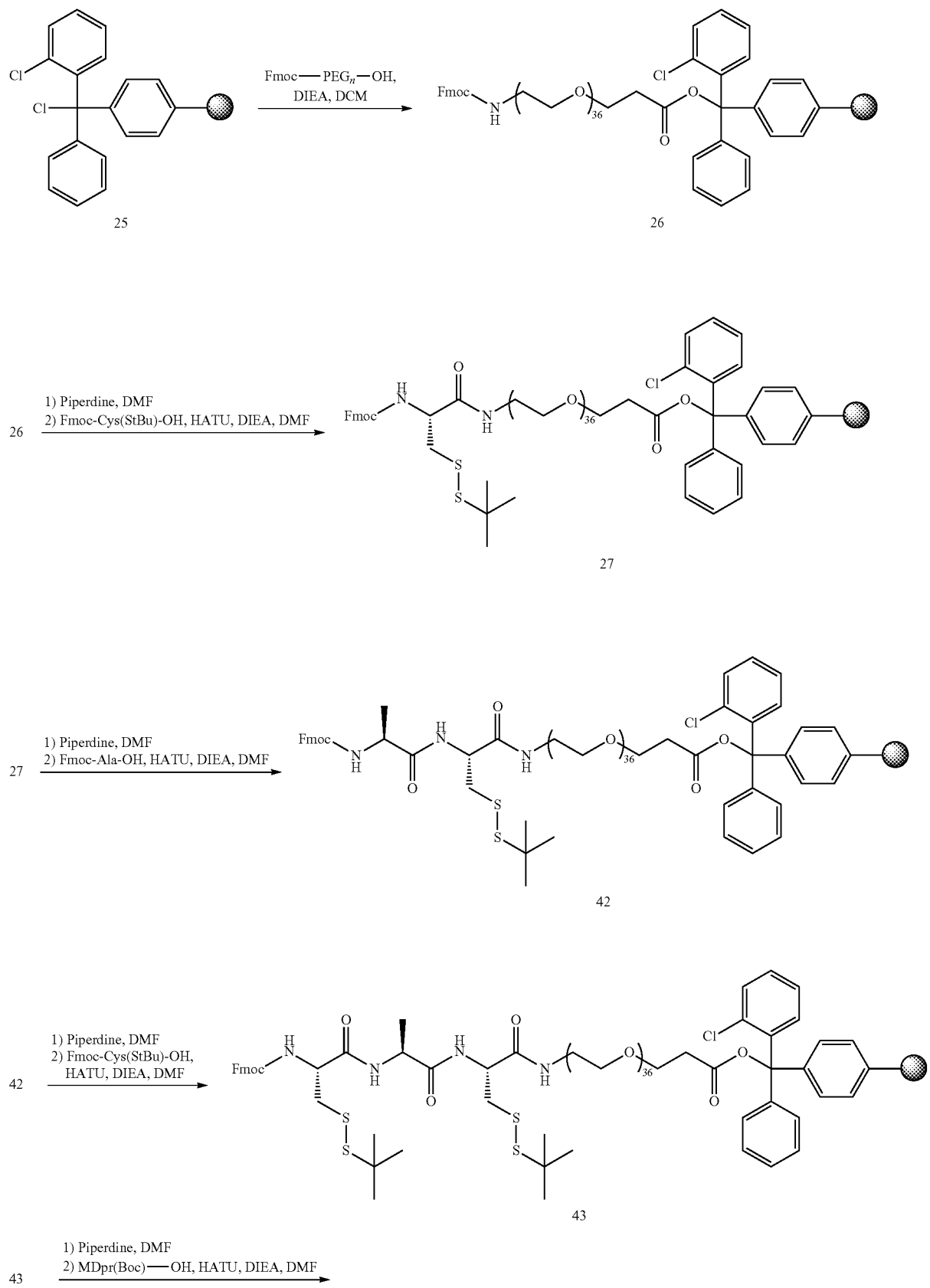

-continued
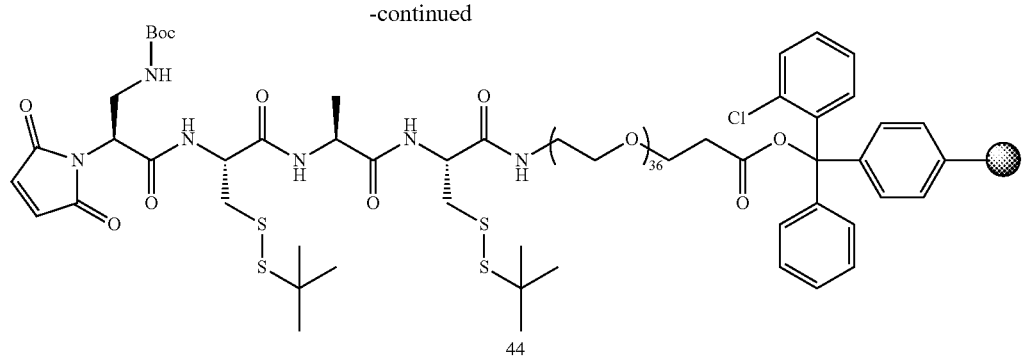
44
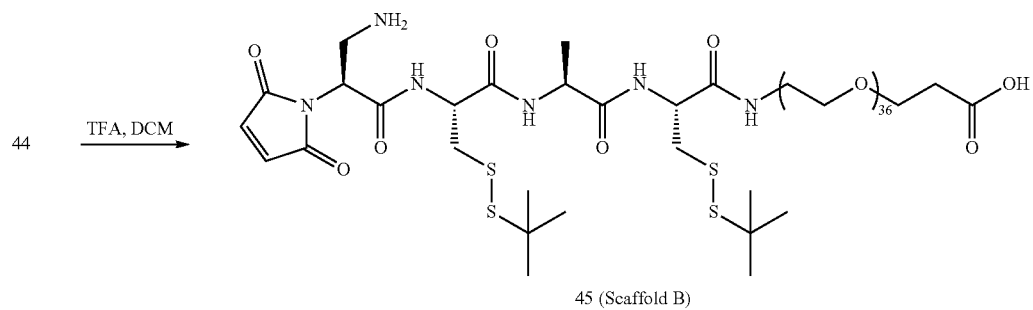
45 (Scaffold B)
Scheme 13: Synthesis of mPEG$_{24}$-Cys(StBu)-Lys(MDpr)-Cys(SBu)-PEG$_{24}$-OH (Scaffold A)
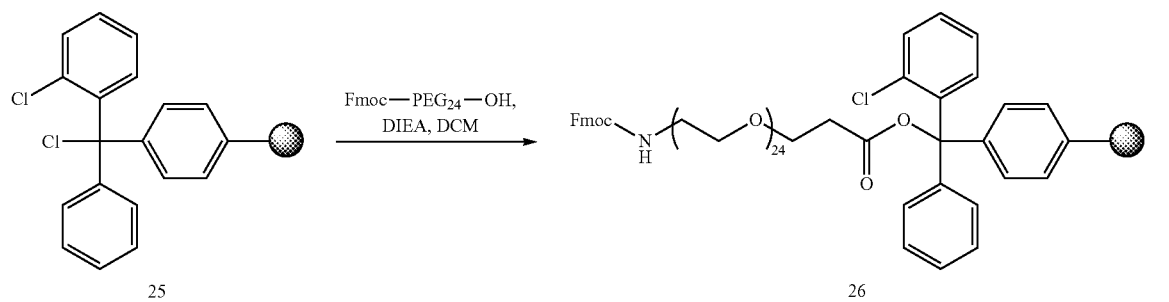
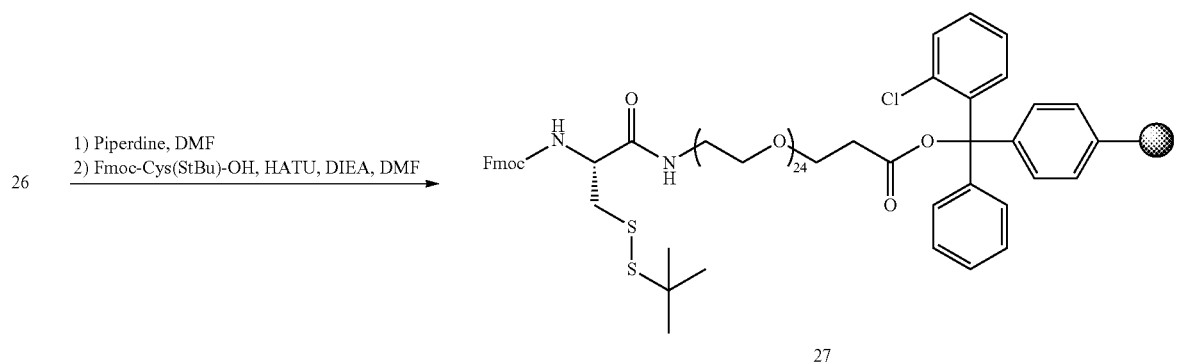

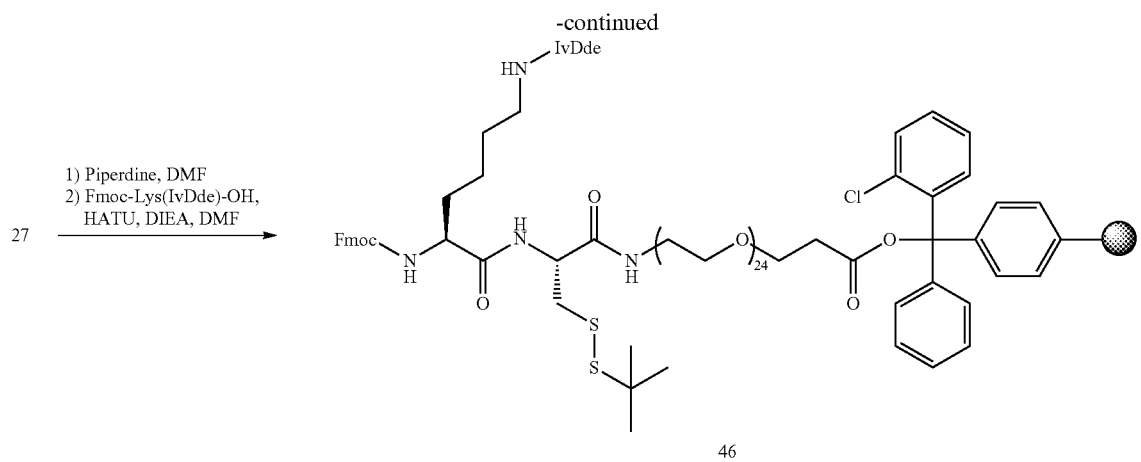
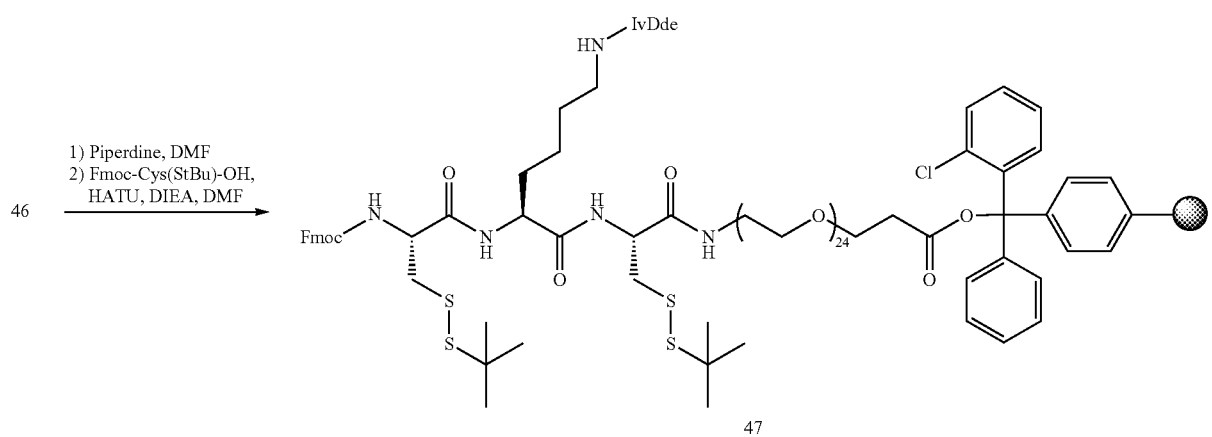

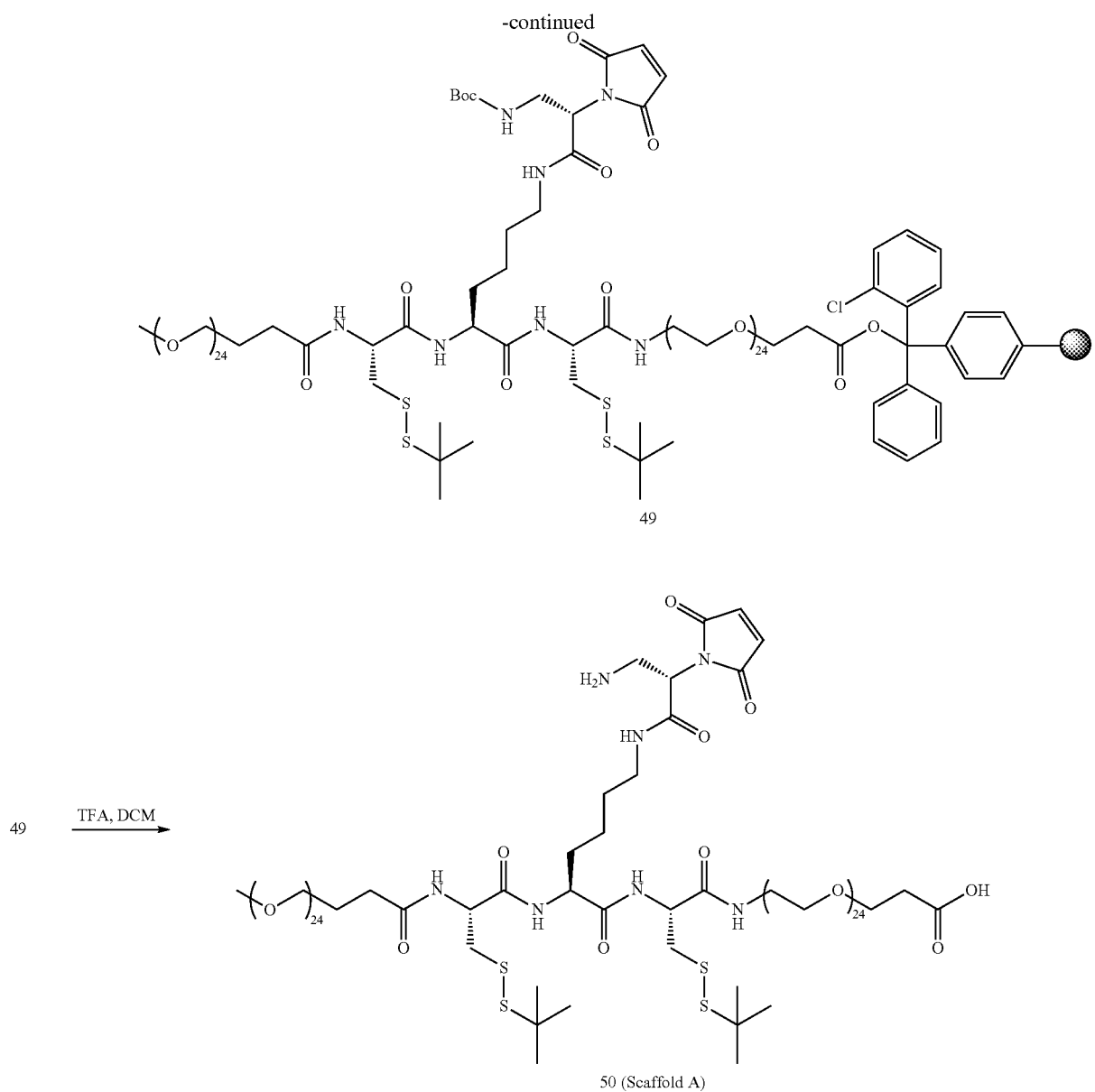
49
50 (Scaffold A)
Scheme 14: Branched PEGylated Drug-Carrier Scaffold (Scaffold C)
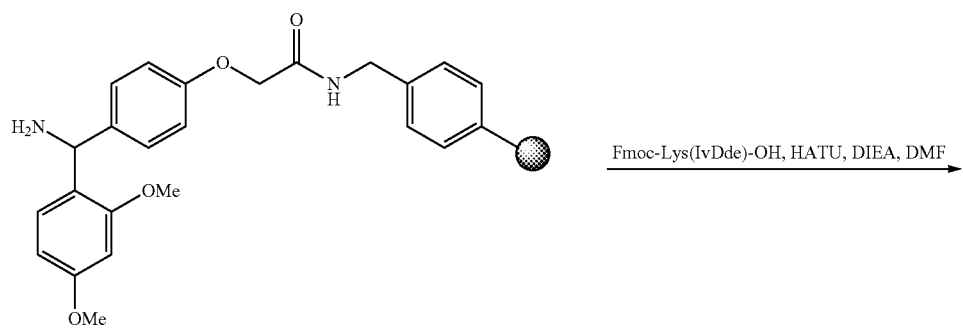
51

-continued
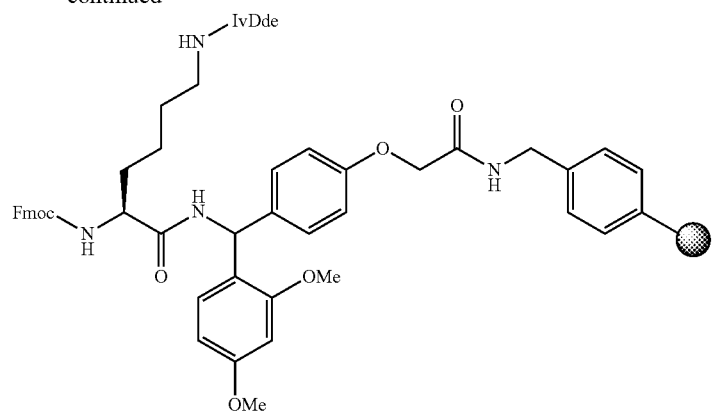
52
52 →  1) Piperdine, DMF
2) Fmoc-Lys(Fmoc)-OH, HATU, DIEA, DMF
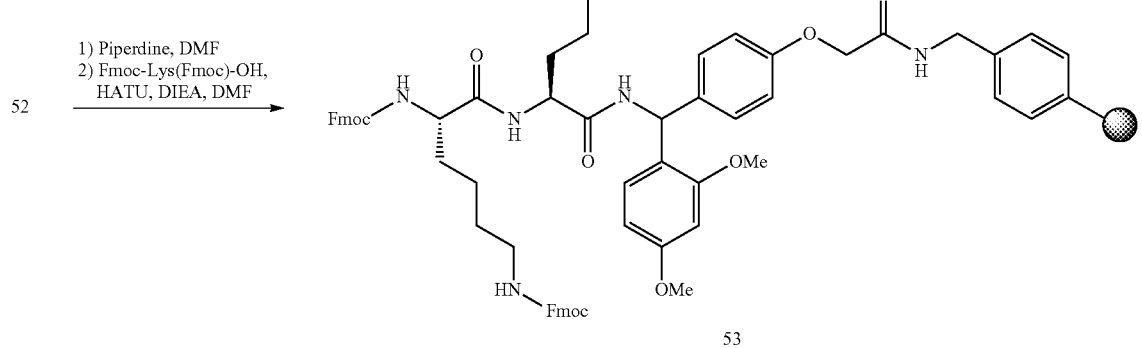
53
53 →  1) Piperdine, DMF
2) Fmoc-Gly-OH, HATU, DIEA, DMF
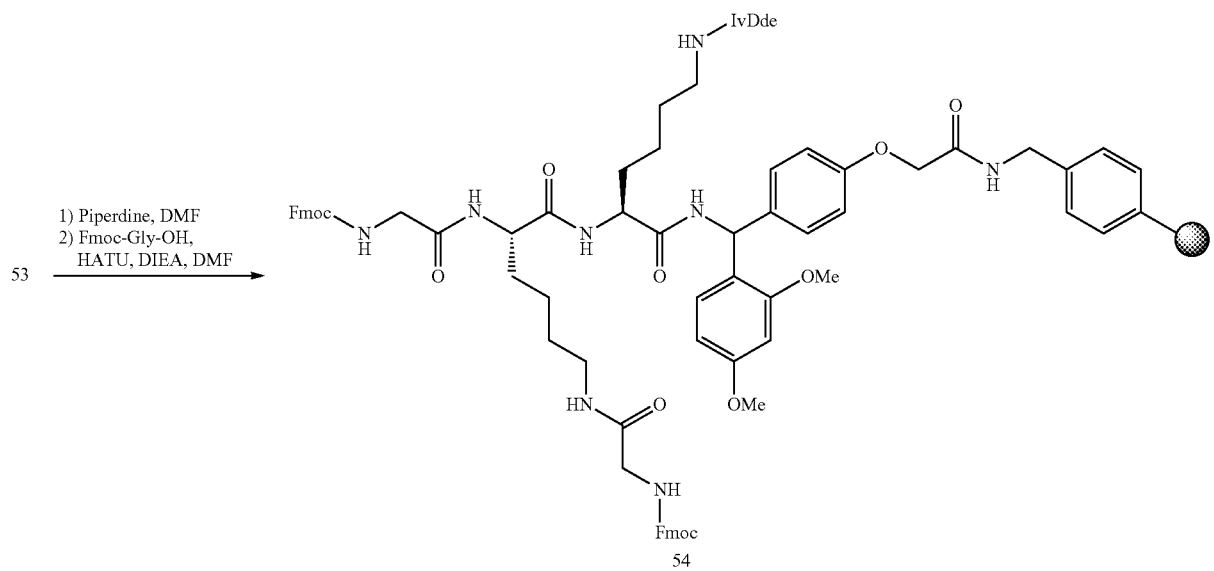
54
54 →  1) Piperdine, DMF
2) Fmoc-Cyc(StBu)-OH, HATU, DIEA, DMF -continued
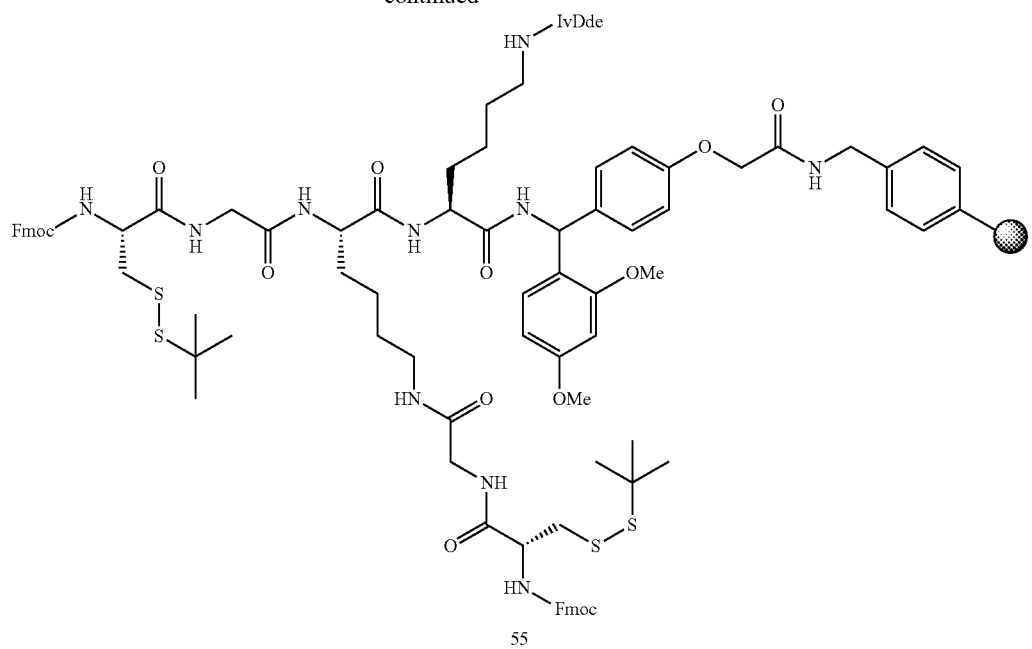
55
1) Piperdine, DMF
2) Fmoc-Gly-OH, HATU, DIEA, DMF
55 →
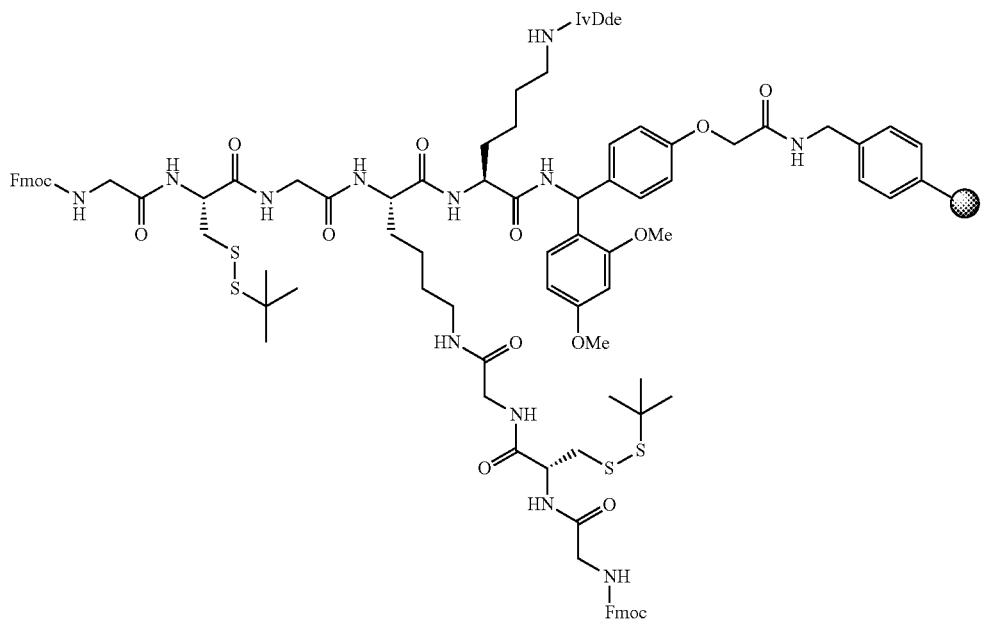
56
1) Piperdine, DMF
2) Fmoc-Cyc(StBu)-OH, HATU, DIEA, DMF
56 →

-continued
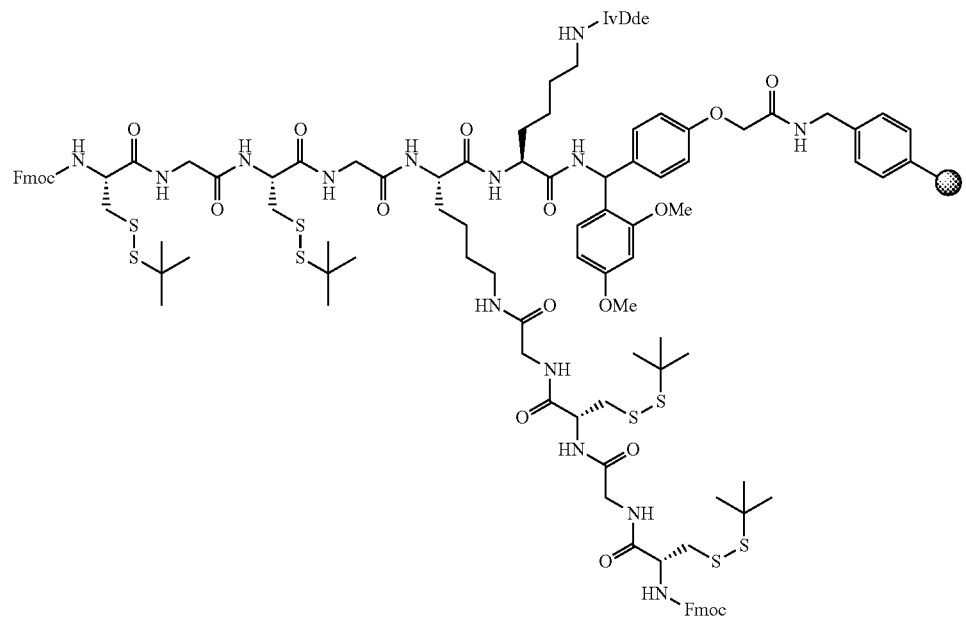
57
1) Piperdine, DMF
2) Fmoc-Gly-OH, HATU, DIEA, DMF
57 →
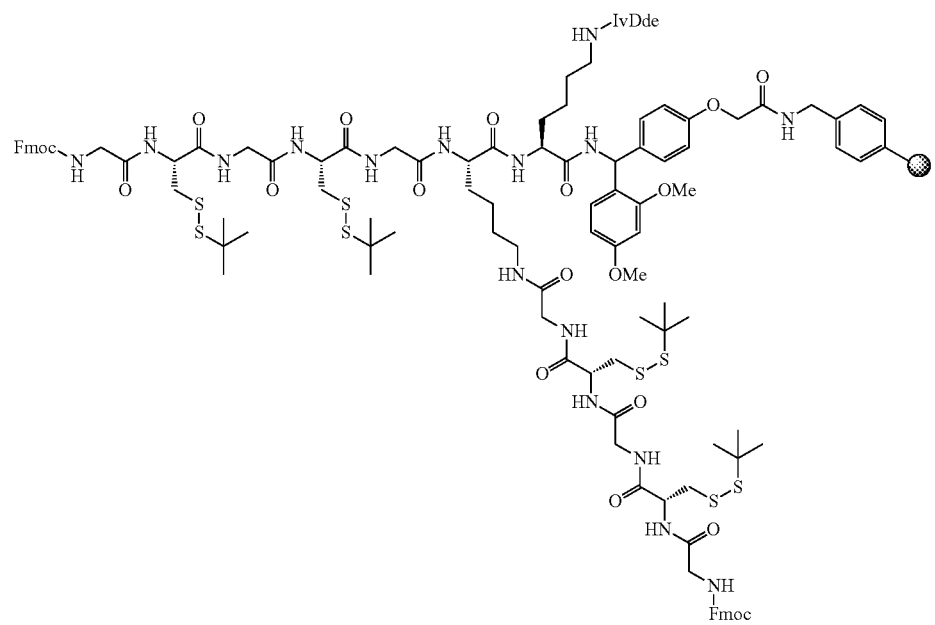
58

-continued
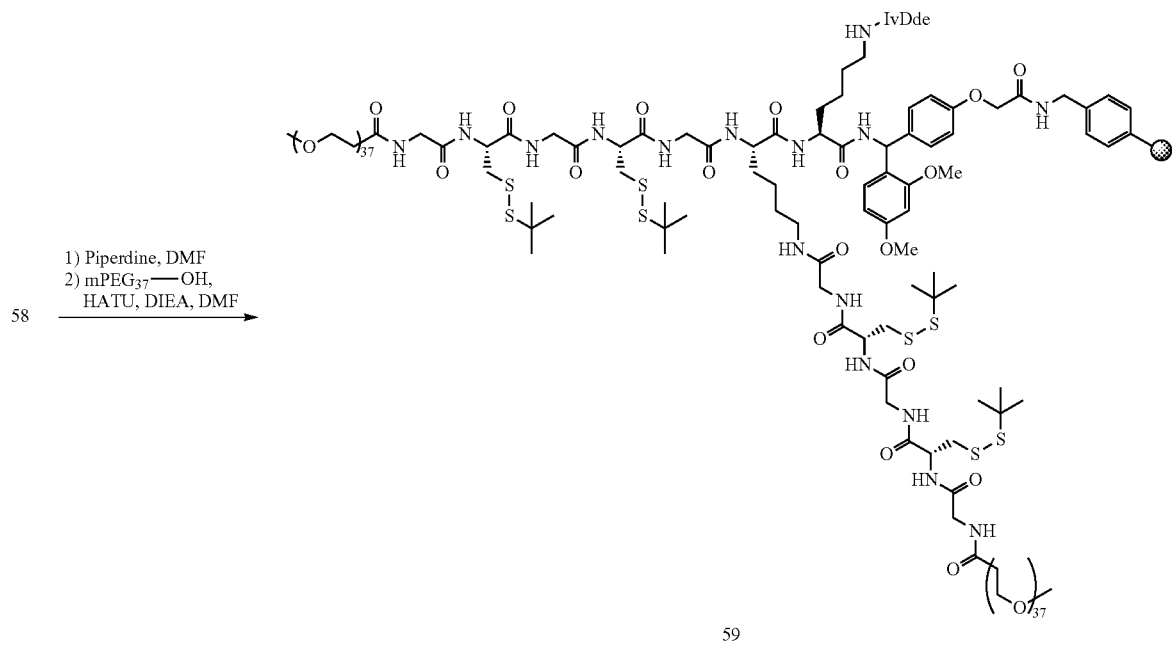
58 →
1) Piperdine, DMF
2) mPEG$_{37}$—OH, HATU, DIEA, DMF
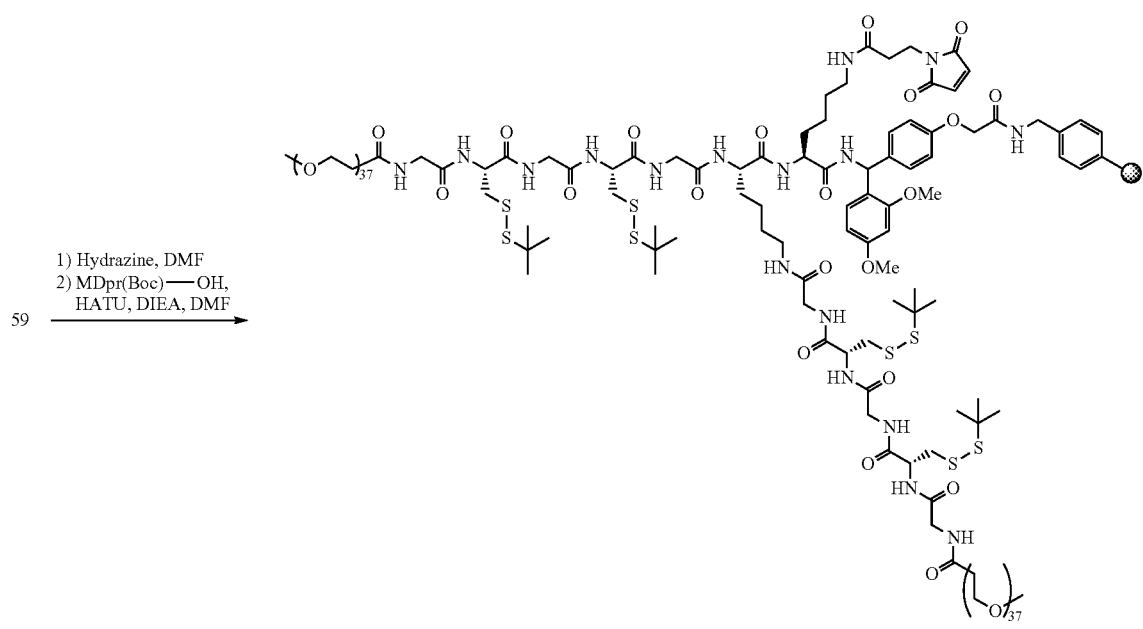
59 →
1) Hydrazine, DMF
2) MDpr(Boc)—OH, HATU, DIEA, DMF -continued

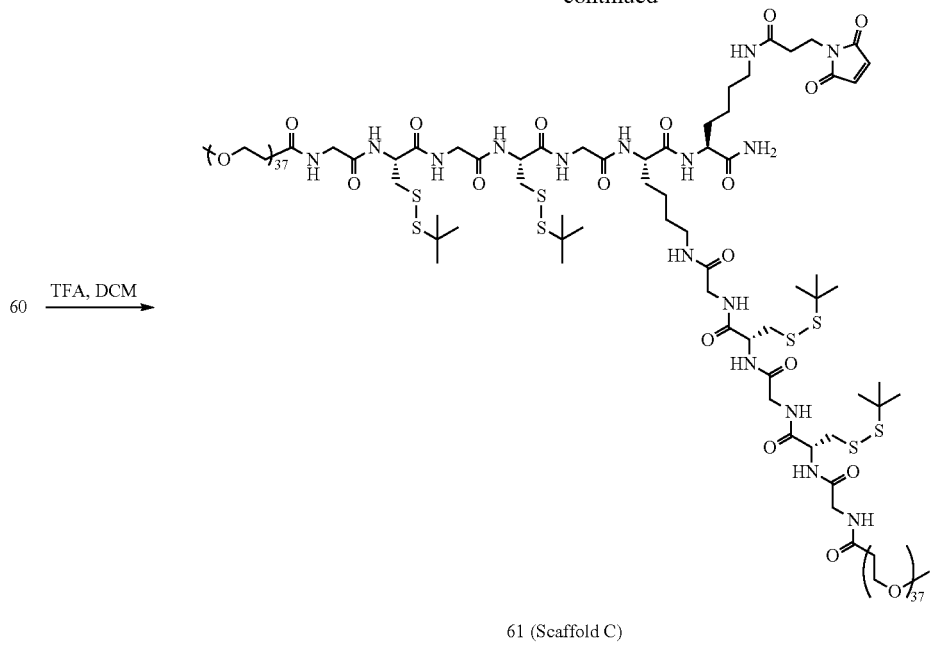

61 (Scaffold C)

MS Data for Scaffolds A, B and C prepared according to Schemes 12-14 are give in Table 6

TABLE 6

Mass Spectrometry Data for Multiplexed PEGylated Scaffolds

| PEGylated Drug Scaffold | Calculated Mass | Found Mass |
|---|---|---|
| Branched Drug Carrier Scaffold (Scaffold C wherein n is 37) | 4872.5 | 1624.92 as (M + 3H)/3 |
| MDpr-Cys(StBu)-Ala-Cys(StBu)-PEG36-OH (Scaffold B wherein n is 36) | 2293.2 | 1147.85 as (M + 2H)/2 |
| mPEG$_{24}$-Cys(StBu)-Lys(MDpr)-Cys(StBu)-PEG$_{24}$-OH (Scaffold A wherein n is 23) | 2920.5 | 1461.32 as (M + 2H)/2 |

Example 23

Preparation of ADCs Incorporating Multiplex PEGylated Scaffolds

Schemes 15-16 depict conjugation of PEGylated scaffolds to Antibody and Drug-Linker. To a solution of fully reduced antibody (34) at a concentration of approximately 10 mg/mL in PBS containing EDTA (2 mM) and buffered with additional potassium phosphate (100 mM, pH 7.4) was added 12 molar equivalents of PEGylated Branched Drug Carrier Scaffold from a 5-20 mM DMSO stock solution. The resulting solution was left at room temperature for 30 min. Complete conjugation was confirmed by reversed phase chromatography. Additional PEG reagent was added if the conjugation was incomplete. After conjugation, the antibody solution bound to a 1 mL HiTrap MabSelect SuRe column (GE Healthcare Bio-Sciences, Pittsburgh, Pa.) using a syringe pump and washed with 10 mL of PBS containing EDTA (2 mM) at 1 mL/min. To remove the t-butylthiol protecting groups, the column was washed with 3 mL of 10 mM TCEP buffered with additional potassium phosphate (100 mM, pH 7.4) over 1 hour at 37° C. The column was then washed with 10 mL of PBS containing EDTA (2 mM) at 1 mL/min and the purified antibody-scaffold conjugate was eluted with 50 mM glycine (pH 3.0). Protein containing fractions were combined and neutralized with 10% (v/v) 800 mM potassium phosphate, 500 mM NaCl, and 500 mM EDTA (pH 7.4). The resulting solution (36) was filtered through a sterile 0.22 the μm centrifugal filter and used immediately or stored at −80° C.

To a solution of deprotected PEGylated antibody (35) at a concentration of approximately 5 mg/mL in PBS containing EDTA (2 mM) and buffered with additional potassium phosphate (100 mM, pH 7.4) was added 48 molar equivalents of a maleimide containing drug-linker from a 5-20 mM DMSO stock solution. The resulting solution was left at room temperature for 30 min. Complete conjugation was confirmed by reversed phase chromatography. Additional drug-linker was added if the conjugation was incomplete. After conjugation, the antibody solution was desalted into PBS by 3 rounds of dilution and centrifugation at 4,000×g through a 30 kDa MWCO filter. The resulting PEGylated antibody-drug conjugate solution (37) was filtered through a sterile 0.22 μm centrifugal filter, analyzed by size exclusion chromatography (SEC) and reversed phase chromatography, and stored at −80° C.

Scheme 15: Conjugation of Maleimide Containing PEGylated Branched Drug Carrier Scaffold and Removal of t-Butylthiol Protecting Groups
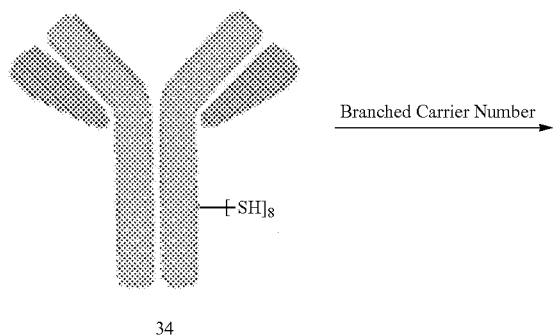
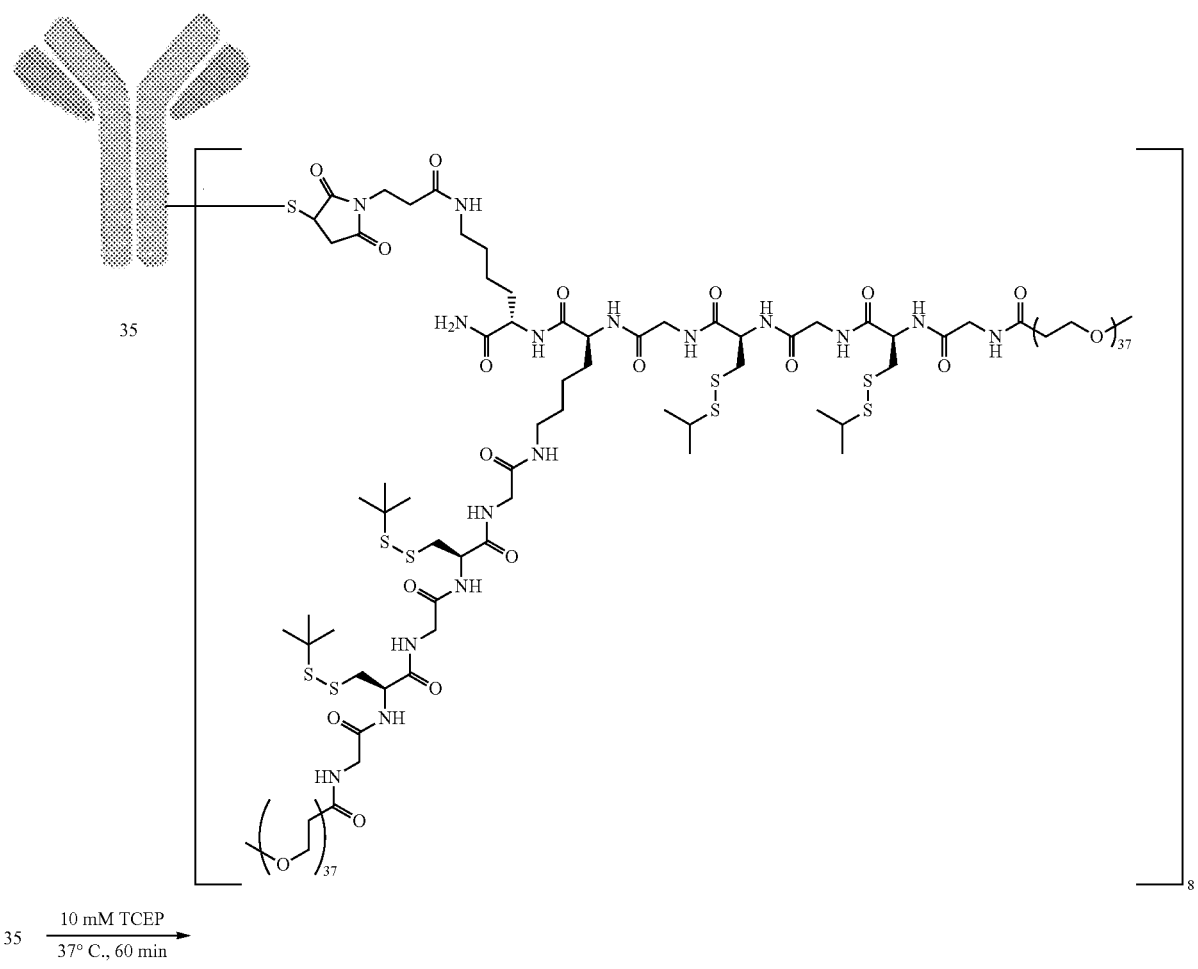

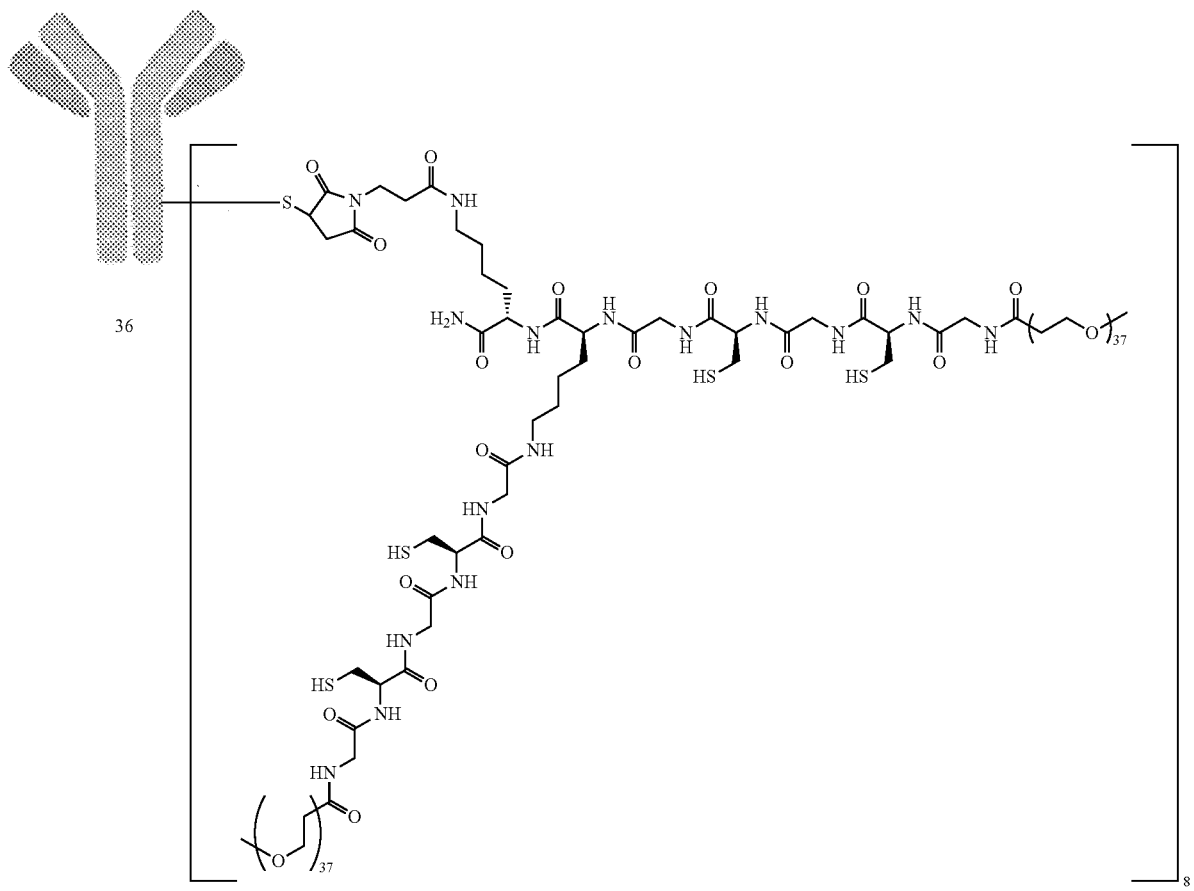
Scheme 16: Conjugation of Maleimide Containing Drug Linkers to Branched Drug Carrier:
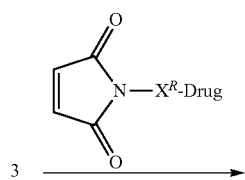

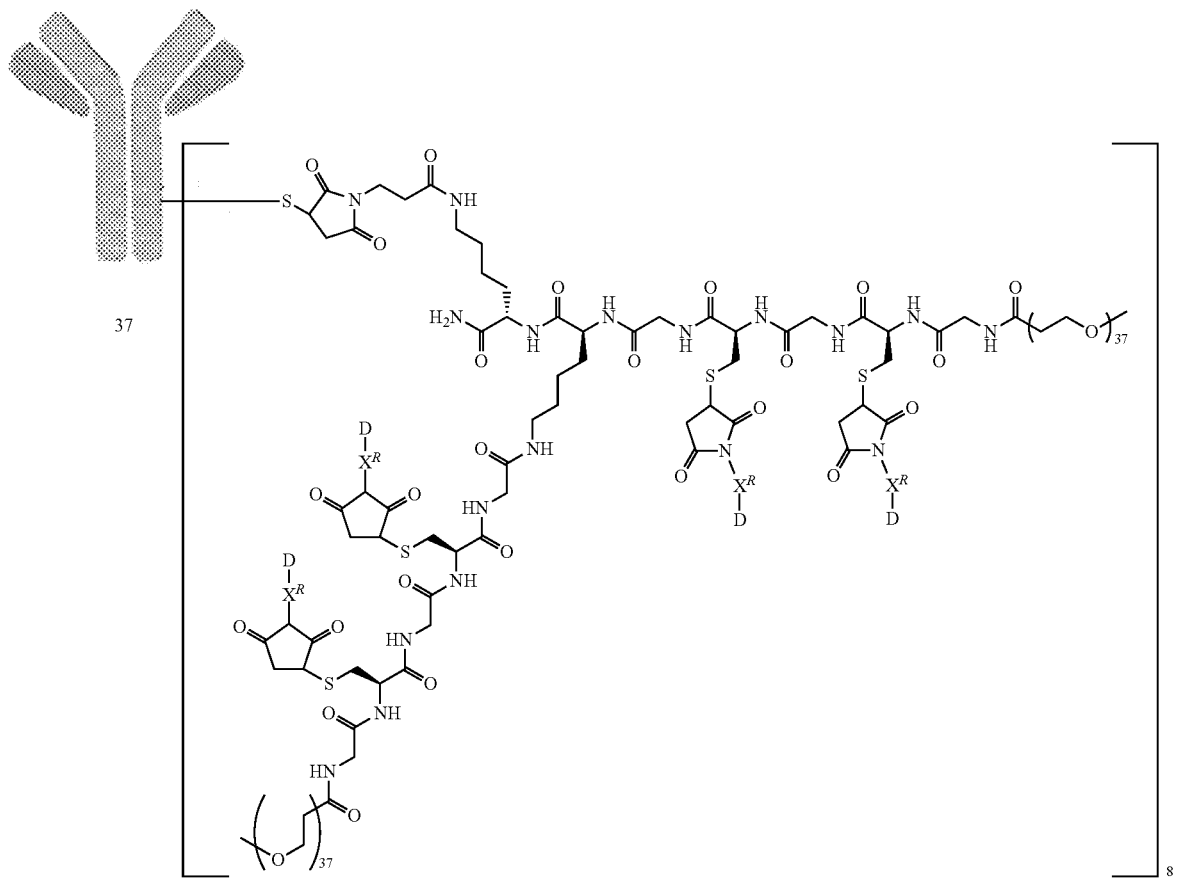

Example 24

Preparation and Biological Activity of ADCs Having Multiplexed PEGylated Scaffolds 32-Load auristatin and Camptothecin ADCs were prepared from the PEGylated multiplexed scaffold C, wherein n=37, using the procedures of Example 23. The amount of aggregation was below the level of quantification, but size exclusion chromatography showed that 32-Load MMAE ADCs may exist in dimeric form.

The cAC10 32-load conjugate having the -X-D moiety of mc-VC-PABA-MMAE showed >5× improvement in cytotoxicity towards L540cy (CD30 copy number 433K) in comparison to 8-load ADC, even though there was only a 4× increase in drug loading. Even more significantly the 32 load conjugate had activity against L-428, which is another Hodgkin Lymphoma cell line, despite that cell line having a much lower copy number of targeted antigen (CD30 copy number 77K) while the 8-load conjugate was considered inactive ($IC_{50}$>1 μM). Also, the 32-load MMAE conjugate had cytotoxic activity against a CD30+ multi-drug resistant ALCL cell line. In contrast the 8-load MMAE conjugate was considered inactive against both multi-drug resistant cell lines although it had similar activity to the 32 load conjugate against the parental cell line.

The cAC10 32-load conjugate that has the -X-D moiety of MDpr-PAB(gluc) Camptothecin showed 3-4× improvement in cytotoxicity against L540cy in comparison to the 8-load conjugate, but like the 8 load conjugate was considered inactive against L-428. The 32-load conjugate had >5× the cytotoxicity against ALCL multi-drug resistant cell lines in comparison to the 8-load conjugates.

The hBU12 32-load conjugate also having the -X-D moiety of MDpr-PAB(gluc)-Camptothecin also showed >5× improvement in cytotoxicity in comparison to the 8-load conjugate against Raj and Ramos and was active against RL, which has the lowest C19 copy number. In contrast the 8-load conjugate was inactive.

TABLE 7

Mass Spectrometry Data for ADCs having Multiplexed PEGylated Scaffolds

| ADC | Calculated Mass (light chain, heavy chain) | Found Mass (light chain, heavy chain) |
|---|---|---|
| 16-load MDpr-glucuronide-Camptothecin cOKT9 ADC[1] | 29,092, ND | 29,094, ND |
| 32-load MDpr-glucuronide-Camptothecin cAC10 ADC[2] | 32,501, ND | 32,505, ND |

TABLE 7-continued

Mass Spectrometry Data for ADCs having Multiplexed PEGylated Scaffolds

| ADC | Calculated Mass (light chain, heavy chain) | Found Mass (light chain, heavy chain) |
|---|---|---|
| 16-load MDpr-VC-MMAE cAC10 ADC[1] | 29,104, 66,460 | 29,108, 66,465 |
| 16-load mc-VC-MMAE cAC10 ADC[3] | 28,476, 64,575 | 28,481, 64,582 |
| 32-load mc-VC-MMAE cAC10 ADC[2] | 33,514, 79,690 | 33,514, 79,691 |
| 32-load MDpr-glucuronide-MMAE cAC10 ADC[2] | 33,505, 79,664 | 33,504, 79,665 |

[1] Prepared with mPEG$_{24}$-Cys(StBu)-Lys(MDpr)-Cys(StBu)-PEG$_{24}$OH
[2] Prepared with PEG$_{37}$ Branched Drug Carrier Scaffold
[3] Prepared with MDpr-Cys(StBu)-Ala-Cys(StBu)-PEG36-OH

---

What is claimed is:

1. A Drug-Linker Compound of formula IV:

$$Z'-L^P-A_s-(X-D)_m$$

(with PEG attached to $L^P$)

(IV)

or a pharmaceutically acceptable salt thereof, wherein

D is a hydrophobic Drug Unit corresponding in structure to a hydrophobic cytotoxic, cytostatic or immunosuppressive agent;

PEG is a Polyethylene Glycol Unit, wherein the Polyethylene Glycol Unit has the formula of:

$$-R^{20}-(CH_2CH_2O)_n-R^{21}$$

$$-R^{20}-(CH_2CH_2O)_{n'}-R^{22}-(CH_2CH_2O)_{n'}-R^{21} \text{ or}$$

$$-R^{20}-(CH_2CH_2O)_{n'}-(R^{22}-(CH_2CH_2O)_{n'})_e-R^{21}$$

wherein the wavy line indicates the site of covalent attachment to $L^P$;

$R^{20}$ is a PEG Attachment Unit, wherein the PEG Attachment Unit is —C(O)—, —O—, —S—, —S(O)—, —NH—, —C(O)O—, —C(O)$C_1$-$C_{10}$ alkyl, —C(O)$C_1$-$C_{10}$ alkyl-O—, —C(O)$C_1$-$C_{10}$ alkyl-$CO_2$—, —C(O)$C_1$-$C_{10}$alkyl-NH—, —C(O)$C_1$-$C_{10}$ alkyl-S—, —C(O)$C_1$-$C_{10}$alkyl-C(O)—NH—, —C(O)$C_1$-$C_{10}$alkyl-NH—C(O)—, —$C_1$-$C_{10}$ alkyl, —$C_1$-$C_{10}$alkyl-O—, —$C_1$-$C_{10}$alkyl-$CO_2$—, —$C_1$-$C_{10}$alkyl-NH—, —$C_1$-$C_{10}$ alkyl-S—, —$C_1$-$C_{10}$ alkyl-C(O)—NH—, —$C_1$-$C_{10}$ alkyl-NH—C(O)—, —$CH_2$$CH_2$$SO_2$—$C_1$-$C_{10}$ alkyl-, —$CH_2$C(O)—$C_{1-10}$ alkyl-, =N—(O or N)—$C_1$-$C_{10}$ alkyl-O—, =N—(O or N)—$C_1$-$C_{10}$ alkyl-NH—, =N—(O or N)—$C_1$-$C_{10}$ alkyl-$CO_2$—, =N—(O or N)—$C_{1-10}$ alkyl-S—,

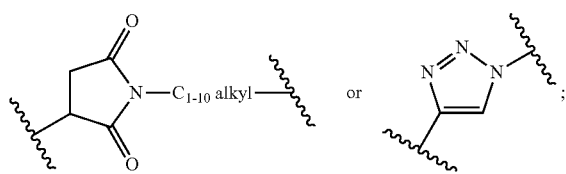

$R^{21}$ is a PEG Capping Unit; wherein the PEG Capping Unit is —$C_1$-$C_{10}$ alkyl, —$C_2$-$C_{10}$ alkyl-$CO_2$H, —$C_2$-$C_{10}$ alkyl-OH, —$C_2$-$C_{10}$ alkyl-$NH_2$, $C_2$-$C_{10}$ alkyl-NH($C_1$-$C_3$ alkyl), or $C_2$-$C_{10}$ alkyl-N($C_1$-$C_3$ alkyl)$_2$;

$R^{22}$ is an PEG Coupling Unit for coupling multiple PEG subunit chains together, wherein the PEG Coupling Unit is —$C_{1-10}$ alkyl-C(O)—NH—, —$C_{1-10}$ alkyl-NH—C(O)—, —$C_{2-10}$ alkyl-NH—, —$C_2$-$C_{10}$ alkyl-O—, —$C_1$-$C_{10}$ alkyl-S—, or —$C_2$-$C_{10}$ alkyl-NH—;

subscript n is independently selected from 8 to 72;
subscript e is selected from 2 to 5;
each n' is independently selected from 6 to 72;
Z' is a Stretcher Unit, wherein the Stretcher Unit comprises maleimide moiety capable of reacting with a thiol functional group from an antibody or antigen-binding fragment thereof to form a thio-substituted succinimide moiety, or wherein the Stretcher Unit has the structure of:

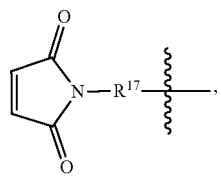

wherein
the wavy line adjacent to $R^{17}$ indicates the site of covalent attachment to $L^P$; and
$R^{17}$ is —$C_1$-$C_{10}$ alkylene-, —$C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, —$C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$ alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S— or —($C_3$-$C_8$ heterocyclo)-$C_1$-$C_{10}$ alkylene-S—, wherein $R^{17}$ is optionally substituted by —$(CH_2)_xNH_2$, —$(CH_2)_xNHR^a$ or —$(CH_2)_xNR^a_2$, wherein subscript x is an integer selected from 1-4 and each $R^a$ is independently $C_{1-6}$ alkyl, or two $R^a$ groups are combined with the nitrogen atom to which they are attached to form an azetidinyl, pyrrolidinyl or piperidinyl;

X is a Releasable Assembly Unit, wherein each Releasable Assembly Unit is capable of releasing free drug upon enzymatic cleavage of the Releasable Assembly Unit; and wherein the Releasable Assembly Unit has the formula of:

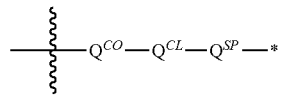

wherein $Q^{CO}$ is an optional Covalent Attachment Unit;
$Q^{SP}$ is an optional Spacer Unit;
$Q^{CL}$ is a Cleavable Unit; and
the asterisk indicates the site of covalent attachment to the Drug Unit; and the wavy line indicates covalent attachment to $L^P$ or A,
wherein the Cleavable Unit is a peptide Cleavable Unit comprising an amino acid or is a peptide sequence with a cleavable bond to $Q^{SP}$ or D, depending on the presence or absence, respectively, of $Q^{SP}$, wherein said cleavable bond is capable of enzymatic cleavage by a tumor associated protease for said releasing of free drug; and
wherein the Spacer Unit when present comprises a para-aminobenzyl (PAB) moiety that is linked to the amino acid or peptide sequence of the peptide Cleavable Unit via the amino nitrogen atom of the PAB moiety, and is connected directly to the Drug Unit via a carbonate, carbamate or ether functional group, wherein the PAB moiety and the adjacent carbonyl group of the carbonate or carbamate functional group that is part of the Spacer Unit, or wherein the Spacer Unit has the formula of:

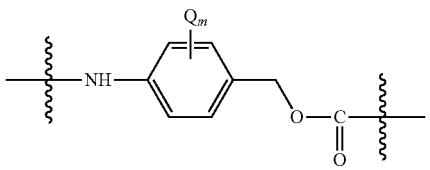

wherein Q is —$C_1$-$C_8$ alkyl, —O—($C_1$-$C_8$ alkyl), -halogen, -nitro or -cyano; and subscript m is an integer selected from 0-4; and the wavy line adjacent to the nitrogen atom indicates the site of covalent attachment to the dipeptide of the peptide Cleavable Unit and the wavy line adjacent to carbonyl carbon atom indicates the site of covalent attachment to an oxygen or nitrogen atom of the Drug Unit, or wherein the Cleavable Unit has the formula of:

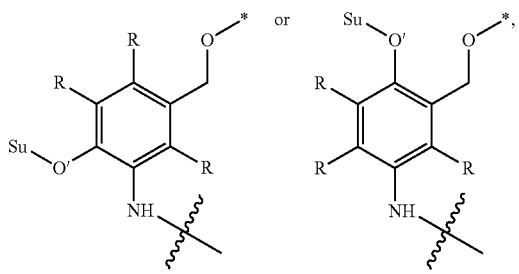

wherein Su is a Sugar moiety;
—O'— represents an oxygen glycosidic bond that is capable of enzymatic cleavable by a glycosidase for said free drug release;

each R is independently hydrogen, a halogen, —CN, or —$NO_2$; and wherein the wavy line indicates the site of covalent attachment to $L^P$ or A, depending on the absence or presence of A, respectively, either directly or indirectly through the Covalent Attachment Unit, and the asterisk indicates the site of covalent attachment to the Drug Unit, either directly or indirectly through the Spacer Unit; and the Spacer Unit when present is —C(=O)—;

$L^P$ is a Parallel Connector Unit that connects the Stretcher Unit to the hydrophobic Drug Unit(s) through intermediacy of a Releasable Assembly Unit for each Drug Unit, and connects the Polyethylene Glycol Unit in parallel orientation relative to the hydrophobic Drug Unit(s) and wherein the Parallel Connector Unit or subunit thereof has the structure of:

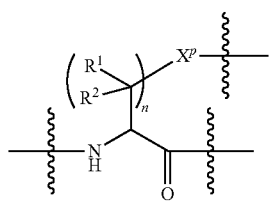

wherein subscript n is an integer selected from 1 to 4;
$X^p$ is selected from the group consisting of —O—, —NH—, —S—, —S(=O)—, —C(=O)—, and —$C_2$-$C_8$ heterocyclo-; and
$R^1$ and $R^2$ are independently selected from the group consisting of —H, —$C_1$-$C_3$ alkyl, -phenyl and —$C_2$-$C_5$ heterocycle; and
the wavy lines indicate the sites of covalent attachment within the Drug-Linker Compound, or
the Parallel Connector Unit or subunit thereof has the formula of:

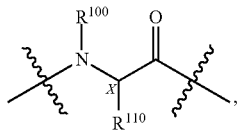

wherein $R^{100}$ is independently selected from the group consisting of —H and —$C_1$-$C_3$ alkyl; and
$R^{110}$ is selected from the group consisting of:

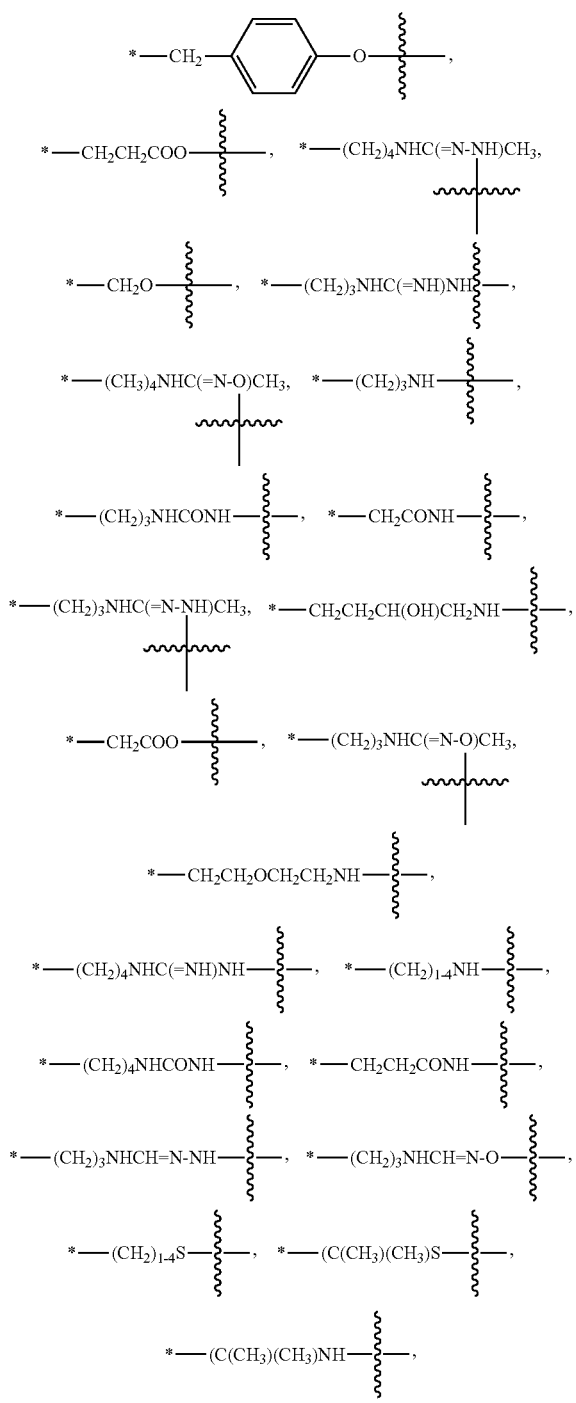

257

-continued

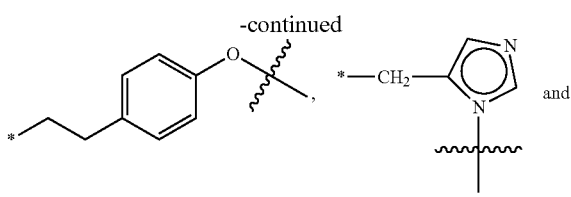

and

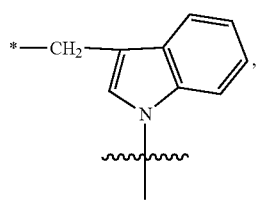

wherein the asterisk indicates the site of covalent attachment to the carbon labeled x and the wavy lines indicate the sites of covalent attachments within the Drug-Linker Compound, or the Parallel Connector Unit or subunit thereof is a trifunctional amino acid residue, or has the structure of:

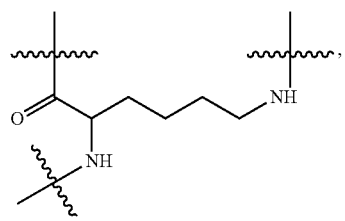

258

-continued

[structure], or

[structure], wherein the wavy lines indicate the sites of covalent attachment within the Drug-Linker compound;

A is an optional Branching Unit;

subscript m is an integer ranging from 1 to 4; and subscript s is 0 or 1, with the proviso that when subscript s is 0, subscript m is 1 and when subscript s is 1, subscript m is 2, 3 or 4.

2. The Drug-Linker Compound of claim 1, or a pharmaceutically acceptable salt thereof, wherein the Drug-Linker Compound has the structure of:

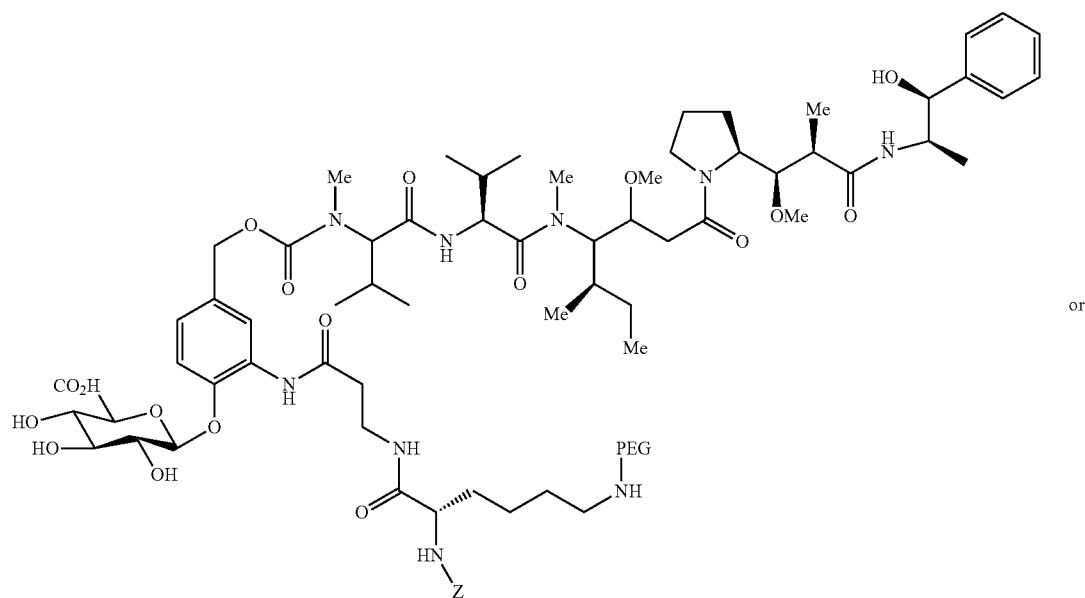

or

-continued
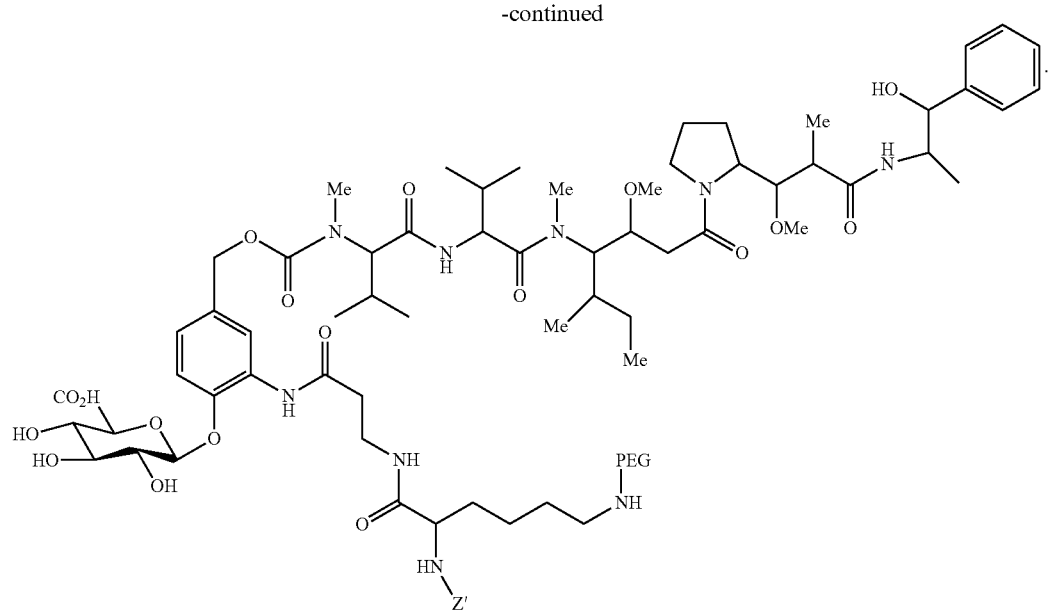
3. The Drug-Linker Compound of claim 1, or a pharmaceutically acceptable salt thereof, wherein the Drug-Linker Compound has the structure of:
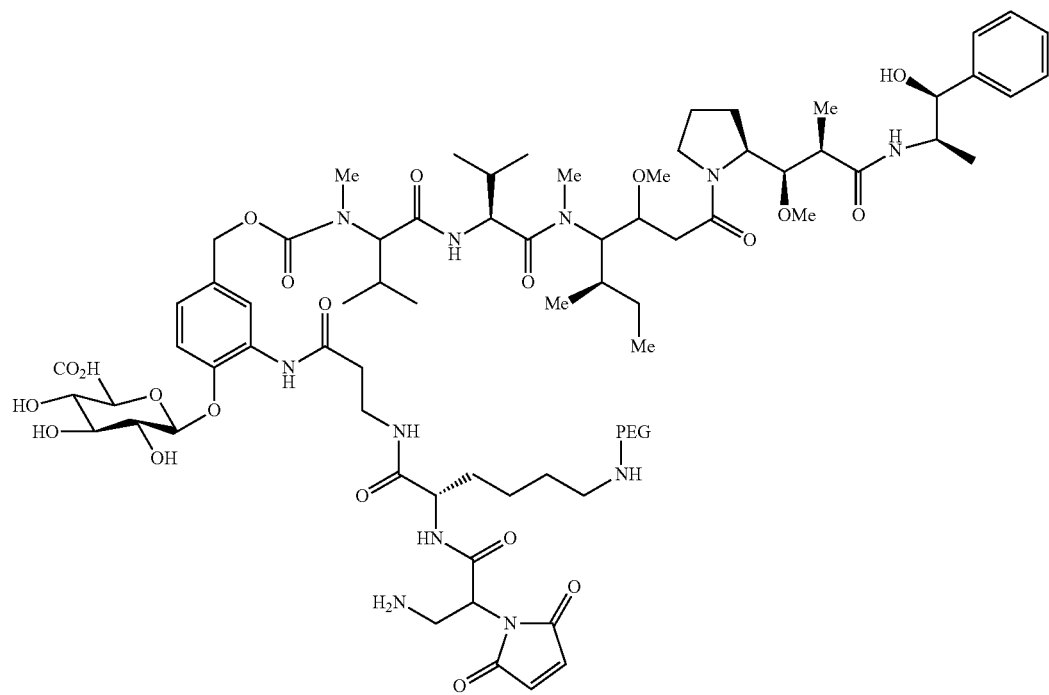
or

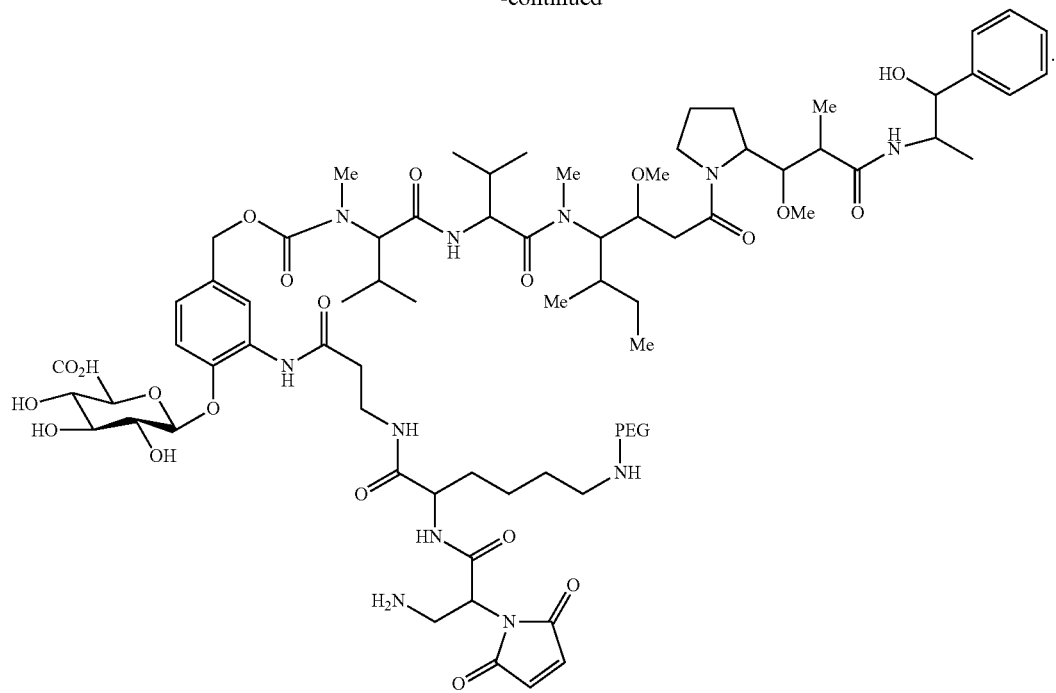
4. The Drug-Linker Compound of claim 1, or a pharmaceutically acceptable salt thereof, wherein the Drug-Linker Compound has the structure of:
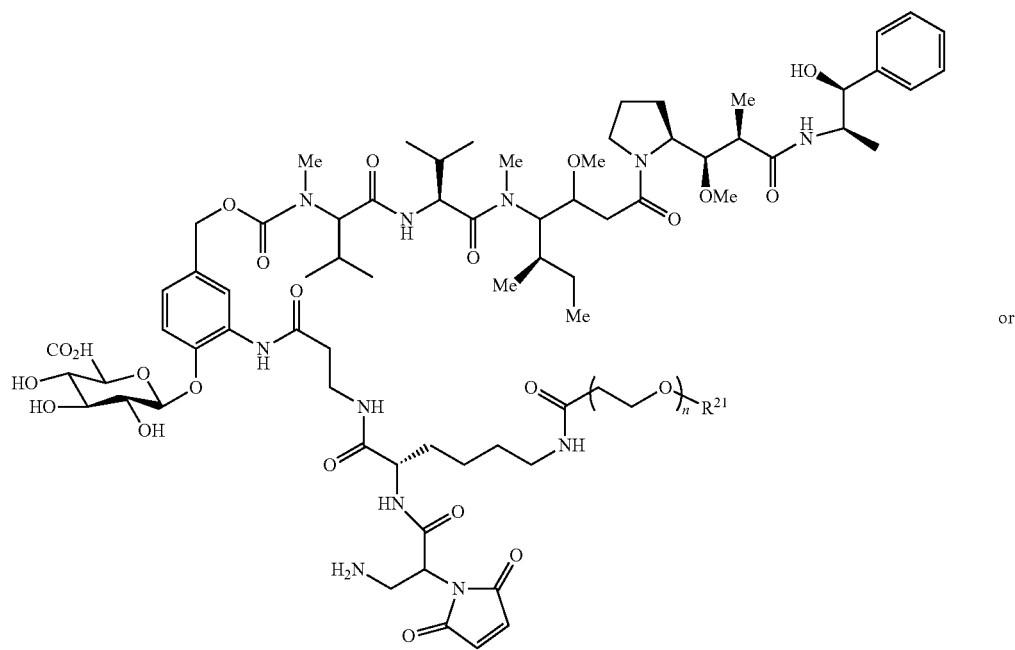
or -continued
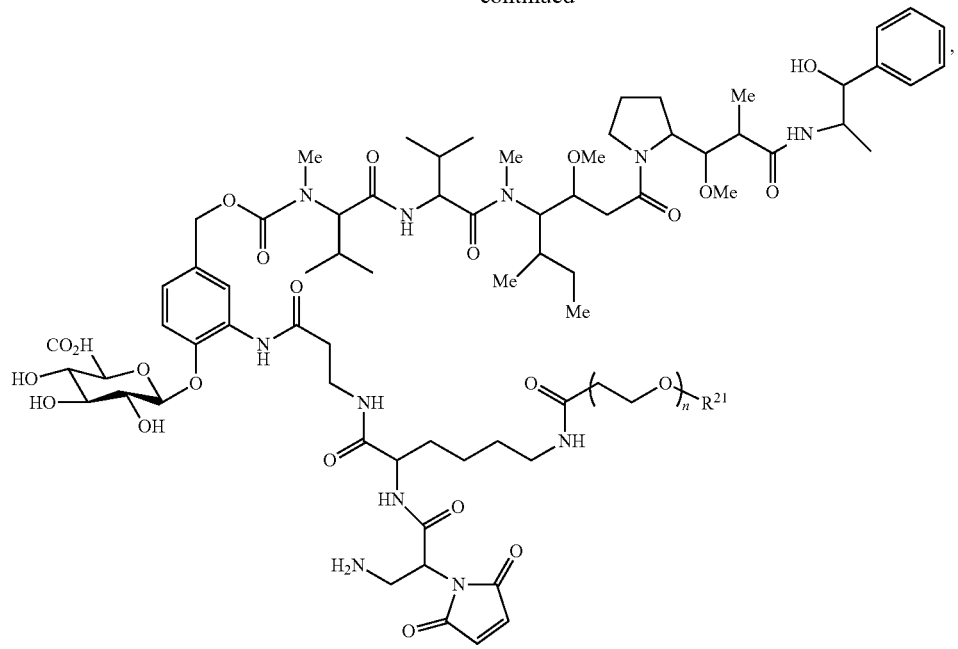
wherein R²¹ is a PEG Capping Unit and subscript n is an integer ranging from 6 to 72.
5. The Drug-Linker Compound of claim 1, or a pharmaceutically acceptable salt thereof, wherein the Drug-Linker Compound has the structure of
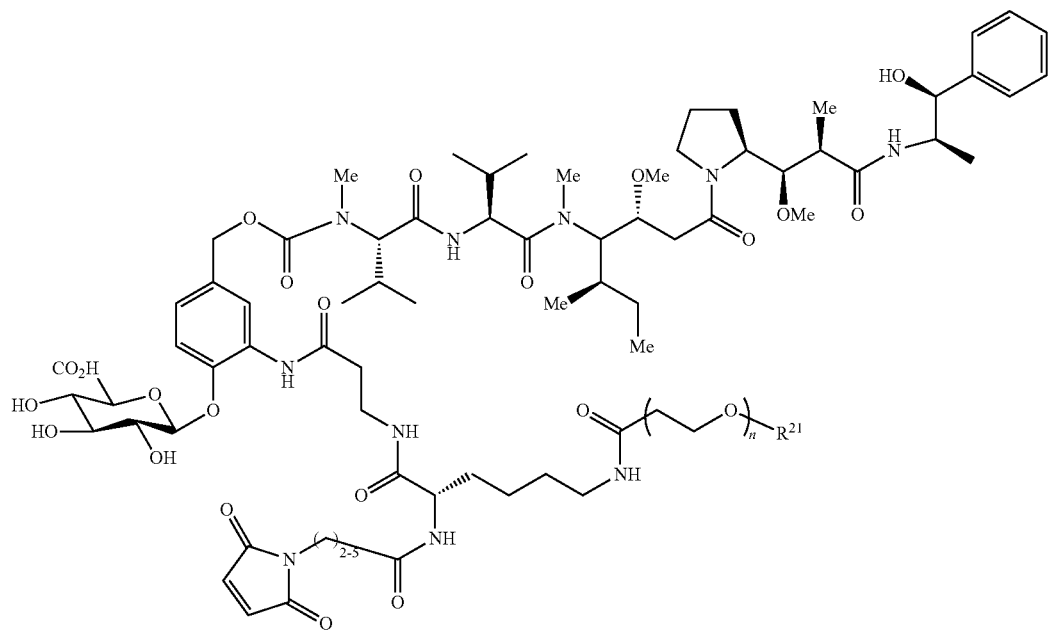
or

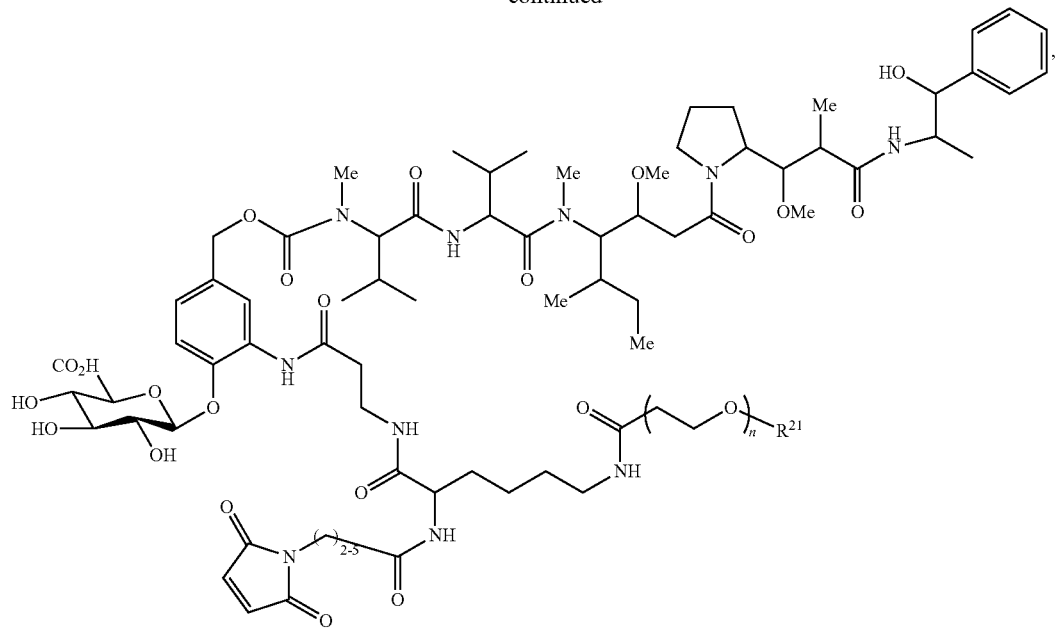

wherein $R^{21}$ is a PEG Capping Unit selected from the group consisting of methyl, ethyl, and propyl, and subscript n is an integer ranging from 6 to 72.

6. The Drug-Linker Compound of claim 1, or a pharmaceutically acceptable salt thereof, wherein the Drug-Linker Compound has the structure of:

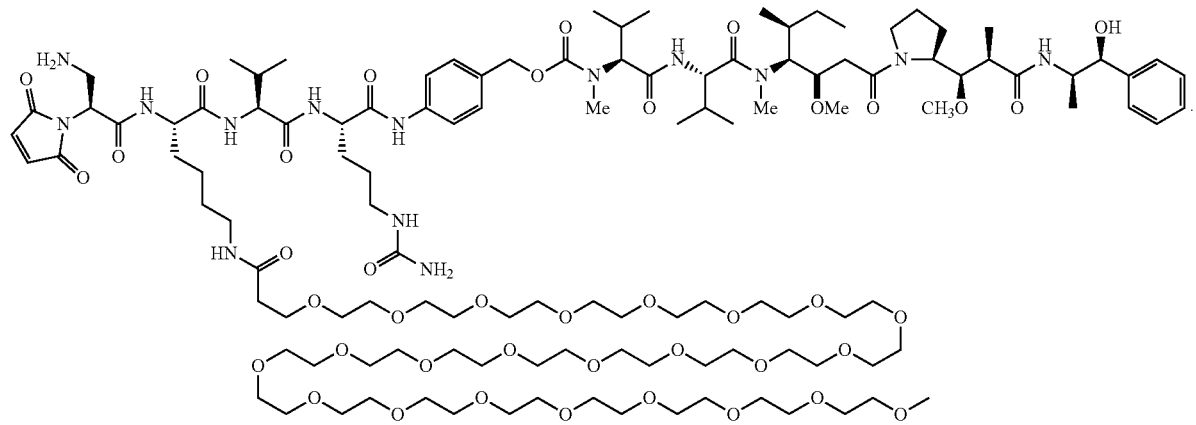

7. The Drug-Linker compound of claim 4, or a pharmaceutically acceptable salt thereof, wherein the PEG Capping Unit is methyl, ethyl, or propyl; and subscript n is an integer ranging from 8 to 24.

8. A Drug-Linker Compound, or a pharmaceutically acceptable salt thereof, wherein the compound has the structure of:

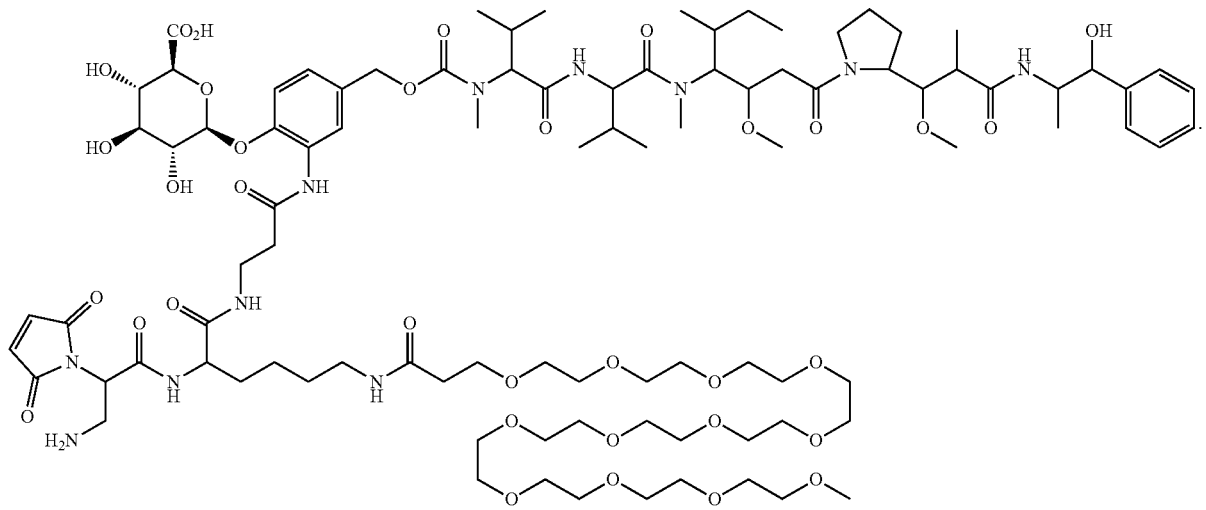 [SMILES: CCC(C)C(C(CC(=O)N1CCCC1C(OC)C(C)C(=O)NC(C)C(O)c1ccccc1)OC)N(C)C(=O)C(NC(=O)C(C(C)C)N(C)C(=O)OCc1ccc(O[C@@H]2O[C@H](C(=O)O)[C@@H](O)[C@H](O)[C@H]2O)c(NC(=O)CCNC(=O)C(CCCCNC(=O)CCOCCOCCOCCOCCOCCOCCOCCOCCOCCOCCOCCOC)NC(=O)C(CN)N2C(=O)C=CC2=O)c1)C(C)C]

9. A Drug-Linker Compound, or a pharmaceutically acceptable salt thereof, wherein the compound has the structure of:

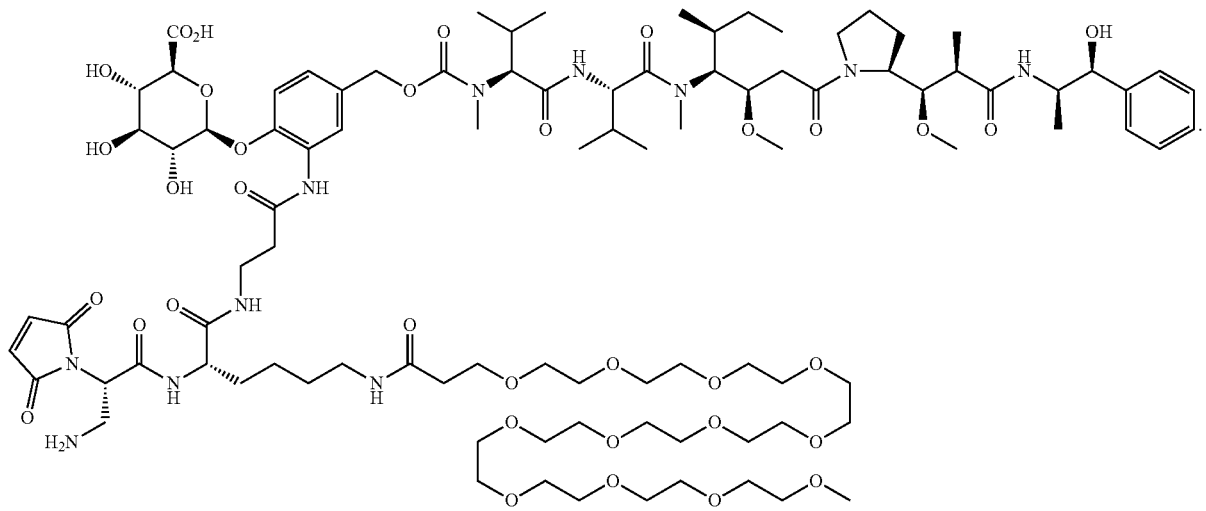 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c(NC(=O)CCNC(=O)[C@H](CCCCNC(=O)CCOCCOCCOCCOCCOCCOCCOCCOCCOCCOCCOCCOC)NC(=O)[C@H](CN)N2C(=O)C=CC2=O)c1)C(C)C]

10. A Ligand-Drug Conjugate compound of formula I:

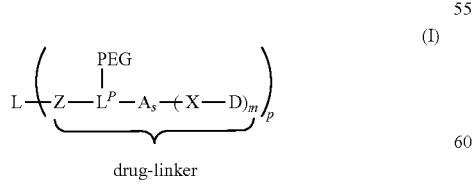

or a pharmaceutically acceptable salt thereof, wherein

L is a Ligand Unit, which is an antibody or antigen-binding fragment thereof;

D is a hydrophobic Drug Unit corresponding in structure to a hydrophobic cytotoxic, cytostatic or immunosuppressive agent;

PEG is a Polyethylene Glycol Unit, wherein the Polyethylene Glycol Unit has the formula of:

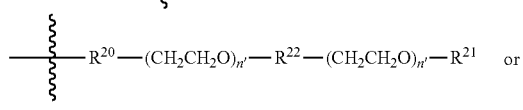

-continued

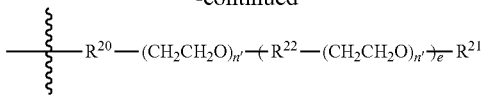

wherein the wavy line indicates the site of covalent attachment to $L^P$;

$R^{20}$ is a PEG Attachment Unit, wherein the PEG Attachment Unit is —C(O)—, —O—, —S—, —S(O)—, —NH—, —C(O)O—, —C(O)C$_1$-C$_{10}$ alkyl, —C(O)C$_1$-C$_{10}$ alkyl-O—, —C(O)C$_1$-C$_{10}$ alkyl-CO$_2$—, —C(O)C$_1$-C$_{10}$alkyl-NH—, —C(O)C$_1$-C$_{10}$ alkyl-S—, —C(O)C$_1$-C$_{10}$alkyl-C(O)—NH—, —C(O)C$_1$-C$_{10}$alkyl-NH—C(O)—, —C$_1$-C$_{10}$ alkyl, —C$_1$-C$_{10}$alkyl-O—, —C$_1$-C$_{10}$alkyl-CO$_2$—, —C$_1$-C$_{10}$alkyl-NH—, —C$_1$-C$_{10}$ alkyl-S—, —C$_1$-C$_{10}$ alkyl-C(O)—NH—, —C$_1$-C$_{10}$ alkyl-NH—C(O)—, —CH$_2$CH$_2$SO$_2$—C$_1$-C$_{10}$ alkyl-, —CH$_2$C(O)—C$_{1-10}$ alkyl-, =N—(O or N)—C$_1$-C$_{10}$ alkyl-O—, =N—(O or N)—C$_1$-C$_{10}$ alkyl-NH—, =N—(O or N)—C$_1$-C$_{10}$ alkyl-CO$_2$—, =N—(O or N)—C$_1$-C$_{10}$ alkyl-S—,

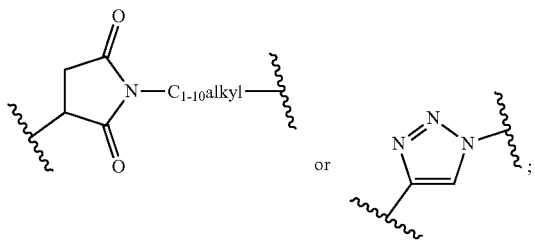

or $R^{21}$ is a PEG Capping Unit; wherein the PEG Capping Unit is —C$_1$-C$_{10}$ alkyl, —C$_2$-C$_{10}$ alkyl-CO$_2$H, —C$_2$-C$_{10}$ alkyl-OH, —C$_2$-C$_{10}$ alkyl-NH$_2$, C$_2$-C$_{10}$ alkyl-NH(C$_1$-C$_3$ alkyl), or C$_2$-C$_{10}$ alkyl-N(C$_1$-C$_3$ alkyl)$_2$;

$R^{22}$ is an PEG Coupling Unit for coupling multiple PEG subunit chains together, wherein the PEG Coupling Unit is —C$_{1-10}$ alkyl-C(O)—NH—, —C$_{1-10}$ alkyl-NH—C(O)—, —C$_{2-10}$ alkyl-NH—, —C$_2$-C$_{10}$ alkyl-O—, —C$_1$-C$_{10}$ alkyl-S—, or —C$_2$-C$_{10}$ alkyl-NH—;

subscript n is independently selected from 8 to 72;
subscript e is selected from 2 to 5;
each n' is independently selected from 6 to 72;
Z is a Stretcher Unit, wherein the Stretcher Unit comprises a succinimide moiety that is connected to a thiol functional group from the antibody or antigen-binding fragment thereof to form a thio-substituted succinimide moiety, or wherein the Stretcher Unit has the structure of:

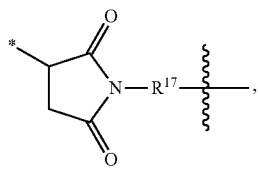

wherein
the asterisk indicates covalent attachment of each Z to the Ligand Unit and the wavy line adjacent to $R^{17}$ indicates the site of covalent attachment to $L^P$; and
$R^{17}$ is —C$_1$-C$_{10}$ alkylene-, —C$_1$-C$_{10}$ heteroalkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —C$_1$-C$_{10}$ alkylene-C(=O)—, —C$_1$-C$_{10}$ heteroalkylene-C(=O)—, —C$_3$-C$_8$ carbocyclo-C(=O)—, —O—(C$_1$-C$_8$ alkyl)-C(=O)—, -arylene-C(=O)—, —C$_1$-C$_{10}$ alkylene-arylene-C(=O)—, -arylene-C$_1$-C$_{10}$ alkylene-C(=O)—, —C$_1$-C$_{10}$ alkylene-(C$_3$-C$_8$ carbocyclo)-C(=O)—, —(C$_3$-C$_8$ carbocyclo)-C$_1$-C$_{10}$ alkylene-C(=O)—, —C$_3$-C$_8$ heterocyclo-C(=O)—, —C$_1$-C$_{10}$ alkylene-(C$_3$-C$_8$ heterocyclo)-C(=O)—, —(C$_3$-C$_8$ heterocyclo)-C$_1$-C$_{10}$ alkylene-C(=O)—, —C$_1$-C$_{10}$ alkylene-NH—, C$_1$-C$_{10}$ heteroalkylene-NH—, —C$_3$-C$_8$ carbocyclo-NH—, —O—(C$_1$-C$_8$ alkyl)-NH—, -arylene-NH—, —C$_1$-C$_{10}$ alkylene-arylene-NH—, -arylene-C$_1$-C$_{10}$ alkylene-NH—, —C$_1$-C$_{10}$ alkylene-(C$_3$-C$_8$ carbocyclo)-NH—, —(C$_3$-C$_8$ carbocyclo)-C$_1$-C$_{10}$ alkylene-NH—, —C$_3$-C$_8$ heterocyclo-NH—, —C$_1$-C$_{10}$ alkylene-(C$_3$-C$_8$ heterocyclo)-NH—, —(C$_3$-C$_8$ heterocyclo)-C$_1$-C$_{10}$ alkylene-NH—, —C$_1$-C$_{10}$ alkylene-S—, C$_1$-C$_{10}$ heteroalkylene-S—, —C$_3$-C$_8$ carbocyclo-S—, —O—(C$_1$-C$_8$ alkyl)-S—, -arylene-S—, —C$_1$-C$_{10}$ alkylene-arylene-S—, -arylene-C$_1$-C$_{10}$ alkylene-S—, —C$_1$-C$_{10}$ alkylene-(C$_3$-C$_8$ carbocyclo)-S—, —(C$_3$-C$_8$ carbocyclo)-C$_1$-C$_{10}$ alkylene-S—, —C$_3$-C$_8$ heterocyclo-S—, —C$_1$-C$_{10}$ alkylene-(C$_3$-C$_8$ heterocyclo)-S— or —(C$_3$-C$_8$ heterocyclo)-C$_1$-C$_{10}$ alkylene-S—, wherein $R^{17}$ is optionally substituted by —(CH$_2$)$_x$NH$_2$, —(CH$_2$)$_x$NHR$^a$ or —(CH$_2$)$_x$NR$^a_2$, wherein subscript x is an integer selected from 1-4 and each R$^a$ is independently C$_{1-6}$ alkyl, or two R$^a$ groups are combined with the nitrogen atom to which they are attached to form an azetidinyl, pyrrolidinyl or piperidinyl;

X is a Releasable Assembly Unit, wherein each Releasable Assembly Unit is capable of releasing free drug upon enzymatic cleavage of the Releasable Assembly Unit; and wherein the Releasable Assembly Unit has the formula of:

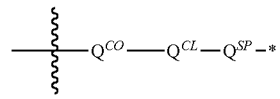

wherein $Q^{CO}$ is an optional Covalent Attachment Unit;
$Q^{SP}$ is an optional Spacer Unit;
$Q^{CL}$ is a Cleavable Unit; and
the asterisk indicates the site of covalent attachment to the Drug Unit; and the wavy line indicates covalent attachment to $L^P$ or A,
wherein the Cleavable Unit is a peptide Cleavable Unit comprising an amino acid or is a peptide sequence with a cleavable bond to $Q^{SP}$ or D, depending on the presence or absence, respectively, of $Q^{SP}$, wherein said cleavable bond is capable of enzymatic cleavage by a tumor associated protease for said releasing of free drug; and
wherein the Spacer Unit when present comprises a para-aminobenzyl (PAB) moiety that is linked to the amino acid or peptide sequence of the peptide Cleavable Unit via the amino nitrogen atom of the PAB moiety, and is connected directly to the Drug Unit via a carbonate, carbamate or ether functional group, wherein the PAB moiety and the adjacent carbonyl group of the carbonate or carbamate functional group that is part of the Spacer Unit, or wherein the Spacer Unit has the formula of:

271

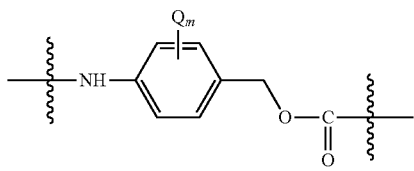

wherein Q is —C$_1$-C$_8$ alkyl, —O—(C$_1$-C$_8$ alkyl), -halogen, -nitro or -cyano; and subscript m is an integer selected from 0-4; and the wavy line adjacent to the nitrogen atom indicates the site of covalent attachment to the dipeptide of the peptide Cleavable Unit and the wavy line adjacent to carbonyl carbon atom indicates the site of covalent attachment to an oxygen or nitrogen atom of the Drug Unit, or wherein the Cleavable Unit has the formula of:

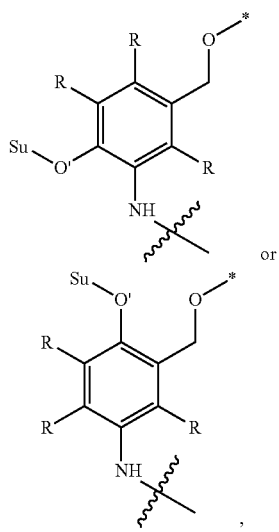

wherein Su is a Sugar moiety;

—O'— represents an oxygen glycosidic bond that is capable of enzymatic cleavable by a glycosidase for said free drug release;

each R is independently hydrogen, a halogen, —CN, or —NO$_2$; and wherein the wavy line indicates the site of covalent attachment to L$^P$ or A, depending on the absence or presence of A, respectively, either directly or indirectly through the Covalent Attachment Unit, and the asterisk indicates the site of covalent attachment to the Drug Unit, either directly or indirectly through the Spacer Unit; and the Spacer Unit when present is —C(=O)—;

L$^P$ is a Parallel Connector Unit that connects the Stretcher Unit to the hydrophobic Drug Unit(s) through intermediacy of a Releasable Assembly Unit for each Drug Unit, and connects the Polyethylene Glycol Unit in parallel orientation relative to the hydrophobic Drug Unit(s) and wherein the Parallel Connector Unit or subunit thereof has the structure of:

272

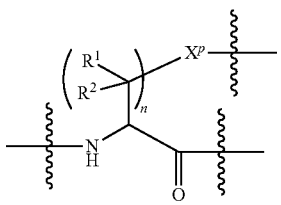

wherein subscript n is an integer selected from 1 to 4;

X$^P$ is selected from the group consisting of —O—, —NH—, —S—, —S(=O)—, —C(=O)—, and —C$_2$-C$_8$ heterocyclo-; and R$^1$ and R$^2$ are independently selected from the group consisting of —H, —C$_1$-C$_3$ alkyl, -phenyl and —C$_2$-C$_5$ heterocycle; and the wavy lines indicate the sites of covalent attachment within the Ligand-Drug Conjugate compound, or the Parallel Connector Unit or subunit thereof has the formula of:

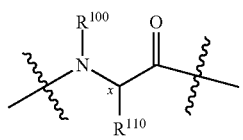

wherein R$^{100}$ is independently selected from the group consisting of —H and —C$_1$-C$_3$ alkyl; and R$^{110}$ is selected from the group consisting of:

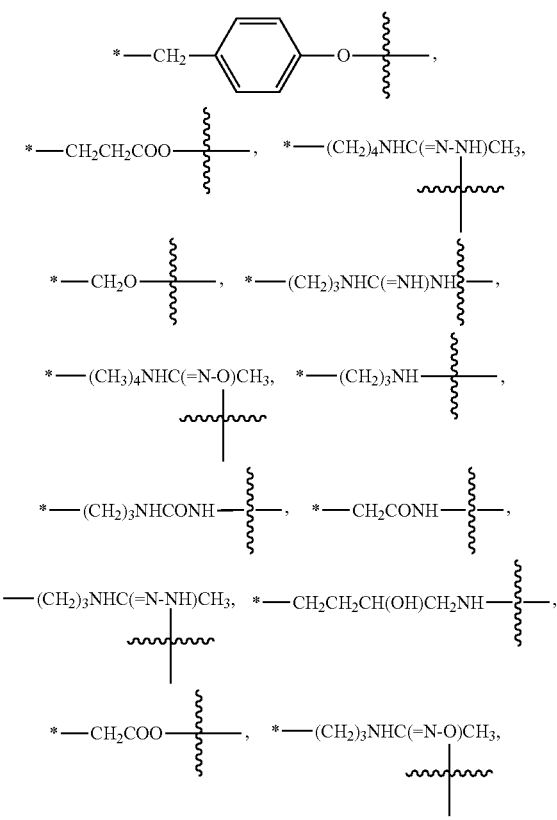

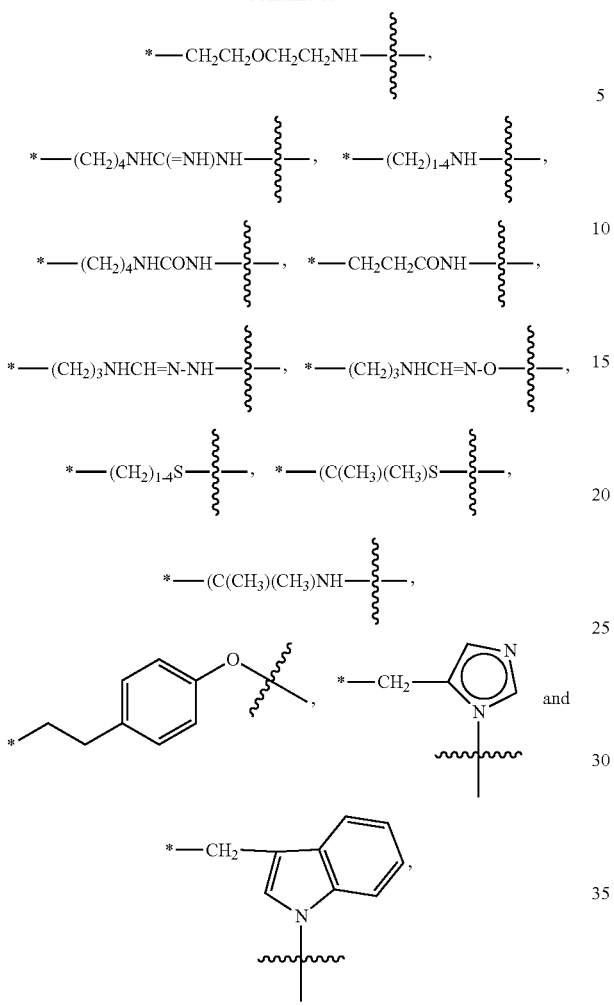

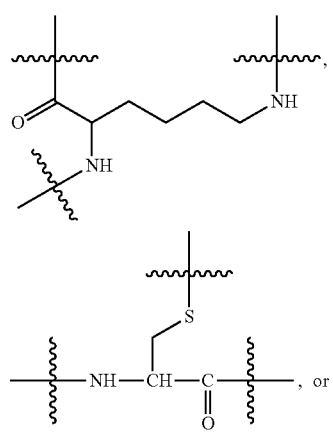

wherein the asterisk indicates the site of covalent attachment to the carbon labeled x and the wavy lines indicate the sites of covalent attachments within the Ligand-Drug Conjugate compound, or the Parallel Connector Unit or subunit thereof is a trifunctional amino acid residue, or has the structure of:

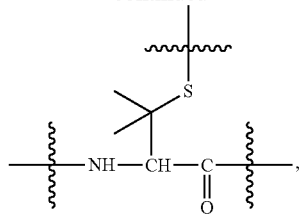

wherein the wavy lines indicate the sites of covalent attachment within the Ligand-Drug Conjugate compound;

A is an optional Branching Unit;

subscript m is an integer ranging from 1 to 4;

subscript s is 0 or 1, with the proviso that when subscript s is 0, subscript m is 1 and when subscript s is 1, subscript m is 2, 3 or 4; and subscript p is an integer ranging from 1 to 14.

11. The Ligand-Drug Conjugate compound of claim 10, or a pharmaceutically acceptable salt thereof, wherein the PEG Unit is

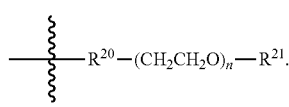

12. The Ligand-Drug Conjugate compound of claim 11, or a pharmaceutically acceptable salt thereof, wherein:

$R^{20}$ is —C(O)—, and $R^{21}$ is $C_1$-$C_{10}$ alkyl.

13. The Ligand-Drug Conjugate compound of claim 10, or a pharmaceutically acceptable salt thereof, wherein Z is

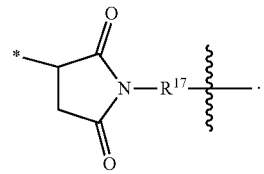

14. The Ligand-Drug Conjugate compound of claim 13, or a pharmaceutically acceptable salt thereof, wherein $R^{17}$ is —$C_1$-$C_{10}$ alkylene-C(=O)—, optionally substituted by —(CH$_2$)$_x$NH$_2$.

15. The Ligand-Drug Conjugate compound of claim 14, or a pharmaceutically acceptable salt thereof, wherein the Cleavable Unit has the formula:

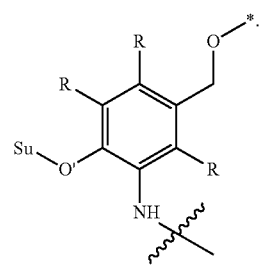

16. The Ligand-Drug Conjugate compound of claim 15, or a pharmaceutically acceptable salt thereof, wherein the Spacer Unit is —C(=O)—.

17. The Ligand-Drug Conjugate compound of claim 10, or a pharmaceutically acceptable salt thereof, wherein $L^P$ has the structure of:

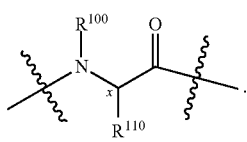

18. The Ligand-Drug Conjugate compound of claim 17, or a pharmaceutically acceptable salt thereof, wherein $R^{100}$ is H and $R^{110}$ has the structure of:

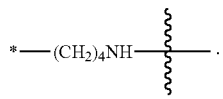

19. The Ligand-Drug Conjugate compound of claim 10, or a pharmaceutically acceptable salt thereof, wherein D is an auristatin Drug Unit represented by the structure of formula $D_E$:

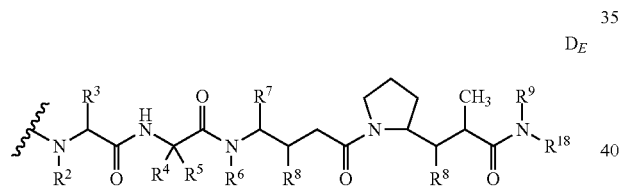

wherein, independently at each location:

$R^2$ is selected from the group consisting of H and $C_1$-$C_8$ alkyl;

$R^3$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from the group consisting of H and methyl;

or $R^4$ and $R^5$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle and n is selected from the group consisting of 2, 3, 4, 5 and 6;

$R^6$ is selected from the group consisting of H and $C_1$-$C_8$ alkyl;

$R^7$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from the group consisting of H, OH, $C_1$-$C_8$ alkyl, $C_3$-$C_8$ carbocycle and O—($C_1$-$C_8$ alkyl);

$R^9$ is selected from the group consisting of H and $C_1$-$C_8$ alkyl; and $R^{18}$ is selected from the group consisting of —C($R^8$)$_2$—C($R^8$)$_2$-aryl, —C($R^8$)$_2$—C($R^8$)$_2$—($C_3$-$C_8$ heterocycle), and —C($R^8$)$_2$—C($R^8$)$_2$—($C_3$-$C_8$ carbocycle).

20. The Ligand-Drug Conjugate compound of claim 10, or a pharmaceutically acceptable salt thereof, wherein the compound has the structure of:

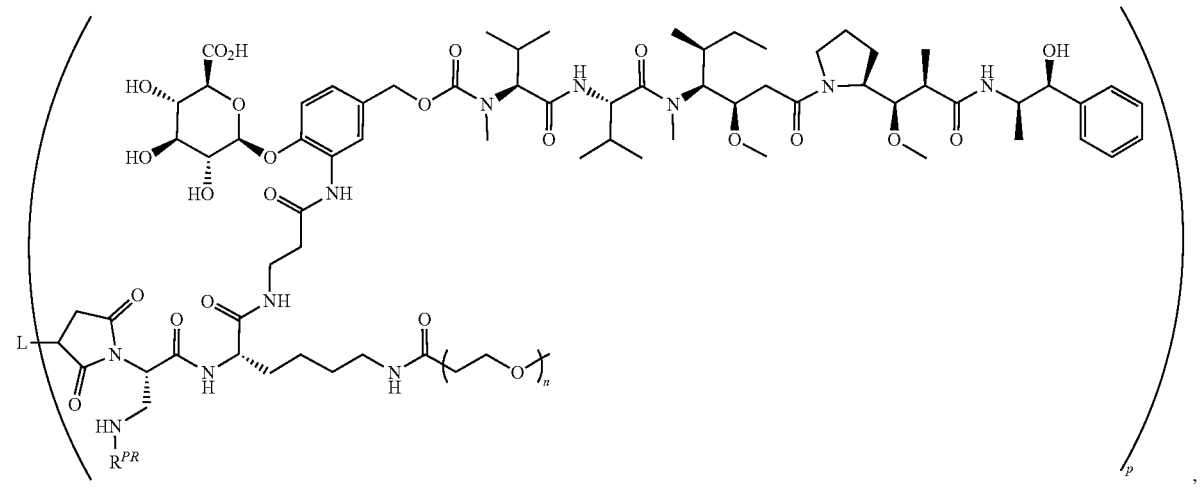

wherein
$R^{PR}$ is hydrogen or a protecting group; and
subscript n is 8, 10, 12, or 24.

21. A Ligand-Drug Conjugate compound, or a pharmaceutically acceptable salt thereof, wherein the compound has the structure of:

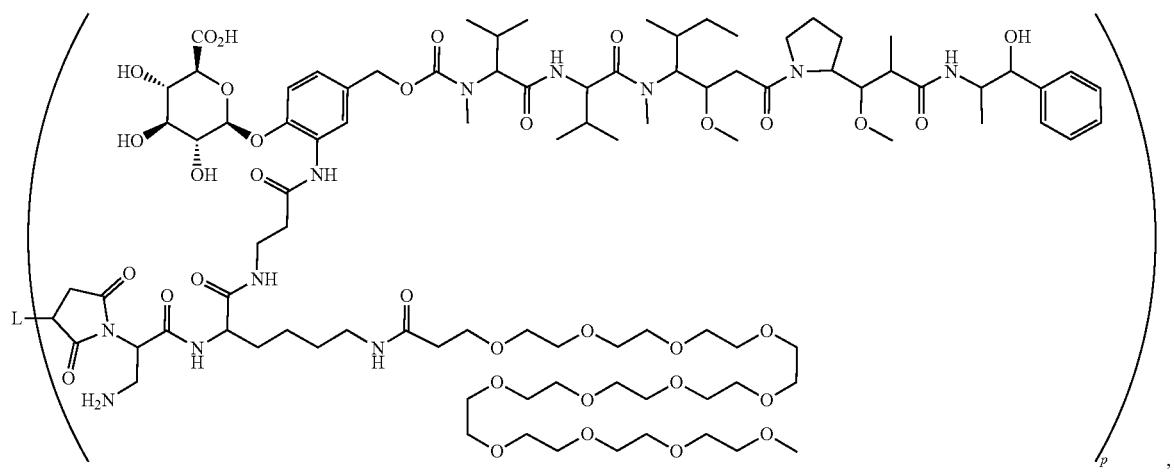

wherein L is a Ligand Unit, which in an antibody or antigen-binding fragment thereof, and
wherein subscript p is an integer ranging from 1 to 14.

22. A Ligand-Drug Conjugate compound, or a pharmaceutically acceptable salt thereof, wherein the compound has the structure of:

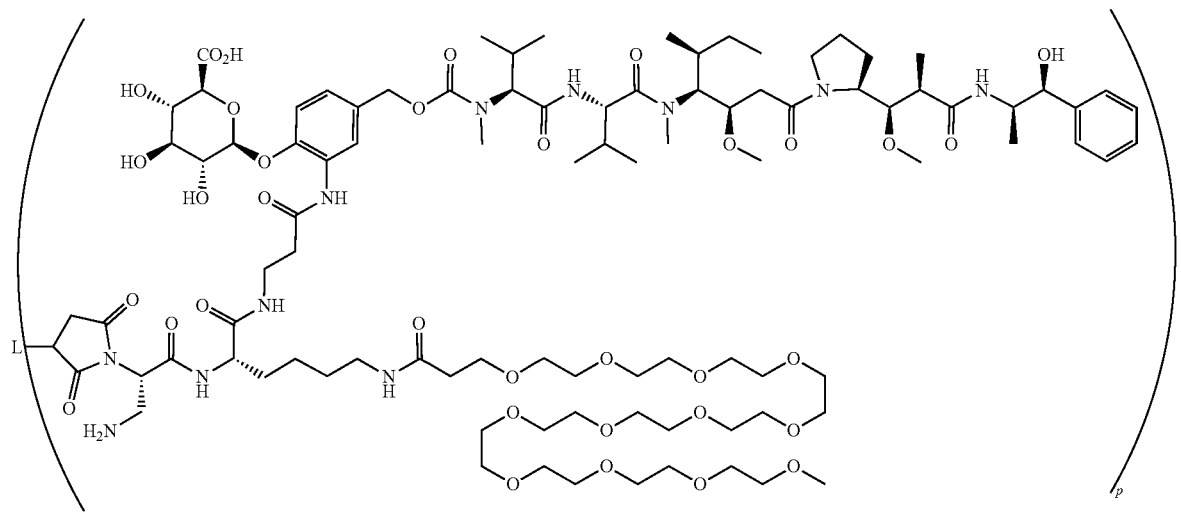

wherein L is a Ligand Unit, which in an antibody or antigen-binding fragment thereof, and
wherein subscript p is an integer ranging from 1 to 14.

23. A pharmaceutical composition comprising a population of Ligand-Drug Conjugate compounds or pharmaceutically acceptable salts thereof of claim 21, wherein the average p value for the population of Ligand-Drug Conjugate compounds ranges from 1 to 14.

24. The pharmaceutical composition of claim 23, wherein the average p value for the population of Ligand-Drug Conjugate compounds ranges from 6 to 12.

25. A pharmaceutical composition comprising a population of Ligand-Drug Conjugate compounds or pharmaceutically acceptable salts thereof of claim 22 wherein the average p value for the population of Ligand-Drug Conjugate compounds ranges from 1 to 14.

26. The pharmaceutical composition of claim 25, wherein the average p value for the population of Ligand-Drug Conjugate compounds ranges from 6 to 12.

* * * * *

UNITED STATES PATENT AND TRADEMARK OFFICE
CERTIFICATE OF CORRECTION

| | |
|---|---|
| PATENT NO. | : 11,103,593 B2 |
| APPLICATION NO. | : 15/029584 |
| DATED | : August 31, 2021 |
| INVENTOR(S) | : Lyon et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this
Eighteenth Day of June, 2024

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 117
<212> TYPE: PRT
<213> ORGANISM: Mus musculus

<400> SEQUENCE: 1

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115
```

<210> SEQ ID NO 2
<211> LENGTH: 111
<212> TYPE: PRT
<213> ORGANISM: mus musculus

<400> SEQUENCE: 2

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95
```

```
Glu Asp Pro Trp Thr Phe Gly Gly Gly Thr Lys Leu Glu Ile Lys
                100                 105                 110
```

<210> SEQ ID NO 3
<211> LENGTH: 118
<212> TYPE: PRT
<213> ORGANISM: Artificial
<220> FEATURE:
<223> OTHER INFORMATION: Humanized murine sequence

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115
```

<210> SEQ ID NO 4
<211> LENGTH: 112
<212> TYPE: PRT
<213> ORGANISM: Artificial
<220> FEATURE:
<223> OTHER INFORMATION: Humanized murine sequence

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
            100                 105                 110
```

<210> SEQ ID NO 5
<211> LENGTH: 120
<212> TYPE: PRT
<213> ORGANISM: Artificial
<220> FEATURE:
<223> OTHER INFORMATION: Humanized murine sequence

<400> SEQUENCE: 5

```
Gln Val Gln Leu Gln Glu Ser Gly Pro Gly Leu Val Lys Pro Ser Gln
```

```
                1               5                  10                 15
            Thr Leu Ser Leu Thr Cys Thr Val Ser Gly Gly Ser Ile Ser Thr Ser
                            20                  25                 30
            Gly Met Gly Val Gly Trp Ile Arg Gln His Pro Gly Lys Gly Leu Glu
                        35                  40                  45
            Trp Ile Gly His Ile Trp Trp Asp Asp Lys Arg Tyr Asn Pro Ala
                    50                  55                  60
            Leu Lys Ser Arg Val Thr Ile Ser Val Asp Thr Ser Lys Asn Gln Phe
             65                 70                  75                  80
            Ser Leu Lys Leu Ser Ser Val Thr Ala Ala Asp Thr Ala Val Tyr Tyr
                            85                  90                  95
            Cys Ala Arg Met Glu Leu Trp Ser Tyr Tyr Phe Asp Tyr Trp Gly Gln
                            100                 105                 110
            Gly Thr Leu Val Thr Val Ser Ser
                            115                 120
```

<210> SEQ ID NO 6
<211> LENGTH: 107
<212> TYPE: PRT
<213> ORGANISM: Artificial
<220> FEATURE:
<223> OTHER INFORMATION: Humanized murine sequence

<400> SEQUENCE: 6

```
            Glu Ile Val Leu Thr Gln Ser Pro Ala Thr Leu Ser Leu Ser Pro Gly
             1                5                  10                 15
            Glu Arg Ala Thr Leu Ser Cys Ser Ala Ser Ser Val Ser Tyr Met
                            20                  25                  30
            His Trp Tyr Gln Gln Lys Pro Gly Gln Ala Pro Arg Leu Leu Ile Tyr
                        35                  40                  45
            Asp Thr Ser Lys Leu Ala Ser Gly Ile Pro Ala Arg Phe Ser Gly Ser
                    50                  55                  60
            Gly Ser Gly Thr Asp Phe Thr Leu Thr Ile Ser Ser Leu Glu Pro Glu
             65                 70                  75                  80
            Asp Val Ala Val Tyr Tyr Cys Phe Gln Gly Ser Val Tyr Pro Phe Thr
                            85                  90                  95
            Phe Gly Gln Gly Thr Lys Leu Glu Ile Lys Arg
                            100                 105
```

<210> SEQ ID NO 7
<211> LENGTH: 330
<212> TYPE: PRT
<213> ORGANISM: homo sapiens

<400> SEQUENCE: 7

```
            Ala Ser Thr Lys Gly Pro Ser Val Phe Pro Leu Ala Pro Ser Ser Lys
             1                5                  10                 15
            Ser Thr Ser Gly Gly Thr Ala Ala Leu Gly Cys Leu Val Lys Asp Tyr
                            20                  25                  30
            Phe Pro Glu Pro Val Thr Val Ser Trp Asn Ser Gly Ala Leu Thr Ser
                        35                  40                  45
            Gly Val His Thr Phe Pro Ala Val Leu Gln Ser Ser Gly Leu Tyr Ser
                    50                  55                  60
            Leu Ser Ser Val Val Thr Val Pro Ser Ser Ser Leu Gly Thr Gln Thr
             65                 70                  75                  80
            Tyr Ile Cys Asn Val Asn His Lys Pro Ser Asn Thr Lys Val Asp Lys
                            85                  90                  95
```

```
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 106
<212> TYPE: PRT
<213> ORGANISM: homo sapiens

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 9
<211> LENGTH: 117
<212> TYPE: PRT
```

```
<213> ORGANISM: Artificial
<220> FEATURE:
<223> OTHER INFORMATION: heavy chain variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 10
<211> LENGTH: 111
<212> TYPE: PRT
<213> ORGANISM: Artificial
<220> FEATURE:
<223> OTHER INFORMATION: light chain variable region

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110
```